US008399232B2

(12) United States Patent
Shimada et al.

(10) Patent No.: US 8,399,232 B2

(45) Date of Patent: Mar. 19, 2013

(54) ENZYME ASSOCIATED WITH EQUOL SYNTHESIS

(75) Inventors: Yoshikazu Shimada, Osaka (JP); Setsuko Yasuda, Tokushima (JP); Masayuki Takahashi, Osaka (JP); Takashi Hayashi, Osaka (JP); Norihiro Miyazawa, Osaka (JP); Yasuhiro Abiru, Osaka (JP); Tadaaki Ohtani, Osaka (JP); Ikutaro Sato, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 230 days.

(21) Appl. No.: 12/810,742

(22) PCT Filed: Dec. 25, 2008

(86) PCT No.: PCT/JP2008/073649

§ 371 (c)(1),
(2), (4) Date: Aug. 20, 2010

(87) PCT Pub. No.: WO2009/084603

PCT Pub. Date: Jul. 9, 2009

(65) Prior Publication Data

US 2010/0330627 A1 Dec. 30, 2010

(30) Foreign Application Priority Data

| | | |
|---|---|---|
| Dec. 27, 2007 | (JP) | 2007-336227 |
| Mar. 5, 2008 | (JP) | 2008-054874 |
| Mar. 26, 2008 | (JP) | 2008-080570 |

(51) Int. Cl.

| | |
|---|---|
| ***C12N 9/02*** | (2006.01) |
| ***C12N 15/00*** | (2006.01) |
| ***C12N 1/20*** | (2006.01) |
| ***C12P 21/06*** | (2006.01) |
| ***C12P 21/04*** | (2006.01) |
| ***C12P 21/02*** | (2006.01) |
| ***C07H 21/04*** | (2006.01) |

(52) U.S. Cl. ..... 435/189; 435/155; 435/440; 435/252.3; 435/320.1; 435/69.1; 435/71.1; 536/23.2

(58) Field of Classification Search ........................ None
See application file for complete search history.

(56) References Cited

U.S. PATENT DOCUMENTS

| | | | |
|---|---|---|---|
| 2003/0233675 | A1 | 12/2003 | Cao et al. |
| 2004/0091987 | A1 | 5/2004 | Spellig |
| 2006/0148045 | A1 | 7/2006 | Uchiyama et al. |

FOREIGN PATENT DOCUMENTS

| | | | |
|---|---|---|---|
| EP | 1 306 438 | A1 | 5/2003 |
| EP | 1 649 760 | A1 | 4/2006 |
| EP | 1 792 986 | A1 | 6/2007 |
| JP | 2006-296434 | A | 11/2006 |
| WO | 00/66576 | A1 | 11/2000 |
| WO | 2007/099764 | A1 | 9/2007 |

OTHER PUBLICATIONS

Branden et al. Introduction to Protein Structure, Garland Publishing Inc., New York, p. 247, 1991.*

Kimiko Minamida et al., "Production of Equol from Daidzein by Gram-Positive Rod-Shaped Bacterium Isolated from Rat Intestine", Journal of Bioscience and Bioengineering, vol. 102, No. 3, pp. 247-250 (Sep. 1, 2006).

Kenneth D.R. Setchell et al., "The Clinical Importance of the Metabolite Equol: A Clue to the Effectiveness of Soy and Its Isoflavones", Journal of Nutrition, vol. 132, No. 12, pp. 3577-3584 (Dec. 2002).

G. E. Joannou et al., "A Urinary Profile Study of Dietary Phytoestrogens. The Identification and Mode of Metabolism of New Isoflavonoids", Journal of Steroid Biochemistry and Molecular Biology, vol. 54, No. 3-4, pp. 167-184 (Jan. 1, 1995).

Yoshikazu Shimada et al., "Cloning and Expression of a Novel NADP(H)-Dependent Daidzein Reductase, an Enzyme Involved in the Metabolism of Daidzein, from Equol-Producing Lactococcus Strain 20-92", Applied and Environmental Microbiology, American Society for Microbiology, vol. 76, No. 17, pp. 5892-5901 (Sep. 1, 2010).

T. Ueno et al., "Identification of the specific intestinal bacteria capable of metabolising soy isoflavone to equol", Annals of Nutrition and Metabolism, vol. 45, p. 114 (Jan. 1, 2001).

Extended European Search Report dated Dec. 1, 2010 on corresponding European Patent Application No. 08867315.

Examination Report dated Jul. 20, 2012 in Singapore Patent Application No. 201004399-0.

Xiu-Ling Wang et al., "Enantioselective Synthesis of *S*-Equol from Dihydrodaidzein by a Newly Isolated Anaerobic Human Intestinal Bacterium", Applied and Environmental Microbiology, 2005, 71(1):214-219.

APKG3142.g2 HF4000_Dec. 21, 2003 Uncultured Marine Microorganism HF4000_Dec. 21, 2003 genomic clone HF4000_[384]008K17, genomic survey sequence; Database accession No. DU772802.

Bacterial Polynucleotide #4802, Database accession No. ADS50059.

Community Genomics Among Stratified Microbial Assemblages in the Ocean's Interior, Science, vol. 311, No. 5760, Jan. 27, 2006, pp. 496-503.

(Continued)

*Primary Examiner* — Yong Pak
(74) *Attorney, Agent, or Firm* — Sughrue Mion, PLLC

(57) ABSTRACT

An object of the present invention is to provide enzymes associated with equol synthesis, genes coding such enzymes, and a process for producing equol and its intermediates using the enzymes and genes.

The present invention provides a dihydrodaidzein synthesizing enzyme, tetrahydrodaidzein synthesizing enzyme, equol synthesizing enzyme, and genes coding these enzymes. The present invention also provides a process for synthesizing dihydrodaidzein, tetrahydrodaidzein, and/or equol using these enzymes.

5 Claims, 33 Drawing Sheets

OTHER PUBLICATIONS

European Search Report dated Dec. 13, 2011 for EP Application No. 11170947.3.

European Search Report dated Dec. 13, 2011 for EP Appln. No. 11170943.2.

*Pseudomonas aeruginosa* polynucleotide #12355. Database Accession No. ABD13751.

Soybean Metabolite—The Equol Research Progress, Progress in Physiology, vol. 37, No. 4, pp. 359-361 (2006).

* cited by examiner

Fig. 2
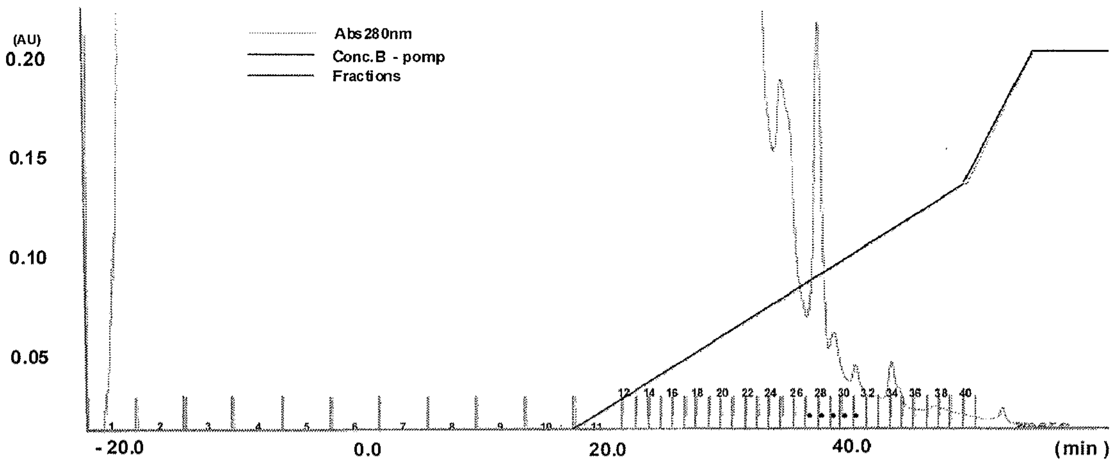
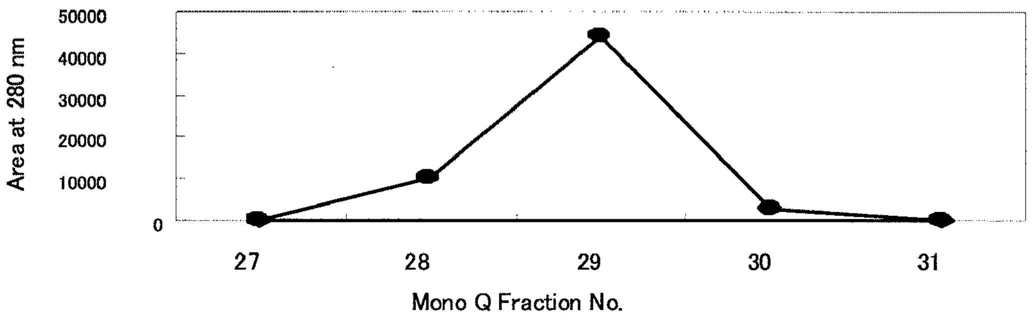

Fig. 16-1-a
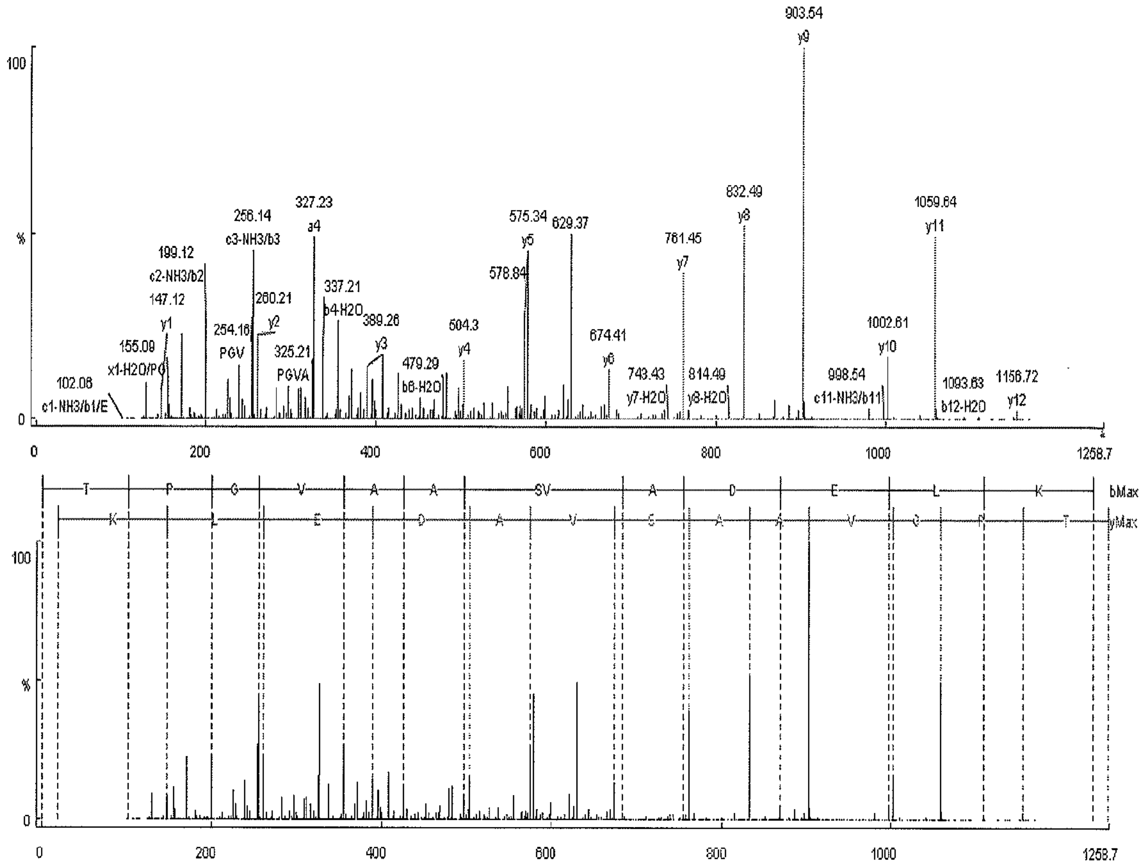

Fig. 16-1-b
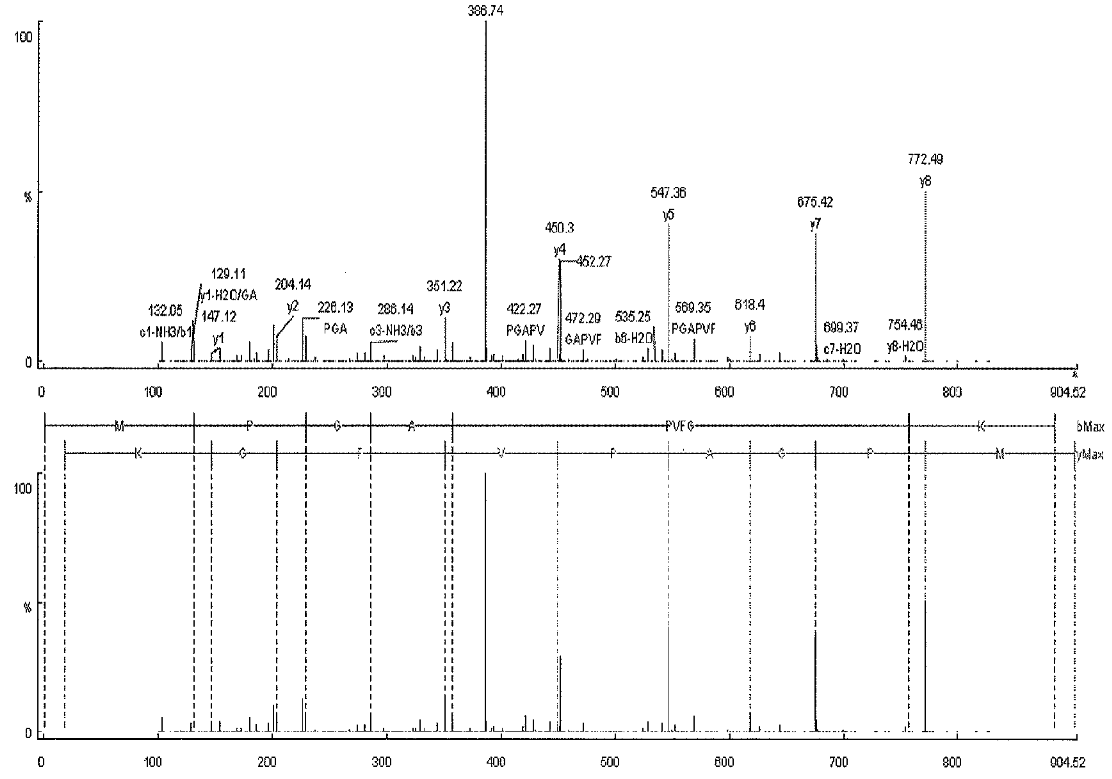

Fig. 16-2-a
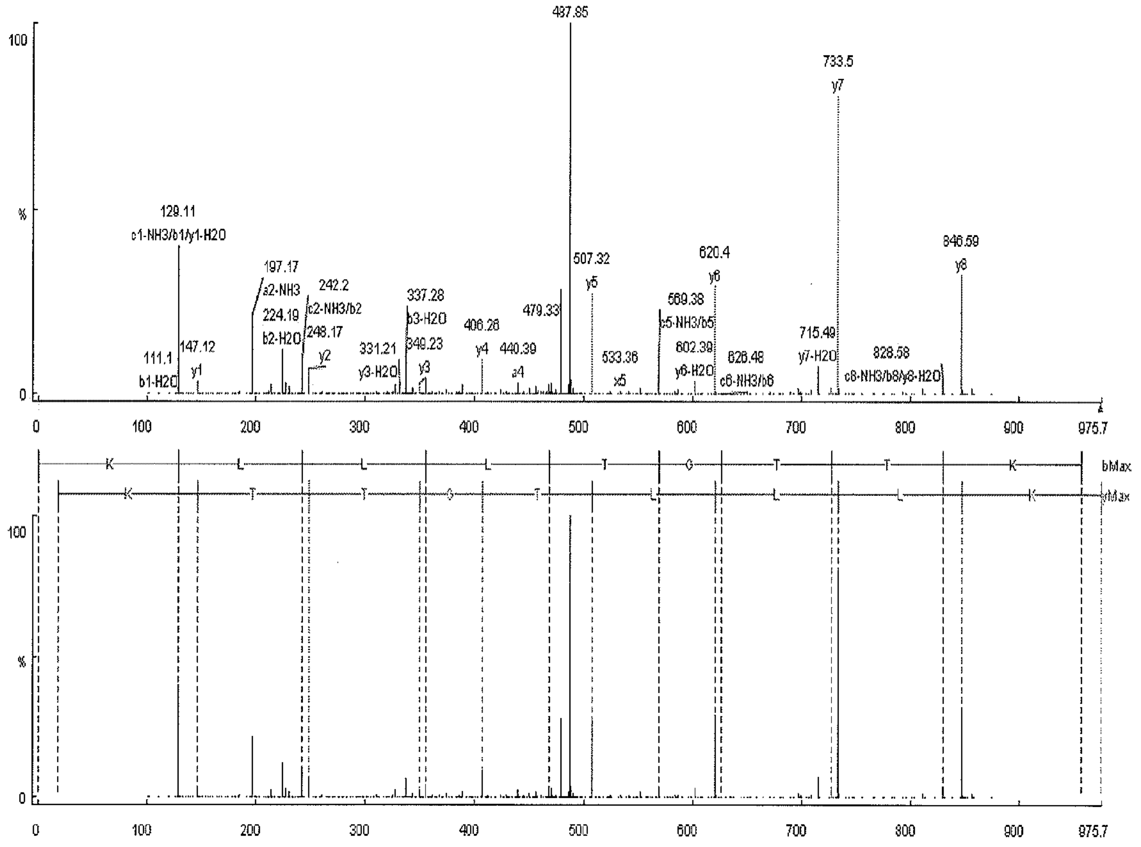

Fig. 16-2-b
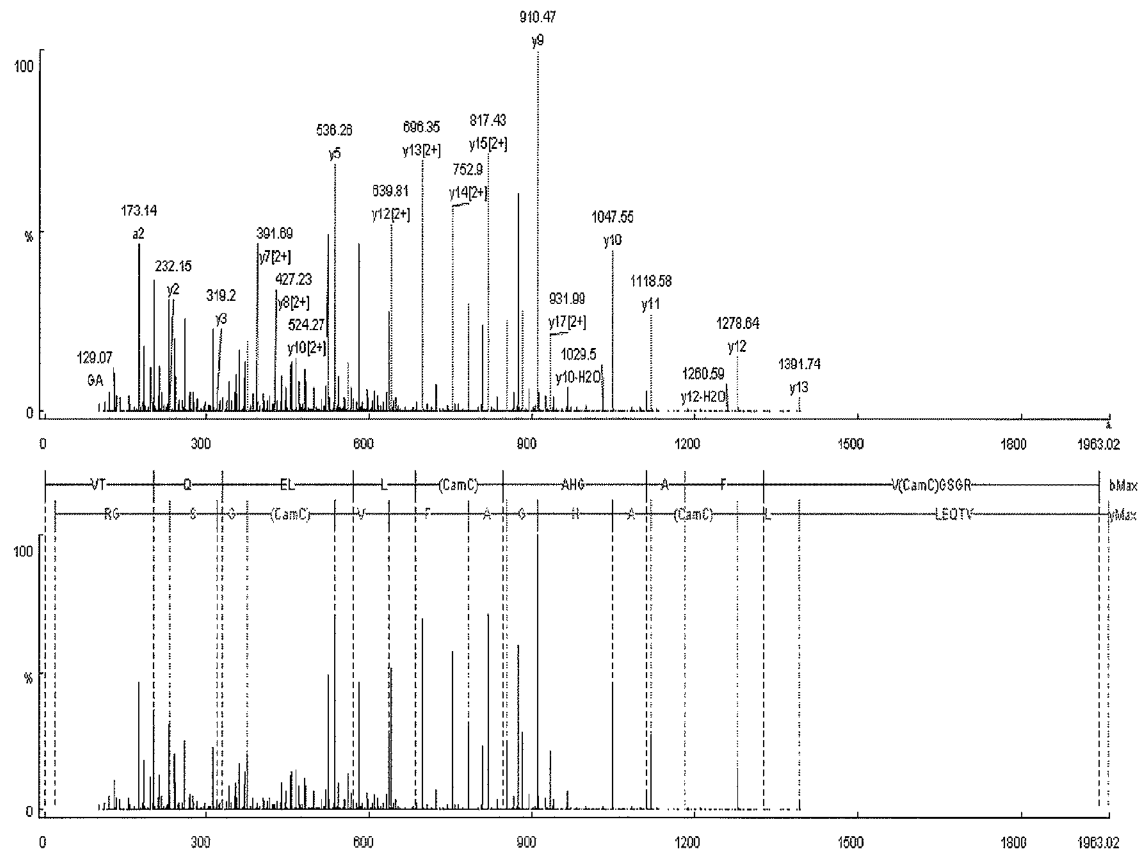

Fig. 19
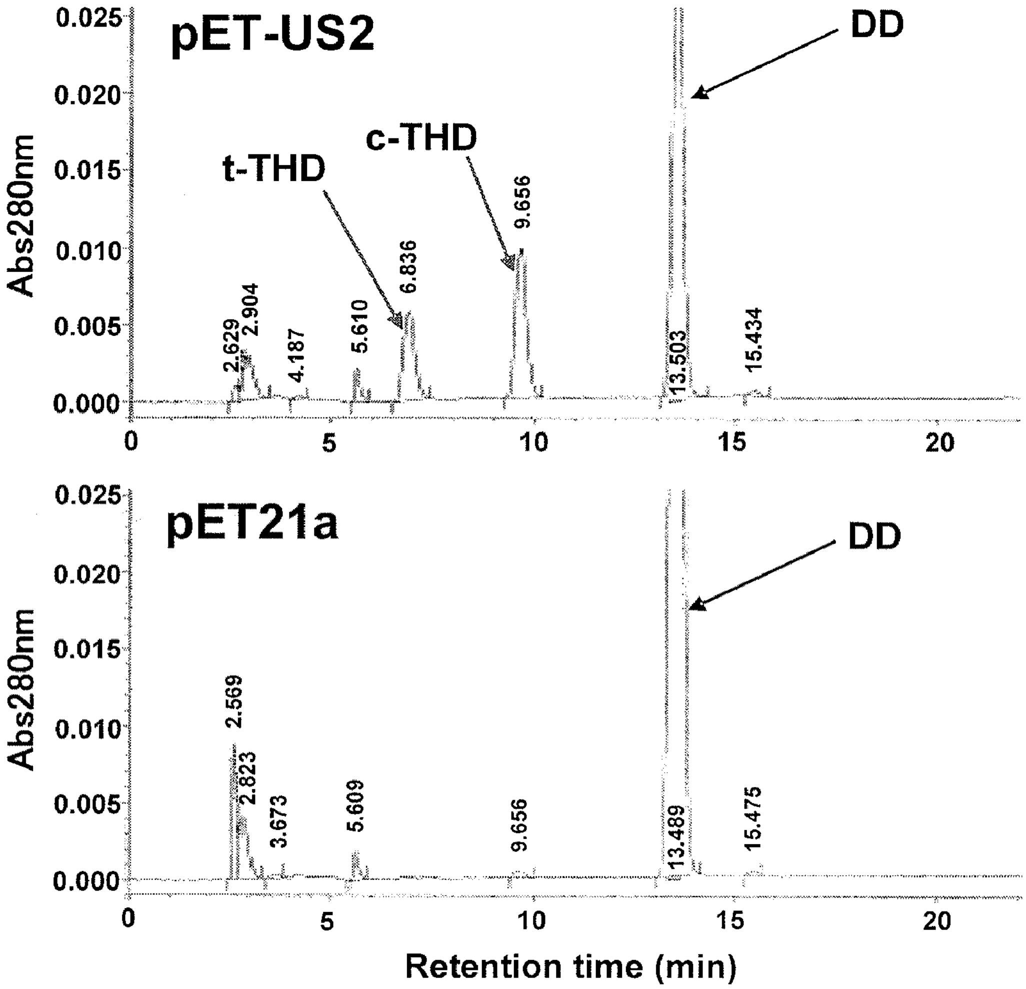
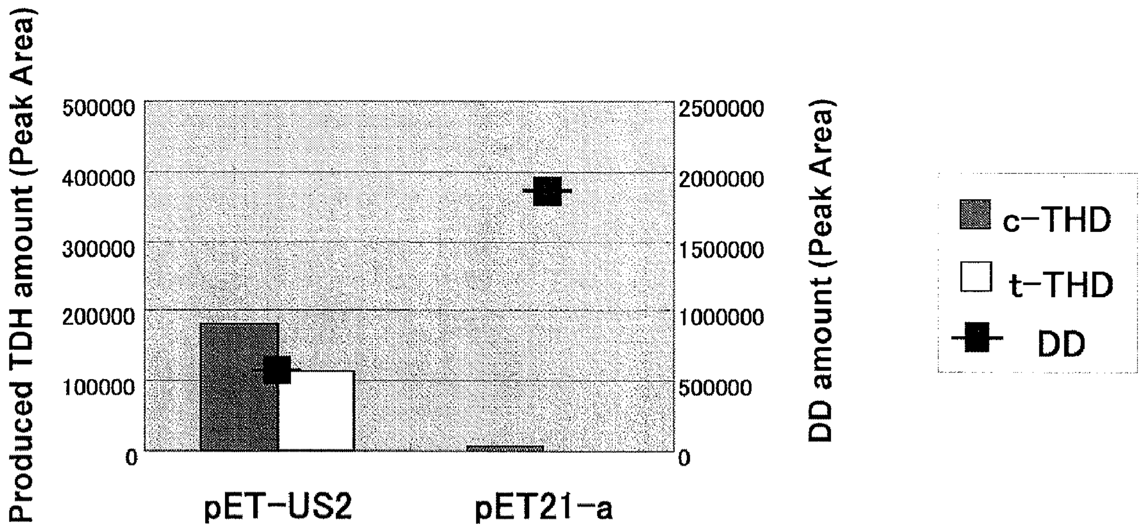

Fig. 27

```
                                                                                         NADPH-binding domain
Lactococcus_E1    MKNKFYPKTFERGYIGNLEVENRAIRMPMGTELGNPDGSPSWASLKAYAEAADGGTGIVFMDNAGVTQFHHVGLSLASDNYIGPMSVLAKTIKQHGAIPGLQIVHPGRDAAFVRGDDLIS
Bacteroides_E1    MKNKFYPKTFERGYIGNLEVENRAIRMPMGTELGNPDGSPSWASFKAYAEAADGGTGIVFMDNAGVTQFHHVGLSLASDNYIGPMSVLAKTIKQHGAIPGLQIVHPGRDAAFVRGDDLIS
Streptcoccus_E1   MKNKFYPKTFERGYIGNLEVENRAIRMPMGTELGNPDGSPSWASLKAYAEAADGGTGIVFMDNAGVTQFHHVGLSLASDKYIGPMSVLAKTIKQHGAIPGLQIVHPGRDAAFVRGDDLIS

                  OYE like FMN family sequence
Lactococcus_E1    SSRIQWEPWYENGGAVPRELTIEEIHDFVGYFGDCALRAQTAGFEIVDVHAACGVLLSNFLSPRNNTRNDMYGGSLHNRARFLLEVIRDIKKKCPNLPLAIRLSGIDFEPDGITIEETCE
Bacteroides_E1    SSRIQWEPWYENGGAVPRELTIEEIHDFVGYFGDCALRAQTAGFEIVDVHAACGVLLSNFLSPRNNTRNDMYGGSLHNRARFLLEVIRDIKKKCPNLPLAIRLSGIDFEPDGITIEETCE
Streptcoccus_E1   SSRIQWEPWYENGGAVPRELTIEEIHDFVGYFGDCALRAQTAGFEIIDVHAACGVLLSNFLSPRNNTRNDMYGGSLHNRARFLLEVIRDIKKKCPNLPLAIRLSGIDFEPGGITVEETCE

                                                                                         Iron-Sulfur Protein Fe4S4 Cluster
Lactococcus_E1    VAKNCEAAGADAINITWGSHAEVINAAGLLSKHGANHVEAAKMIKDAVSIPTMLCGGIYSPEIGEKLLEDGVCDFIGIGKPALADPMWAKKAAEGRPEDIRPCIGCGVGCHDRGMLSGGV
Bacteroides_E1    VAKNCEAAGADAINITWGSHAEVINAAGLLSKHGANHVEAAKMIKDAVSIPTMLCGGIYSPEIGEKLLEDGVCDFIGIGKPALADPMWAKKAAEGRPEDIRPCIGCGVGCHDRGMLSGGV
Streptcoccus_E1   VAKNCEAAGADAINITWGSHAEVINAAGLLSKHGANHVEAAKMIKDAVSIPTMLCGGIYSPEIGEKLLEDGVCDFIGIGKPALADPMWAKKAAEGRPEDIRPCIGCGVGCHDRGMLSGGV

                  FAD-dependent pyridine nucleotide reductase signat
Lactococcus_E1    VQCAVNAALYKFDEPVYPQAEVPKKVIIGAGPAGCEAAITAKKCGHDVTIYEKRKIGGVLKEATVSDSKEDLGRLITYYETQLKKEGIEVIYEEATADTVVAGGFDVAIVACGATVRNL
Bacteroides_E1    VQCAVNAALYKFDEPVYPQAEVPKKVIIGAGPAGCEAAITAKKCGHDVTIYEKRKIGGVLKEATVSDSKEDLGRLITYYETQLKKEGIEVIYEEATADTVVAGGFDVAIVACGATVRNL
Streptcoccus_E1   VQCAVNAALYKFDEPVYPQAEVPKKVIIGAGPAGCEAAITAKKCGHDVTIYEKRKIGGVLKEATVSDSKEDLGYLITYYETQLKKEGIEVIYEEATASTVAAGGFDVAIVACGATVRNL

                  FAD-dependent pyridine nucleotide reductase signat
Lactococcus_E1    NIDGQDDPSVVYAMDFLDNDCKSDADRVVVVGGGIVGAETALILAEERGKDVTITTRSPEFFVSGVMGIAYMVRLGMAGVTIKPSTQLVAVKDGKPMFAGPRGLETLDVDQTIISSGFVP
Bacteroides_E1    NIDGQDDPSVVYAMDFLDNDCKSDADRVVVVGGGIVGAETALILAEERGKDVTITTRSPEFFVPGVMGIAYMVRLGMAGVTIKPSTQLVAVKDGKPMFAGPRGLETLDVDQTIISSGFVP
Streptcoccus_E1   NIDGQDDPSVVYAMDFLDNDCKSDADRVVVVGGGIVGAETALILAEEQGKDVTITTRSPEFFVPGVMGIAYMVRLGMAGVTIKPSTQLVAVKDGKPMFAGPRGLETLDVDQTIISSGFVP

Lactococcus_E1    TFNQFRAQIEEKCEDVRVIGIGDCKASRMVMDAVHEGYIAGCNL
Bacteroides_E1    TFNQFRAQIEEKCEDVRVIGIGDCKASRMVMDAVHEGYLAGCNL
Streptcoccus_E1   TFNQFRAQIEEKCEDVRVIGIGDCKASRMVMDAVHEGYIAGCNL
```

♦ : FMN binding site (conserved)

♦ : FMN binding site (not conserved?)

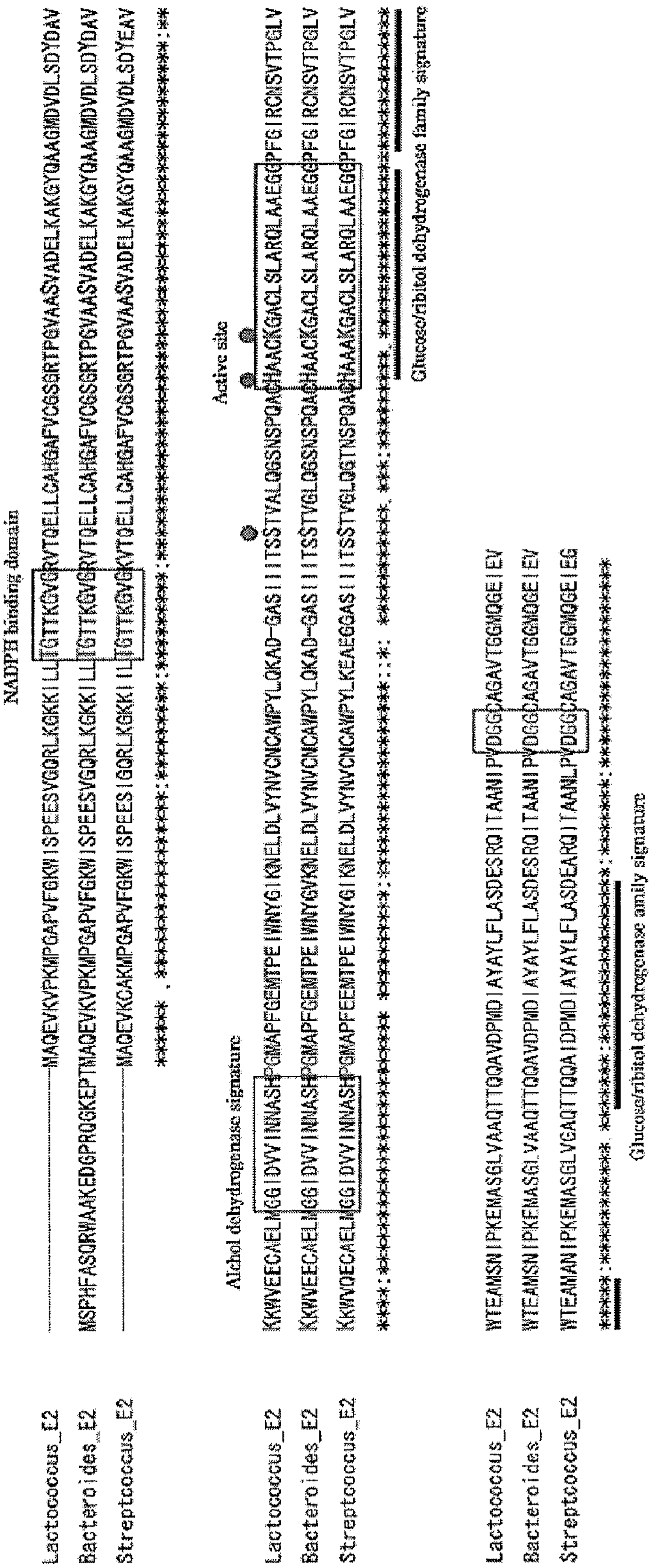

Fig. 28

```
                                                       NADPH binding domain
Lactococcus_E2      ----------------------MAQEVKVPKMPGAPVFGKWISPEESVGQRLKGKKILL|GTTKGVGRVTQELLCAHGAFVCGSGRTPGVAASVADELKAKGYQAAGMDVDLSDYDAV
Bacteroides_E2      MSPHFASQRWAAKEDGPRQGKEPTMAQEVKVPKMPGAPVFGKWISPEESVGQRLKGKKILL|GTTKGVGRVTQELLCAHGAFVCGSGRTPGVAASVADELKAKGYQAAGMDVDLSDYDAV
Streptococcus_E2    ----------------------MAQEVKCAKMPGAPVFGKWISPEESIGQRLKGKKILL|GTTKGVGKVTQELLCAHGAFVCGSGRTPGVAASVADELKAKGYQAAGMDVDLSDYEAV
                                          *****  *********** *****  *******:*********************************************** ***

                                                                                              Active site
Lactococcus_E2      KKWVEECAELMGGIDVVINNASH|PGWAPFGEMTPEIWNYGIKNELDLVYNVCNCAWPYLQKAD-GASIIITSSTVALQGSNSPQACHAACKGACLSLARQLAAEGGPFGIRCNSVTPGLV
Bacteroides_E2      KKWVEECAELMGGIDVVINNASH|PGWAPFGEMTPEIWNYGVKNELDLVYNVCNCAWPYLQKAD-GASIIITSSTVGLQGSNSPQACHAACKGACLSLARQLAAEGGPFGIRCNSVTPGLV
Streptococcus_E2    KKWVQECAELMGGIDVVINNASH|PGWAPFGEMTPEIWNYGIKNELDLVYNVCNCAWPYLKEAEGGASIIITSSTVGLGTNSPQACHAAAKGACLSLARQLAAEGGPFGIRCNSVTPGLV
                    **** ****************** ****************:***********:**:  * ***:**:*** ** ******* ***:***************************
                                Alchol dehydrogenase signature                                        Glucose/ribitol dehydrogenase family signature

Lactococcus_E2      WTEAMSNIPKEMASGLVAAQTTQQAVDPMIDIAYAYLFLASDESRQITAANIPVDGGCAGAVTGGMQGEIEV
Bacteroides_E2      WTEAMSNIPKFMASGIVAAQTTQQAVDPMIDIAYAYLFLASDESRQITAANIPVDGGCAGAVTGGMQGEIEV
Streptococcus_E2    WTEAMANIPKEMASGLVEAQTTQQAIDPMIDIAYAYLFLASDEARQITAANLPVDGGCAGAVTGGMQGEIEG
                    ***** ***** *** * *******:***************:*******:*****************:*
                    Glucose/ribitol dehydrogenase family signature
```

ENZYME ASSOCIATED WITH EQUOL SYNTHESIS

TECHNICAL FIELD

The present invention relates to a polypeptide having an activity to synthesize dihydrodaidzein using daidzein as a substrate, a polypeptide having an activity to synthesize tetrahydrodaidzein using dihydrodaidzein as a substrate, and a polypeptide having an activity to synthesize equol using tetrahydrodaidzein as a substrate, as well as a polynucleotide that encodes these polypeptides. The invention further relates to processes for producing dihydrodaidzein, tetrahydrodaidzein, and equol using the above polypeptides, and a production apparatus used in the processes. The invention also provides techniques concerning thereto.

BACKGROUND ART

Isoflavone derivatives are believed to possess various physiological and pharmacological activities. For this reason, isoflavone derivatives are used as material for food and pharmaceuticals. As studies uncover the functions of isoflavone derivatives, there have been reports that the estrogen-like activity of isoflavone derivatives is not, as conventionally believed, due to the action of the isoflavone derivatives themselves, but due to the strong estrogen-like activity found throughout the body exhibited by equol, which is absorbed in the intestines after being released from various kinds of intestinal bacteria metabolizing (biosynthesizing) the isoflavone derivatives to produce equol. In humans, not all individuals have the ability to produce equol in the intestines, and such an equol-producing ability varies among different individuals. For example, some individuals may have no equol-producing bacteria in the intestines, while others may have such bacteria, but with only a limited ability to produce equol.

Accordingly, it would be beneficial in countries with aging populations, such as Japan, to make effective use of equol in the body, particularly in consideration of chronic disorders such as osteoporosis affecting the elderly. Given the fact that equol-producing bacteria are not found in all individuals, there is a need to find an equol synthesis material which enables efficient artificial equol production.

Under these circumstances, it is very important, in terms of providing an equol synthesis material, to identify and use enzymes involved in the equol biosynthetic pathway. However, no information is available concerning enzymes producing or catalyzing some of the intermediates involved in the biosynthetic pathway. Accordingly, the identification of enzymes associated with the synthesis of such intermediates is desired.

Patent Document 1: JP-A-2006-296434

DISCLOSURE OF INVENTION

Technical Problem

It is an object of the present invention to provide an enzyme associated with the synthesis of dihydrodaidzein that can be used as a material of equol synthesis. Specifically, the invention aims to provide a polypeptide having an activity to synthesize dihydrodaidzein using daidzein as a substrate. The invention also aims to provide a polynucleotide that encodes such a polypeptide, and techniques concerning dihydrodaidzein synthesis using such a polypeptide.

It is another object of the present invention to provide an enzyme associated with the synthesis of tetrahydrodaidzein that can be used as a material of equol synthesis. Specifically, the invention aims to provide a polypeptide having an activity to synthesize tetrahydrodaidzein using dihydrodaidzein as a substrate. The invention also aims to provide a polynucleotide that encodes such a polypeptide, and techniques concerning tetrahydrodaidzein synthesis using such a polypeptide.

It is another object of the present invention to provide an enzyme associated with equol synthesis. Specifically, the invention aims to provide a polypeptide having an activity to synthesize equol using tetrahydrodaidzein as a substrate. The invention also aims to provide a polynucleotide that encodes such a polypeptide, and techniques concerning equol synthesis using such a polypeptide.

It is another object of the present invention to provide a process for producing intermediates such as dihydrodaidzein and tetrahydrodaidzein generated in the production of equal from daidzein, and a process for producing equol using the obtained intermediates. The invention also aims to provide a producing apparatus for use in the production.

Technical Solution

The inventors of the present invention conducted intensive studies to solve the foregoing problems, and successfully isolated from equol-producing intestinal bacteria an enzyme capable of synthesizing dihydrodaidzein, an enzyme capable of synthesizing tetrahydrodaidzein, and an enzyme capable of synthesizing equol, used as starting materials of equol synthesis, and revealed the structures of these enzymes. Moreover, the inventors conducted further studies, and succeeded in the artificial production of dihydrodaidzein, tetrahydrodaidzein, and equol, using the above enzymes. The present invention was accomplished upon further studies based on these findings.

Specifically, in one aspect, the present invention provides:

Item A1. A polypeptide selected from:

(Aa) a polypeptide consisting of the amino acid sequence of SEQ ID NO: 1;

(Ab) a polypeptide consisting of the amino acid sequence of SEQ ID NO: 1 with the substitution, deletion, insertion, and/or addition of one or more amino acids, and having an activity to synthesize dihydrodaidzein using daidzein as a substrate; and (Ac) a polypeptide consisting of an amino acid sequence having 60% or more identity with the amino acid sequence of SEQ ID NO: 1, and having an activity to synthesize dihydrodaidzein using daidzein as a substrate.

Item A2. A polynucleotide selected from:

(Ad) a polynucleotide consisting of the nucleotide sequence of SEQ ID NO: 4;

(Ae) a polynucleotide that encodes a polypeptide consisting of the amino acid sequence of SEQ ID NO: 1; and (Af) a polynucleotide that hybridizes under stringent conditions with the complementary strand of the polynucleotide (Ad) or (Ae), and that encodes a polypeptide having an activity to synthesize dihydrodaidzein using daidzein as a substrate.

Item A3. An expression vector including the polynucleotide of Item A2.

Item A4. A recombinant cell transformed with the expression vector of Item A3.

Item A5. A recombinant cell according to Item A4, wherein the recombinant cell is a bacterial prokaryotic cell.

Item A6. A recombinant cell according to Item A5, wherein the bacterial prokaryotic cell belongs to the genus *Lactococcus.*

Item A7. A process for producing a polypeptide, comprising culturing the cell of any one of Items A4 through A6 to obtain a polypeptide having an activity to synthesize dihydrodaidzein using daidzein as a substrate.

Item A8. A polypeptide obtained by the process of Item A7.

Item. A9. A process for producing dihydrodaidzein, comprising having the polypeptide of Item A1 or A8, and NADPH and/or NADH act on daidzein.

Item A10. A process for producing dihydrodaidzein, comprising having the cell of any one of Items A4 through A6 act on daidzein.

Item A11. An antibody having affinity to the polypeptide of Item A1, or the polypeptide encoded by the polynucleotide of Item A2.

Item A12. An immunological method for detecting or measuring the polypeptide of Item A1 or the polypeptide encoded by the polynucleotide of Item A2, the method comprising having the antibody of Item A11 contact a test sample.

Item A13. A method according to Item A12, wherein the polypeptide to be detected or measured exists in a bacterial prokaryotic cell.

Item A14. A probe having a nucleotide sequence capable of hybridizing under stringent conditions with a polynucleotide that encodes the polypeptide of Item A1, or with the polynucleotide of Item A2.

Item A15. A primer having a nucleotide sequence capable of hybridizing under stringent conditions with a polynucleotide that encodes the polypeptide of Item A1, or with the polynucleotide of Item A2.

Item A16. A method for detecting or measuring a polynucleotide that encodes the polypeptide of Item A1, or the polynucleotide of Item A2, using the probe of Item A14.

Item A17. A method according to Item A16, wherein the polypeptide to be detected or measured exists in a bacterial prokaryotic cell.

Item A18. A method according to Item A16, comprising PCR amplifying all of or part of a polynucleotide that encodes the polypeptide of Item A1, or the polynucleotide of Item A2.

Item A19. A dihydrodaidzein synthesizing enzyme composition, comprising the polypeptide of Item A1, or a polypeptide encoded by the polynucleotide of Item A2.

Item A20. A composition according to Item A19, further comprising NADPH and/or NADH.

Item A21. A dihydrodaidzein synthesis composition, comprising:

(Ai) the polypeptide of Item A1, or a polypeptide encoded by the polynucleotide of Item A2;

(Aii) NADPH and/or NADH; and (Aiii) daidzein.

Item A22. A dihydrodaidzein synthesis composition, comprising:

(Aiv) the cell of any one of Items A4 through A6; and (Aiii) daidzein.

Item A23. A dihydrodaidzein synthesis kit, comprising:

(Ai) the polypeptide of Item A1, or a polypeptide encoded by the polynucleotide of Item A2;

(Aii) NADPH and/or NADH; and (Aiii) daidzein.

Item A24. A dihydrodaidzein synthesis kit, comprising:

(Aiv) the cell of any one of Items A4 through A6; and (Aiii) daidzein.

Item A25. An immunological measurement kit for measuring the polypeptide of Item A1, or a polypeptide encoded by the polynucleotide of Item A2, the kit comprising at least the antibody of Item A11.

Item A26. A PCR kit for detecting a polynucleotide encoding the polynucleotide of Item A1, or the polynucleotide of of Item A2, the PCR kit comprising at least the primer of Item A15.

Item A27. A kit according to Item A26, wherein the kit is for identifying a cell containing a polynucleotide encoding the polypeptide of Item A1, or the polynucleotide of Item A2.

Item A28. A PCR kit according to Item A27, wherein the kit is for PCR.

Item A29. A dihydrodaidzein synthesizing enzyme, which consists of the polypeptide of Item A1.

Item B1. A polypeptide selected from:

(Ba) a polypeptide consisting of the amino acid sequence of SEQ ID NO: 7;

(Bb) a polypeptide consisting of the amino acid sequence of SEQ ID NO: 7 with the substitution, deletion, insertion, and/or addition of one or more amino acids, and having an activity to synthesize tetrahydrodaidzein using dihydrodaidzein as a substrate; and (Bc) a polypeptide consisting of an amino acid sequence having 60% or more identity with the amino acid sequence of SEQ ID NO: 7, and having an activity to synthesize tetrahydrodaidzein using dihydrodaidzein as a substrate.

Item B2. A polynucleotide selected from:

(Bd) a polynucleotide consisting of the nucleotide sequence of SEQ ID NO: 10;

(Be) a polynucleotide that encodes a polypeptide consisting of the amino acid sequence of SEQ ID NO: 7; and (Bf), a polynucleotide that hybridizes under stringent conditions with the complementary strand of the polynucleotide (Bd) or (Be), and that encodes a polypeptide having an activity to synthesize tetrahydrodaidzein using dihydrodaidzein as a substrate.

Item B3. An expression vector including the polynucleotide of Item B2.

Item B4. A recombinant cell transformed with the expression vector of Item B3.

Item B5. A recombinant cell according to Item B4, wherein the recombinant cell is a bacterial prokaryotic cell.

Item B6. A recombinant cell according to Item B5, wherein the bacterial prokaryotic cell belongs to the genus *Lactococcus*.

Item B7. A process for producing a polypeptide, comprising culturing the cell of any one of Items B4 through B6 to obtain a polypeptide having an activity to form tetrahydrodaidzein using dihydrodaidzein as a substrate.

Item B8. A polypeptide obtained by the process of Item B7.

Item B9. A process for producing tetrahydrodaidzein, comprising having the polypeptide of Item B1 or B8, and NADPH and/or NADH act on dihydrodaidzein.

Item B10. A process for producing tetrahydrodaidzein, comprising having the cell of any one of Items B4 through B6 act on dihydrodaidzein.

Item B11. An antibody having affinity to the polypeptide of Item B1, or the polypeptide encoded by the polynucleotide of Item B2.

Item B12. An immunological method for detecting or measuring the polypeptide of Item B1 or the polypeptide encoded by the polynucleotide of Item B2, the method comprising having the antibody of Item B11 contact a test sample.

Item B13. A method according to Item B12, wherein the polypeptide to be detected or measured exists in a bacterial prokaryotic cell.

Item B14. A probe having a nucleotide sequence capable of hybridizing under stringent conditions with a polynucleotide that encodes the polypeptide of Item B1, or with the polynucleotide of Item B2.

Item B15. A primer having a nucleotide sequence capable of hybridizing under stringent conditions with a polynucleotide that encodes the polypeptide of Item B1, or with the polynucleotide of Item B2.

Item B16. A method for detecting or measuring a polynucleotide that encodes the polypeptide of Item B1, or the polynucleotide of Item B2, using the probe of Item B14.

Item B17. A method according to Item B16, wherein the polypeptide to be detected or measured exists in a bacterial prokaryotic cell.

Item B18. A method according to Item B16, comprising PCR amplifying all of or part of a polynucleotide that encodes the polypeptide of Item B1, or the polynucleotide of Item B2.

Item B19. A tetrahydrodaidzein synthesizing enzyme composition, comprising the polypeptide of Item B1, or a polypeptide encoded by the polynucleotide of Item B2.

Item B20. A composition according to Item B19, further comprising NADPH and/or NADH.

Item B21. A tetrahydrodaidzein synthesis composition, comprising:

(Bi) the polypeptide of Item B1, or a polypeptide encoded by the polynucleotide of Item B2;

(Bii) NADPH and/or NADH; and (Biii) dihydrodaidzein.

Item B22. A tetrahydrodaidzein synthesis composition, comprising:

(Biv) the cell of any one of Items B4 through B6; and (Biii) dihydrodaidzein.

Item B23. A tetrahydrodaidzein synthesis kit, comprising:

(Bi) the polypeptide of Item B1, or a polypeptide encoded by the polynucleotide of Item B2;

(Bii) NADPH and/or NADH; and (Biii) dihydrodaidzein.

Item B24. A tetrahydrodaidzein synthesis kit, comprising:

(Biv) the cell of any one of Items B4 through B6; and (Biii) dihydrodaidzein.

Item B25. An immunological measurement kit for measuring the polypeptide of Item B1, or a polypeptide encoded by the polynucleotide of Item B2, the kit comprising at least the antibody of Item B11.

Item B26. A PCR kit for detecting a polynucleotide encoding the polypeptide of Item B1, or the polynucleotide of Item B2, the PCR kit comprising at least the primer of Item B15.

Item B27. A kit according to Item B26, wherein the kit is for identifying a cell containing the polynucleotide encoding the polypeptide of Item B1, or the polynucleotide of Item B2.

Item B28. A PCR kit according to Item B27, wherein the kit is for PCR.

Item B29. A tetrahydrodaidzein synthesizing enzyme, which consists of the polypeptide of Item B1.

Item C1. A polypeptide selected from:

(Ca) a polypeptide consisting of the amino acid sequence of SEQ ID NO: 13;

(Cb) a polypeptide consisting of the amino acid sequence of SEQ ID NO: 13 with the substitution, deletion, insertion, and/or addition of one or more amino acids, and having an activity to synthesize equol using tetrahydrodaidzein as a substrate; and (Cc) a polypeptide consisting of an amino acid sequence having 60% or more identity with the amino acid sequence of SEQ ID NO: 13, and having an activity to synthesize equol using tetrahydrodaidzein as a substrate.

Item C2. A polynucleotide selected from:

(Cd) a polynucleotide consisting of the nucleotide sequence of SEQ ID NO: 16;

(Ce) a polynucleotide that encodes a polypeptide consisting of the amino acid sequence of SEQ ID NO: 13; and (Cf) a polynucleotide that hybridizes under stringent conditions with the complementary strand of the polynucleotide (Cd) or (Ce), and that encodes a polypeptide having an activity to synthesize equol using tetrahydrodaidzein as a substrate.

Item C3. An expression vector including the polynucleotide of Item C2.

Item C4. A recombinant cell transformed with the expression vector of Item C3.

Item C5. A recombinant cell according to Item C4, wherein the recombinant cell is a bacterial prokaryotic cell.

Item C6. A recombinant cell according to Item C5, wherein the bacterial prokaryotic cell belongs to the genus *Lactococcus.*

Item C7. A process for producing a polypeptide, comprising culturing the cell of any one of Items C4 through C6 to obtain a polypeptide having an activity to form equol using tetrahydrodaidzein as a substrate.

Item C8. A polypeptide obtained by the process of Item C7.

Item C9. A process for producing equol, comprising having the polypeptide of Item C1 or C8 act on tetrahydrodaidzein.

Item C10. A process for producing equol, comprising having the cell of any one of Items C4 through C6 act on tetrahydrodaidzein.

Item C11. An antibody having affinity to the polypeptide of Item C1, or the polypeptide encoded by the polynucleotide of Item C2.

Item C12. An immunological method for detecting or measuring the polypeptide of Item C1 or the polypeptide encoded by the polynucleotide of Item C2, the method comprising having the antibody of Item C11 contact a test sample.

Item C13. A method according to Item C12, wherein the polypeptide to be detected or measured exists in a bacterial prokaryotic cell.

Item C14. A probe having a nucleotide sequence capable of hybridizing under stringent conditions with a polynucleotide that encodes the polypeptide of Item C1, or with the polynucleotide of Item C2.

Item C15. A primer having a nucleotide sequence capable of hybridizing under stringent conditions with a polynucleotide that encodes the polypeptide of Item C1, or with the polynucleotide of Item C2.

Item C16. A method for detecting or measuring a polynucleotide that encodes the polypeptide of Item C1, or the polynucleotide of Item C2, using the probe of Item C14.

Item C17. A method according to Item C16, wherein the polypeptide to be detected or measured exists in a bacterial prokaryotic cell.

Item C18. A method according to Item C16, comprising PCR amplifying all of or part of a polynucleotide that encodes the polypeptide of Item C1, or the polynucleotide of Item C2.

Item C19. An equol synthesizing enzyme composition, comprising the polypeptide of Item C1, or a polypeptide encoded by the polynucleotide of Item C2.

Item C20. An equol synthesis composition comprising:

(Ci) the polypeptide of Item C1, or a polypeptide encoded by the polynucleotide of Item C2; and (Cii) tetrahydrodaidzein.

Item C21. An equol synthesis composition comprising:
(Ciii) the cell of any one of Items C4 through C6; and
(Cii) tetrahydrodaidzein.

Item C22. An equol synthesis kit comprising:
(Ci) the polypeptide of Item C1, or a polypeptide encoded by the polynucleotide of Item C2; and
(Cii) tetrahydrodaidzein.

Item C23. An equol synthesis kit comprising:
(Ciii) the cell of any one of Items C4 through C6; and
(Cii) tetrahydrodaidzein.

Item C24. An immunological measurement kit for measuring the polypeptide of Item C1, or a polypeptide encoded by the polynucleotide of Item C2,
the kit comprising at least the antibody of Item C11.

Item C25. A PCR kit for detecting a polynucleotide encoding the polypeptide of Item C1, or the polynucleotide of Item C2,
the PCR kit comprising at least the primer of Item C15.

Item C26. A kit according to Item C25, wherein the kit is for identifying a cell containing a polynucleotide encoding the polypeptide of Item C1, or the polynucleotide of Item C2.

Item C27. A kit according to Item C26, wherein the kit is for PCR.

Item C28. An equol synthesizing enzyme, which consists of the polypeptide of Item C1.

Item D1. A process for producing tetrahydrodaidzein comprising the following First Step and Second Step, First Step comprising a step of having an enzyme consisting of one of the following (Aa) to (Ac) polypeptides, and NADPH and/or NADH act on daidzein, thereby producing dihydrodaidzein, (Aa) a polypeptide consisting of the amino acid sequence of SEQ ID NO: 1;

(Ab) a polypeptide consisting of the amino acid sequence of SEQ ID NO: 1 with the substitution, deletion, insertion, and/or addition of one or more amino acids, and having an activity to synthesize dihydrodaidzein using daidzein as a substrate; and (Ac) a polypeptide consisting of an amino acid sequence having 60% or more identity with the amino acid sequence of SEQ ID NO: 1, and having an activity to synthesize dihydrodaidzein using daidzein as a substrate, Second Step comprising a step of having an enzyme consisting of one of the following (Ba) to (Bc) polypeptides and NADPH and/or NADH act on dihydrodaidzein, thereby producing tetrahydrodaidzein, (Ba) a polypeptide comprising the amino acid sequence of SEQ ID NO: 7;

(Bb) a polypeptide consisting of the amino acid sequence of SEQ ID NO: 7 with the substitution, deletion, insertion, and/or addition of one or more amino acids, and having an activity to synthesize tetrahydrodaidzein using dihydrodaidzein as a substrate; and (Bc) a polypeptide consisting of an amino acid sequence having 60% or more identity with the amino acid sequence of SEQ ID NO: 7, and having an activity to synthesize tetrahydrodaidzein using dihydrodaidzein as a substrate.

Item D2. A product containing tetrahydrodaidzein, produced by the process according to Item D1.

Item D3. A process for producing equol comprising the following Second Step and Third Step, Second Step comprising a step of having an enzyme consisting of one of the following (Ba) to (Bc) polypeptides and NADPH and/or NADH act on dihydrodaidzein, thereby producing tetrahydrodaidzein, (Ba) a polypeptide consisting of the amino acid sequence of SEQ ID NO: 7;

(Bb) a polypeptide consisting of the amino acid sequence of SEQ ID NO: 7 with the substitution, deletion, insertion, and/or addition of one or more amino acids, and having an activity to synthesize tetrahydrodaidzein using dihydrodaidzein as a substrate; and (Bc) a polypeptide consisting of an amino acid sequence having 60% or more identity with the amino acid sequence of SEQ ID NO: 7, and having an activity to synthesize tetrahydrodaidzein using dihydrodaidzein as a substrate, Third Step comprising a step of having an enzyme consisting of one of the following (Ca) to (Cc) polypeptides to act on tetrahydrodaidzein, thereby producing equol, (Ca) a polypeptide consisting of the amino acid sequence of SEQ ID NO: 13;

(Cb) a polypeptide consisting of the amino acid sequence of SEQ ID NO: 13 with the substitution, deletion, insertion, and/or addition of one or more amino acids, and having an activity to synthesize equol using tetrahydrodaidzein as a substrate; and (Cc) a polypeptide consisting of an amino acid sequence having 60% or more identity with the amino acid sequence of SEQ ID NO: 13, and having an activity to synthesize equol using tetrahydrodaidzein as a substrate.

Item D4. A product containing equol, produced by the process according to Item D3.

Item D5. A process for producing equol comprising First Step through Third Step.

Item D6. A product containing equol, produced by the process according to Item D5.

Item D7. An expression vector having at least one polynucleotide selected from the group consisting of the following (Ad) to (Af), (Bd) to (Bf), and (Cd) to (Cf), (Ad) a polynucleotide consisting of the nucleotide sequence of SEQ ID NO: 4;

(Ae) a polynucleotide that encodes a polypeptide consisting of the amino acid sequence of SEQ ID NO: 1;

(Af) a polynucleotide that hybridizes under stringent conditions with the complementary strand of the polynucleotide (Ad) or (Ae), and that encodes a polypeptide having an activity to synthesize dihydrodaidzein using daidzein as a substrate;

(Bd) a polynucleotide consisting of the nucleotide sequence of SEQ ID NO: 10;

(Be) a polynucleotide that encodes a polypeptide consisting of the amino acid sequence of SEQ ID NO: 7;

(Bf) a polynucleotide that hybridizes under stringent conditions with the complementary strand of the polynucleotide (Bd) or (Be), and that encodes a polypeptide having an activity to synthesize tetrahydrodaidzein using dihydrodaidzein as a substrate;

(Cd) a polynucleotide consisting of the nucleotide sequence of SEQ ID NO: 16;

(Ce) a polynucleotide that encodes a polypeptide consisting of the amino acid sequence of SEQ ID NO: 13; and (Cf) a polynucleotide that hybridizes under stringent conditions with the complementary strand of the polynucleotide (Cd) or (Ce), and that encodes a polypeptide having an activity to synthesize equol using tetrahydrodaidzein as a substrate.

Item D8. A recombinant cell transformed with the expression vector of Item 7.

Item D9. A recombinant cell according to Item 8, wherein the recombinant cell is a bacterial prokaryotic cell.

Item D10. A recombinant cell according to Item 9, wherein the bacterial prokaryotic cell belongs to the genus *Lactococcus.*

Item D11. A process for producing dihydrodaidzein, tetrahydrodaidzein, and/or equal, comprising at least two of the following Fourth Step to Sixth Step, Fourth Step comprising a step of having a recombinant cell-comprising one of the following (Ad) to (Af) polynucleotides act on daidzein, thereby producing dihydrodaidzein, (Ad) a polynucleotide consisting of the nucleotide sequence of SEQ ID NO: 4;

(Ae) a polynucleotide that encodes a polypeptide consisting of the amino acid sequence of SEQ ID NO: 1; and (Af) a polynucleotide that hybridizes under stringent conditions with the complementary strand of the polynucleotide (Ad) or (Ae), and that encodes a polypeptide having an activity to synthesize dihydrodaidzein using daidzein as a substrate, Fifth Step comprising a step of having a recombinant cell comprising one of the following (Bd) to (Bf) polynucleotides act on dihydrodaidzein, thereby producing tetrahydrodaidzein, (Bd) a polynucleotide consisting of the nucleotide sequence of SEQ ID NO: 10;

(Be) a polynucleotide that encodes a polypeptide consisting of the amino acid sequence of SEQ ID NO: 7; and (Bf) a polynucleotide that hybridizes under stringent conditions with the complementary strand of the polynucleotide (Bd) or (Be), and that encodes a polypeptide having an activity to synthesize tetrahydrodaidzein using dihydrodaidzein as a substrate, Sixth Step comprising a step of having a recombinant cell comprising one of the following (Cd) to (Cf) polynucleotides act on tetrahydrodaidzein, thereby producing equol, (Cd) a polynucleotide consisting of the nucleotide sequence of SEQ ID NO: 16;

(Ce) a polynucleotide that encodes a polypeptide consisting of the amino acid sequence of SEQ ID NO: 13; and (Cf) a polynucleotide that hybridizes under stringent conditions with the complementary strand of the polynucleotide (Cd) or (Ce), and that encodes a polypeptide having an activity to synthesize equol using tetrahydrodaidzein as a substrate, wherein at least two polynucleotides selected from the group consisting of (Ad) to (Af), (Bd) to (Bf), and (Cd) to (Cf) may exist in a single recombinant cell.

Item D12. A recombinant cell according to Item 11, wherein the recombinant cell is a bacterial prokaryotic cell.

Item D13. A recombinant cell according to Item 12, wherein the bacterial prokaryotic cell belongs to the genus *Lactococcus.*

Item D14. A product containing dihydrodaidzein, tetrahydrodaidzein, and/or equal, produced by any of the processes according to Items D11 to D13.

Item D15. A device for producing dihydrodaidzein, tetrahydrodaidzein, and/or equal, comprising at least one of the following First to Third reaction vessels, First reaction vessel having a reaction means in which an enzyme consisting of one of (Aa) to (Ac) polypeptides is immobilized, the reaction vessel being used for production of dihydrodaidzein from daidzein using the enzyme, the reaction means being disposed in a position allowing contact with daidzein;

Second reaction vessel having a reaction means in which an enzyme consisting of one of (Ba) to (Bc) polypeptides is immobilized, the reaction vessel being used for production of tetrahydrodaidzein from dihydrodaidzein using the enzyme, the reaction means being disposed in a position allowing contact with dihydrodaidzein; and Third reaction vessel having a reaction means in which an enzyme consisting of one of (Ca) to (Cc) polypeptides is immobilized, the reaction vessel being used for production of equol from tetrahydrodaidzein using the enzyme, the reaction means being disposed in a position allowing contact with tetrahydrodaidzein.

Item D16. A device for producing dihydrodaidzein, tetrahydrodaidzein, and/or equal, comprising at least one of the following Fourth to Sixth reaction vessels, Fourth reaction vessel having a reaction means in which a recombinant cell comprising one of (Ad) to (Af) polynucleotides is immobilized, the reaction vessel being used for production of dihydrodaidzein from daidzein using the reaction means, the reaction means being disposed in a position allowing contact with daidzein;

Fifth reaction vessel having a reaction means in which a recombinant cell comprising one of (Bd) to (Bf) polynucleotides is immobilized, the reaction vessel being used for production of tetrahydrodaidzein from dihydrodaidzein using the reaction means, the reaction means being disposed in a position allowing contact with dihydrodaidzein; and Sixth reaction vessel having a reaction means in which a recombinant cell comprising one of (Cd) to (Cf) polynucleotides is immobilized, the reaction vessel being used for production of equol from tetrahydrodaidzein using the reaction means, the reaction means being disposed in a position allowing contact with tetrahydrodaidzein.

Effects of the Invention

The present invention provides polypeptides capable of: (1) synthesizing dihydrodaidzein using daidzein as a substrate, (2) synthesizing tetrahydrodaidzein using dihydrodaidzein as a substrate, and (3) synthesizing equol using tetrahydrodaidzein as a substrate. Thus, the present invention is useful for industrial synthesis of dihydrodaidzein and/or tetrahydrodaidzein, which are intermediates generated in the production of equol from daidzein, as well as industrial equol synthesis. The present invention will open the door for the industrial production of equol, without using the difficult-to-handle anaerobic bacterial strains traditionally used for equol production.

BEST MODE FOR CARRYING OUT THE INVENTION

In the following, all abbreviations used to represent the names of substances, including amino acids, polypeptides, base sequences, and nucleic acids, follow the nomenclature specified by the IUPAC-IUB (IUPAC-IUB Communication on Biological Nomenclature, Eur. J. Biochem., 138: 9 (1984)), the Guideline for Drafting Specifications containing Base Sequence or Amino Acid Sequence (Japan Patent Office), and other conventional symbols commonly used in the field.

The following describes the present invention in detail.

A: Dihydrodaidzein Synthesizing Enzyme

This section describes a dihydrodaidzein synthesizing enzyme (hereinafter also referred to as E1 enzyme) in detail. Except as otherwise described, general explanation of the dihydrodaidzein synthesizing enzyme is applied to a tetrahydrodaidzein synthesizing enzyme and equol synthesizing enzyme, described later.

A-1. Polypeptide

The present invention provides a polypeptide (hereinafter also referred to as "E1 polypeptide") for the synthesis of dihydrodaidzein using daidzein as a substrate. Specifically, the invention provides:

(Aa) a polypeptide consisting of the amino acid sequence of SEQ ID NO: 1; for example, the range is from 1 to 250, preferably 1 to 200, more preferably 1 to 150, more preferably 1 to 100, more preferably 1 to 50, more preferably 1 to 30, more preferably 1 to 15, more preferably 1 to 5, further preferably 1 to 4, even more preferably 1 to 3, and particularly preferably 1 or 2.

(Ab) a polypeptide consisting of the amino acid sequence of SEQ ID NO: 1 with the substitution, deletion, insertion, and/or addition of one or more amino acids, and having an activity to synthesize dihydrodaidzein using daidzein as a substrate; and (Ac) a polypeptide consisting of an amino acid sequence having 60% or more identity with the amino acid sequence of SEQ ID NO: 1, and having an activity to synthesize dihydrodaidzein using daidzein as a substrate.

In polypeptide (Ab), the range of "one or more amino acids" is not particularly limited as long as the polypeptide has the activity to synthesize dihydrodaidzein using daidzein as a substrate. Examples of (Ab) polypeptide includes a polypeptide consisting of the amino acid sequence of SEQ ID NO: 2 and a polypeptide consisting of the amino acid sequence of SEQ ID NO: 3. Compared with the amino acid sequence of SEQ ID NO: 1, the amino acid sequence of SEQ ID NO: 2 contains three substituted amino acids. Compared with the amino acid sequence of SEQ ID NO: 1, the amino acid sequence of SEQ ID NO: 3 contains ten substituted amino acids. The amino acid sequence of SEQ ID NO: 2 corresponds to the E1 enzyme polypeptide from *Bacteroides ovatus* E-23-15 strain (FERM BP-6435). The amino acid sequence of SEQ ID NO: 3 corresponds to the E1 enzyme polypeptide from *Streptococcus constellatus* A6G-225 (FERM BP-6437).

Further, the type of amino acid substitution in (Ab) polypeptide is not particularly limited. However, from the standpoint of preventing phenotypic change in the polypeptide, it is preferable that the substitution be made between analogous amino acids. Analogous amino acids may be classified as follows.

Aromatic amino acid: Phe, Trp, Tyr

Aliphatic amino acid: Ala, Leu, Ile, Val

Polar amino acid: Gln, Asn

Basic amino acid: Lys, Arg, His

Acidic amino acid: Glu, Asp

Amino acids with a hydroxyl group: Ser, Thr

Amino acids with a short side chain: Gly, Ala, Ser, Thr, Met

In (Ab) polypeptide, it is preferable that the amino acid substitution, deletion, insertion, or addition occur in regions where the amino acid change does not have large effects on the higher-order structures of the polypeptide, or where the change does not adversely affect the active center of the dihydrodaidzein synthesizing enzyme. Examples of such regions include low-conserved regions among the amino acid sequences of SEQ ID NOs: 1, 2, and and vicinities thereof, and the N-terminal region or C-terminal region. Specific examples include leucine at position 45, asparagine at position 80, valine at position 167, aspartic acid at position 231, isoleucine at position 233, arginine at position 435, aspartic acid at position 459, valine at position 462, arginine at position 528, serine at position 540, isoleucine at position 639, in the amino acid sequence of SEQ ID NO: 1, and adjacent regions of these amino acids. The "adjacent region" means regions where the dihydrodaidzein synthesizing enzyme activity is not affected. Examples includes those within five amino acids from one of the exemplified amino acids, preferably those within four amino acids from one of the exemplified amino acids, more preferably those within three amino acids from one of the exemplified amino acids, even more preferably those within two amino acids from one of the exemplified amino acids, particularly preferably those within one amino acid from one of the exemplified amino acids.

In the amino acid sequence of SEQ ID NO: 1, the sequence of the amino acids at positions 112 to 116 is considered to correspond to the NADPH binding domain. As long as functions of the NADPH domain are not inhibited, there may be substitution, deletion, insertion, or addition of amino acid in the sequence of the five amino acids. In said sequence, the number of mutated amino acids is preferably not more than three, more preferably not more than two, and even more preferably one. Most preferred is no mutation in the amino acid sequence. Particularly, there is preferably no substitution, deletion, insertion, or addition of the amino acids at positions 112, 115, and 116.

Histidine at position 260 in the amino acid sequence of SEQ ID NO: 1 is also considered to be associated with the proton relay site. Accordingly, as long as functions of proton relay site are not inhibited, said histidine may be replaced by another amino acid, but is preferably not replaced.

In the amino acid sequence of SEQ ID NO: 1, the sequence of the amino acids at positions 343 to 363 is considered to correspond to the Fe—S cluster motif. As long as functions of the motif are not inhibited, there may be substitution, deletion, insertion, or addition of an arbitrary amino acid in the sequence. It is however preferred that cysteines at positions 343, 346, 350, and 363 are not mutated. When the sequence has one or more amino acid substitutions at positions other than said three amino acids, it is preferred that the number of substituted amino acids is preferably not more than four, more preferably not more than three, even more preferably not more than two, and particularly preferably one. Most preferred is no amino acid substitution, deletion, insertion, or addition in the sequence.

In the amino acid sequence of SEQ ID NO: 1, the sequence of the amino acids at positions 390 to 413 is considered to correspond to the FAD binding domain. Accordingly, as long as functions of the domain are not inhibited, there may be substitution, deletion, insertion, or addition of an arbitrary amino acid in the sequence. It is however preferred that glycines at positions 390, 392, and 395 are not mutated. When the sequence has one or more amino acid substitutions, deletions, insertions, or additions, the number of mutated amino acids is preferably not more than four, more preferably not more than three, even more preferably not more than two, and particularly preferably one. Most preferred is no mutation in the amino acid sequence.

In the amino acid sequence of SEQ. ID NO: 1, the sequence of the amino acids at positions 512 to 540 is also considered to correspond to the FAD binding domain. Accordingly, as long as functions of the domain are not inhibited, there may be substitution, deletion, insertion, or addition of an arbitrary amino acid in the sequence. It is however preferred that glycines at positions 512, 514, and 517 are not mutated. When the sequence has one or more amino acid substitutions, deletions, insertions, or additions, the number of mutated amino acids is preferably not more than four, more preferably not more than three, even more preferably not more than two, and particularly preferably one. Most preferred is no mutation in the amino acid sequence.

An alignment, which indicates the regions of amino acid sequences with possible functions as described above, is shown in FIG. 27.

The substitution, deletion, insertion or addition of one or several amino acids in a specific amino acid sequence is possible by known techniques.

In (Ac) polypeptide, the amino acid sequence has, for example, 60% or more identity with the amino acid sequence of SEQ ID NO: 1. It is preferable, however, that the amino acid sequence have generally 80% or more, preferably 85% or more, more preferably 90% or more, further preferably 95% or more, even more preferably 98% or more, and particularly preferably 99% or more identity with the amino acid sequence of SEQ ID NO: 1.

Specifically, (Ac) polypeptide may be a polypeptide consisting of the amino acid sequence of SEQ ID NO: 2 or a polypeptide consisting of the amino acid sequence of SEQ ID NO: 3. The amino acid identity between the amino acid sequence of SEQ ID NO: 1 and the amino acid sequence of SEQ ID NO: 2 is 99.5% (Blast2). The amino acid identity between the amino acid sequence of SEQ ID NO: 1 and the amino acid sequence of SEQ ID NO: 3 is 98.6% (Blast2). Accordingly, in a preferred embodiment of the invention, (Ac) polypeptide comprises an amino acid sequence having 98.6% or more, and more preferably 99.5% identity to the amino acid sequence of SEQ ID NO: 1.

The identity of the amino acid sequence can be calculated, using analysis tools such as, for example, FASTA, BLAST, PSI-BLAST, SSEARCH, or other kinds of software available either commercially or through telecommunication lines (the Internet). Specifically, a BLAST query is generally performed under the following initial conditions to calculate the identity (%) of the amino acid sequence.

Advanced BLAST 2.1:

Program: blastp

Expect value: 10

Filters: all OFF

Matrix: BLOSUM62

Gap existence cost: 11 (default)

Per residue gap cost: 1 (default)

Lambda ratio: 0.85 (default)

Other parameters (default)

Regarding polypeptides (Ab) and (Ac), the activity to synthesize dihydrodaidzein using daidzein as a substrate can be confirmed as follows. First, a polypeptide of interest is added to a substrate solution of the composition below at a concentration of 0.001 mg/mL. The solution is then incubated at 37° C. for 2 hours to check for the presence or absence of dihydrodaidzein in the solution. The presence of dihydrodaidzein in the solution after incubation is used as an indicator of the polypeptide's activity to synthesize dihydrodaidzein using daidzein as a substrate.

Composition of Substrate Solution 0.1 M potassium phosphate buffer 1 mM PMSF (phenylmethylsulfonyl fluoride)

2 mM dithiothreitol 5 mM sodium hydrosulfite 2 mM NADPH or NADH

40 μM daidzein pH 7.0

Enzyme Property

Since E1 polypeptide has an enzyme activity to synthesize dihydrodaidzein using daidzein as a substrate, E1 polypeptide is also referred to as E1 enzyme. E1 enzyme is activated by the presence of a reducing agent such as $Na_2S_2O_4$ and metal ions such as $Fe^{2+}$ and $Mn^{2+}$. In addition, E1 enzyme requires NADPH or NADH as a coenzyme. The optimal temperature of E1 enzyme is in the vicinity of 30° C., and the optimal pH-is 7.0. E1 enzyme can not only synthesize dihydrodaidzein using daidzein as a substrate, but also synthesize daidzein from dihydrodaidzein, as a reverse reaction.

E1 polypeptide can be produced by genetic engineering techniques to be described later, or by isolation and purification from microorganisms capable of producing it. Further, common chemical synthesis methods may be used to produce E1 polypeptide, based on the information of the amino acid sequence of SEQ ID NO: 1, 2, or 3. Such chemical synthesis methods include common liquid-phase or solid-phase peptide synthesis methods.

The following describes a method for the isolation and purification of E1 polypeptide from a microorganism capable of producing E1 polypeptide. First, the cells of a microorganism capable of producing E1 polypeptide are disrupted to obtain a crude extract of the microorganism. Here, the cells can be disrupted by methods used in common cell-disruption processes, such as disruption using a French press, a cell mill, and other disrupters, and sonication in a hypotonic solution. The crude extract may be supplemented with an appropriate buffer. When E1 polypeptide is anaerobically conditioned, it is desirable to add a suitable reducing agent to the crude extract to keep the E1 polypeptide active. To improve purity, the crude extract may be further purified by processes such as ammonium sulfate precipitation, organic solvent precipitation using ethanol or the like, and isoelectric precipitation. A fraction containing E1 polypeptide can then be obtained by subjecting the crude extract to processes such as ion-exchange chromatography, gel filtration chromatography, hydrophobic chromatography, various types of affinity chromatography, reverse-phase chromatography, and hydroxyapatite column chromatography. These chromatography processes may use an open column, or HPLC may be used, as required. The purity of the fraction including E1 polypeptide can be easily estimated by visualization through electrophoresis, and particularly, through SDS-PAGE. Confirmation of E1 polypeptide is also possible by analysis of the amino acid sequence, mass spectrometry using a mass spectrometer such as MALDI-TOF MS, ESI Q-TOF MS, and MALDI Q-TOF MS, and peptide mass fingerprinting, for example.

Here, the microorganism capable of producing E1 polypeptide is preferably cultured in a medium containing a desired amount of daidzein (e.g., but not limited to, a medium containing at least 0.01 μg/mL of daidzein) in terms of efficient production of E1 polypeptide.

E1 polypeptide may be monomeric, or dimeric or polymeric, as long as it can synthesize dihydrodaidzein. Further, to improve stability and other characteristics, E1 polypeptide may be modified as required, by adding polyethylene glycol or a sugar chain.

E1 polypeptide can serve as a catalyst that converts daidzein (a substrate) into dihydrodaidzein. Dihydrodaidzein is further converted to equol by tetrahydrodaidzein synthesize enzyme and equol synthesize enzyme as described below. Equol is believed to exhibit various physiological activities in the body. In this respect, E1 polypeptide, capable of providing the material for equol synthesis, is considered important.

A-2. Polynucleotide

The present invention also provides a polynucleotide (hereinafter also referred to as "E1 polynucleotide") that encodes a polypeptide having an activity to synthesize dihydrodaidzein using daidzein as a substrate. Specifically, the invention provides:

(Ad) a polynucleotide consisting of the nucleotide sequence of SEQ ID NO: 4;

(Ae) a polynucleotide that encodes a polypeptide consisting of the amino acid sequence of SEQ ID NO: 1; and (Af) a polynucleotide that hybridizes under stringent conditions with the complementary strand of the polynucleotide (Ad) or (Ae), and that encodes a polypeptide having an activity to synthesize dihydrodaidzein using daidzein as a substrate.

The amino acid sequence of SEQ ID NO: 1 corresponds to the amino acid sequence encoded by the nucleotide sequence of SEQ ID NO: 4. The amino acid sequence of SEQ ID NO: 2 corresponds to the amino acid sequence encoded by the nucleotide sequence of SEQ ID NO: 5. The amino acid sequence of SEQ ID NO: 3 corresponds to the amino acid sequence encoded by the nucleotide sequence of SEQ ID NO: 6.

Regarding polynucleotide (Af), the phrase "hybridizes under stringent conditions" describes hybridization between two polynucleotide fragments under ordinary hybridization conditions as described by Sambrook et al. in Molecular Cloning: A laboratory Manual (1989), Cold Spring Harbor Laboratory Press, New York, USA. More specifically, "stringent conditions" means hybridization in 6.0×SSC at about 45° C., and washing with 2.0×SSC at 50° C. Examples of (Af) polynucleotide include the nucleotide sequence of SEQ ID NO: 5 and the nucleotide sequence of SEQ ID NO: 6.

The "polynucleotide that hybridizes under stringent conditions" generally has above a certain level of identity with the nucleotide sequence of the polynucleotide used as a probe. The identity is, for example, 60% or more, preferably 70% or more, more preferably 80% or more, further preferably 90% or more, even more preferably 95% or more, and particularly preferably 98% or more. The identity of the nucleotide sequence can be calculated using analysis tools such as, for example, FASTA, BLAST, PSI-BLAST, SSEARCH, or other kinds of software available either commercially or through telecommunication lines (the Internet). Specifically, a BLAST query is generally performed under the following initial conditions to calculate the identity (%) of the nucleotide sequence.

Advanced BLAST 2.1:

Program: blastn

Parameters: default

The base sequence homology between the nucleotide sequence of SEQ ID NO: 4 and the nucleotide sequence of SEQ ID NO: 5 is 99.6% (Blast2). The base sequence homology between the nucleotide sequence of SEQ ID NO: 4 and the nucleotide sequence of SEQ ID NO: 6 is 97.6% (Blast2). Accordingly, in a preferred embodiment of the invention, a polynucleotide (Af) comprises a base sequence having 97.6% homology, and more preferably 99.6% homology to the base sequence of SEQ ID NO: 4.

Regarding polynucleotide (Af), the "activity to synthesize dihydrodaidzein using daidzein as a substrate" can be confirmed by the method used for polypeptides (Ab) and (Ac).

E1 polynucleotide can be produced or obtained by chemical DNA synthesis methods, based on the sequence information of SEQ ID NOs: 4, 5, and 6. Generally, E1 polynucleotide can be easily produced or obtained by common genetic engineering techniques (see, for example, Molecular Cloning 2d Ed, Cold Spring Harbor Lab. Press (1989); and Zoku Seikagaku Jikken Kouza, Gene Kennkyu-hou I, II, III, the Japanese Biochemical Society (1986)).

An example of such chemical DNA synthesis methods is a solid-phase synthesis method using the phosphoramidite method, which may employ an autosynthesizer.

In a specific example of common genetic engineering techniques, a cDNA library is prepared by an ordinary method from a suitable source expressing E1 polynucleotide, and the library is screened for desired clones using a suitable probe or antibody specific to E1 polynucleotide (see, for example, Proc. Natl. Acad. Sci., USA., 78, 6613 (1981); Science, 222, 778 (1983)).

The cDNA source is not particularly limited as long as it is an organism expressing E1 polynucleotide. Specific examples include microorganisms capable of producing equol, preferably lactic acid bacteria, bacteria beloinging to the genera *Bacteroides* and *Streptococcus* capable of producing equol, more preferably *Lactococcus garvieae, Bacteroides ovatus* and *Streptococcus constellatus* capable of producing equol, further preferably fecal *Lactococcus garvieae* capable of producing equol, and particularly preferably *Lactococcus* 20-92 strain, *Bacteroides ovatus* E-23-15 strain, *Streptococcus constellatus* A6G-225 (FERM BP-10036, FERM BP-6435, and FERM BP-6437, respectively; deposited with the International Patent Organism Depositary, National Institute of Advanced Industrial Science and Technology, 1-1-1 Higashi, Tsukuba, Ibaraki, Japan), strains of fecal *Lactococcus garvieae* capable of producing equol.

Ordinary methods can be used for procedures including the separation of total RNA, the separation and purification of mRNA, and the preparation and cloning of cDNA. The method of screening the cDNA library for a polynucleotide of the present invention is not particularly limited, and an ordinary method can be used. For example, polypeptides produced from cDNA may be screened for by selecting corresponding cDNA clones by an immunological screening using a polypeptide-specific antibody. Further, the screening may be made by hybridization techniques such as plaque hybridization and colony hybridization, which use probes that specifically bind to target nucleotide sequences. Further, a combination of these different techniques may be used.

Generally, the probe may be, for example, chemically synthesized DNA obtained based on information concerning the nucleotide sequence of E1 polynucleotide (e.g., the nucleotide sequence of SEQ ID NO: 4, 5, or 6). Further, the probe used for screening may be a sense primer and/or an antisense primer designed based on the information of the base sequence of a polynucleotide of the present invention.

E1 polynucleotide can be suitably obtained by the PCR method (Science, 130, 1350 (1985)), or by variants of the PCR method, such as a DNA or RNA amplification method. Any difficulty in screening the library for full-length cDNA can be circumvented by using suitable techniques such as the'RACE method (Rapid amplification of cDNA ends, Experimental Medicine, 12(6), 35 (1994)); and particularly the 5'-RACE method (M. A. Frohman, et al., Proc. Natl. Acad. Sci., USA., 8, 8998 (1988)). The Race method and the 5'-RACE method are useful for obtaining E1 polypeptide from eukaryote.

The primers used for the PCR method can be appropriately designed based on the sequence information of E1 polynucleotide. Such primers can be synthesized by an ordinary method. As noted above, the isolation and purification of amplified DNA or RNA fragments can be performed by an ordinary method such as gel electrophoresis and hybridization.

E1 polynucleotide readily enables mass, stable production of the polynucleotide product (the polypeptide), using common genetic engineering techniques. The successful isolation of E1 polynucleotide by the present invention will open the door for the industrial production of equol, without using the difficult-to-handle anaerobic bacterial strains traditionally used for equol production.

A-3. Expression Vector

An expression vector of the present invention is not particularly limited as long as it includes E1 polynucleotide and is capable of expressing E1 polynucleotide. Generally, it is appropriately selected according to the type of host cell.

When the host cell is a prokaryotic cell, the expression vector may be, for example, an expression plasmid vector, replicable in the host cell, prepared by adding promoters and a SD (Shine-Dalgarno) base sequence upstream of the polynucleotide to cause expression of the polynucleotide. A specific example is an expression plasmid using a $P_L$ promoter, a T7 promoter, and a lac promoter. Other examples of preferable bacterial expression vectors include plasmid pKK233-2 and plasmid pKK233-3 using a tac promoter or trc promoter. These are non-limiting examples, and other known bacterial strains and vectors may be used, as well.

When the host cell is a eukaryotic cell, the expression vector may generally include promoters upstream of the polynucleotide to be expressed, and other specific sequences including an RNA splice site, a polyadenylation site, and a transcription termination sequence. The expression vector may further include a replication origin. There are a number of well-known eukaryotic vectors useful for the insertion of the polynucleotide. Examples of such suitable eukaryotic vectors include pCD and pCMV. Other examples include pMSG and pSVL, which make use of MMTV or SV40 late promoter as required. These are non-limiting examples, and various known eukaryotes and vectors can be used, as well.

A-4. Recombinant Cell

The present invention provides a recombinant cell (transformant) transformed with an expression vector including E1 polynucleotide.

The host cell used for the recombinant cell may be a prokaryotic cell or a eukaryotic cell.

Suitable examples of a prokaryotic host cell include: bacterial prokaryotic cells of genus *Lactococcus*, such as lactic acid bacteria; and bacterial prokaryotic cells such as, for example, *Escherichia coli, Streptomyces, Bacillus subtilis, Streptococcus*, and *Staphylococcus*, which can grow under aerobic conditions.

Examples of a eukaryotic host cell include: eukaryotic microorganisms such as yeast and *Aspergillus*; insect cells such as *Drosophila* S2 and *Spodoptera* Sf9; and animal and plant cells such as L cells, CHO cells, COS cells, HeLa cells, C127 cells, BALB/c3T3 cells (including mutant strains lacking dihydrofolate reductase or thymidine kinase), BHK21 cells, HEK293 cells, Bowes melanoma cells, and oocytes.

The method used to introduce the expression vector into the host cell is not particularly limited, and a variety of common methods can be used. For example, the expression vector can be introduced into the host cell according to the methods of many standard laboratory manuals, including, for example, Davis et al., Basic Methods in Molecular Biology, 1986, and Sambrook et al., Molecular Cloning: A Laboratory Manual, 2nd Ed., Cold Spring Harbor Laboratory Press, Cold Spring Harbor, N.Y., 1989. Specific examples include calcium phosphate transfection, DEAE-dextran mediated transfection, transvection, microinjection, cationic lipid-mediated transfection, electroporation, transduction, scrape loading, ballistic introduction, and infection.

Because the recombinant cell is capable of producing E1 polypeptide (a dihydrodaidzein-converting enzyme), it can be used to produce a dihydrodaidzein-converting enzyme. The recombinant cell can also be used to produce dihydrodaidzein in a cell form.

A-5. Polypeptide Production Using Recombinant Cell

E1 polypeptide can be produced by culturing a recombinant cell into which E1 polynucleotide is introduced and collecting E1 polypeptide from the cell and culture.

The culture may be subculture or batch culture using a suitable medium for the host. The cells may be cultured until an adequate quantity of E1 polypeptide is obtained, using the level of E1 polypeptide inside and outside of the recombinant cells as an index.

The culture medium can be appropriately selected from common media according to the type of host cell used. The culture may be incubated under suitable growth conditions for the host cell.

The resulting E1 polypeptide may be optionally separated and purified by various kinds of separation techniques utilizing the physical and chemical properties of E1 polypeptide (see, for example, Biochemistry Data Book II, pp. 1175-1259, 1st ed., 1st print, Jun. 23, 1980, Tokyo Kagaku Dozin Co., Ltd.; Biochemistry, 25(25), 8274 (1986); and Eur. J. Biochem., 163, 313 (1987)). Specifically, E1 polypeptide may be separated and purified, for example, as in the "method for isolation and purification of E1 polypeptide from microorganisms capable of producing E1 polypeptide" described in Section A-1 under the heading "Polypeptide".

A-6. Dihydrodaidzein Production Using E1 Polypeptide

The present invention provides a process for producing dihydrodaidzein using E1 polypeptide. In the producing process, daidzein can be converted into dihydrodaidzein by having E1 polypeptide act on daidzein in the presence of NADPH and/or NADH. Preferably, daidzein can be converted into dihydrodaidzein by having E1 polypeptide act on daidzein in the presence of NADPH.

Since the dihydrodaidzein synthesizing enzyme activity of E1 polypeptide is activated by the presence of $Mn^{2+}$ and $Fe^{2+}$, E1 peptide is preferably to have E1 polypeptide act on on daidzein in the presence of $Mn^{2+}$ and/or $Fe^{2+}$. The concentration of $Mn^{2+}$ and/or $Fe^{2+}$ in the reaction solution is not particularly limited as long as the enzyme activity of E1 polypeptide can be activated. The concentration of $Fe^{2+}$ is preferably 2 mM and more, more preferably 2 mM to 100 mM, more preferably 10 mM to 40 mM. The concentration of $Mn^2$+ is preferably 0.2 μM and more, more preferably, more preferably 0.2 μM to 100 mM and even more preferably 1.0 μM to 40 mM.

The reaction used in the producing process may be performed in a suitable buffer. Examples of such suitable buffers include phosphate buffer, carbonate buffer, acetate buffer, Tris buffer, and borate buffer. The pH condition of the reaction can be suitably selected so as not to inactivate the desired enzyme activity of E1 polypeptide. For example, the reaction may be performed in a pH range of preferably 5.0 to 10.0, and more preferably 6.0 to 8.0.

In the reaction, an appropriate amount of protease inhibitor such as PMSF or EDTA may be added as required. Further, considering that the polypeptide derives from anaerobic bacteria, an appropriate amount of reducing agent, such as DTT, 2ME, DET, and $Na_2S_2O_4$ may be added as well.

The reaction used in the producing process is performed under such conditions that, for example, each component is added in a medium in the concentration ranges shown below at the start of reaction so as to prepare a mixure. The mixture is incubated for 0.5 to 10 hours, preferably 1 to 6 hours, and more preferably 2 to 4 hours at temperatures of 20 to 45° C., preferably 25 to 40° C., and more preferably 30 to 38° C. The initial concentration of each components are as follows:

the polypeptide content is 0.0001 to 1.0 weight %, preferably 0.001 to 0.1 weight %, and more preferably 0.001 to 0.01 weight %;

the daidzein content is 0.0001 to 10.0 weight %, preferably 0.001 to 1.0 weight %, and more preferably 0.001 to 0.1 weight %;

the NADPH and/or NADH content is 0.01 to 5 weight %, preferably 0.05 to 1 weight %, and more preferably 0.1 to 0.5 weight %.

The present invention also provides a material mixture for the synthesis of dihydrodaidzein, specifically, a composition for synthesizing dihydrodaidzein including (Ai) E1 polypeptide, (Aii) NADPH and/or NADH, and (Aiii) daidzein. Additionally, the present invention provides a material mixture for the synthesis of dihydrodaidzein, specifically a dihydrodaidzein synthesis material composition including (Ai) E1 polypeptide, (Aii) NADPH and/or NADH, (Aiii) daidzein, and (Aiv) $Mn^{2+}$ and/or $Fe^{2+}$. By incubating the composition under the above-mentioned conditions, the daidzein contained in the composition can be converted to dihydrodaidzein. The synthesis material composition corresponds to the above-mentioned material mixture used to initiate the reaction to produce dihydrodaidzein. Further, the concentrations of E1 polypeptide, NADPH and/or NADH, and daidzein in the composition, and other components that can be added to the synthesis starting-material composition are essentially as in the reaction system (a mixture of starting materials at the start of reaction) used in the above-mentioned producing process.

The present invention also provides a kit for synthesizing dihydrodaidzein, specifically, a dihydrodaidzein synthesis kit including (Ai) E1 polypeptide, (Aii) NADPH and/or NADH, and (Aiii) daidzein. Additionally, the present invention provides a kit for synthesizing dihydrodaidzein, specifically a dihydrodaidzein synthesis kit including (Ai) E1 polypeptide, (Aii) NADPH and/or NADH, (Aiii) daidzein, and (Aiv) $Mn^{2+}$ and/or $Fe^{2+}$. The components may optionally be stored separately in the synthesis kit so as to conveniently enable dihydrodaidzein synthesis from daidzein under the foregoing conditions. The synthesis kit may further include a buffer as required. The synthesis kit may also include any necessary tools or operation manuals that help perform dihydrodaidzein synthesis.

A-7. Dihydrodaidzein Synthesizing Enzyme Composition

The present invention also provides a dihydrodaidzein synthesizing enzyme composition including E1 polypeptide. The enzyme composition can be suitably used as a dihydrodaidzein synthesizing enzyme in the producing process of dihydrodaidzein using E1 polypeptide.

The enzyme composition may be a crude purified E1 polypeptide, or the enzyme composition may be a crude purified or purified E1 polypeptide formulated with a suitable support.

The proportion of E1 polypeptide in the enzyme composition is not particularly limited as long as the composition can be used as a dihydrodaidzein synthesizing enzyme in the producing process of dihydrodaidzein. Specifically, the E1 polypeptide content is, for example, 0.001 to 20.0 weight %, preferably 0.005 to 5.0 weight %, and more preferably 0.01 to 1.0 weight %, with respect to the total of the enzyme composition.

The enzyme composition may include NADPH and/or NADH, which act as a coenzyme of E1 polypeptide. When contained in the enzyme composition, the proportion of NADPH and/or NADH, though not particularly limited, is 0.0005 to 25.0 weight %, preferably 0.005 to 5.0 weight %, and more preferably 0.01 to 2.5 weight %, with respect to the total of the enzyme composition.

Moreover, in a preferable embodiment, the enzyme composition may include $Mn^{2+}$ and/or $Fe^{2+}$. When contained in the enzyme composition, the proportion of $Mn^{2+}$ and/or $Fe^{2+}$ is not particularly limited as long as the dihydrodaidzein synthesizing enzyme activity of E1 polypeptide can be activated. The proportion of $Fe^{2+}$ is preferably 2 mM or more, more preferably 2 mM to 100 mM, and even more preferably 10 mM to 40 mM with respect to the total of the composition. The proportion of $Mn^{2+}$ is preferably 0.2 μM or more, more preferably 0.2 μM to 100 mM, and even more preferably 1.0 μM to 40 mM with respect to the total of the composition.

To improve the stability of the polypeptide, the enzyme composition may further include antioxidants such as sulfite, ascorbic acid, α-tocopherol, and cysteine, in addition to E1 polypeptide. Further, to ensure the preservability of the enzyme composition, the enzyme composition may include preservatives such as p-hydroxybenzoates, chlorobutanol, benzyl alcohol, 2-phenylethyl alcohol, dehydroacetic acid, and sorbic acid, as required.

A-8. Producing Process of Dihydrodaidzein Using Recombinant Cell

The present invention provides a producing process of dihydrodaidzein using recombinant cells including E1 polynucleotide. Specifically, in the producing process, daidzein is converted into dihydrodaidzein by having the recombinant cell act on daidzein.

The reaction used in the producing process is performed in conditions that allow the recombinant cell to survive, and daidzein to be converted into dihydrodaidzein.

Specifically, appropriate amounts of recombinant cells and daidzein are added and cultured in a medium that allows for growth of the recombinant cells.

The medium used in the producing process is suitably selected from various kinds of conventional media according to the type of the cell used as the host recombinant cell.

The medium may be supplemented with appropriate amounts of protease inhibitors such as PMSF and EDTA, as required. Further, considering that the polypeptide derives from anaerobic bacteria, appropriate amounts of reducing agents such as DTT, 2ME, DET, and $Na_2S_2O_4$ may also be added. When using the recombinant cell, the medium may be supplemented with NADPH and/or NADH as required, though it is not essential. Moreover, the medium may be supplemented with $Mn^{2+}$ and/or $Fe^{2+}$.

Specifically, the producing process is performed as follows. First, the recombinant cells are inoculated in medium containing 0.001 to 1 weight %, preferably 0.01 to 1 weight %, and more preferably 0.01 to 0.5 weight % of daidzein, and the culture is incubated under permissive temperature conditions for 6 to 30 hours, preferably 7 to 24 hours, and more preferably 7 to 18 hours.

The present invention also provides a material mixture for synthesizing dihydrodaidzein, specifically, a dihydrodaidzein synthesis material composition containing (Aiv) the recombinant cell and (Aiii) daidzein. By culturing the synthesis material composition under the above-mentioned conditions, the dihydrodaidzein in the composition can be converted to dihydrodaidzein. The composition corresponds to the above-mentioned starting material mixture used to initiate the reaction to produce dihydrodaidzein. Further, the concentrations of the recombinant cell and daidzein in the composition, and other components that can be added to the synthesis starting-material composition, are essentially as in the conditions used in the foregoing producing process.

The present invention also provides a kit for synthesizing dihydrodaidzein, specifically, a dihydrodaidzein synthesis kit including (Aiv) the recombinant cell and (Aiii) daidzein. Additionally, the present invention provides a kit for synthesizing dihydrodaidzein, specifically a dihydrodaidzein synthesis kit including (Aiv) the recombinant cell, (Aiii) daidzein, and (Aiv) $Mn^{2+}$ and/or $Fe^{2+}$. The synthesis kit may include the recombinant cell and daidzein separately as required, so as to conveniently enable dihydrodaidzein synthesis from daidzein under the above-mentioned conditions. The synthesis kit may further include a buffer or a medium, as required. The synthesis kit may also include any necessary tools or operation manuals that help perform dihydrodaidzein synthesis.

The recombinant cells included in the synthesis kit may be preserved therein by known methods. There are a number of known recombinant cell preservation techniques. For example, there is a method in which the recombinant cells are preserved at 4 to 25° C. after being treated with a lyophilizer to evacuate the ampule storing the recombinant cells in a solvent such as dimethylformamide. Another example is a liquid nitrogen method, in which the cells are suspended in a preserving medium supplemented with 10% glycerol, which is then stored in a specific ampule and kept in a liquid nitrogen tank (at −150 to −196° C.)

A-9. Antibody Having Affinity to the Polypeptide

The present invention also provides an antibody (an IgG antibody) having affinity to E1 polypeptide.

The monoclonal antibody can be prepared by an ordinary method. Specifically, the method described by Harlow, H. and Lane, D. in Antibody: Laboratory Manual, Cold Spring Harbor Lab., New York, pp. 139-240 (1988) can be used.

The polyclonal antibody can also be prepared by an ordinary method. Specifically, the method described in, for example, Cell Engineering Experiment Protocol, Department of Oncology, The Institute of Medical Science, The University of Tokyo, 1992, pp. 155-173, can be used.

The polyclonal IgG antibody and monoclonal IgG antibody can be purified by common methods, such as a sulfuric acid ammonium precipitation method, and protein A chromatography.

A-10. Immunological Method for the Detection or Measurement of the Polypeptide

The present invention also provides an immunological method for detecting or measuring E1 polypeptide using the antibody. Specifically, the immunological method is performed by having the antibody contact a test sample. More specifically, the polypeptide in the test sample can be detected or measured as follows. First, the antibody is made to contact a test sample to check for the presence of E1 polypeptide in the test sample. If present, the antibody specifically binds to E1 polypeptide. Then, the antibody bound to E1 polypeptide is detected and optionally quantified.

Here, the test sample is a sample used for the detection or measurement of E1 polypeptide. Because E1 polypeptide is expected to exist in bacterial prokaryotic cells, the immunological method is suitable for the detection and measurement of E1 polypeptide residing in bacterial prokaryotic cells. In the detection and measurement of E1 polypeptide in the cell, the test sample can be prepared from disrupted cells, or cells subjected to protein purification after disruption.

Techniques to detect or measure a target polypeptide by the immunological method using the antibody are known, and it would be obvious for the skilled artisan to appropriately set various conditions suitable for the immunological method. For example, methods such as radioimmunoassay and ELISA may be used under appropriately set conditions.

The present invention also provides an immunological detection kit including the antibody, used for the detection or measurement of E1 polypeptide. The detection kit may also include a standard E1 polypeptide, as required. The detection kit may further include, as required, additional reagents that facilitate the easy detection of E1 polypeptide under the foregoing conditions. The detection kit may also include any necessary tools or operation manuals that facilitate easy E1 polypeptide detection.

A-11. Method for Detection or Measurement of Polynucleotide that Encodes the Polypeptide The present invention also provides a method for detecting or measuring E1 polynucleotide. Specifically, the method is performed by causing an E1 polynucleotide-binding probe to contact a test sample. To be more specific, E1 polynucleotide in the test sample can be detected or measured as follows. First, the probe is made to contact a test sample to hybridize with the test sample, which occurs when E1 polynucleotide is present in the test sample. Then, the presence or absence of the double strand is detected, and the double strand, if present, is optionally quantified.

Here, the test sample is a sample used for the detection or measurement of E1 polynucleotide. Because E1 polynucleotide is expected to exist in bacterial prokaryotic cells, the method is suitable for the detection and measurement of E1 polynucleotide residing in bacterial prokaryotic cells. In the detection and measurement of E1 polynucleotide in the cell, the test sample can be prepared from disrupted cells, or cells subjected to nucleic acid purification after disruption.

The probe used in the method has a nucleotide sequence that can hybridize with the polynucleotide under stringent conditions. As used herein, "stringent conditions" describe, for example, conditions common to probes and primers, and specifically, conditions described in the above Section A-2.

The probe may be chemically synthesized based on information concerning the nucleotide sequence of E1 polynucleotide (e.g., the nucleotide sequence of SEQ ID NO: 4, 5, or 6), or may be a previously produced E1 polynucleotide or a fragment of E1 polynucleotide. The probe may be labeled or unlabeled, though labeled probes are generally used. Further, when the probe is used as a PCR primer (a sense primer or an antisense primer), the probe length is, for example, about 10 to 40 nucleotides, and preferably about 20 to 30 nucleotides.

Examples of methods to specifically detect the polynucleotide include: plaque hybridization, colony hybridization, Southern blotting, Northern blot, and the PCR method. From the standpoint of sensitivity, a PCR method that uses the probes as primers to amplify part of or all of E1 polynucleotide is preferably used.

The PCR method may be, for example, RT-PCR method, or various types of variant methods used in the art. The PCR method can be used to assay the presence and the quantity of E1 polynucleotide. Examples of such PCR methods include a competitive assay such as MSSA (Kinoshita, M., et al., CCA, 228, 83-90 (1994)), and the PCR-SSCP method, which is a known method of detecting mutations based on changes in mobility of single-stranded DNA due to different higher-order structures (Orita, M., et al., Genomics, 5, 874-879 (1989)).

The present invention also provides a kit for detecting or measuring E1 polynucleotide, specifically an E1 polynucleotide detection kit including the probe. For ease of E1 polynucleotide detection under the above-mentioned conditions, the detection kit may include additional reagents or the like as required, in addition to the probe. Further, the detection kit can be used to identify cells containing E1 polynucleotide. From the standpoint of enabling accurate detection, the detection kit may preferably be provided as a kit for performing detection using PCR.

B. Tetrahydrodaidzein Synthesizing Enzyme

B-1. Polypeptide

The present invention provides a polypeptide (hereinafter also referred to as "E2 polypeptide") for the synthesis of tetrahydrodaidzein using dihydrodaidzein as a substrate. Specifically, the invention provides:

(Ba) a polypeptide consisting of the amino acid sequence of SEQ ID NO: 7;

(Bb) a polypeptide consisting of the amino acid sequence of SEQ ID NO: 7 with the substitution, deletion, insertion, and/or addition of one or more amino acids, and having an activity to synthesize tetrahydrodaidzein using dihydrodaidzein as a substrate; and (Bc) a polypeptide consisting of an amino acid sequence having 60% or more identity with the amino acid sequence of SEQ ID NO: 7, and having an activity to synthesize tetrahydrodaidzein using dihydrodaidzein as a substrate.

In polypeptide (Bb), the range of "one or more amino acids" is not particularly limited as long as the polypeptide has the activity to synthesize tetrahydrodaidzein using dihydrodaidzein as a substrate. For example, the range is from 1 to 50, preferably 1 to 30, more preferably 1 to 15, more preferably 1 to 5, further preferably 1 to 4, even more preferably 1 to 3, and particularly preferably 1 or 2.

Examples of (Bb) polypeptide includes a polypeptide consisting of the amino acid sequence of SEQ ID NO: 8 and a polypeptide consisting of the amino acid sequence of SEQ ID NO: 9. Compared with the amino acid sequence of SEQ ID NO: 7, the amino acid sequence of SEQ ID NO: 8 contains two substituted amino acids and an amino acid sequence having 24 amino acids at the N terminus. Compared with the amino acid sequence of SEQ ID NO: 7, the amino acid sequence of SEQ ID NO: 9 contains 20 substituted amino acids and loses 1 amino acid. The amino acid sequence of SEQ ID NO: 8 corresponds to the E2 enzyme polypeptide from *Bacteroides ovatus* E-23-15 strain (FERM BP-6435). The amino acid sequence of SEQ ID NO: 9 corresponds to the E2 enzyme polypeptide from *Streptococcus constellatus* A6G-225 (FERM BP-6437).

In (Bb) polypeptide, the amino acid substitution, deletion, insertion, or addition can be made as in the amino acid substitution, deletion, insertion, or addition in E1 polypeptide described in Section A-1. It is preferable that the amino acid substitution, deletion, insertion, or addition in polypeptide (Bb) is in regions where the amino acid change does not have large effects on the higher-order structures of the polypeptide, or where the change does not adversely affect the active center of the tetrahydrodaidzein synthesizing enzyme. Examples of such regions include low-conserved regions among the amino acid sequences of SEQ ID NOs: 7, 8, and 9, and vicinities thereof, and the N-terminal region or C-terminal region. Specific examples include valine at position 7, proline at position 8, valine at position 26, leucine at position 36, arginine at position 46, aspartic acid at position 94, glutamic acid at position 101, glycine at position 126, isoleucine at position 137, glutamine at position 156, lysine at position 157, aspartic acid at position 159, alanine at positions 160 and 171, cysteine at position 185, serine at position 221, alanine at position 233, valine at position 241, serine at position 258, isoleucine at position 266, and valine at position 286, in the amino acid sequence of SEQ ID NO: 7; and adjacent regions of these amino acids. The "adjacent region" means regions where the tetrahydrodaidzein synthesizing enzyme activity is not affected. Examples of said regions includes amino acids within five amino acids from one of the exemplified amino acids, preferably those within four amino acids from one of the exemplified amino acids, more preferably those within three amino acids from one of the exemplified amino acids, even more preferably those within two amino acids from one of the exemplified amino acids, and particularly preferably one amino acid from one of the exemplified amino acids.

In the amino acid sequence of SEQ ID NO: 7, the sequence of the amino acids at positions 38 to 45 is considered to correspond to the NADPH binding domain. Accordingly, as long as functions of the domain are not inhibited, there may be substitution, deletion, insertion, or addition of an arbitrary amino acid in the sequence. It is however preferred that threonine at position 38, glycine at position 39, glycine at position 43, and glycine at position 45 are not mutated. When the sequence contains one or more amino acid substitutions, deletions, insertions, or additions, the number of mutated amino acids is preferably not more than four, more preferably not more than three, even more preferably not more than two, and most preferably one.

In the amino acid sequence of SEQ ID NO: 7, the sequence of the amino acids at positions 115 to 118 is considered to correspond to the motif highly conserved among SDR family. When the sequence contains one or more amino acid substitutions, deletions, insertions, or additions in the sequence, the number of mutated amino acids is preferably not more than three, more preferably not more than two, and even more preferably one. Most preferred is no mutation in the sequence.

In the amino acid sequence of SEQ ID NO: 7, serine at position 168, histidine at position 182, and lysine at position 186 are considered to be associated with the activity center of E2 enzyme. Accordingly, as long as the enzyme activity is not inhibited, the three amino acids may be substituted by other arbitrary amino acids. It is however preferred that these amino acids are not mutated.

In the amino acid sequence of SEQ ID NO: 7, the sequence of the amino acids at positions 212 to 217 is considered to be associated with binding to cofactors. Accordingly, as long as the function is not inhibited, there may be substitution, deletion, insertion, or addition of an arbitrary amino acid in the sequence. It is however preferred that proline at position 212, glycine at position 213, and threonine at position 217 are not mutated. When the sequence contains one or more amino acid substitutions, deletions, insertions, or additions, the number of mutated amino acids is preferably not more than three, more preferably not more than two, and even more preferably one. Particularly preferred is no mutation in the sequence. An alignment, which indicates the regions of amino acid sequences with possible functions as described above, is shown in FIG. 28.

In polypeptide (Bc), the amino acid sequence has, for example, 60% or more identity with the amino acid sequence of SEQ ID NO: 7. It is preferable, however, that the amino acid sequence have generally 80% or more, preferably 85% or more, more preferably 90% or more, further preferably 95% or more, even more preferably 98% or more, and particularly preferably 99% or more identity with the amino acid sequence of SEQ ID NO: 7.

Specifically, (Bc) polypeptide may be a polypeptide consisting of the amino acid sequence of SEQ ID NO: 8 or a polypeptide consisting of the amino acid sequence of SEQ ID NO: 9. The identity between the amino acid sequence of SEQ ID NO: 7 and the amino acid sequence of SEQ ID NO: 8 is 99.3% (Blast2). The identity between the amino acid sequence of SEQ ID NO: 7 and the amino acid sequence of SEQ ID NO: 9 is 93.0% (Blast 2). Accordingly, in a preferred embodiment of the invention, (Bc) polypeptide comprises an amino acid sequence having 93.0% or more, and more preferably 99.3% identity to the amino acid sequence of SEQ ID NO: 7.

Regarding polypeptides (Bb) and (Bc), the activity to synthesize tetrahydrodaidzein using dihydrodaidzein as a substrate can be confirmed as follows. First, a polypeptide of interest is added to a substrate solution of the composition below at a concentration of 0.001 mg/mL. The solution is then incubated at 37° C. for 2 hours to check for the presence or absence of tetrahydrodaidzein in the solution. The presence of tetrahydrodaidzein in the solution after incubation is used as an indicator of the polypeptide's activity to synthesize tetrahydrodaidzein using dihydrodaidzein as a substrate.

Composition of Substrate Solution 0.1 M potassium phosphate buffer (pH 7.0)
1 mM PMSF (phenylmethylsulfonyl fluoride)
2 mM dithiothreitol
5 mM sodium hydrosulfite
2 mM NADPH
2 mM NADH
40 μM dihydrodaidzein Enzyme Property Since E2 polypeptide has an enzyme activity to synthesize tetrahydrodaidzein using dihydrodaidzein as a substrate, E2 polypeptide is also referred to as E2 enzyme. E2 enzyme requires NADPH or NADH as a coenzyme. The optimal temperature of E2 enzyme is in the vicinity of 37° C., and the optimal pH is 4.5. E2 enzyme can not only synthesize tetrahydrodaidzein using dihydrodaidzein as a substrate, but also synthesize dihydrodaidzein from tetrahydrodaidzein, as a reverse reaction.

Similarly to E1 polypeptide, E2 polypeptide can be produced by genetic engineering techniques based on the information of the nucleotide sequence of SEQ ID NO: 10, 11, or 12. Further, common chemical synthesis methods may be used to produce E2 polypeptide, based on the information of the amino acid sequence of SEQ ID NO: 7, 8, or 9. E2 polypeptide can also be produced by isolation and purification from microorganisms capable of producing it. These methods can be performed according to the description in the foregoing Section A-1.

The microorganism capable of producing E2 polypeptide may be cultured in a medium containing a desired amount of dihydrodaidzein, and additionally, daidzein. E2 polypeptide can also be produced in this way in microorganisms capable of producing E2 polypeptide.

E2 polypeptide may be monomeric, or dimeric or polymeric, as long as it can synthesize tetrahydrodaidzein. Further, to improve stability and other characteristics, E2 polypeptide may be modified as required, by adding polyethylene glycol or a sugar chain.

E2 polypeptide can serve as a catalyst that converts dihydrodaidzein (a substrate) into tetrahydrodaidzein. Tetrahydrodaidzein is further converted into equol by equol synthesize enzyme as described below. Equol is believed to exhibit various physiological activities in the body. In this respect, E2 polypeptide, capable of providing a starting material of equol synthesis, is considered important. The present invention therefore provides a tetrahydrodaidzein synthesizing enzyme including any of polypeptides (Ba) through (Bc).

B-2. Polynucleotide

The present invention also provides a polynucleotide (hereinafter also referred to as "E2 polynucleotide") that encodes a polypeptide having an activity to synthesize tetrahydrodaidzein using dihydrodaidzein as a substrate. Specifically, the invention provides:

(Bd) a polynucleotide consisting of the nucleotide sequence of SEQ ID NO: 10;

(Be) a polynucleotide that encodes a polypeptide consisting of the amino acid sequence of SEQ ID NO: 7; and (Bf) a polynucleotide that hybridizes under stringent conditions with the complementary strand of the polynucleotide (Bd) or (Be), and that encodes a polypeptide having an activity to synthesize tetrahydrodaidzein using dihydrodaidzein as a substrate.

The amino acid sequence of SEQ ID NO: 7 corresponds to the amino acid sequence encoded by the nucleotide sequence of SEQ ID NO: 10. The amino acid sequence of SEQ ID NO: 8 corresponds to the amino acid sequence encoded by the nucleotide sequence of SEQ ID NO: 11. The amino acid sequence of SEQ ID NO: 9 corresponds to the amino acid sequence encoded by the nucleotide sequence of SEQ ID NO: 12.

Regarding polynucleotide (Bf), the phrase "hybridizes under stringent conditions" is synonymous with the phrase "hybridizes under stringent conditions" in Section A-2. Examples of polynucleotide (Bf) include the nucleotide sequence of SEQ ID NO: 11 and the nucleotide sequence of SEQ ID NO: 12. The base sequence homology between the nucleotide sequence of SEQ ID NO: 10 and the nucleotide sequence of SEQ ID NO: 11 is 99.7% (Blast2). The base sequence homology between the nucleotide sequence of SEQ ID NO: 10 and the nucleotide sequence of SEQ ID NO: 12 is 91.0% (Blast2). Accordingly, in a preferred embodiment of the invention, a polynucleotide (Bf) comprises a base sequence having 91.0% homology, and more preferably 99.7% homology to the base sequence of SEQ ID NO: 10.

Regarding polynucleotide (Bf), the "activity to synthesize tetrahydrodaidzein using dihydrodaidzein as a substrate" can be confirmed by the same method used for polypeptides (Bb) and (Bc).

E2 polynucleotide can be produced or obtained by chemical synthesis methods or genetic engineering techniques, based on the sequence information of SEQ ID NO: 10, 11, or 12. Specifically, the methods described for E1 polynucleotide in Section A-2 can be employed. The method may be modified or changed, as required.

The cDNA source of E2 polynucleotide is not particularly limited as long as it is a microorganism expressing E2 polynucleotide. Specific examples include microorganisms capable of producing equol, preferably lactic acid bacteria, bacteria beloinging to the genera *Bacteroides* and *Streptococcus* capable of producing equol, more preferably *Lactococcus garvieae, Bacteroides ovatus* and *Streptococcus constellatus* capable of producing equol, further preferably fecal *Lactococcus garvieae* capable of producing equol, and particularly preferably *Lactococcus* 20-92 strain, *Bacteroides ovatus* E-23-15 strain, *Streptococcus constellatus* A6G-225 (FERM BP-10036, FERM BP-6435, and FERM BP-6437, respectively; deposited with the International Patent Organism Depositary, National Institute of Advanced Industrial Science and Technology, 1-1-1 Higashi, Tsukuba, Ibaraki, Japan), strains of fecal *Lactococcus garvieae* capable of producing equol.

Expression of E2 polynucleotide using common genetic engineering techniques readily enables mass, stable production of the polynucleotide product (the polypeptide). The successful isolation of E2 polynucleotide by the present invention will open the door for the industrial production of equol, without using the difficult-to-handle anaerobic bacterial strains traditionally used for equol production.

B-3. Expression Vector

An expression vector of the present invention is not particularly limited as long as it includes E2 polynucleotide and is capable of expressing E2 polynucleotide. Generally, it is appropriately selected according to the type of host cell, similar to the expression vector including E1 polynucleotide. Specifically, the host cell described in Section A-3 may be used.

B-4. Recombinant Cell

The present invention provides a recombinant cell (transformant) transformed with an expression vector including E2 polynucleotide. The host cell used for the recombinant cell may be those described in Section A-4, without limitation. Further, the expression vector may be introduced into the host cell by the method described in Section A-4.

Because the recombinant cell is capable of producing E2 polypeptide (a tetrahydrodaidzein-converting enzyme), it can be used to produce a tetrahydrodaidzein-converting enzyme. The recombinant cell can also be used to produce tetrahydrodaidzein in a cell form.

B-5. Polypeptide Production Using Recombinant Cell

E2 polypeptide can be produced by culturing a recombinant cell into which E2 polynucleotide is introduced and collecting E2 polypeptide from the cell and culture. The recombinant cells can be cultured according to the description of Section A-5.

B-6. Tetrahydrodaidzein Production Using E2 Polypeptide

The present invention provides a process for producing tetrahydrodaidzein using E2 polypeptide. In the producing process, dihydrodaidzein can be converted into tetrahydrodaidzein by having E2 polypeptide act on dihydrodaidzein in the presence of NADPH and/or NADH.

The reaction used in the producing process may be performed in a suitable buffer such as one described in Section A-6.

The reaction used in the producing process is performed under such conditions that, for example, each component is added in a medium in the concentration ranges shown below at the start of reaction so as to prepare a mixture. The mixture is incubated for 0.5 to 10 hours, preferably 1 to 6 hours, and more preferably 2 to 4 hours at temperatures that do not alter or inactivate the starting materials, including the E2 polypeptide and dihydrodaidzein, and the product, including tetrahydrodaidzein. The reaction temperature is not particularly limited. For example, when the reaction temperature is 0° C. or less, the reaction uses, for example, a buffer that does not freeze at such reaction temperatures. The reaction temperature is, for example, preferably 0 to 45° C., and more preferably 0 to 37° C. Regarding tetrahydrodaidzein, the compound exists either in a cis form or a trans form. However, the formation of cis- and trans-configurations can be controlled by varying reaction conditions such as reaction temperature and reaction time. For example, a mixture of cis- and trans-tetrahydrodaidzeins can be produced by setting the reaction temperature at 0° C., or the reaction may be controlled to favor the trans form by setting the reaction temperature at 37° C.

The concentration of each component in the above producing process are as follows.

The E2 polypeptide content is 0.0001 to 1.0 weight %, preferably 0.001 to 0.1 weight %, and more preferably 0.001 to 0.01 weight %;

the dihydrodaidzein content is 0.0001 to 10.0 weight %, preferably 0.001 to 1.0 weight %, and more preferably 0.001 to 0.1 weight %; and the NADPH and/or NADH content is 0.01 to 5 weight %, preferably 0.05 to 1 weight %, and more preferably 0.1 to 0.5 weight %.

The present invention also provides a material mixture for the synthesis of tetrahydrodaidzein, specifically, a tetrahydrodaidzein synthesis material composition including (Bi) E2 polypeptide, (Bii) NADPH and/or NADH, and (Biii) dihydrodaidzein. By incubating the composition under the above-mentioned conditions, the dihydrodaidzein contained in the synthesis starting-material composition can be converted to tetrahydrodaidzein. The composition corresponds to the above-mentioned starting material mixture used to initiate the reaction to produce tetrahydrodaidzein. Further, the concentrations of E2 polypeptide, NADPH and/or NADH, and dihydrodaidzein in the composition, and other components that can be added to the synthesis starting-material composition are essentially as in the reaction system (a starting material mixture at the start of reaction) used in the above-mentioned producing process.

The present invention also provides a kit for synthesizing tetrahydrodaidzein, specifically, a tetrahydrodaidzein synthesis kit including (Bi) E2 polypeptide, (Bii) NADPH and/or NADH, and (Biii) dihydrodaidzein. The synthesis kit may include the components in compartments as required, so as to conveniently enable tetrahydrodaidzein synthesis from dihydrodaidzein under the foregoing conditions. The synthesis kit may further include a buffer as required. The synthesis kit may also include any necessary tools or operation manuals that help perform tetrahydrodaidzein synthesis.

B-7. Tetrahydrodaidzein Synthesizing Enzyme Composition

The present invention also provides a tetrahydrodaidzein synthesizing enzyme composition including E2 polypeptide. The enzyme composition can be suitably used as a tetrahydrodaidzein synthesizing enzyme in the producing process of tetrahydrodaidzein using E2 polypeptide.

The enzyme composition may be a crude purified E2 polypeptide, or the enzyme composition may be a crude purified or purified E2 polypeptide formulated with a suitable support. The support does not have any adverse effect on the activity of E2 polypeptide, and is used in a suitable amount.

The proportion of E2 polypeptide in the enzyme composition is not particularly limited as long as the composition can be used as a tetrahydrodaidzein synthesizing enzyme in the producing process of tetrahydrodaidzein. Specifically, the E2 polypeptide content is, for example, 0.001 to 20.0 weight %, preferably 0.005 to 5.0 weight %, and more preferably 0.01 to 1.0 weight %, with respect to the total of the enzyme composition.

The enzyme composition may include NADPH and/or NADH, which act as a coenzyme of E2 polypeptide. When contained in the enzyme composition, the proportion of NADPH and/or NADH, though not particularly limited, is 0.005 to 50.0 weight %, preferably 0.05 to 10.0 weight %, and more preferably 0.1 to 5.0 weight %, with respect to the total of the enzyme composition.

To improve the stability of the polypeptide and/or to ensure the preservability of the enzyme composition, the enzyme composition may further include various antioxidants and preservatives described in Section A-7, in addition to E2 polypeptide.

B-8. Producing Process of Tetrahydrodaidzein Using Recombinant Cell

The present invention provides a producing process of tetrahydrodaidzein using recombinant cells including E2 polynucleotide. Specifically, in the producing process, dihydrodaidzein is converterd into tetrahydrodaidzein by having the recombinant cell act on dihydrodaidzein.

The reaction used in the producing process is performed in conditions that allow the recombinant cell to survive, and dihydrodaidzein to be converted into tetrahydrodaidzein.

Specifically, appropriate amounts of recombinant cells and dihydrodaidzein are added and cultured in a medium that allows for growth of the recombinant cells.

The medium used in the producing process is suitably selected from various kinds of conventional media according to the type of the cell used as the host recombinant cell.

The medium may be supplemented with appropriate amounts of protease inhibitors such as PMSF and EDTA, as required. Further, considering that the polypeptide derives from anaerobic bacteria, appropriate amounts of reducing agents such as DTT, 2ME, DET, and $Na_2S_2O_4$ may also be added. When using the recombinant cell, the medium may be supplemented with NADPH and/or NADH as required, though it is not essential.

Specifically, the producing process is performed as follows. First, the recombinant cells are inoculated in medium containing 0.001 to 1 weight %, preferably 0.01 to 0.5 weight %, and more preferably 0.01 to 0.1 weight % of dihydrodaidzein, and the culture is incubated under permissive temperature conditions for 7 to 30 hours, preferably 15 to 24 hours, and more preferably 17 to 20 hours. Here, the permissive temperature conditions are not particularly limited, and are essentially as in the foregoing Section B-6 under the heading "Tetrahydrodaidzein Production Using E2 Polypeptide".

The present invention also provides a material mixture for synthesizing tetrahydrodaidzein, specifically, a tetrahydrodaidzein synthesis material composition containing (Biv) the recombinant cell and (Biii) dihydrodaidzein. By culturing the composition under the above-mentioned conditions, the dihydrodaidzein in the composition can be converted to tetrahydrodaidzein. The composition corresponds to the foregoing starting material mixture used to initiate the reaction to produce tetrahydrodaidzein. Further, the concentrations of the recombinant cell and dihydrodaidzein in the synthesis starting-material composition, and other components that can be added to the synthesis starting-material composition, are essentially as in the conditions used in the foregoing producing process.

The present invention also provides a kit for synthesizing tetrahydrodaidzein, specifically, a tetrahydrodaidzein synthesis kit including (Biv) the recombinant cell and (Biii) dihydrodaidzein. The synthesis kit may include the recombinant cell and dihydrodaidzein separately as required, so as to conveniently enable tetrahydrodaidzein synthesis from dihydrodaidzein under the above-mentioned conditions. The synthesis kit may further include a buffer or a medium, as required. The synthesis kit may also include any necessary tools or operation manuals that help perform tetrahydrodaidzein synthesis.

The recombinant cells included in the synthesis kit may be preserved therein by known methods. There are a number of known recombinant cell preservation techniques. For example, there is a method in which the recombinant cells are preserved at 4 to 25° C. after being treated with a lyophilizer to evacuate the ampule storing the recombinant cells in a solvent such as dimethylformamide. Another example is a liquid nitrogen method, in which the cells are suspended in a preserving medium supplemented with 10% glycerol, which is then stored in a specific ampule and kept in a liquid nitrogen tank (at −150 to −196° C.)

B-9. Antibody Having Affinity to the Polypeptide

The present invention also provides an antibody (an IgG antibody) having affinity to E2 polypeptide.

The monoclonal antibody and polyclonal antibody can be prepared by an ordinary method. Specifically, these antibodies can be prepared by the method described in Section A-9.

B-10. Immunological Method for the Detection or Measurement of the Polypeptide

The present invention also provides an immunological method for detecting or measuring E2 polypeptide using the antibody. Specifically, the immunological method can be performed according to the method described in Section A-10.

The present invention also provides an immunological detection kit including the antibody, used for the detection or measurement of E2 polypeptide. The detection kit may also include a standard E2 polypeptide, as required. The detection kit may further include, as required, additional reagents that facilitate the easy detection of E2 polypeptide under the foregoing conditions. The detection kit may also include any necessary tools or operation manuals that facilitate easy E2 polypeptide detection.

B-11. Method for Detection or Measurement of Polynucleotide that Encodes the Polypeptide The present invention also provides a method for detecting or measuring E2 polynucleotide. Specifically, the method is performed by having an E2 polynucleotide-binding probe contact a test sample, according to the method described in Section A-11.

The present invention also provides a kit for detecting or measuring E2 polynucleotide, specifically an E2 polynucleotide detection kit including the probe. For ease of E2 polynucleotide detection under the foregoing conditions, the detection kit may include additional reagents or the like as required, in addition to the probe. Further, the detection kit can be used to identify cells containing E2 polynucleotide. From the standpoint of enabling accurate detection, the detection kit may preferably be provided as a kit for performing detection using PCR.

C. Equol Synthesizing Enzyme

C-1. Polypeptide

The present invention provides a polypeptide (hereinafter also referred to as "E3 polypeptide") for the synthesis of equol using tetrahydrodaidzein as a substrate. Specifically; the invention provides:

(Ca) a polypeptide consisting of the amino acid sequence of SEQ ID NO: 13;

(Cb) a polypeptide consisting of the amino acid sequence of SEQ ID NO: 13 with the substitution, deletion, insertion, and/or addition of one or more amino acids, and having an activity to synthesize equol using tetrahydrodaidzein as a substrate; and (Cc) a polypeptide consisting of an amino acid sequence having 60% or more identity with the amino acid sequence of SEQ ID NO: 13, and having an activity to synthesize equol using tetrahydrodaidzein as a substrate.

In polypeptide (Cb), the range of "one or more amino acids" is not particularly limited as long as the polypeptide has the activity to synthesize equol using tetrahydrodaidzein as a substrate. For example, the range is from 1 to 200, preferably 1 to 150, more preferably 1 to 100, more preferably 1 to 50, more preferably 1 to 45, more preferably 1 to 40, more preferably 1 to 30, more preferably 1 to 15, more preferably 1 to 5, further preferably 1 to 4, even more preferably 1 to 3, and particularly preferably 1 or 2.

Examples of (Cb) polypeptide includes a polypeptide consisting of the amino acid sequence of SEQ ID NO: 14 or a polypeptide consisting of the amino acid sequence of SEQ ID NO: 15. Compared with the amino acid sequence of SEQ ID NO: 13, the amino acid sequence of SEQ ID NO: 14 contains two substituted amino acids. Compared with the amino acid sequence of SEQ ID NO: 13, the amino acid sequence of SEQ ID NO: 15 contains 42 substituted amino acids and one additional amino acid (glutamic acid) at the C terminus. The amino acid sequence of SEQ ID NO: 14 corresponds to the E3 enzyme polypeptide from *Bacteroides ovatus* E-23-15 strain (FERN BP-6435). The amino acid sequence of SEQ ID NO: 15 corresponds to the E3 enzyme polypeptide from *Streptococcus constellatus* A6G-225 (FERN BP-6437).

In (Cb) polypeptide, "the amino acid substitution, deletion, insertion, or addition" can be made as in the amino acid substitution, deletion, insertion, or addition in E1 polypeptide described in Section A-1. It is preferable that the amino acid substitution, deletion, insertion, or addition in polypeptide (Cb) is in regions where the amino acid change does not have large effects on the higher-order structures of the polypeptide, or where the change does not affect the active center of the equol synthesizing enzyme. Examples of such regions include low-conserved regions among the amino acid sequences of SEQ ID NOs: 13, 14, and 15, and vicinities thereof, and the N-terminal region or C-terminal region. Specific examples include glutamic acid at position 3, arginine at position 28, glutamic acid at position 29, arginine at position 32, asparagine at position 61, isoleucine at position 80, asparagine at position 92, aspartic acid at position 112, alanine at position 119, asparagine at position 129, aspartic acid at position 172, alanine at position 174, serine at position 204, glutamic acid at position 206, threonine at position 223, valine at position 230, proline at position 244, thyrosin at position 246, threonine at position 280, arginine at position 282, alanine at position 285, valine at position 307, alanine at position 322, glutamic acid at position 347, glycine at position 359, serine at position 360, alanine at position 366, leucine at position 367, isoleucine at position 368, valine at position 372, aspartic acid at position 373, threonine at position 374, alanine at position 377, alanine at position 380, aspartic acid at position 381, glutamine at position 399, proline at position 403, methionine at position 404, valine at position 405, glutamic acid at position 406, glycine at position 407, arginine at position 426, valine at position 434, alanine at position 436, thyrosin at position 438, and alanine at position 440, in the amino acid sequence of SEQ ID NO: 13; and adjacent regions of these amino acids. The "adjacent region" means regions where the equol synthesizing enzyme activity is not affected. Examples of said regions includes amino acids within five amino acids from one of the exemplified amino acids, preferably those within four amino acids from one of the exemplified amino acids, more preferably those within three amino acids from one of the exemplified amino acids, even more preferably those within two amino acids from one of the exemplified amino acids, and particularly preferably one amino acid from one of the exemplified amino acids. Preferable examples of the regions with low preservability and their vicinities include the region corresponding to positions 25 to 35, the region corresponding to positions 170 to 177, the region corresponding to positions 201 to 208, the region corresponding to positions 242 to 248, the region corresponding to positions 276 to 289, the region corresponding to positions 355 to 385, the region corresponding to positions 396 to 409, and the region corresponding to positions 431 to 443, in the amino acid sequence of SEQ ID NO: 13.

In the amino acid sequence of SEQ ID NO: 13, the sequence ranging from the amino acid at position 14 to the amino acid at position 19 is considered to correspond to the FAD binding domain. Accordingly, as long as functions of the domain are not inhibited, there may be substitution, deletion, insertion, or addition of an arbitrary amino acid in the sequence. It is however preferred that glycine at position 14, glycine at position 16, and glycine at position 19 are not mutated. In the amino acid substitution, deletion, insertion, or addition in the sequence, the number of mutated amino acids is preferably not more than 3, more preferably not more than 2, even more preferably 1. Most preferred is no mutation in the sequence.

FIG. 29 shows an alignment of the amino acid sequences of SEQ ID Nos. 13, 14 and 15.

In (Cc) polypeptide, the amino acid sequence has, for example, 60% or more identity with the amino acid sequence of SEQ ID NO: 13. It is preferable that the amino acid sequence have generally 80% or more, preferably 85% or more, more preferably 90% or more, further preferably 95% or more, even more preferably 98% or more, and particularly preferably 99% or more identity with the amino acid sequence of SEQ ID NO: 13.

Specifically, (Cc) polypeptide may be a polypeptide consisting of the amino acid sequence of SEQ ID NO: 14 or a polypeptide consisting of the amino acid sequence of SEQ ID NO: 15. The amino acid identity between the amino acid sequence of SEQ ID NO: 13 and the amino acid sequence of SEQ ID NO: 14 is 99.6% (Blast2). The amino acid identity between the amino acid sequence of SEQ ID NO: 13 and the amino acid sequence of SEQ ID NO: 15 is 90.9% (Blast 2). Accordingly, in a preferred embodiment of the invention, (Bc) polypeptide comprises an amino acid sequence having 90.9% or more, and more preferably 99.6% identity to the amino acid sequence of SEQ ID NO: 13.

Regarding polypeptides (Cb) and (Cc), the activity to synthesize equol using tetrahydrodaidzein as a substrate can be confirmed as follows. First, a polypeptide of interest is added to a substrate solution of the composition below at a concentration of 0.001 mg/mL. The solution is then incubated at 37° C. for 2 hours to check for the presence or absence of equol in the solution. The presence of equol in the solution after incubation is used as an indicator of the polypeptide's activity to synthesize equol using tetrahydrodaidzein as a substrate.

Composition of Substrate Solution 0.1 M potassium phosphate buffer (pH 7.0)
1 mM PMSF (phenylmethylsulfonyl fluoride)
2 mM dithiothreitol
5 mM sodium Sodium hydrosulfite
40 μM dihydrodaidzein Enzyme Property Since E3 polypeptide has an enzyme activity to synthesize equol using tetrahydrodaidzein as a substrate, E3 polypeptide is also referred to as E3 enzyme. The optimal temperature of E3 enzyme is in the vicinity of about 23 to 37° C., and the optimal pH is 4.5. E3 enzyme can also synthesize tetrahydrodaidzein from equol.

Similarly to E1 polypeptide and E2 polypeptide, E3 polypeptide can be produced by genetic engineering techniques based on the information of the nucleotide sequence of SEQ ID NO: 16, 17, or 18. Further, common chemical synthesis methods may be used to produce E3 polypeptide, based on the information of the amino acid sequence of SEQ ID NO: 13, 14, or 15. E3 polypeptide can also be produced by isolation and purification from microorganisms capable of producing it. These methods can be performed according to the description in the foregoing Section A-1.

The microorganism capable of producing E3 polypeptide may be cultured in a medium containing a desired amount of tetrahydrodaidzein. E3 polypeptide can also be produced in this way in microorganisms capable of producing E3 polypeptide.

E2 polypeptide may be monomeric, or dimeric or polymeric, as long as it can synthesize tetrahydrodaidzein. Further, to improve stability and other characteristics, E3 polypeptide may be modified as required, by adding polyethylene glycol or a sugar chain.

E3 polypeptide can serve as a catalyst that converts tetrahydrodaidzein (a substrate) into equol. Equol is believed to exhibit various physiological activities in the body. In this respect, E3 polypeptide, capable of providing equol, is considered important. The present invention therefore provides a equol synthesizing enzyme including any of polypeptides (Ca) through (Cc).

C-2. Polynucleotide

The present invention also provides a polynucleotide (hereinafter also referred to as "E3 polynucleotide") that encodes a polypeptide having an activity to synthesize equol using tetrahydrodaidzein as a substrate. Specifically, the invention provides:

(Cd) a polynucleotide consisting of the nucleotide sequence of SEQ ID NO: 16;

(Ce) a polynucleotide that encodes a polypeptide consisting of the amino acid sequence of SEQ ID NO: 13; and (Cf) a polynucleotide that hybridizes under stringent conditions with the complementary strand of the polynucleotide (Cd) or (Ce), and that encodes a polypeptide having an activity to synthesize equol using tetrahydrodaidzein as a substrate.

The amino acid sequence of SEQ ID NO: 13 corresponds to the amino acid sequence encoded by the nucleotide sequence of SEQ ID NO: 16. The amino acid sequence of SEQ ID NO: 14 corresponds to the amino acid sequence encoded by the nucleotide sequence of SEQ ID NO: 17. The amino acid sequence of SEQ ID NO: 15 corresponds to the amino acid sequence encoded by the nucleotide sequence of SEQ ID NO: 18.

Regarding polynucleotide (Cf), the phrase "hybridizes under stringent conditions" is synonymous with the phrase "hybridizes under stringent conditions" in Section A-2. Examples of polynucleotide (Cf) include the nucleotide sequence of SEQ ID NO: 17 and the nucleotide sequence of SEQ ID NO: 18. The base sequence homology between the nucleotide sequence of SEQ ID NO: 16 and the nucleotide sequence of SEQ ID NO: 17 is 99.8% (Blast2). The homology between the nucleotide sequence of SEQ ID NO: 16 and the nucleotide sequence of SEQ ID NO: 18 is 85.2% (Blast2). Accordingly, in a preferred embodiment of the invention, a polynucleotide (Cf) comprises a base sequence having 85.2% homology, and more preferably 99.8% homology to the base sequence of SEQ ID NO: 16.

Regarding polynucleotide (Cf), the "activity to synthesize equol using tetrahydrodaidzein as a substrate" can be confirmed by the same method used for polypeptides (Cb) and (Cc).

E3 polynucleotide can be produced or obtained by chemical DNA synthesis methods or genetic engineering techniques, based on the sequence information of SEQ ID NO: 16, 17 or 18. Specifically, the method described for E1 polynucleotide in Section A-2 can be employed.

The cDNA source of E3 polynucleotide is not particularly limited as long as it is a microorganism expressing E3 polynucleotide. Specific examples include microorganisms capable of producing equol, preferably lactic acid bacteria, bacteria belonging to the genera *Bacteroides* and *Streptococcus* capable of producing equol, more preferably *Lactococcus garvieae, Bacteroides ovatus*, and *Streptococcus constellatus* capable of producing equol, further preferably fecal *Lactococcus garvieae* and particularly preferably *Lactococcus* 20-92 strain, *Bacteroides ovatus* E-23-15 strain, *Streptococcus constellatus* A6G-225 (FERM BP-10036, FERM BP-6435, and FERM BP-6437, respectively; deposited with the International Patent Organism Depositary, National Institute of Advanced Industrial Science and Technology, 1-1-1 Higashi, Tsukuba, Ibaraki, Japan), strains of fecal *Lactococcus garvieae* capable of producing equol.

Expression of E3 polynucleotide using common genetic engineering techniques readily enables mass, stable production of the polynucleotide product (the polypeptide). The successful isolation of E3 polynucleotide by the present invention will open the door for the industrial production of equol, without using the difficult-to-handle anaerobic bacterial strains traditionally used for equol production.

C-3. Expression Vector

An expression vector of the present invention is not particularly limited as long as it includes E3 polynucleotide and is capable of expressing E3 polynucleotide. Generally, it is appropriately selected according to the type of host cell, similar to the expression vector including E1 polynucleotide. Specifically, the host cell described in Section A-3 may be used.

C-4. Recombinant Cell

The present invention provides a recombinant cell (transformant) transformed with an expression vector including E3 polynucleotide. The host cell used for the recombinant cell may be any of those described in Section A-4. Further, the expression vector may be introduced into the host cell by the method described in Section A-4.

Because the recombinant cell is capable of producing E3 polypeptide (an equol-converting enzyme), it can be used to produce an equol-converting enzyme. The recombinant cell can also be used to produce equol in a cell form.

C-5. Polypeptide Production Using Recombinant Cell

E3 polypeptide can be produced by culturing a recombinant cell into which E3 E3 polynucleotide is introduced, and collecting E3 polypeptide from the cell and culture. The recombinant cells can be cultured according to the description of Section A-5.

C-6. Equol Production Using E3 Polypeptide

The present invention provides a process for producing equol using E3 polypeptide. In the producing process, tetrahydrodaidzein can be converted into equol by having E3 polypeptide act on tetrahydrodaidzein.

The reaction used in the producing process may be performed in a suitable buffer. Specifically, the buffers described in Section A-6 can be used.

The reaction used in the producing process is performed under such conditions that, for example, each component is added in a medium in the concentration rages described below at the start of reaction so as to prepare a mixture. The mixture is incubated for 0.5 to 10 hours, preferably 1 to 6 hours, and more preferably 2 to 4 hours at temperatures that do not alter or inactivate the starting materials, including the E3 polypeptide and tetrahydrodaidzein, and the product, including equol. The reaction temperature is not particularly limited. For example, when the reaction temperature is 0° C. or less, the reaction uses, for example, a buffer that does not freeze at such reaction temperatures. The reaction temperature is, for example, preferably 0 to 45° C., and more preferably 0 to 37° C.

The E3 polypeptide content is 0.0001 to 1.0 weight %, preferably 0.001 to 0.1 weight %, and more preferably 0.001 to 0.01 weight %; and the tetrahydrodaidzein content is 0.0001 to 10.0 weight %, preferably 0.001 to 1.0 weight %, and more preferably 0.001 to 0.1 weight %.

The present invention also provides a material mixture for the synthesis of equol, specifically, an equol synthesis material composition including (Ci) E3 polypeptide, (Cii) tetrahydrodaidzein. By incubating the composition under the foregoing conditions, the tetrahydrodaidzein contained in the composition can be converted to equol. The composition corresponds to the foregoing starting material mixture used to initiate the reaction to produce equol. Further, the concentrations of E3 polypeptide, and tetrahydrodaidzein in the composition, and other components that can be added to the composition are essentially as in the reaction system (a starting material mixture at the start of reaction) used in the foregoing producing process.

The present invention also provides a kit for synthesizing equol, specifically, an equol synthesis kit including (Ci) E3 polypeptide and (Cii) tetrahydrodaidzein. The synthesis kit may include the components in compartments as required, so as to conveniently enable equol synthesis from tetrahydrodaidzein under the foregoing conditions. The synthesis kit may further include a buffer as required. The synthesis kit may also include any necessary tools or operation manuals that help perform equol synthesis.

C-7. Equol Synthesizing Enzyme Composition

The present invention also provides an equol synthesizing enzyme composition including E3 polypeptide. The enzyme composition can be suitably used as an equol synthesizing enzyme in the producing process of equol using E3 polypeptide.

The enzyme composition may be a crude purified E3 polypeptide, or the enzyme composition may be a crude purified or purified E3 polypeptide formulated with a suitable support. The support does not have any adverse effect on the activity of E3 polypeptide, and is used in a suitable amount.

The proportion of E3 polypeptide in the enzyme composition is not particularly limited as long as the composition can be used as an equol synthesizing enzyme in the producing process of equol. Specifically, the E3 polypeptide content is, for example, 0.001 to 20.0 weight %, preferably 0.005 to 5.0 weight %, and more preferably 0.01 to 1.0 weight %, with respect to the total of the enzyme composition.

To improve the stability of the polypeptide and/or to ensure the preservability of the enzyme composition, the enzyme composition may further include various antioxidants and preservatives described in Section A-7, in addition to E3 polypeptide.

C-8. Producing Process of Equol Using Recombinant Cell

The present invention provides a producing process of equol using recombinant cells including E3 polynucleotide. Specifically, in the producing process, tetrahydrodaidzein is converted into equol by having the recombinant cell act on tetrahydrodaidzein to convert.

The reaction used in the producing process is performed in an environment that allows the recombinant cell to survive, and tetrahydrodaidzein to be converted into equol.

Specifically, appropriate amounts of recombinant cells and tetrahydrodaidzein are added and cultured in a medium that allows for growth of the recombinant cells.

The medium used in the producing process is suitably selected from various kinds of conventional media according to the type of the cell used as the host recombinant cell.

The medium may be supplemented with appropriate amounts of protease inhibitors such as PMSF and EDTA, as required. Further, considering that the polypeptide derives from anaerobic bacteria, appropriate amounts of reducing agents such as DTT, 2ME, DET, and $Na_2S_2O_4$ may also be added. When using the recombinant cell, the medium may be supplemented with NADPH and/or NADH as required, though it is not essential.

Specifically, the producing process is performed as follows. First, the recombinant cells are inoculated in medium containing 0.001 to 1 weight %, preferably 0.01 to 0.5 weight %, and more preferably 0.01 to 0.1 weight % of tetrahydrodaidzein, and the culture is incubated under permissive temperature conditions for 7 to 30 hours, preferably 15 to 24 hours, and more preferably 17 to 20 hours. Here, the permissive temperature conditions are not particularly limited, and are essentially as in the foregoing Section C-6.

The present invention also provides a material mixture for synthesizing equol, specifically, a equol synthesis material composition containing (Ciii) the recombinant cell and (Cii) tetrahydrodaidzein. By culturing the composition under the foregoing conditions, the tetrahydrodaidzein in the composition can be converted to equol. The composition corresponds to the foregoing starting material mixture used to initiate the reaction to produce equol. Further, the concentrations of the recombinant cell and tetrahydrodaidzein in the composition, and other components that can be added to the composition, are essentially as in the conditions used in the foregoing producing process.

The present invention also provides a kit for synthesizing equol, specifically, an equol synthesis kit including (Ciii) the recombinant cell and (Cii) tetrahydrodaidzein. The synthesis kit may include the recombinant cell and tetrahydrodaidzein in compartments as required, so as to conveniently enable equol synthesis from dihydrodaidzein under the foregoing conditions. The synthesis kit may further include a buffer or a medium, as required. The synthesis kit may also include any necessary tools or operation manuals that help perform equol synthesis.

The recombinant cells included in the synthesis kit may be preserved therein by known methods. There are a number of known recombinant cell preservation techniques. For example, there is a method in which the recombinant cells are preserved at 4 to 25° C. after being treated with a lyophilizer to evacuate the ampule storing the recombinant cells in a solvent such as dimethylformamide. Another example is a liquid nitrogen method, in which the cells are suspended in a preserving medium supplemented with 10% glycerol, which is then stored in a specific ampule and kept in a liquid nitrogen tank (at −150 to −196° C.).

C-9. Antibody Having Affinity to the Polypeptide

The present invention also provides an antibody (an IgG antibody) having affinity to E3 polypeptide.

The monoclonal antibody and polyclonal antibody can be prepared by an ordinary method. Specifically, these antibodies can be produced by the methods described in Section A-9.

C-10. Immunological Method for the Detection or Measurement of the Polypeptide

The present invention also provides an immunological method for detecting or measuring E3 polypeptide using the antibody. Specifically, the immunological method can be performed according to the method described in Section A-10.

The present invention also provides an immunological detection kit including the antibody, used for the detection or measurement of E3 polypeptide. The detection kit may also include a standard E3 polypeptide, as required. The detection kit may further include, as required, additional reagents that facilitate the easy detection of E3 polypeptide under the foregoing conditions. The detection kit may also include any necessary tools or operation manuals that facilitate easy E3 polypeptide detection.

C-11. Method for Detection or Measurement of Polynucleotide that Encodes the Polypeptide The present invention also provides a method for detecting or measuring E3 polynucleotide. Specifically, the method is performed by causing an E3 polynucleotide-binding probe to contact a test sample, according to the method described in Section A-11.

The present invention also provides a kit for detecting or measuring E3 polynucleotide, specifically an E3 polynucleotide detection kit including the probe. For ease of E3 polynucleotide detection under the foregoing conditions, the detection kit may include additional reagents or the like as required, in addition to the probe. Further, the detection kit can be used to identify cells containing E3 polynucleotide. From the standpoint of enabling accurate detection, the detection kit may preferably be provided as a kit for performing detection using PCR.

D. Process for Producing Equol Using E1-E3 Enzymes, or Intermediate of Those

D-I-1. Process for Producing Tetrahydrodaidzein Comprising First Step and Second Step The present invention provides a process for producing tetrahydrodaidzein comprising the following First Step and Second Step (hereinafter, this process is occasionally referred to as "First Production Method"). First Step produces dihydrodaidzein from daidzein. Second Step produces tetrahydrodaidzein from dihydrodaidzein.

First Step comprises a step of causing an enzyme consisting of one of the following (Aa) to (Ac) polypeptides, and NADPH and/or NADH to act on daidzein, thereby producing dihydrodaidzein.

(Aa) a polypeptide consisting of the amino acid sequence of SEQ ID NO: 1.

(Ab) a polypeptide consisting of the amino acid sequence of SEQ ID NO: 1 with the substitution, deletion, insertion, and/or addition of one or more amino acids, and having an activity to synthesize dihydrodaidzein using daidzein as a substrate.

(Ac) a polypeptide consisting of an amino acid sequence having 60% or more identity with the amino acid sequence of SEQ ID NO: 1, and having an activity to synthesize dihydrodaidzein using daidzein as a substrate.

Second Step comprises a step of having an enzyme consisting of one of the following (Ba) to (Bc) polypeptides, and NADPH and/or NADH act on dihydrodaidzein, thereby producing tetrahydrodaidzein.

(Ba) a polypeptide consisting of the amino acid sequence of SEQ ID NO: 7.

(Bb) a polypeptide consisting of the amino acid sequence of SEQ ID NO: 7 with the substitution, deletion, insertion, and/or addition of one or more amino acids, and having an activity to synthesize tetrahydrodaidzein using dihydrodaidzein as a substrate.

(Bc) a polypeptide consisting of an amino acid sequence having 60% or more identity with the amino acid sequence of SEQ ID NO: 7, and having an activity to synthesize tetrahydrodaidzein using dihydrodaidzein as a substrate.

First Production Method of the present invention enables production of tetrahydrodaidzein from dihydrodaidzein, and equol from tetrahydrodaidzein.

First Step

In First Step, daidzein is converted into dihydrodaidzein by having an enzyme consisting of E1 polypeptide act on daidzein in the presence of NADPH and/or NADH. The reaction in First Step is performed through incubation in a solution containing an enzyme consisting of E1 polypeptide, daidzein, and NADPH and/or NADH at temperatures that do not alter or inactivate the starting materials, including the polypeptide and daidzein, and the product, including dihydrodaidzein; namely the conditions detailed in the foregoing section A-6.

When First Step and the later-described Second Step are performed under the same conditions, the reaction is performed under such conditions that the components satisfy the concentration ranges as shown below in a reaction system at the start of reaction (in a mixture of starting materials at the start of reaction), and that the mixture is incubated for 0.5 to 10 hours, preferably 1 to 6 hours, and more preferably 2 to 4 hours, at 15 to 45° C., preferably 25 to 40° C., and more preferably 30 to 38° C. With this arrangement, both First and Second Step are efficiently carried out. The content of the enzyme consisting of E1 polypeptide is 0.0001 to 1.0 weight %, preferably 0.001 to 0.1 weight %, and more preferably 0.001 to 0.01 weight %. The daidzein content is 0.0001 to 10.0 weight %, preferably 0.001 to 1.0 weight %, and more preferably 0.001 to 0.1 weight %. The NADPH and/or NADH content is 0.01 to 5 weight %, preferably 0.05 to 1 weight %, and more preferably 0.1 to 0.5 weight %.

The source of daidzein used as a substrate in First Step is not limited. For example, commercially-available daidzeins or daidzeins produced or synthesized through appropriate methods may be used.

Further, for example, a dihydrodaidzein synthesis material composition containing (Ai) an enzyme consisting of E1 polypeptide; (Aii) NADPH and/or NADH; and (Aiii) daidzein may be used as the mixture of starting materials in the production of dihydrodaidzein in First Step. By incubating the composition under the foregoing conditions, the daidzein in the composition is converted into dihydrodaidzein. The composition is specifically described in the foregoing sections A-6 and A-7.

Second Step

In Second Step, dihydrodaidzein is converted into tetrahydrodaidzein by having an enzyme consisting of E2 polypeptide act on dihydrodaidzein in the presence of NADPH and/or NADH.

The reaction in Second Step is performed through incubation in a solution containing an enzyme consisting of E2 polypeptide, dihydrodaidzein, and NADPH and/or NADH at temperatures that do not alter or inactivate the starting materials, including the enzyme consisting of the polypeptide E2 and dihydrodaidzein, and the product, including tetrahydrodaidzein; namely the conditions detailed in the foregoing section B-6.

Regarding tetrahydrodaidzein, the compound exists either in a cis form or a trans form. The formation of cis- and trans-configurations can be controlled by varying reaction conditions such as reaction temperature and reaction time. For example, a mixture of cis- and trans-tetrahydrodaidzeins can be produced by setting the reaction temperature at 0° C., or the reaction may be controlled to favor the trans form by setting the reaction temperature at 37° C.

When First Step and Second Step are performed under the same conditions, the reaction is performed through incubation under the aforementioned conditions for carrying out First Step and Second Step under the same conditions, that are detailed in the foregoing explanation of First Step. With this arrangement, both First and Second Step are efficiently carried out. In this case, the contents of the enzyme consisting of E2 polypeptide, dihydrodaidzein, and NADPH and/or NADH are adjusted as follows:

the content of the enzyme consisting of E2 polypeptide is 0.0001 to 1.0 weight %, preferably 0.001 to 0.1 weight %, and more preferably 0.001 to 0.01 weight %;

the dihydrodaidzein content is 0.0001 to 10.0 weight %, preferably 0.001 to 1.0 weight %, and more preferably 0.001 to 0.1 weight %; and the NADPH and/or NADH content is 0.01 to 5 weight %, preferably 0.05 to 1 weight %, and more preferably 0.1 to 0.5 weight %.

However, when being performed in the presence of the enzyme consisting of E1 polypeptide or the enzyme consisting of E2 polypeptide, First Step and Second Step require use of NADPH to increase efficiency in the dihydrodaidzein producing reaction. The concentration of NADPH is determined based on the aforementioned conditions for carrying out First Step and Second Step under the same conditions, that are detailed in the foregoing explanation of First Step. The concentration of NADH, which is used with NADPH, is 0.01 to 5 wt %, preferably 0.05 to 1 wt %, more preferably 0.1 to 0.5 wt %.

The source of dihydrodaidzein used as a substrate in Second Step is not limited.

For example, the dihydrodaidzein produced in First Step from daidzein may be used as a substrate for Second Step. The dihydrodaidzein is used either in the form of the solution containing dihydrodaidzein as produced in First Step, or in a roughly-refined state or properly refined state.

Commercially-available dihydrodaidzeins or dihydrodaidzeins synthesized through appropriate methods may also be used.

Further, a tetrahydrodaidzein synthesis material composition containing (Bi) an enzyme consisting of E2 polypeptide; (Bii) NADPH and/or NADH; and (Biii) dihydrodaidzein may be used as the mixture of starting materials in the production of tetrahydrodaidzein in Second Step. By incubating the composition under the foregoing conditions, the dihydrodaidzein in the composition is converted into tetrahydrodaidzein. The synthesis composition is specifically described in the foregoing sections A-6 and A-7.

In Second Step, it is preferable to use dihydrodaidzein, produced in First Step using daidzein as a substrate; however, commercially-available dihydrodaidzein, the synthesis starting-material composition, the enzyme composition etc. may be mixed with the dihydrodaidzein produced in First Step.

E1 Polypeptide and E2 Polypeptide

First Production Method of the present invention uses the enzyme consisting of E1 polypeptide as detailed in the foregoing section A-1, and the enzyme consisting of E2 polypeptide as detailed in the foregoing section B-1.

D-I-2. Product Containing Tetrahydrodaidzein, Produced by First Production Method The present invention provides a product containing tetrahydrodaidzein, produced by the foregoing process comprising First Step and Second Step (First Production Method).

As described above, First Production Method of the present invention enables production of dihydrodaidzein from daidzein, and tetrahydrodaidzein from dihydrodaidzein.

Accordingly, the product produced by First Production Method of the present invention contains not only tetrahydrodaidzein, but also dihydrodaidzein and/or daidzein.

The product of the present invention may be used in the form of the solution as produced in First Production Method, or may be a tetrahydrodaidzein product obtained by roughly or properly refining the solution.

The product of the present invention may be incorporated in foods, drinks, or makeup product materials, medicinal products etc., or may be used as a substrate.

D-I-3. Equol Production Process Comprising Second Step and Third Step

The present invention provides a process for producing equol comprising the following Second Step and Third Step (hereinafter, this process is occasionally referred to as "Second Production Method"). Second Step produces tetrahydrodaidzein from dihydrodaidzein. Third Step produces equol from tetrahydrodaidzein.

Second Step comprises a step of having an enzyme consisting of one of the following (Ba) to (Bc) polypeptides, and NADPH and/or NADH act on dihydrodaidzein, thereby producing tetrahydrodaidzein.

(Ba) a polypeptide consisting of the amino acid sequence of SEQ ID NO: 7.

(Bb) a polypeptide consisting of the amino acid sequence of SEQ ID NO: 7 with the substitution, deletion, insertion, and/or addition of one or more amino acids, and having an activity to synthesize tetrahydrodaidzein using dihydrodaidzein as a substrate.

(Bc) a polypeptide consisting of an amino acid sequence having 60% or more identity with the amino acid sequence of SEQ ID NO: 7, and having an activity to synthesize tetrahydrodaidzein using dihydrodaidzein as a substrate.

Third Step comprises a step of having an enzyme consisting of one of the following (Ca) to (Cc) polypeptides act on tetrahydrodaidzein, thereby producing equol.

(Ca) a polypeptide consisting of the amino acid sequence of SEQ ID NO: 13.

(Cb) a polypeptide consisting of the amino acid sequence of SEQ ID NO: 13 with the substitution, deletion, insertion, and/or addition of one or more amino acids, and having an activity to synthesize equol using tetrahydrodaidzein as a substrate.

(Cc) a polypeptide consisting of an amino acid sequence having 60% or more identity with the amino acid sequence of SEQ ID NO: 13, and having an activity to synthesize equol using tetrahydrodaidzein as a substrate.

Second Production Method of the present invention enables production of equol from tetrahydrodaidzein, and equol from tetrahydrodaidzein.

Second Step

Second Step of Second Production Method of the present invention is the same as Second Step of First Production Method.

When Second Step and the later-described Third Step are performed under the same conditions, the reaction is performed under such conditions that the components satisfy the concentration ranges below in a reaction system at the start of reaction (in a mixture of starting materials at the start of reaction), and that the mixture is incubated for 0.5 to 10 hours, preferably 1 to 6 hours, and more preferably 2 to 4 hours, at 15 to 45° C., preferably 25 to 40° C., and more preferably 30 to 38° C. With this arrangement, both First and Second Step are efficiently carried out.

The content of the enzyme consisting of E2 polypeptide is 0.0001 to 1.0 weight %, preferably 0.001 to 0.1 weight %, and more preferably 0.001 to 0.01 weight %. The dihydrodaidzein content is 0.0001 to 10.0 weight %, preferably 0.001 to 1.0 weight %, and more preferably 0.001 to 0.1 weight %. The NADPH and/or NADH content is 0.01 to 5 weight %, preferably 0.05 to 1 weight %, and more preferably 0.1 to 0.5 weight %.

Third Step

Third Step causes an enzyme consisting of E3 polypeptide to act on tetrahydrodaidzein, thereby converting tetrahydrodaidzein into equol.

The reaction in Third Step is performed through incubation in a solution containing an enzyme consisting of E3 polypeptide, and tetrahydrodaidzein at temperatures that do not alter or inactivate the starting materials, including the enzyme consisting of the polypeptide E3 and tetrahydrodaidzein, and the product, including equol; namely the conditions detailed in the foregoing section A-6.

When Second Step and Third Step are performed under the same conditions, the reaction is performed through incubation under the aforementioned conditions for carrying out Second Step and Third Step under the same conditions, that are detailed in the foregoing explanation of Second Step. With this arrangement, both Second and Third Step are efficiently carried out. In this case, the contents of the enzyme consisting of E3 polypeptide, tetrahydrodaidzein, and NADPH and/or NADH are adjusted as follows:

the content of the enzyme consisting of E3 polypeptide is 0.0001 to 1.0 weight %, preferably 0.001 to 0.1 weight %, and more preferably 0.001 to 0.01 weight %;

the tetrahydrodaidzein content is 0.0001 to 10.0 weight %, preferably 0.001 to 1.0 weight %, and more preferably 0.001 to 0.1 weight %; and the NADPH and/or NADH content is 0.01 to 5 weight %, preferably 0.05 to 1 weight %, and more preferably 0.1 to 0.5 weight %.

The source of tetrahydrodaidzein used as a substrate in Third Step is also not limited.

For example, the tetrahydrodaidzein produced in Second Step from dihydrodaidzein may be used as a substrate for Third Step. The tetrahydrodaidzein is used either in the form of the solution containing tetrahydrodaidzein as produced in Second Step, or in a roughly-refined state or properly refined state.

Commercially-available tetrahydrodaidzeins or tetrahydrodaidzeins synthesized through appropriate methods may also be used.

Further, a tetrahydrodaidzein synthesis material composition containing (Ci) an enzyme consisting of E3 polypeptide; and (Cii) tetrahydrodaidzein may be used as the mixture of starting materials in the production of tetrahydrodaidzein in Third Step. By incubating the composition under the foregoing conditions, the tetrahydrodaidzein in the composition is converted into equol. The composition is specifically described in the foregoing sections C-6 and C-7.

In Third Step, it is preferable to use tetrahydrodaidzein, produced in Second Step using dihydrodaidzein as a substrate; however, commercially-available tetrahydrodaidzein, the synthesis starting-material composition, the enzyme composition etc. may be mixed with the tetrahydrodaidzein produced in Second Step.

E2 Polypeptide and E3 Polypeptide

Second Production Method of the present invention uses an enzyme consisting of E2 polypeptide described in the foregoing section B-1, and an enzyme consisting of E3 polypeptide described in the foregoing section C-1.

D-I-4. Product Containing Equol, Produced by Second Production Method

The present invention provides a product containing equol, produced by the foregoing process comprising Second Step and Third Step (Second Production Method).

As described above, Second Production Method of the present invention enables production of tetrahydrodaidzein from dihydrodaidzein, and equol from tetrahydrodaidzein.

Accordingly, the product produced by Second Production Method of the present invention contains not only equol, but also tetrahydrodaidzein and/or dihydrodaidzein.

The product of the present invention may be used in the form of the solution as produced in Second Production Method, or may be an equol product obtained by roughly or properly refining the solution.

The product of the present invention may be incorporated in foods, drinks, makeup product materials, medicinal products etc., or may be used as a substrate.

D-I-5. Equol Production Method Comprising First Step to Third Step

The present invention provides an equol production method comprising First Step, Second Step and Third Step (hereinafter, this process is occasionally referred to as "Third Production Method").

Third Production Method of the present invention enables production of dihydrodaidzein from daidzein, tetrahydrodaidzein from dihydrodaidzein, and equol from tetrahydrodaidzein.

First Step

In First Step of Third Production Method of the present invention, daidzein is converted into dihydrodaidzein by having an enzyme consisting of E1 polypeptide act on daidzein in the presence of NADPH and/or NADH. First Step of Third Production Method of the present invention is the same as the aforementioned First Step.

When First Step and Second Step are performed under the same conditions, when First Step and Third Step are performed under the same conditions, or when First Step through Third Step are performed under the same conditions, the reaction is performed through incubation under the aforementioned conditions/concentrations for carrying out First Step and Second Step under the same conditions, that are detailed in the foregoing explanation of First Step. With this arrangement, both First and Second Step are efficiently carried out.

Second Step

In Second Step of Third Production Method of the present invention, dihydrodaidzein is converted into tetrahydrodaidzein by having an enzyme consisting of E2 polypeptide act on dihydrodaidzein in the presence of NADPH and/or NADH. Second Step of Third Production Method of the present invention is the same as the aforementioned Second Step.

When First Step and Second Step are performed under the same conditions, or when First Step through Third Step are performed under the same conditions, the reaction is performed through incubation under the aforementioned conditions/concentrations for carrying out First Step and Second Step under the same conditions, that are detailed in the foregoing explanation of Second Step. With this arrangement, both First and Second Step are efficiently carried out.

Further, when First Step and Second Step are performed in the presence of the enzyme consisting of E1 polypeptide and the enzyme consisting of E2 polypeptide, or when First Step through Third Step are performed in the presence of the enzyme consisting of E1 polypeptide, the enzyme consisting of E2 polypeptide, and the enzyme consisting of E3 polypeptide, the reaction is performed through the incubation in the presence of the enzyme consisting of E1 polypeptide and the enzyme consisting of E2 polypeptide, under the aforementioned conditions/concentrations, that is detailed in the explanation of Second Step, for example.

When Second Step and Third Step are performed under the same conditions, the reaction is performed through incubation under the aforementioned conditions/concentrations for carrying out Second Step and Third Step under the same conditions, that are detailed in the foregoing explanation of Second Step. With this arrangement, both Second and Third Step are efficiently carried out.

Third Step

In Third Step of Third Production Method of the present invention, tetrahydrodaidzein is converted into equol by having an enzyme consisting of E3 polypeptide act on tetrahydrodaidzein in the presence of NADPH and/or NADH, thereby converting tetrahydrodaidzein into equol. Third Step of Third Production Method of the present invention is the same as the aforementioned Third Step.

When First Step and Third Step are performed under the same conditions, or when First Step through Third Step are performed under the same conditions, the reaction is performed through incubation under the aforementioned conditions for carrying out First Step and Second Step under the same conditions, that are detailed in the foregoing explanation of First Step. With this arrangement, both First and Second Step are efficiently carried out. In this case, the contents of the enzyme consisting of E3 polypeptide, tetrahydrodaidzein, and NADPH and/or NADH are adjusted as follows:

the content of the enzyme consisting of E3 polypeptide is 0.0001 to 1.0 weight %, preferably 0.001 to 0.1 weight %, and more preferably 0.001 to 0.01 weight %;

the tetrahydrodaidzein content is 0.0001 to 10.0 weight %, preferably 0.001 to 1.0 weight %, and more preferably 0.001 to 0.1 weight %; and the NADPH and/or NADH content is 0.01 to 5 weight %, preferably 0.05 to 1 weight %, and more preferably 0.1 to 0.5 weight %.

However, when being performed in the presence of the enzyme consisting of E1 polypeptide and the enzyme consisting of E3 polypeptide, First Step and Third Step require use of NADPH to increase efficiency in the dihydrodaidzein producing reaction using the enzyme consisting of E1 polypeptide. Similarly, when being performed in the presence of the enzyme consisting of E1 polypeptide, the enzyme consisting of E2 polypeptide, and the enzyme consisting of E3 polypeptide, First Step through Third Step require use of NADPH to increase efficiency in the dihydrodaidzein producing reaction using the enzyme consisting of E1 polypeptide. In this case, the concentration of NADPH is determined based on the aforementioned conditions for carrying out First Step and Second Step under the same conditions, that are detailed in the foregoing explanation of First Step. The concentration of NADH, which is used with NADPH, is determined based on the aforementioned conditions for carrying out reaction in the presence of the enzyme consisting of E1 polypeptide, the enzyme consisting of E2 polypeptide, that are detailed in the foregoing explanation of Second Step, and the aforementioned conditions for carrying out Second Step and Third Step under the same conditions, that are detailed in the foregoing explanation of Second Step.

E1 to E3 Polypeptides

Third Production Method of the present invention uses the enzyme consisting of E1 polypeptide, the enzyme consisting of E2 polypeptide, and the enzyme consisting of E3 polypeptide. The peptides E1 to E3 are same as those described above.

D-I-6. Equol Containing Product, Produced by Third Production Method

The present invention provides a product containing equol, produced by the foregoing process comprising First Step through Third Step (Third Production Method).

As described above, Third Production Method of the present invention enables production of dihydrodaidzein from daidzein, tetrahydrodaidzein from dihydrodaidzein, and equol from tetrahydrodaidzein.

Accordingly, the product produced by Third Production Method of the present invention contains not only equol, but also tetrahydrodaidzein, dihydrodaidzein and/or daidzein.

The product of the present invention may be used in the form of the solution as produced in Third Production Method, or may be a tetrahydrodaidzein product obtained by roughly or properly refining the solution.

The product of the present invention may be incorporated in foods, drinks, or makeup product materials, medicinal products etc., or may be used as a substrate.

D-I-7. Process for Producing Dihydrodaidzein, Tetrahydrodaidzein and/or Equol, Comprising at Least Two of Fourth Step to Sixth Step The present invention provides a process for producing dihydrodaidzein, tetrahydrodaidzein, and/or equal, comprising at least two of the following Fourth Step to Sixth Step (hereinafter, this process is occasionally referred to as "Fourth Production Method"). Fourth Step produces dihydrodaidzein from daidzein. Fifth Step produces tetrahydrodaidzein from dihydrodaidzein, and Sixth Step produces equol from tetrahydrodaidzein.

Fourth Step comprises a step of having a recombinant cell consisting of one of the following (Ad) to (Af) polynucleotides act on daidzein, thereby producing dihydrodaidzein.

(Ad) a polynucleotide consisting of the nucleotide sequence of SEQ ID NO: 4;

(Ae) a polynucleotide that encodes a polypeptide consisting of the amino acid sequence of SEQ ID NO: 1; and (Af) a polynucleotide that hybridizes under stringent conditions with the complementary strand of the polynucleotide (Ad) or (Ae), and that encodes a polypeptide having an activity to synthesize dihydrodaidzein using daidzein as a substrate.

Fifth Step comprises a step of having a recombinant cell consisting of one of the following (Bd) to (Bf) polynucleotides act on dihydrodaidzein, thereby producing tetrahydrodaidzein.

(Bd) a polynucleotide consisting of the nucleotide sequence of SEQ ID NO: 10;

(Be) a polynucleotide that encodes a polypeptide consisting of the amino acid sequence of SEQ ID NO: 7; and (Bf) a polynucleotide that hybridizes under stringent conditions with the complementary strand of the polynucleotide (Bd) or (Be), and that encodes a polypeptide having an activity to synthesize tetrahydrodaidzein using dihydrodaidzein as a substrate.

Sixth Step comprises a step of having a recombinant cell consisting of one of the following (Cd) to (Cf) polynucleotides to act on tetrahydrodaidzein, thereby producing equol.

(Cd) a polynucleotide consisting of the nucleotide sequence of SEQ ID NO: 16;

(Ce) a polynucleotide that encodes a polypeptide consisting of the amino acid sequence of SEQ ID NO: 13; and (Cf) a polynucleotide that hybridizes under stringent conditions with the complementary strand of the polynucleotide (Cd) or (Ce), and that encodes a polypeptide having an activity to synthesize equol using tetrahydrodaidzein as a substrate.

Fourth Production Method of the present invention produces dihydrodaidzein, tetrahydrodaidzein and/or equol by appropriately combining Fourth to Sixth Steps.

Fourth Production Method of the present invention comprises at least two of Fourth Step, Fifth Step and Sixth Step.

For example, a Fourth Production Method of the present invention that comprises Fourth Step and Fifth Step and does not comprise Sixth Step produces dihydrodaidzein from daidzein, and tetrahydrodaidzein from dihydrodaidzein.

For example, a Fourth Production Method of the present invention that comprises Fifth Step and Sixth Step and does not comprise Fourth Step produces tetrahydrodaidzein from dihydrodaidzein, and equol from tetrahydrodaidzein.

And, for example, a Fourth Production Method of the present invention that comprises all of Fourth Step, Fifth Step and Sixth Step produces dihydrodaidzein from daidzein, tetrahydrodaidzein from dihydrodaidzein, and equol from tetrahydrodaidzein.

Each recombinant cell used for Fourth Production Method of the present invention may contain one or more polynucleotides selected from the group consisting of (Ad) to (Af), (Bd) to (Bf) and (Cd) to (Cf).

For example, when the cell contains two polynucleotides: a polynucleotides selected from the group consisting of (Ad) to (Af), and a polynucleotides selected from the group consisting of (Bd) to (Bf), Fourth Step and Fifth Step can be carried out with this cell, i.e., Fourth Step and Fifth Step can be carried out with one kind of recombinant cell.

Similarly, when the cell contains three polynucleotides: a polynucleotides selected from the group consisting of (Ad) to (Af), a polynucleotides selected from the group consisting of (Bd) to (Bf), and a polynucleotides selected from the group consisting of (Cd) to (Cf), Fourth Step to Sixth Step can be carried out with this cell, i.e., Fourth Step to Sixth Step can be carried out with one kind of recombinant cell.

In Fourth Production Method of, the present invention, Fourth Step to Sixth Step may also be carried out using a recombinant cell containing two polynucleotides: a polynucleotide selected from the group consisting of (Ad) to (Af), a polynucleotide selected from the group consisting of (Bd) to (Bf); and another recombinant cell containing a polynucleotides selected from the group consisting of (Cd) to (Cf).

Similarly, In Fourth Production Method of the present invention, Fourth Step to Sixth Step may also be carried out using a recombinant cell containing two polynucleotides: a polynucleotide selected from the group consisting of (Ad) to (Af), a polynucleotide selected from the group consisting of (Cd) to (Cf); and another recombinant cell containing a polynucleotides selected from the group consisting of (Bd) to (Bf).

Fourth Step

Fourth Step causes a recombinant cell having the E1 polynucleotide as detailed in the section A-2 to act on daidzein, thereby converting daidzein into dihydrodaidzein.

The reaction in Fourth Step may be carried out under the same conditions as those of First Step. More specifically, the recombinant cell is inoculated in the culture medium containing 0.001 to 1 wt %, preferably 0.01 to 1 wt %, more preferably 0.01 to 0.5 wt % of daidzein, and incubated for 6 to 30 hours, preferably 7 to 24 hours, more preferably 7 to 18 hours at a temperature allowing the cell growth. The temperature is not limited, and may be the temperature adopted in First Step.

Recombinant Cell Used in Fourth Step

Any recombinant cell may be used in Fourth Step as long as the cell contains E1 polynucleotide and is capable of expressing E1 polynucleotide. Recombinant cells detailed in the section A-4 can be used in the step.

Production of Enzyme Consisting of E1 Polypeptide Using Recombinant Cell Having E1 Polynucleotide The enzyme consisting of E1 polypeptide may be produced by culturing the recombinant cell after E2 polynucleotide introduction and by collecting E1 polypeptide from the cell culture. More specifically, E1 polypeptide can be produced by culturing the recombinant cell under the conditions detailed in the section A-5.

Fifth Step

Fifth Step causes a recombinant cell having the E2 polynucleotide as detailed in the section B-2 to act on dihydrodaidzein, thereby converting dihydrodaidzein into tetrahydrodaidzein.

The reaction in Fifth Step may be carried out under the same conditions as those of Second Step. More specifically, the recombinant cell is inoculated in the culture medium containing 0.001 to 1 wt %, preferably 0.01 to 0.5 wt %, more preferably 0.01 to 0.1 wt % of daidzein, and incubated for 7 to 30 hours, preferably 15 to 24 hours, more preferably 17 to 20 hours at a temperature allowing the cell growth. The temperature is not limited, and may be the temperature adopted in Second Step.

Recombinant Cell Used in Fifth Step

Any recombinant cell may be used in Fifth Step as long as the cell contains E2 polynucleotide described in B-2 section and is capable of expressing E2 polynucleotide. One example is a recombinant cell detailed in the section B-4.

Production of Enzyme Consisting of E2 Polypeptide Using Recombinant Cell Having E2 Polynucleotide The enzyme consisting of E2 polypeptide may be produced by culturing the recombinant cell after E2 polynucleotide introduction and by collecting E2 polypeptide from the cells and/or culture.

The same manners and conditions as those in the section "Production of enzyme consisting of E1 polypeptide using recombinant cell having E1 polynucleotide" may be used for incubation of recombinant cell supplied with E2 polynucleotide, culture medium, and isolation/purification of E2 polypeptide.

Sixth Step

Sixth Step causes a recombinant cell having the E3 polynucleotide as detailed in the section C-2 to act on tetrahydrodaidzein, thereby converting tetrahydrodaidzein into equol.

The reaction in Sixth Step may be carried out under the same conditions as those of Third Step. More specifically, the recombinant cell is inoculated in the culture medium containing 0.001 to 1 wt %, preferably 0.01 to 0.5 wt %, more preferably 0.01 to 0.1 wt % of tetrahydrodaidzein, and incubated for 7 to 30 hours, preferably 15 to 24 hours, more preferably 17 to 20 hours at a temperature allowing the cell growth. The temperature is not limited, and may be the temperature adopted in Third Step.

The source of tetrahydrodaidzein used as a substrate in Sixth Step is also not limited.

For example, the tetrahydrodaidzein produced in Fifth Step from dihydrodaidzein may be used as a substrate for Sixth Step. The tetrahydrodaidzein is used either in the form of the solution containing tetrahydrodaidzein as produced in Fifth Step, or in a roughly-refined state or properly refined state.

Commercially-available tetrahydrodaidzeins or tetrahydrodaidzeins synthesized through appropriate methods may also be used.

Further, a tetrahydrodaidzein synthesis material composition containing recombinant cells containing E3 polynucleotide; and tetrahydrodaidzein may be used as the mixture of starting materials in the production of tetrahydrodaidzein in Sixth Step. By incubating the composition under the foregoing conditions, the tetrahydrodaidzein in the composition is converted into equol. The same conditions and restrictions as above are applied to determine the concentrations of the recombinant cells and tetrahydrodaidzein in the composition, other ingredients added to the composition, reaction condition, etc.

In Sixth Step, it is preferable to use tetrahydrodaidzein, produced in Fifth Step using dihydrodaidzein as a substrate; however, commercially-available tetrahydrodaidzein, the synthesis starting-material composition, the enzyme composition etc. may be mixed with the tetrahydrodaidzein produced in Fifth Step.

Recombinant Cell Used in Sixth Step

Any recombinant cell may be used in Sixth Step as long as the cell contains E3 polynucleotide described in the C-2 section and is capable of expressing E3 polynucleotide. One example is a recombinant cell detailed in the section C-4.

Production of Enzyme Consisting of E3 Polypeptide Using Recombinant Cell Having E3 Polynucleotide The enzyme consisting of E3 polypeptide may be produced by culturing the recombinant cell after E3 polynucleotide introduction and by collecting E3 polypeptide from the cells and/or culture.

The same manners and conditions as those in the section "Production of enzyme consisting of E1 polypeptide using recombinant cell having E1 polynucleotide" may be used for incubation of recombinant cell supplied with E3 polynucleotide, culture medium, and isolation/purification of E3 polypeptide.

E1 to E3 Polynucleotides

Fourth Production Method of the present invention uses at least one of E1 to E3 polynucleotides, that are detailed in the foregoing sections A-2, B-2 and C-2, respectively.

D-I-8. Product Containing Dihydrodaidzein, Tetrahydrodaidzein and/or Equol, Produced by Fourth Production Method The present invention provides a product containing dihydrodaidzein, tetrahydrodaidzein and/or equol, produced by the foregoing Fourth Production Method.

As described above, Fourth Production Method of the present invention enables production of dihydrodaidzein, tetrahydrodaidzein, and/or equol by appropriately combining Fourth to Sixth Steps.

Accordingly, the product produced by Fourth Production Method of the present invention contains dihydrodaidzein, tetrahydrodaidzein, and/or equol.

The product of the present invention may be used in the form of the solution as produced in Fourth Production Method, or may be a dihydrodaidzein product, a tetrahydrodaidzein product or an equol product obtained by roughly or properly purifying the solution.

The product of the present invention may be incorporated in foods, drinks, or makeup product materials, medicinal products etc., or may be used as a substrate.

D-II-1. A Device for Producing Dihydrodaidzein, Tetrahydrodaidzein and/or Equol, Provided with at Least One of First Reaction Vessel to Third Reaction Vessel The present invention provides a device for producing dihydrodaidzein, tetrahydrodaidzein and/or equol, provided with at least one of the following First Reaction Vessel to Third Reaction Vessel (hereinafter, this device is occasionally referred to as "First Production Device").

First Reaction Vessel

First Reaction Vessel is a reaction vessel having a reaction means (hereinafter, this means is occasionally referred to as "reaction means 1") in which an enzyme consisting of one of (Aa) to (Ac) polypeptides (E1 polypeptides) is immobilized. This reaction vessel is used for production of dihydrodaidzein from daidzein using the polypeptide. In this reaction vessel, the reaction means is disposed in a position allowing contact with daidzein.

Second Reaction Vessel

Second Reaction Vessel is a reaction vessel having a reaction means (hereinafter, this means is occasionally referred to as "reaction means 2") in which an enzyme consisting of one of (Ba) to (Bc) polypeptides (E2 polypeptides) is immobilized. This reaction vessel is used for production of tetrahydrodaidzein from dihydrodaidzein using the polypeptide. In the reaction vessel, the reaction means is disposed in a position allowing contact with dihydrodaidzein.

Third Reaction Vessel

Third Reaction Vessel is a reaction vessel having a reaction means (hereinafter, this means is occasionally referred to as "reaction means 3") in which an enzyme consisting of one of (Ca) to (Cc) polypeptides (E3 polypeptides) is immobilized. This reaction vessel is used for production of equol from tetrahydrodaidzein using the polypeptide. In the reaction vessel, the reaction means is disposed in a position allowing contact with tetrahydrodaidzein.

First Production Device of the present invention enables production of dihydrodaidzein, tetrahydrodaidzein and/or equol by appropriately combining First through Third Reaction Vessels.

First Production Device of the present invention has at least one of First Reaction Vessel, Second Reaction Vessel and Third Reaction Vessel.

For example, when First Production Device of the present invention has First Reaction Vessel, and does not have Second Reaction Vessel and Third Reaction Vessel, First Production Device of the present invention enables production of dihydrodaidzein from daidzein.

For example, when First Production Device of the present invention has Second Reaction Vessel, and does not have First Reaction Vessel and Third Reaction Vessel, First Production Device of the present invention enables production of tetrahydrodaidzein from dihydrodaidzein.

For example, when First Production Device of the present invention has Third Reaction Vessel, and does not have First Reaction Vessel and Second Reaction Vessel, First Production Device of the present invention enables production of equol from tetrahydrodaidzein.

For example, when First Production Device of the present invention has First Reaction Vessel and Second Reaction Vessel, and does not have Third Reaction Vessel, First Production Device of the present invention enables production of dihydrodaidzein from daidzein, and tetrahydrodaidzein from dihydrodaidzein.

For example, when First Production Device of the present invention has Second Reaction Vessel and Third Reaction Vessel, and does not have First Reaction Vessel, First Production Device of the present invention enables production of tetrahydrodaidzein from dihydrodaidzein, and equol from tetrahydrodaidzein.

For example, when First Production Device of the present invention has First Reaction Vessel, Second Reaction Vessel, and Third Reaction Vessel, First Production Device of the present invention enables production of dihydrodaidzein from daidzein, tetrahydrodaidzein from dihydrodaidzein, and equol from tetrahydrodaidzein.

In First Production Device of the present invention, a single reaction vessel may have two of the reaction means 1 to 3.

For example, when reaction means 1 and 2 are provided in a single reaction vessel, the respective reactions performed in First Reaction Vessel and Second Reaction Vessel may be performed in a reaction vessel. Further, for example, when the reaction means 1 through 3 are provided in a single reaction vessel, the respective reactions performed in First to Third Reaction Vessels may be performed in a reaction vessel.

Insofar as the desired effect is ensured, the way of mounting of these reaction means to the reaction vessel is not limited.

Further, when First Production Device of the present invention has at least two of the reaction means 1 to 3 and plural different reaction vessels, the reaction vessels are connected via a supply means.

For example, when First production Device of the present invention has First Reaction Vessel and Second Reaction Vessel, and does not have Third Reaction Vessel, in which First Reaction Vessel and Second Reaction Vessel are independent units and First Reaction Vessel and Second Reaction Vessel contain the reaction means 1 and 2, respectively; the First Reaction Vessel and Second Reaction Vessel are connected via a supply, means for supplying a dihydrodaidzein product, produced in First Reaction Vessel, to Second Reaction Vessel.

Further, for example, when First Production Device of the present invention comprises the reaction means 1 and 2 in a reaction vessel, and the reaction means 3 in another reaction vessel; the reaction vessel containing the reaction means 1 and 2 and the reaction vessel containing the reaction means 3 are connected via a supply means for supplying a product, produced in the reaction vessel containing the reaction means 1 and 2, to the reaction vessel containing the reaction means 3.

The product may be a form of solution as produced, or may be a dihydrodaidzein product etc. obtained by roughly or properly purifying the solution.

Reaction Vessel

The shapes, sizes, materials etc. of the First Reaction Vessel to Third Reaction Vessel provided in First Production Device of the present invention are not limited, given that each vessel is capable of containing a reaction means, and appropriately producing dihydrodaidzein, tetrahydrodaidzein and/or equol.

Reaction Means

The reaction means 1 to 3 to be used in First Production Device of the present invention are not limited as long as they each contain an respective immobilized enzyme, and is capable of appropriately producing dihydrodaidzein, tetrahydrodaidzein and/or equol.

The respective enzyme immobilized in each reaction means may be roughly or properly (purely) purified. Immobilization of the enzyme consisting of one of the polypeptides in the reaction means is carried out using a known method.

For example, when the enzyme is immobilized in a carrier, the carrier is not limited as long as the desired activity of the enzyme can be exhibited. Examples of the carrier include a carrier having a functional group bondable with the enzyme through covalent bond, such as amino groups, carboxyl groups, or hydroxyl groups; and a carrier connectable with the enzyme consisting of the polypeptide via a linker. The shape of the carrier is not limited. The carrier, functioning group, and linker etc. are appropriately selected according to the adopted known technique for immobilizing an enzyme in the carrier. The immobilization of the enzyme consisting of the polypeptide in the carrier is also carried out using a known method.

Supply Means

The supply means provided in First Production Device of the present invention is not limited as long as it is capable of connecting plural different reaction vessels used in First Production Device of the present invention, and capable of producing dihydrodaidzein, tetrahydrodaidzein and/or equol in First Production Device of the present invention. The supply means is realized by an appropriate means according to a suitable known technology.

E1 to E3 Polypeptide

E1 to E3 polypeptides used in First Production Device of the present invention are the same as those above.

Production of Dihydrodaidzein in First Reaction Vessel

First Reaction Vessel causes an enzyme consisting of E1 polypeptide immobilized in the reaction means 1 to act on daidzein in the presence of NADPH and/or NADH, thereby converting daidzein into dihydrodaidzein. The enzyme consisting of E1 polypeptide may be immobilized in the reaction means together with NADPH and/or NADH that serves as a coenzyme of the enzyme consisting of E1 polypeptide. The reaction in First Reaction Vessel is carried out according to the method detailed in the foregoing explanation of "First Step".

Production of Tetrahydrodaidzein in Second Reaction Vessel

Second Reaction Vessel causes an enzyme consisting of E2 polypeptide immobilized in the reaction means 2 to act on dihydrodaidzein in the presence of NADPH and/or NADH, thereby converting dihydrodaidzein into tetrahydrodaidzein. The enzyme consisting of E2 polypeptide may be immobilized in the reaction means together with NADPH and/or NADH that serves as a coenzyme of the enzyme consisting of E2 polypeptide. The reaction in Second Reaction Vessel is carried out according to the method detailed in the foregoing explanation of "Second Step".

Production of Equol in Third Reaction Vessel

Third Reaction Vessel causes an enzyme consisting of E3 polypeptide immobilized in the reaction means 3 to act on tetrahydrodaidzein, thereby converting tetrahydrodaidzein into equol. The reaction in Third Reaction Vessel is carried out according to the method detailed in the foregoing explanation of "Third Step".

D-II-2. A Device for Producing Dihydrodaidzein, Tetrahydrodaidzein and/or Equol, Comprising at Least One of Fourth to Sixth Reaction Vessels The present invention provides a device for producing dihydrodaidzein, tetrahydrodaidzein and/or equol, comprising at least one of the following Fourth to Sixth Reaction Vessels (hereinafter, this device is occasionally referred to as "Second Production Device").

Fourth Reaction Vessel

Fourth Reaction Vessel is a reaction vessel having a reaction means (hereinafter, this means is occasionally referred to as "reaction means 4") in which a recombinant cell consisting of one of (Ad) to (Af) polynucleotides (E1 polynucleotides) is immobilized. This reaction vessel is used for production of dihydrodaidzein from daidzein using the polynucleotide. In this reaction vessel, the reaction means is disposed in a position allowing contact with daidzein.

Fifth Reaction Vessel

Fifth Reaction Vessel is a reaction vessel having a reaction means (hereinafter, this means is occasionally referred to as "reaction means 5") in which a recombinant cell consisting of one of (Bd) to (Bf) polynucleotides (E2 polynucleotides) is immobilized. This reaction vessel is used for production of tetrahydrodaidzein from dihydrodaidzein using the polynucleotide. In the reaction vessel, the reaction means is disposed in a position allowing contact with dihydrodaidzein.

Sixth Reaction Vessel

Sixth Reaction Vessel is a reaction vessel having a reaction means (hereinafter, this means is occasionally referred to as "reaction means 6") in which a recombinant cell consisting of one of (Cd) to (Cf) polynucleotides (E3 polynucleotides) is immobilized. This reaction vessel is used for production of equol from tetrahydrodaidzein using the polynucleotide. In the reaction vessel, the reaction means is disposed in a position allowing contact with tetrahydrodaidzein.

Second Production Device of the present invention enables production of dihydrodaidzein, tetrahydrodaidzein and/or equol by appropriately combining Fourth through Sixth Reaction Vessels.

Second Production Device of the present invention has at least one of Fourth Reaction Vessel, Fifth Reaction Vessel and Sixth Reaction Vessel.

For example, when Second Production Device of the present invention has Fourth Reaction Vessel, and does not have Fifth Reaction Vessel and Sixth Reaction Vessel, Second Production Device of the present invention enables production of dihydrodaidzein from daidzein.

For example, when Second Production Device of the present invention has Fifth Reaction Vessel, and does not have Fourth Reaction Vessel and Sixth Reaction Vessel, Second Production Device of the present invention enables production of tetrahydrodaidzein from dihydrodaidzein.

For example, when Second Production Device of the present invention has Sixth Reaction Vessel, and does not have Fourth Reaction Vessel and Fifth Reaction Vessel, Second Production Device of the present invention enables production of equol from tetrahydrodaidzein.

For example, when Second Production Device of the present invention has Fourth Reaction Vessel and Fifth Reaction Vessel, and does not have Sixth Reaction Vessel, Second Production Device of the present invention enables production of dihydrodaidzein from daidzein, and tetrahydrodaidzein from dihydrodaidzein.

For example, when Second Production Device of the present invention has Fifth Reaction Vessel and Sixth Reaction Vessel, and does not have Fourth Reaction Vessel, Second Production Device of the present invention enables production of tetrahydrodaidzein from dihydrodaidzein, and equol from tetrahydrodaidzein.

For example, when Second Production Device of the present invention has Fourth Reaction Vessel, Fifth Reaction Vessel, and Sixth Reaction Vessel, Second Production Device of the present invention enables production of dihydrodaidzein from daidzein, tetrahydrodaidzein from dihydrodaidzein, and equol from tetrahydrodaidzein.

In Second Production Device of the present invention, a single reaction vessel may have two of the reaction means 4 to 6.

For example, when reaction means 4 and 5 are provided in a single reaction vessel, the respective reactions performed in Fourth Reaction Vessel and Fifth Reaction Vessel may be performed in a reaction vessel. Further, for example, when the reaction means 4 through 6 are provided in a single reaction vessel, the respective reactions performed in Fourth to Sixth Reaction Vessels may be performed in a reaction vessel.

Insofar as the desired effect is ensured, the way of mounting of these reaction means to the reaction vessel is not limited.

Further, when Second Production Device of the present invention has at least two of the reaction means 4 to 6 and plural different reaction vessels, the reaction vessels are connected via a supply means.

For example, when Second Production Device of the present invention has Fourth Reaction Vessel and Fifth Reaction Vessel, and does not have Sixth Reaction Vessel, in which Fourth Reaction Vessel and Fifth Reaction Vessel are independent units and Fourth Reaction Vessel and Fifth Reaction Vessel contain the reaction means 4 and 5, respectively; the Fourth Reaction Vessel and Fifth Reaction Vessel are connected via a supply means for supplying a dihydrodaidzein product, produced in Fourth Reaction Vessel, to Fifth Reaction Vessel.

Further, for example, when Second Production Device of the present invention comprises the reaction means 4 and 5 in a reaction vessel, and the reaction means 6 in another reaction vessel; the reaction vessel containing the reaction means 4 and 5 and the reaction vessel containing the reaction means 6 are connected via a supply means for supplying a product, produced in the reaction vessel containing the reaction means 4 and 5, to the reaction vessel containing the reaction means 6.

The product may be a form of solution as produced, or may be a dihydrodaidzein product etc. obtained by roughly or properly purifying the solution.

Reaction Vessel

The shapes, sizes, materials etc. of the Fourth Reaction Vessel to Sixth Reaction Vessel provided in Second Production Device of the present invention are not limited, given that each vessel is capable of containing a reaction means, and appropriately producing dihydrodaidzein, tetrahydrodaidzein and/or equol.

Reaction Means

The reaction means 4 to 6 to be used in Second Production Device of the present invention are not limited as long as they each contain a respective immobilized recombinant cell, and is capable of appropriately producing dihydrodaidzein, tetrahydrodaidzein and/or equol.

Immobilization of the recombinant cell in the reaction means is not limited as long as the desired activity of the recombinant cell can be exhibited, and carried out using a known method. The recombinant cell may be incubated or incubatable in the reaction means. The conditions for the incubation of the recombinant cells are determined according to the foregoing explanations of “Fourth Step”, “Fifth Step”, and “Sixth Step”.

Supply Means

The supply means provided in Second Production Device of the present invention is not limited as long as it is capable of connecting plural different reaction vessels used in Second Production Device of the present invention, and capable of producing dihydrodaidzein, tetrahydrodaidzein and/or equol in Second Production Device of the present invention. The supply means is realized by an appropriate means according to a suitable known technology.

Recombinant Cells

The recombinant cells used in Second Production Device of the present invention are the same as those detailed in the foregoing sections “Recombinant cells used in Fourth Step”, “Recombinant cell used in Fifth Step”, and “Recombinant cell used in Sixth Step”.

E1 to E3 Polypeptide

E1 to E3 polynucleotides used in Second Production Device of the present invention are the same as those above.

Production of Dihydrodaidzein in Fourth Reaction Vessel

Fourth Reaction Vessel converts daidzein into dihydrodaidzein using a recombinant cell consisting of E1 polynucleotide immobilized in the reaction means 4. The reaction in Fourth Reaction Vessel is carried out according to the method detailed in the foregoing explanation of “Fourth Step”.

Production of Tetrahydrodaidzein in Fifth Reaction Vessel

Fifth Reaction Vessel converts dihydrodaidzein into tetrahydrodaidzein using a recombinant cell consisting of E2 polynucleotide immobilized in the reaction means 5. The reaction in Fifth Reaction Vessel is carried out according to the method detailed in the foregoing explanation of “Fifth Step”.

Production of Equol in Sixth Reaction Vessel

Sixth Reaction Vessel converts tetrahydrodaidzein into equol using a recombinant cell consisting of E3 polynucleotide immobilized in the reaction means 6. The reaction in Sixth Reaction Vessel is carried out according to the method detailed in the foregoing explanation of “Sixth Step”.

D-II-3. Device for Producing Dihydrodaidzein, Tetrahydrodaidzein and/or Equol, Comprising at Least One of First to Third Reaction Vessels, and at Least One of Fourth to Sixth Reaction Vessels The present invention provides a device for producing dihydrodaidzein, tetrahydrodaidzein and/or equol, comprising at least one of First to Third Reaction Vessels, and at least one of Fourth to Sixth Reaction Vessels (hereinafter, this device is occasionally referred to as “Third Production Device”).

The combinations of the reaction vessels, reaction means in Third Production Device are made according to those of the foregoing First and Second Production Devices. The reaction vessels, reaction means, polynucleotides, recombinant cells, and the reaction processes in the reaction vessels in Third Production Device are the same as those for the foregoing First and Second Production Devices.

EXAMPLES

Example A

Reference Example A1

A *Lactococcus* 20-92 strain (FERM BP-10036) was inoculated in a daidzein-containing amplification liquid medium (a modified GAM broth medium (Nissui Pharmaceutical Co. Ltd.) in which daidzein was added in an amount of 10 μg/mL), and the culture was incubated at 37° C. for appropriate hours from 7 to 18 hours under anaerobic conditions (BBL Gas Pack systems). After incubation, the cells were collected by centrifugation and cryogenically preserved to be used in the Examples below.

Example A1

Confirmation of Dihydrodaidzein Biosynthesis Activity in Centrifuged Supernatant of Disrupted Cell Material, and Confirmation of NADPH Dependency The frozen cells (67 mL bottle×2) were thawed, and centrifuged at 4° C. at 8,000 rpm for 10 minutes. The pellet was used in the test below. First, the pellet was suspended in 2 ml of a 0.1 M phosphate-potassium solution containing 1 mM PMSF (Wako Pure Chemical Industries, Ltd.), 2 mM DTT (Wako Pure Chemical Industries, Ltd.) and 5 mM sodium hydrosulfite (Wako Pure Chemical Industries, Ltd.). The suspension was supplied to two 2 ml tubes with screw caps (Assist) and pre-supplemented with 0.1 mM zirconia/silica beads (BioSpec Products, Inc.). The cells were disrupted using FastPrep® FP100A (Thermo ELECTRON CORPORATION) (6500 rpm, 10 seconds, ice cooling×8). The resulting liquid was centrifuged to obtain supernatant. The suspension of disrupted cell was centrifuged at about 10,000 rpm at 4° C. for 10 minutes to obtain a supernatant, which was then diluted to 4.5 mL with 0.1 M potassium phosphate solution containing 1 mM PMSF, 2 mM DTT and 5 mM sodium hydrosulfite. This was used as an enzyme source.

An enzyme reaction mixture of the composition below was prepared, and the mixture was incubated at 37° C. for 2 hour. After incubation, 3 mL of ethyl acetate was added to the enzyme reaction mixture for extraction. After drying, the extract was dissolved by the mobile phase (eluent). The dissolved product was analyzed by HPLC. As the standard solution for HPLC analysis, a mixed solution of daidzein (2 μg/mL; Funakoshi Corporation), equol (2 μg/mL; Funakoshi Corporation), dihydrodaidzein (2 μg/mL; Toronto Research Chemicals Inc.) was used.

| Composition of Enzyme Reaction Mixture | |
|---|---|
| Supernatant of disrupted cells (enzyme source): | 250 μl |
| Sterilized water, NADH (100 mM) or NADPH (100 mM): | 5 μl |
| Dihydrodaidzein (1 mg/ml): | 10 μl |
| 0.1M potassium phosphate buffer pH 7/1 mM DTT/5 mM sodiumhydrosulfite: | 735 μl |
| Total: | 1,000 μl |

The results are shown in FIG. 1. The results confirmed the presence of dihydrodaidzein biosynthesis activity in the centrifuged supernatant of the disrupted cell material. It was also confirmed that the conversion of daidzein into dihydrodaidzein is dependent on the coenzyme NADH.

Example A2

Purification of Dihydrodaidzein Synthesizing Enzyme

*Lactococcus* 20-92 strain cells were incubated for 18 hours in a modified GAM broth medium (Nissui Pharmaceutical Co. Ltd.), 67 ml per incubation bottle. The cultured cells from nine such bottles were centrifuged, and suspended in a 0.1 M potassium phosphate buffer (pH 7) containing 2 mM DTT (1,4-Dithiothreitol, Merck), 5 mM sodium hydrosulfite (Wako Pure Chemical Industries, Ltd.) and proteinase inhibitor (complete proteinase inhibitor cocktail EDTA-free, Roche Diagnostics). The suspension was supplied to three 2 ml tubes with screw caps (Assist) that each previously contain 0.1 mM zirconia/silica beads (BioSpec Products, Inc.). The cells were disrupted using FastPrep® FP100A (Thermo ELECTRON CORPORATION) (6500 rpm, 20 seconds×4). The resulting liquid was centrifuged to obtain supernatant. *Lactococcus* 20-92 strain cells were incubated for 18 hours in the same liquid medium, 200 ml per incubation bottle. The cultured cells from eight such bottles were centrifuged to obtain supernatant equivalent to eight bottles.

Purification was performed using a 0.1 M potassium phosphate buffer (pH 7.0) ("Buffer A", hereinafter) containing 1 mM PMSF (phenylmethylsulfonyl fluoride, Sigma Aldrich), 2 mM DTT and 5 mM sodium hydrosulfite. The disrupted supernatant of the cells were mixed with Buffer A containing the same quantity of 2 M ammonium sulfate, and placed in micro bio spin columns (×11, Bio-Red Laboratories, Inc.) filled with Butyl Sepharose 4 Fast Flow (the gel was about 0.3 ml per bottle, GE Healthcare) and equilibrated with Buffer A containing 1 M ammonium sulfate. After being washed with Buffer A containing 1 M ammonium sulfate and subsequent two-times rinsing with 0.75 ml of Buffer A containing 0.5 M ammonium sulfate, 0.75 ml and then 0.5 ml of Buffer A were added to elute a fraction having a dihydrodaidzein synthesis activity. Hereinafter, the eluate obtained by adding 0.75 ml of Buffer A is referred to as an eluate I, and the eluate obtained by adding 0.5 ml of Buffer A is referred to as an eluate II.

0.3 ml and 0.2 ml of Buffer A containing 3.4M ammonium sulfate were added to the eluate I (with 0.75 ml of Buffer A) and the eluate II (with 0.5 ml of Buffer A), respectively. Then, the two eluates were mixed to be subjected to HPLC using TSKgel Ether-5PW column (TOSOH) equilibrated with an eluent containing 1 M ammonium sulfate. 0.5 ml of the mixed solution was poured to the column 2 to 9 times, followed by washing at a flow rate of 0.1 ml/min using an eluent containing 1 M ammonium sulfate (Eluent B). Thereafter, the mixture ratio of Eluent B to Eluent A was changed using a program so that the concentration of ammonium sulfate linearly goes down to 0M (Eluent A) in 15 minutes. The enzymatic activity was seen in the elution position of about 0.6 M to 0.35M ammonium sulfate, and the total eluate was about 3.5 ml. The following shows the conditions in the HPLC. 280 nm protein absorption was observed.

Column: TSKgel Ether-5PW

Flow Rate: 0.05 to 0.1 ml/min on sample supply, 0.1 ml/min on elution

Eluent A: 0.1 M potassium phosphate buffer (pH 7.0)/2 mM DTT/2.5 mM sodium hydrosulfite/1% 2-propanol Eluent B: Eluent A containing 1M ammonium sulfate The eluate of the elution position where the enzymatic activity was seen was diluted with Buffer A, and the diluted liquid was subjected to micro bio spin column filled with 2'5' ADP Sepharose 4B (GE Healthcare; the gel was about 0.3 ml per bottle), equilibrated with Buffer A. After washing the column with Buffer A, the fraction having the dihydrodaidzein synthesis activity was eluted with 0.7 ml, and then 0.6 ml of pH 7.5 Buffer A composition liquid containing 20 mM NADPH.

The obtained eluate was subjected to HPLC using a Mono Q column (GE Healthcare) equilibrated with Eluent C (pH 7.5). Eluent C was supplied to the column at a flow rate=0.1 ml/min. After washing, the mixture ratio of Eluent C to Eluent D was changed to carry out a program for linearly turning it into 0.65 M NaCl for 32.5 minutes. The following shows the conditions in the HPLC. 280 nm protein absorption was observed.

column: Mono Q PC 1.6/5
Eluent C: 0.1 M potassium phosphate buffer pH 7.5/3 mM DTT/2.5 mM sodium hydrosulfite/1% 2-propanol
Eluent D: Eluent C containing 1M NaCl The enzymatic activity was observed in 0.4 to 0.46 M NaCl fraction (fraction No. 28 to 30).

FIG. 2 shows the result of Mono Q HPLC and the enzymatic activity. FIG. 3 shows the result of SDS-PAGE for the fractions No. 27 to 31. According to these results, a 70 kDa band was observed in the fraction having a dihydrodaidzein synthesis activity under reducing condition.

Example A3

Determination of N Terminus Amino Acid Sequence

30 μl of 0.1% trifluoroacetic acid (TFA) was added to 70 μl of fraction, No. 29 having a dihydrodaidzein synthesis activity obtained by the Mono Q HPLC (100 μl in total).

A PVDF membrane of ProSorb cartridge (Applied Biosystems Japan) was moistened with 10 μl methanol, and the foregoing mixed liquid was added. After absorbing water using a ProSorb filter (Applied Biosystems Japan), the membrane was dried, and then cut off using a membrane punch (Applied Biosystems Japan). The membrane was washed five times with 20% methanol, and dried. The membrane was subjected to N terminus amino acid sequence analysis using a protein sequencer (Applied Biosystems, Procise 494cLC), thereby finding a continuous amino acid sequence having the following 22 residues.

```
                                       (SEQ ID NO: 19)
Met Lys Asn Lys Phe Tyr Pro Lys Thr Phe Glu Arg

Gly Tyr Ile Gly Asn Leu Glu Val Glu Asn
```

Example A4

Determination of Amino Acid Sequence

The enzyme protein exhibiting a dihydrodaidzein synthesis activity was fragmented using a digest enzyme into a peptide. The internal amino acid sequence was found by analyzing the amino acid sequence in the N terminus of the peptide.

(1) Preparation of Sample

*Lactococcus* 20-92 strain cells were incubated for 18 hours in a modified GAM broth medium (Nissui Pharmaceutical Co. Ltd.), 200 ml per culture bottle. Three strains of the cultured cells were centrifuged and suspended in a 0.1 M potassium phosphate buffer (pH 7.0) containing 2 mM DTT (1,4-Dithiothreitol, Merck), 5 mM sodium hydrosulfite (Wako Pure Chemical Industries, Ltd.) and proteinase inhibitor (complete proteinase inhibitor cocktail EDTA-free, Roche Diagnostics). The suspension was then transferred to a 2 ml tube (Assist) that has a screw cap and contains 0.1 mM zirconia/silica beads (BioSpec Products, Inc.). The cells were disrupted using FastPrep® FP100A (Thermo ELECTRON CORPORATION) (6500 rpm, 20 seconds×4). The resulting liquid was centrifuged to obtain supernatant.

A 0.1 M potassium phosphate buffer (pH 7) ("Buffer A", hereinafter) containing 1 mM PMSF (phenylmethylsulfonyl fluoride, Sigma Aldrich), 2 mM DTT and 5 mM sodium hydrosulfite was used in the following process. The disrupted supernatant of the cells were mixed with Buffer A containing the equivalent quantity of 2 M ammonium sulfate, and placed in micro bio spin columns (×3, Bio-Red Laboratories, Inc.) filled with Butyl Sepharose 4 Fast Flow (the gel was about 0.3 ml per bottle, GE Healthcare), equilibrated with Buffer A containing 1 M ammonium sulfate. After being washed with Buffer A containing 1 M ammonium sulfate and subsequent two-times rinsing with 0.75 ml of Buffer A containing 0.5 M ammonium sulfate, 0.75 ml of Buffer A were added twice to elute a fraction having a dihydrodaidzein synthesis activity.

A micro bio spin column filled with 2'5'ADP Sepharose 4B was equilibrated with Buffer A, and then 1.5 ml of the solution eluted earlier was added. After five times of washing with 0.75 ml of Buffer A, elution was carried out using 0.75 ml, and then 0.45 ml of Buffer A containing 20 mM NADPH. The eluates were mixed and desalinated and concentrated to 5 μl in a micro centrifugation concentration tube (NANOSEP 10K OMEGA, Pall Life Sciences).

The concentrated solution was mixed with a double-concentrated SDS-PAGE sample buffer containing 2-mercaptoethanol; and the mixture was heated for seven minutes at 90° C. before being subjected to SDS-PAGE according to Laemmuli method. The SuperSep HG 10-20% (Wako Pure Chemical Industries, Ltd.) was used as an electrophoresis gel plate. After staining with Colloidal Blue (Invitrogen) and subsequent decoloring with Milli-Q water, a 70 kDa electrophoresis band was excised. As a control, an equimolar and equivalent-sized gel was cut out from the same portion into a strip in the no-protein electrophoresis area, and processed in the same manner. An another group of cells was processed in the same manner, and the cells were transferred to a PVDF membrane after SDS-PAGE. Then, a band in the same position was subjected to N terminus amino acid sequence analysis so as to confirm consistency with the sequence of the fraction No. 29 in the Mono Q HPLC.

(2) Generation of Reduced Carboxamidemethyl and Enzyme Digestion

The excised gels were cut into pieces, decolored using a 50% acetonitrile aqueous solution, dehydrated by acetonitrile, and dried with a centrifugal thickener (SpeedVac A160, Savant). After 100 mM ammonium hydrogencarbonate aqueous solution containing 55 mM of DTT was added, reduction was performed for an hour at 56° C. After removing a DTT solution, a 100 mM ammonium hydrogencarbonate aqueous solution containing 100 mM of iodoacetamide was added, and the mixture blocked by light was gently shaken for 30 minutes to generate carboxamidemethyl. After removing the reaction reagent, the gel was washed sequentially with a 50% acetonitrile aqueous solution, acetonitrile, a 100 mM ammonium hydrogencarbonate aqueous solution, and acetonitrile, before being dried by a centrifugal thickener. 20 mM Tris-HCL buffer (pH 9) containing 2 μg Achromobacter protease I (Wako Pure Chemical Industries, Ltd.) and 0.02% Tween 20 was added, and digestion was performed at 37° C. for seven hours. The centrifuged supernatant was transferred to another tube, and the gel was mixed with 60% acetonitrile-0.1% TFA aqueous solution and heated at 30° C. for 20 minutes. The heated mixture was boltexed for 10 minutes×three times to obtain peptide fragments. The supernatant was collected to be filtered using Ultrafree-MC (0.22 μm, Amicon), followed by centrifugal concentration.

(3) Peptide Mapping

Through reverse phase HPLC, the peptide resulted from the enzyme digestion was isolated.

Column: μRPC C2/C18 SC2.1/10 (GE Healthcare Bio Science)

Flow Rate: 0.1 ml/min

Eluent E: 0.05% TFA

Eluent F: 90% acetonitrile/0.04% TFA

Elute Program: 0 minute: 5% F 3 minutes: 5% F 43 minutes: 65% F 48 minutes: 100% F 68 minutes: 100% F Fraction: 30 μl Detection: 215 nm For example, "0 minute 5% B" denotes usage of an eluent containing Eluent E and Eluent F in an amount of 95% and 5%, respectively, at the time 0 in the elution.

(4) Internal Amino Acid Sequence Analysis

In comparison with the control chromatogram, an enzyme-protein-derived peptide peak exhibiting dihydrodaidzein synthesis activity was selected, and N terminus amino acid sequence analysis was performed using a protein sequencer (Applied Biosystems, Procise 492HT). After the separation using reverse phase HPLC was started, the elution was started at 20.6 minutes. The following shows the amino acid sequence (Peptide 1, hereinafter) of the peak of the elution.

```
                                        (SEQ ID NO: 20)
    Phe Asp Glu Pro Val Tyr Pro Gln Ala Glu
```

The following shows the amino acid sequence (Peptide 2, hereinafter) of the peak of the elution which was started at 22.1 minutes.

```
                                        (SEQ ID NO: 21)
Ala Ser Arg Met Val Met Asp Ala Val His Glu Gly

Tyr Ile Ala Gly
```

The peak of the elution which was started at 26.6 minutes was a peptide that was nonspecifically severed; however, as shown below, its N-terminus had glycine that is the 13th residue from the N terminus of said enzyme protein (the following amino acid sequence is called Peptide 3, hereinafter).

```
                                        (SEQ ID NO: 22)
Gly Tyr Ile Gly Asn Leu Glu Val Glu Asn Arg Ala

Ile Arg Met Pro Met
```

FIG. 4 shows the result of peptide mapping in Example A4, and amino acid sequences corresponding to the respective peaks.

Peak 1 (20.6 minutes)

Peak 2 (22.1 minutes)

Peak 3 (26.6 minutes)

Example A5

Amplification of Dihydrodaidzein Synthesis Enzyme Gene from N Terminus and Partial Amino Acid Sequences of Purified Polypeptide Based on the N terminus and partial amino acid sequences obtained in Examples A3 and A4, a degenerative-primer was designed and created. Using the genome DNA of *Lactococcus* 20-92 strain as a template, amplification of the gene which encodes the dihydrodaidzein synthesis enzyme was attempted by way of degenerative-PCR.

(1) Purification of Genome DNA from *Lactococcus* 20-92 Strain

*Lactococcus* 20-92 strain incubated in a 40 mL modified GAM broth culture medium (Nissui Pharmaceutical Co. Ltd.) under an anaerobic condition was centrifuged for ten minutes, at 5000 rpm, 4° C. The culture medium was removed by decantation, and the bacteria cells were collected. The cells were immediately suspended in a 11 mL of B1 solution (containing 200 μg/mL RNase) in the QIAGEN Genomic DNA Buffer Set (Qiagen), and incubated for 16 hours at 37° C. after mixed with 300 μL of Lysozyme solution (100 mg/mL), and 500 μL of QIAGEN Proteinase K solution (Qiagen). Then, after mixed with 4 mL of B2 solution and several times of end-over-end mixing, three hours incubation was performed at 50° C.

The culture was centrifuged for ten minutes at 5000 rpm, 4° C. The supernatant was poured in a QIAGEN Genomic-tip 500/G (Qiagen) column equilibrated with a QBT solution so that the genome DNA was adhered to the column. After washing the column twice with 30 mL of a QC solution, the genome DNA was eluted from the column using 15 mL of QF; then 10.5 mL of isopropanol was added to salt out the DNA. The precipitated thread-like genome DNA was placed in a 1.5 mL microtube, washed with 75% ethanol, and dried by air, before being dissolved in 250 μL of a TE solution (0.4 μg/μL). The concentration of the genome DNA solution thus obtained was measured, and the solution was then adjusted to 40 ng/μL by adding a TE solution. This DNA solution was used as a template of PCR.

(2) Design and Production of Degenerative-Primer

In the designing of degenerative-primer, to reduce the number of degeneracy, the most frequent codon in each amino acid was used for the sequence on the 5' end according to the codon usage information (Codon Usage Database http://www.kazusa.or.jp/codon/) of *Lactococcus garvieae*. Further, a mixed base was used for the sequence of 3' end to avoid mismatch with the dihydrodaidzein synthesis enzyme gene.

The following degenerative-primer was designed and created based on the N terminus sequence: MKNKFYPKTFERGYIGNLEVEN determined in Example A3, to be used for degenerative-PCR.

```
                                        (SEQ ID NO: 23)
E1-N-terminus-31: TGAAGAATAANTTNTAYCCNAARACNTTYGA
```

(In SEQ ID NO: 23, "N" in the 11th and 14th positions represent inosine, and "N" in the 20th and 26th positions represent adenine, guanine, cytosine or thymine.)

```
                                        (SEQ ID NO: 24)
E1-N-terminus-37: TGAAGAATAANTTNTAYCCNAARACNTTYGAR

RGNGG
```

(In SEQ ID NO: 24, "N" in the 11th, 14th, 20th and 26th positions represent inosine, and "N" in the 35th position represents adenine, guanine, cytosine or thymine.)

```
                                        (SEQ ID NO: 25)
E1-N-terminus-F32: ATGAAGAATAAGTTTTAYCCNAARACNTTY

GA
```

(In SEQ ID NO: 25, "N" in the 21st and 27th positions represents adenine, guanine, cytosine or thymine.)

Further, the following degenerative-primer was designed and created based on the internal sequence Peptide 2: ASRMVMDAVHEGYIAG determined in Example A4, to be used for degenerative-PCR.

```
                                        (SEQ ID NO: 26)
E1-internal-RP1: CCTGCAATATAACCTTCATGTACNGCRTCCATN

ACCAT
```

(In SEQ ID NO: 26, "N" in the 24th and 33rd positions represent adenine, guanine, cytosine or thymine.)

The all oligo DNAs used as the primers of the present Example were produced by Sigma-Aldrich Japan K.K.

(3) Amplification of Dihydrodaidzein Synthesis Enzyme Gene Through Degenerative-PCR Using the produced degenerative-primer, amplification of dihydrodaidzein synthesis enzyme gene by way of Degenerative-PCR was attempted.

The followings are the combinations of the degenerative-primers used in the degenerative-PCR.

(i) E1-N-terminus-31 and E1-internal-RP1

(ii) E1-N-terminus-37 and E1-internal-RP1

(iii) E1-N-terminus-F32 and E1-internal-RP1

In the amplification of dihydrodaidzein synthesis enzyme gene through degenerative-PCR, Ex-Tag DNA polymerase (Takara Bio Inc.) was used. The amplification program was: 95° C., 2 min (95° C., 45 sec; 38° C. to 54° C., 30 sec; 72° C., 2 min)×50 cycles, and 72° C., 3 min. In consideration of mismatch with the genome DNA of the degenerative-primer, the annealing was performed in 5 stages, beginning at 38° C., with a 4° C.-temperature increase before each additional stage, until 54° C. After the PCR reaction, 1/10 of 10× Dye was added to the PCR product. 6 μL of the product was subjected to electrophoresis using 0.8% of agarose gel. In the agarose electrophoresis in the present Example, the coloring was performed using ethidium bromide; and λ/StyI (Nippon-gene Co. Ltd.) and 100 bp ladder (Toyobo Co. Ltd.) were used as molecular weight markers.

FIG. 5 shows the result of electrophoresis of degenerative-PCR product. For the combination (E1-N-terminus-F32 and E1-internal-RP1) of the degenerative-primer (iii) in (3) of the present Example, about 1.9 kb amplification was observed in the DNA fragment in any of the annealing temperatures. The most significant increase was observed when the annealing temperature was 54° C.

(4) Determination of Base Sequence of Amplified DNA Fragment

The amplified DNA fragment of about 1.9 kb (annealing temperature=54° C.) was excised from the agarose gel, and purified using a Gel-Extraction kit (Qiagen). The purified DNA fragment was inserted to a pT7-Blue Cloning Vector (Novagen) to determine the base sequence.

The obtained DNA base sequence was assayed using DNA sequence assemble software SEQUENCHER (Gene Codes Inc, USA), with the result that the DNA fragment contained the base sequences corresponding to the amino acid sequences of Peptides 1 and 3 found in Example A4.

Example A6

Determination of Entire Base Sequence of Dihydrodaidzein Synthesis Enzyme Gene To determine the sequences of 5' end and 3' end of the 1.9 kb dihydrodaidzein synthesis enzyme gene obtained in Example A5 so as to determine the entire base sequences, rapid amplification of cDNA terminus sequence (5'-, 3'-RACE) was performed using the genome DNA library of the *Lactococcus* 20-92 strain as a template.

(1) Production of Genome DNA Library

The genome DNA of the *Lactococcus* 20-92 strain purified in Example A5 was fragmented through 16 hours digestion at 37° C., using restriction endonuclease (BamHI, EcoRI, HindIII, KpnI, PstI, SacI, SalI, Sau3AI, XhoI: products of Takara Bio Inc.). After processing with phenol/chloroform, the fragment was purified by ethanol sedimentation. The purified genome DNA fragments were ligated with pUC19 cloning vectors, which were previously excised by corresponding restriction endonuclease and dephosphorylated by Shrimp Alkaline Phosphatase (Takara Bio Inc.), using a TaKaRa Ligation kit var. 2.1 (Takara Bio Inc.), thereby producing a genome DNA library.

(2) Rapid Amplification of cDNA Terminus Sequence (5'-RACE, 3'-RACE)

The genome DNA library (ligation reaction liquid) was diluted 20-fold with sterilized water. Amplification of the sequences of 5' end and 3' end of the dihydrodaidzein synthesis enzyme gene by way of rapid amplification of cDNA terminus sequences (5'-RACE, 3'-RACE) was attempted using a 1 μL template.

(2-1) Primer

The followings are the combinations of primers used for 5'-RACE, 3'-RACE, respectively.

(2-1-1) 5'-RACE

First-PCR: E1-RACE-N-P1 and pUC19-FP-1, E1-RACE-N-P1 and pUC19-RP-1

Nested-PCR: E1-RACE-N-P2 and pUC19-FP-2, E1-RACE-N-P2 and pUC19-RP-2

(2-1-2) 3'-RACE

First-PCR: E1-RACE-RP2-1 and pUC19-FP-1, E1-RACE-RP2-1 and pUC19-RP-1

Nested-PCR: E1-RACE-RP2-2 and pUC19-FP-2, E1-RACE-RP2-2 and pUC19-RP-2

(2-1-3) Sequence of the Primer Used

The followings are the sequences of primers used for 5'-RACE, 3'-RACE, respectively.

```
Primers for Vector:
                                        (SEQ ID NO: 27)
pUC19-FP-1: ACACAGGAAACAGCTATGACCATGATTACG

                                        (SEQ ID NO: 28)
pUC9-RP-1: AGCTGGCGAAAGGGGGATGTGCTGCAAGGC

                                        (SEQ ID NO: 29)
pUC19-FP-2: ATGATTACGCCAAGCTTGCATGCCTGCAGG

                                        (SEQ ID NO: 30)
pUC19-RP-2: CCAGTCACGACGTTGTAAAACGACGGCCAG

Primers for Dihydrodaidzein synthesis enzyme gene
                                        (SEQ ID NO: 31)
E1-RACE-N-P1: ATGCGGATCGCTCGGTTCTCGACCTCTAGGTTAC
```

-continued

```
                                          (SEQ ID NO: 32)
E1-RACE-RP2-1: ATCGAGGAGAAGTGCGAGGACGTCAGGGTCATC

                                          (SEQ ID NO: 33)
E1-RACE-N-P2: TTCTCGACCTCTAGGTTACCGATGTAGCCGC

                                          (SEQ ID NO: 34)
E1-RACE-RP2-2: ACGTCAGGGTCATCGGCATCGGCGACTGCAAG
```

The all oligo DNAs used as the primers in the present Example were produced by Sigma-Aldrich Japan K.K.

(2-2) Amplification of the Sequences of 5' End and 3' End of the Dihydrodaidzein Synthesis Enzyme Gene Using 5'-RACE and 3'-RACE Ex-Taq DNA polymerase (Takara Bio Inc.) was used for 5'-RACE, 3'-RACE. First-PCR and Nested-PCR were performed using the same amplification program: 95° C. 2 min, (95° C. 45 sec, 60° C. 30 sec, 72° C. 1 min)×30 cycles, 72° C. 3 min. In First-PCR, 1 μL (40 ng) of the genome DNA dilution liquid prepared in the aforementioned manner was used as a template. In Nested-PCR, 0.5 μL of First-PCR product was used.

After the Nested-PCR reaction, 1/10 of 10× day was added to the PCR product, and 5 μL of the mixture was subjected to electrophoresis with 0.8% agarose gel. The observed amplification of the DNA fragment was about 1.2 kb (SacI) and about 1.0 kb (Sau3AI) in 5'-RACE, and about 0.6 kb (SacI) and 0.3 kb (KpnI) in 3'-RACE.

In the agarose electrophoresis in the present Example, the coloring was performed using ethidium bromide (Nippongene Co. Ltd.); and λ/StyI (Nippongene Co. Ltd.) and 100 bp ladder (Toyobo Co. Ltd.) were used as molecular weight markers.

The amplified DNA fragments were excised from the agarose gel, and purified using a Gel-Extraction kit (Qiagen). The base sequences of the purified DNA fragments were determined by the direct sequence using the primers used for the amplification, with the result that the sequence of dihydrodaidzein synthesis enzyme gene was observed in those DNA fragments of about 1.2 kb (SacI) and about 1.0 kb (Sau3AI) in 5'-RACE, and that of about 0.6 kb (SacI) in 3'-RACE.

(3) Determination of Entire Base Sequence of Dihydrodaidzein Synthesis Enzyme Gene The DNA base sequence obtained by the degenerative-PCR in Example A5 and the rapid amplification of the cDNA terminus sequence in (2) of the present Example was subjected to assemble assay using DNA sequence assemble software SEQUENCHER (Gene Codes Inc, USA). As a result, the genome structure of 3548 bp in the vicinity of the dihydrodaidzein synthesis enzyme gene was found. This revealed that the dihydrodaidzein synthesis enzyme gene was a polypeptide consisting of 1935 nucleotides and 644 amino acids.

The entire amino acid sequences found by the base sequences, and the partial amino acid sequences found by the amino-acid sequence were collated, with the result that the all partial amino acid sequences found by the amino-acid sequence attributed to the entire amino acid sequences found by the base sequences.

(4) Confirmation of base Sequence in the Coating Region

In the sequence obtained in (3) of the present Example, many portions were observed with the clones having inconsistent bases caused by incorporation error of the bases of DNA polymerase upon PCR amplification. Therefore, using the first strand cDNA as a template, the region (2368 bp) containing the coding region of the dihydrodaidzein synthesis enzyme gene was amplified through PCR using Easy-A®High-Fidelity PCR Cloning Enzyme (Stratagene), that is High-Fidelity DNA-Polymerase.

The followings are the amplification primers used above.

```
                                          (SEQ ID NO: 35)
E1-conf-NP: TGCCGGTGCAATGGCTGACATCATGTTCAACCTG

                                          (SEQ ID NO: 36)
E1-conf-CP: TCCTCCATCGTTCCTCCAATCAGTAAGACACGCG
```

The obtained DNA fragment was purified using a Gel-Extraction kit (Qiagen), and the confirmation and final determination of the sequence was done using direct sequence.

Example A7

Induction of Expression of Dihydrodaidzein Synthesis Enzyme Gene by Adding Daidzein to Amplification Culture Solution As shown in Example A1, when daidzein, that is a substrate, is added to the amplification culture solution of *Lactococcus* 20-92 strain, the cultured cells exhibit a dihydrodaidzein synthesis activity. This leads to an assumption that the addition of daidzein to the amplification culture solution induces transcription of dihydrodaidzein synthesis enzyme gene, and further induces translation into protein. The following test was performed based on this assumption. Two samples of *Lactococcus* 20-92 strain-derived cDNA were incubated in a culture medium containing daidzein and in a culture medium with no daidzein; they were subjected to RT-PCR so as to find out whether the expression of dihydrodaidzein synthesis enzyme gene was induced by the daidzein addition into the amplification culture solution.

(1) Extraction of Entire DNA from *Lactococcus* 20-92 Strain and Purification of the DNA Extraction of the entire DNA from *Lactococcus* 20-92 strain, and purification were carried out in the following manner.

Sealed *Lactococcus* 20-92 strain kept at 4° C. was incubated for eight hours in a modified GAM broth culture medium, that contains 10 mg/L daidzein (Funakoshi Co., Ltd.) or no daidzein, at 37° C. under an anaerobic condition. 25 mL of the culture solution was transferred to a 50 mL tube, and centrifuged for ten minutes at 3500 rpm, 4° C. The culture medium was removed by decantation and cells were collected. The collected cells were immediately frozen by liquid nitrogen. Then, the entire RNA was extracted and purified using 1 mL of TRIzol solution (Invitrogen) according to the instruction. The purified entire RNA was processed by DNase I (Invitrogen) to remove the genome DNA, and used for synthesis of first-strand cDNA.

(2) Synthesis of First-Strand cDNA from the Entire RNA

From 2 μg of the entire RNA thus processed by DNaseI, the first-strand cDNA (reverse transcription) was synthesized using Superscript® First-Strand Synthesis System for RT-PCR (Invitrogen). The synthesis of the first-strand cDNA was carried out using Random Hexamer mix as an extension primer according to the instruction. Further, to confirm that the entire RNA processed by DNase I used for the first-strand cDNA synthesis did not contain genome DNA, another reaction was performed at the same time without reverse transcription. The final reaction liquid was used as a template for RT-PCR.

The followings are the four kinds of final reaction liquids thus prepared.

1. Reverse transcription product of the entire RNA derived from bacteria cells incubated in a medium containing daidzein (DZN(+)RT(+))
2. Reverse transcription product of the entire RNA derived from bacteria cells incubated in a medium with no daidzein (DZN(−)RT(+))
3. Non-reverse transcription product of the entire RNA derived from bacteria cells incubated in a medium containing daidzein (DZN(+)RT(−))
4. Non-reverse transcription product of the entire RNA derived from bacteria cells incubated in a medium with no daidzein (DZN(−)RT(−))

(3) Confirmation of Expression of Dihydrodaidzein Synthesis Enzyme Gene Using RT-PCR The dihydrodaidzein synthesis enzyme gene was amplified through RT-PCR using the four final reaction products as detailed in (2) of the present Example as templates. The expression amounts were compared with each other. As a control, another RT-PCR was performed at the same time using the 16S-ribosome RNA sequence as a control gene.

The followings are amplification conditions in RT-PCR and a primer sequence for each gene amplification. Ex-Taq DNA polymerase (Takara Bio Inc.) was used for RT-PCR. The amplification program was: 95° C. 2 min, (95° C. 30 sec, 56° C. 20 sec, 72° C. 30 sec)×30 cycles, 72° C. 2 min. As a template, 1 μL of each final reaction liquid as in (2) of the present Example was used.

The following shows a primer sequence used for the RT-PCR of the present Example and the size of DNA fragment to be amplified.

```
dihydrodaidzein synthesis enzyme: 239bp
                                        (SEQ ID NO: 37)
E1-FP: CTACATCGGTAACCTAGAGGTCG

                                        (SEQ ID NO: 38)
E1-RP: CCGTGCTGCTTGATGGTCTTTGC

16S-ribosome RNA sequence: 326bp
                                        (SEQ ID NO: 39)
Gar-16S-Ribo-FP: TGCGTAGATATATGGAGGAAC

                                        (SEQ ID NO: 40)
Gar-16S-Ribo-RP: CTTATCTCTAAGGATAGCACG
```

The primer used for the amplification of 16S-ribosome RNA sequence was created based on the sequence of *Lactococcus* garvieae strain FLG12 16S ribosomal RNA gene, partial sequence (Accesion No. AF352163-66) in the DNA database (GenBank) provided by National Center of Biotechnology Information: http://www.ncbi.nlm.nih.gov/

1/10 of 10× day was added to the PCR product, and 5 μL of the mixture was subjected to electrophoresis with 1.5% agarose gel. The amplification of each DNA fragment was observed.

In the agarose electrophoresis in the present Example, the coloring was performed using ethidium bromide (Nippongene Co. Ltd.); and λ/StyI (Nippongene Co. Ltd.) and 100 bp ladder (Toyobo Co. Ltd.) were used as molecular weight markers.

FIG. 6 shows the results.

As evident from the result of the amplification of dihydrodaidzein synthesis enzyme gene through RT-PCR, efficient expression of gene was observed only in the reverse transcription product of the entire RNA derived from bacteria cells incubated in a medium with daidzein. The same level of expression was observed in the amplification of 16S-ribosome RNA sequence used as a control, regardless of incorporation of daidzein. Further, since both the dihydrodaidzein synthesis enzyme gene and the 16S-ribosome RNA sequence were not amplified in the non-reverse transcription product, it was confirmed that the entire RNA processed by DNase I used for the synthesis of first-strand cDNA did not contain genome DNA. These results showed that the addition of daidzein to the medium induced the expression of mRNA of dihydrodaidzein synthesis enzyme gene.

Example A8

Expression of Recombinant E1 Polypeptide Using *Escherichia coli*, and Confirmation of Dihydrodaidzein Synthesis Activity The pET system, a recombinant protein expression system using *Escherichia coli*, was used to express E1 polypeptide, and its dihydrodaidzein synthesis activity was confirmed.

(1) Preparation of E1 Polypeptide Expression Vector

To prepare an E1 polypeptide expression vector (pET21-E1-His), the DNA in the open reading frame region of E1 nucleotide was amplified by PCR.

The following amplification primers were prepared based on the E1 nucleotide sequence determined in Example A6.

```
                                        (SEQ ID NO: 41)
exp.E1 pet F Nde: AGCTCATATGAAGAACAAGTTCTATCCGAA

                                        (SEQ ID NO: 42)
exp.E1 pet His: AATCGAATTCCTACAGGTTGCAGCCAGCGATGT
```

For insertion into pET21a (Novagen), the amplification primers exp.E1 pet F Nde and exp.E1 pet His were designed to include NdeI and EcoRI restriction sequences, respectively.

A PCR reaction was performed using 25 μL of a reaction mixture containing the primers, 5 pmol each; dNTP, 5 nmol each; genomic DNA of *Lactococcus* 20-92 strain purified in Example A5, 40 ng; 10× buffer for KOD-plus DNA polymerase (Toyobo Co., Ltd.), 2.5 μL; KOD-Plus DNA polymerase, 0.3 U (Toyobo Co., Ltd.). Amplification program: 95° C. for 3 min, (94° C. for 30 sec, 60° C. for 30 sec, 68° C. for 2 min)×30 cycles, 68° C. for 7 min. PCR device: GeneAmpPCR System 9700 (Applied Biosystems). Analyzing a part of the PCR reaction mixture by agarose gel electrophoresis detected a band of an expected size. The entire PCR product was collected by a QIAGEN PCR Purification kit (Qiagen).

The DNA fragments so collected were cut with restriction enzymes NdeI and EcoRI, and subjected to agarose gel electrophoresis. Then, a portion containing the target band was excised, and purified and collected with a Qiagen Gel Extraction kit (Qiagen). After collection, the DNA fragments were ligated at 16° C. overnight with pET21a digested with NdeI and EcoRI, using a DNA Ligation Kit ver.2.1 (Takara Bio Inc.). The ligated reaction mixture was then used to transform *Escherichia coli* JM109 strain (Takara Bio Inc.).

The transformant was cultivated at 37° C. overnight on a LB medium agar (GIBCO) plate containing ampicillin (50 μg/mL). The resulting single colonies were cultured overnight in a 3 mL LB medium (GIBCO) containing ampicillin (50 μg/mL). Then, plasmid DNA was extracted using a plasmid auto extractor PI-100 (KURABO).

The base sequence of the inserted DNA in the plasmid was sequenced by the dye terminator method. This confirmed the successful insertion of E1 polynucleotide, as intended. Thus, pET21-E1-His was obtained. In this example, the DNA sequence was determined using DNA sequencer ABI3700 (Applied Biosystems).

(2) Preparation of Recombinant, and Expression and Confirmation of Recombinant E1 Polypeptide in *Escherichia coli*

Recombinant E1 polypeptide-expressing plasmid pET21-E1-His and plasmid pET21a (negative control) were used to transform *Escherichia coli* BL21 (DE3) strain (Novagen). To obtain single colonies, the transformants were cultivated overnight at 37° C. on a LB medium agar plate containing ampicillin (50 μg/mL).

Each *E. coli* BL21 (DE3) transformant was cultured overnight at 37° C. in a 3 mL liquid LB medium containing ampicillin (50 μg/mL). Then, 0.5 mL of the culture was pre-cultured for 3 hours (until OD at 630 nm became about 0.4) by adding 50 mL of liquid LB medium containing the same concentration of ampicillin. After adjusting the final concentration to 1 mM by adding IPTG (isopropyl-β-thiogalactopyranoside; Wako Pure Chemical Industries, Ltd.), the culture was further incubated at 37° C. for 4 hours.

After incubation, the cells were collected by centrifugation (6,000 rpm, 4° C., 15 min) using an Avanti HP25 (Beckman Coulter). The subsequent procedures were performed on ice. After removing the supernatant (the medium), the cells were suspended in 1 mL of 0.1 M potassium phosphate buffer (pH 7.0; KPB-PDH) containing 1 mM PMSF, 2 mM DTT, and 5 mM sodium hydrosulfite. The cell suspension was then placed in a 2 mL assist tube charged with 0.7 mL zirconia-silica beads (BioSpec Products, Inc.) and 400 μL KPB-PDH. The cells were then disrupted by two repeated cycles of a 20-second, 6,500 rpm treatment and 3-minute ice-cooling, using a FastPrep® (Thermo Electron Corporation). As a result, a suspension of disrupted cells was obtained.

The expression of recombinant E1 polypeptide in *E. coli* was confirmed by SDS-polyacrylamide-gel electrophoresis (SDS-PAGE).

2.5 μL of 5× sample buffer. (125 mM Tris-HCl (pH 6.5)/25% glycerol/5% SDS/5% 2-mercaptoethanol/BPB 0.5%) was added to 10 μL of the disrupted cell suspension. After heat-denaturing at 98° C. for 5 minutes, the suspension was ice-cooled, and 5 μL was electrophorased by SDS-PAGE. SDS-PAGE was performed with a commercially available gel plate (SuperSep® 5-20%; Wako Pure Chemical Industries, Ltd.), and Quick CBB (Wako Pure Chemical Industries, Ltd.) for staining. Prestained XL-Ladder Broad range (Apro Science) was used as a molecular weight marker.

The results of SDS-PAGE are shown in FIG. 7. A recombinant E1 polypeptide with a molecular weight of about 70 kDa was confirmed in the disrupted cell suspension derived from pET21-E1-His transformant.

(3) Confirmation of Dihydrodaidzein Synthesis Activity of E1 Polypeptide Obtained from Recombinant The disrupted cell suspension obtained in (2) of this Example was used as an enzyme source to measure the conversion activity from daidzein to dihydrodaidzein. As a result, the activity was confirmed in the expressed recombinant E1 polypeptide.

In this example, the measurement of conversion activity from daidzein to dihydrodaidzein was performed as follows.

An enzyme reaction mixture of the composition below was prepared, and the mixture was incubated at 37° C. for 2. hours.

| Composition of Enzyme Reaction Mixture | |
|---|---|
| Disrupted cell suspension (enzyme source): | 100 μl |
| NADH (100 mM): | 20 μl |
| NADPH (100 mM): | 20 μl |
| Daidzein (2 mg/ml): | 5 μl |
| KPB-PDH: | 855 μl |
| Total: | 1,000 μl |

After incubation, 3 mL of ethyl acetate was added to the enzyme reaction mixture for extraction. After drying, the extract was dissolved by the mobile phase (eluent). The dissolved product was analyzed by HPLC to measure the contents of daidzein and dihydrodaidzein in the enzyme reaction mixture.

The results of HPLC analysis are shown in FIG. 8. In the disrupted cell suspension derived from plasmid pET21-E1-His transformant expressing the recombinant E1 polypeptide, the daidzein (substrate) added to the enzyme reaction mixture was converted to dihydrodaidzein whereas dihydrodaidzein was not detected in the enzyme reaction mixture in pET21a transformant (negative control).

These results show that recombinant E1 polypeptide has the activity to synthesize dihydrodaidzein from daidzein.

Example B

Reference Example B1

Synthesis of Cis-tetrahydrodaidzein and Trans-Tetrahydrodaidzein

Cis-tetrahydrodaidzein and trans-tetrahydrodaidzein were produced according to the reaction flow below. The compounds are designated as follows.

Compound 1 (daidzein): 4',7-dihydroxy isoflavone

Compound 2: 4',7-diacetoxy isoflavone

Compound 3: 4',7-diacetoxy isoflavan-4-one

Compound 4: cis-4',7-diacetoxy isoflavan-4-ol

Compound 5: trans-4',7-diacetoxy isoflavan-4-ol

Compound 6: cis-tetrahydrodaidzein

Compound 7: trans-tetrahydrodaidzein

Formula 1

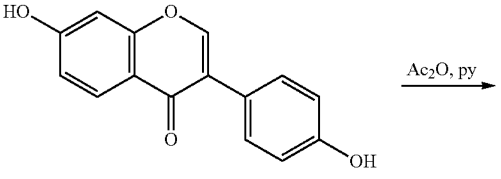

daidzein
(1)

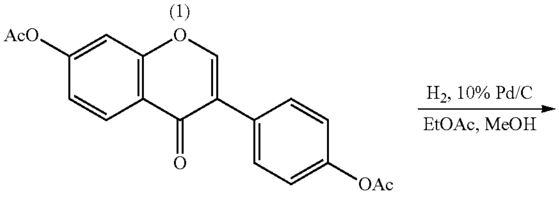

2

-continued

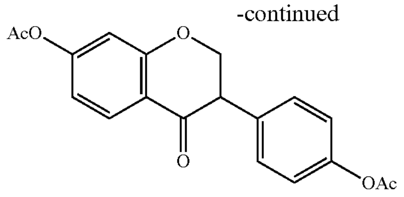

NaBH4

MeOH, CH2Cl2

3

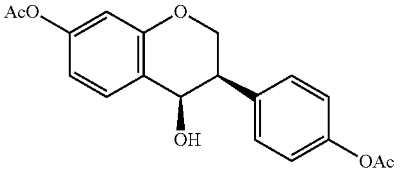

+

4

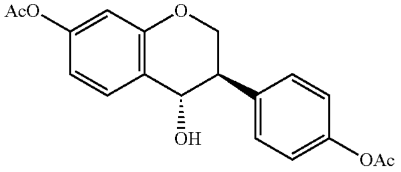

5

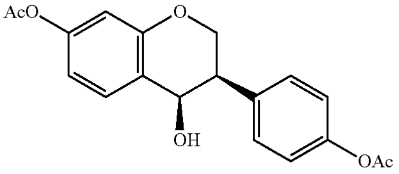

NaOMe

MeOH

4

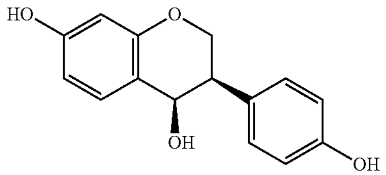

6

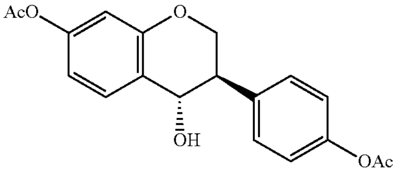

1N NaOH

MeOH

5

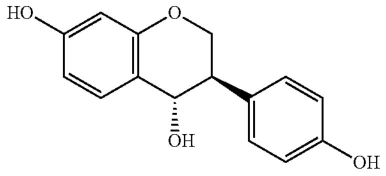

7

Synthesis of Compound 2

0.76 mL (8.0 mmol) of acetic anhydride was added to a pyridine (5 mL) solution containing 500 mg (1.97 mmol) of daidzein (Compound 1), and the mixture was stirred at 60° C. for 2 hours. After adding a minute amount of methanol, the reaction mixture was transferred into 3 N hydrochloric acid. After dilution with water, the resulting solid precipitate was filtered out and rinsed with water. The solid was then air-dried at room temperature to obtain 609 mg of a white, powdery Compound 2 (1.80 mmol, 91% yield).

Compound 2: $^1$H NMR (250 MHz, $CDCl_3$) δ (ppm): 2.33 (3H, s), 2.37 (3H, s), 7.13-7.22 (3H, m), 7.32 (1H, d, J=2.3 Hz), 7.54-7.63 (2H, m), 8.01 (1H, s), 8.33 (1H, d, J=8.8 Hz).

Synthesis of Compound 3

A methanol (6 mL)-ethyl acetate (6 mL) suspension containing 400 mg (1.18 mmol) of Compound 2 and 150 mg of 10% palladium-carbon (hydrous, about 50 wt %) was stirred at room temperature for 2 hours under a hydrogen atmosphere. The reaction mixture was filtered with Celite, and the residues were washed with ethyl acetate. The residues obtained by concentrating the filtrate were purified by silica gel column chromatography (silica gel:dichloromethane/ethyl acetate=100/0-19/1) to obtain 312 mg of a white, powdery Compound 3 (0.917 mmol, 78% yield).

Compound 3: $^1$H NMR (250 MHz, $CDCl_3$) δ (ppm): 2.29 (3H, s), 2.32 (3H, s), 3.93-4.04 (1H, m), 4.60-4.75 (2H, m), 6.76-6.84 (2H, m), 7.04-7.13 (2H, m), 7.27-7.35 (2H, m), 7.93-8.01 (1H, m).

Synthesis of Compound 4 and Compound 5

11 mg (0.29 mmol) of sodium borohydride was added to a methanol (1 mL)-dichloromethane (1 mL) solution containing 100 mg (0.294 mmol) of Compound 3 at 0° C. After stirring the reaction mixture at 0° C. for 30 minutes, 2 mL of 1 N hydrochloric acid and 50 mL of water were successively added, followed by extraction with ethyl acetate. The organic layer was successively washed with saturated sodium bicarbonate water and saturated brine, followed by drying with anhydrous sodium sulfate. The solvent was distilled away, and the resulting residues were purified by silica gel column chromatography (silica gel:dichloromethane/ethyl acetate=19/1-3/1). The resulting diastereomer mixture was purified by medium-pressure column chromatography (Yamazen, Ultra Pack SI-40B: n-hexane/ethyl acetate=3/2) to obtain 44 mg of a colorless, acicular Compound 4 (0.13 mmol, 44% yield), and 26 mg of a colorless, acicular Compound 5 (75 mmol), 26% yield).

Compound 4: $^1$H NMR (250 MHz, $CDCl_3$) δ (ppm): 1.80 (1H, d, J=4.0 Hz), 2.30 (3H, s), 2.31 (3H, s), 3.32 (1H, td, J=3.5, 11.5 Hz), 4.32 (1H, ddd, J=1.3, 3.5, 10.5 Hz), 4.59 (1H, dd, J=10.5, 11.5 Hz), 4.76-4.83 (1H, m), 6.64-6.73 (2H, m), 7.06-7.14 (2H, m), 7.27-7.35 (3H, m).

Compound 5: $^1$H NMR (250 MHz, $CDCl_3$) δ (ppm): 2.02 (1H, d, J=5.5 Hz), 2.29 (3H, s), 2.30 (3H, s), 3.11-3.24 (1H, m), 4.26 (1H, dd, J=9.0, 11.3 Hz), 4.37 (1H, dd, J=3.8, 11.3 Hz), 4.92 (1H, dd, J=5.5, 7.8 Hz), 6.62 (1H, d, J=2.3 Hz), 6.72 (1H, dd, J=2.3, 8.5 Hz), 7.04-7.12 (2H, m), 7.21-7.30 (2H, m), 7.47 (1H, d, J=8.5 Hz).

Synthesis of Compound 6

55 mg (1.0 mmol) of sodium methoxide was added to a methanol (4 mL) solution containing 116 mg (0.339 mmol) of Compound 4, and the mixture was stirred at room temperature for 2 hours. The reaction mixture was neutralized by adding an ion-exchange resin (DOWEX 50×8 W, ammonium form). After filtering out the resin, the solid obtained by concentrating the filtrate was washed with methanol to obtain 62 mg of a white, powdery compound 6 (0.24 mmol, 71% yield).

Compound 6: $^1$H NMR (250 MHz, DMSO-$d_6$) δ (ppm): 3.03 (1H, td, J=3.3, 12.0 Hz), 4.00-4.15 (1H, m), 4.31-4.51 (2H, m, including 4.39, dd, J=10.3, 12.0 Hz), 4.96 (1H, d, J=5.8 Hz), 6.18 (1H, d, J=2.3 Hz), 6.32 (1H, dd, J=2.3, 8.3 Hz), 6.69 (2H, d, J=8.5 Hz), 7.00 (1H, d, J=8.3 Hz), 7.09 (2H, d, J=8.5 Hz), 9.19 (1H, br s), 9.31 (1H, br s).

Synthesis of Compound 7

0.73 mL (0.73 mmol) of 1 N sodium hydroxide was added to a methanol (2 mL) suspension containing 84 mg (0.25 mmol) of Compound 5, and the mixture was stirred at room temperature for 2.5 hours. Then, saturated ammonium chloride water was added to the reaction mixture, followed by extraction with ethyl acetate. The organic layer was successively washed with saturated sodium bicarbonate water and saturated saline, followed by drying with anhydrous sodium sulfate. By distilling away the solvent, 64 mg of a white, powdery Compound 7 (0.25 mmol, quantitative yield) was obtained.

Compound 7: $^1$H NMR (250 MHz, DMSO-$d_6$) δ (ppm): 2.82-2.96 (1H, m), 4.04-4.22 (2H, m), 4.60 (1H, t, J=7.0 Hz), 5.18 (1H, d, J=7.0 Hz), 6.14 (1H, d, J=2.3 Hz), 6.34 (1H, dd, J=2.3, 8.5 Hz), 6.67 (2H, d, J=8.5 Hz), 7.04 (2H, d, J=8.5 Hz), 7.16 (1H, d, J=8.5 Hz), 9.21 (1H, s), 9.28 (1H, s).

Reference Example B2

A *Lactococcus* 20-92 strain (FERM BP-10036) was inoculated in a daidzein-containing amplification liquid medium, and the culture was incubated at 37° C. for 7 to 24 hours under anaerobic conditions. After incubation, the cells were collected and cryogenically preserved to be used in the Examples below.

Example B1

Confirmation of Tetrahydrodaidzein Production

The following experiments were conducted to confirm that tetrahydrodaidzein is the intermediate of equol biosynthesis.

(1) Preparation of Disrupted Cell Material

The *Lactococcus* 20-92 strain cells preserved at −80° C. were quickly thawed. The cells were suspended by tapping, and centrifuged at 4° C. (8,000 rpm×5 min) using a centrifuge VC-960 (Taitec). After removing the supernatant, 0.1 M potassium phosphate buffer/1 mM PMSF (phenylmethanesulfonyl fluoride)/2 mM DTT (dithiothreitol)/5 mM sodium hydrosulfite (pH 7.0) were added to obtain a cell suspension. The cell suspension was placed in a 2 ml tube prepared to include zirconia-silica beads (about 0.8 mL, 0.1 mm, 1 lb; Wakenyaku Co., Ltd.), and the tube was charged with 0.1 M potassium phosphate solution/1 mM PMSF/2 mM DTT/5 mM sodium hydrosulfite (pH 7.0) to fill the tube almost completely. For disruption, the tube was closed and kept on ice, where a cycle of 6,500 rpm×20 sec centrifugation and ice-cooling was repeated four times using FastPrep®-FP100A (Thermo Electron Corporation). The resulting disrupted cell material was used as an enzyme source in an enzyme reaction.

(2) Enzyme Reaction

A 1 mL enzyme reaction mixture of the composition below, containing 0.1 ml of the disrupted cell material obtained in (1) was prepared, and the mixture was incubated at 37° C. for 2 hours. After incubation, 3 mL of ethyl acetate was added to the resulting enzyme reaction product for extraction. The product was dried to prepare a sample for HPLC analysis.

Composition of Enzyme Reaction Mixture 0.1 M potassium phosphate buffer/1 mM PMSF/2 mM DTT/5 mM sodium hydrosulfite (pH 7.0)

2 mM NADPH 2 mM NADH

10 μg/mL dihydrodaidzein or tetrahydrodaidzein (3) Production of Tetrahydrodaidzein from Dihydrodaidzein by Enzyme Reaction FIG. 9 shows the results of HPLC analysis of the enzyme reaction product obtained by using dihydrodaidzein as a substrate and the disrupted cell material as an enzyme source. FIG. 9 also shows the results of HPLC analysis of the tetrahydrodaidzein synthesized in Reference Example B1. The results show that the enzyme reaction product obtained by using dihydrodaidzein as a substrate and the disrupted cell material as an enzyme source includes an intermediate having a retention time corresponding to the retention time of trans-tetrahydrodaidzein, confirming the production of trans-tetrahydrodaidzein.

(4) Production of Equol from Tetrahydrodaidzein by Enzyme Reaction

FIG. 10 shows the results of HPLC analysis of the enzyme reaction product obtained by using cis-tetrahydrodaidzein or trans-tetrahydrodaidzein as a substrate and the disrupted cell material as an enzyme source. As is clear from FIG. 10, equol was produced from both compounds, showing that the tetrahydrodaidzein is used as a substrate in equol biosynthesis, both in cis and trans forms.

Example B2

Confirmation of Tetrahydrodaidzein Biosynthesis Activity in Centrifuged Supernatant of Disrupted Cell Material, and Confirmation of NADH or NADPH Dependency The frozen cells were thawed and centrifuged at 4° C. for 15 minutes (5,000× G). The pellet was used in the test below. First, the pellet (wet weight 2.7 g) was suspended in 10 ml of a 0.1 M phosphate-potassium solution containing 1 mM PMSF and 5 mM sodium hydrosulfite. After preheating at 37° C. for 5 minutes, lysozyme was added in an amount of 100 mg per gram of the pellet (wet weight) to cause a reaction at 37° C. for 1.5 hours. Then, an equivalent amount of 0.1 M dipotassium phosphate solution was added to the reaction mixture, and the mixture was vigorously agitated with a vortex mixer after adding zirconia-silica beads (3 ml). The cells were then disrupted with a sonicator (Branson Sonifier Cell Disruptor 200) (3 cycles of a 5-minute sonication and a 2-minute rest). The disrupted cell suspension was centrifuged at about 10,000× G for 15 minutes to obtain a supernatant, which was then used as an enzyme source.

An enzyme reaction mixture of the composition below was prepared, and was incubated at 37° C. for 2 hours. After incubation, 5 mL of ethyl acetate was added to the enzyme reaction product for extraction. Then, the product was dried to prepare a sample for HPLC analysis.

| Composition of Enzyme Reaction Mixture | |
|---|---|
| Centrifuged supernatant of disrupted cells (enzyme source): | 250 μl |
| NADH (100 mM) or NADPH (100 mM): | 20 μl |
| Dihydrodaidzein (1 mg/ml): | 10 μl |
| 0.1M potassium phosphate buffer pH 7/1 mM DTT/5 mM sodiumhydrosulfite: | 720 μl |
| Total: | 1,000 μl |

The results are shown in FIG. 11. The results confirmed the presence of tetrahydrodaidzein biosynthesis activity in the centrifuged supernatant of the disrupted cell material. It was also confirmed that the conversion of dihydrodaidzein into tetrahydrodaidzein is dependent on the coenzyme NADH, and much more strongly on NADPH.

Example B3

Purification of Tetrahydrodaidzein Synthesizing Enzyme

*Lactococcus* 20-92 strain cells were incubated for 20 hours in 67 ml of a daidzein-containing amplification liquid medium contained in an incubation bottle. The cultured cells from ten such bottles were centrifuged and suspended in a 0.02 M potassium phosphate buffer (pH 7; hereinafter “Buffer A”) containing 1 mM PMSF (phenylmethylsulfonyl fluoride) and 4 mM DTT (dithiothreitol). The cells were disrupted with a French press (SLM Instruments Inc.) six times at 1,800 psi, and the disrupted cell suspension was centrifuged to obtain a supernatant. Separately, *Lactococcus* 20-92 strain cells were incubated for 18 hours in 200 ml of a liquid medium contained in an incubation bottle. The cultured cells from five such bottles were similarly disrupted with a French press, and a supernatant was obtained after centrifugation. These supernatants, 38 ml and 47 ml, were mixed, and 82 ml of the mixture was fed to red-sepharose (about 7 ml) equilibrated with Buffer A. After washing the red-sepharose with 150 ml of Buffer A, the mixture was eluted with Buffer A containing 10 mM NADPH (20 ml/fraction). Each fraction was used as an enzyme source, and the tetrahydrodaidzein biosynthesis activity was measured under the same conditions as the enzyme reaction conditions of Example B2 (using NADPH as a coenzyme). As a result, active fractions No: 1 to 5 were obtained.

Fractions No: 1 to 5 having tetrahydrodaidzein biosynthesis activity were concentrated by ultrafiltration using Amicon Ultra Centrifugal UFC801024 (MW Cut: 10,000) to obtain a concentrate (about 2.1 ml). The concentrate was separated into three portions and fed to HPLC using TSKgel Phenyl-5PW (Tosoh) after mixing each portion with an equivalent amount of Buffer A containing 3 M ammonium sulfate. HPLC conditions are as follows. The protein was assayed by measuring absorbance at 280 nm.

| | | |
|---|---|---|
| Column: | TSKgel Phenyl-5PW | |
| Flow rate: | 1 ml/min | |
| Fraction: | 2 ml/2 min/fraction | |
| Eluent A: | 0.02M potassium phosphate buffer pH 7/1 mM DTT/2.5 mM sodiumhydrosulfite/0.5% isoPrOH | |
| Eluent B: | Eluent A containing 1M ammonium sulfate | |
| | time (min) | (eluent B)/(eluent A + eluent B) |
| Elution program: | 0 | 1 |
| | 5 | 1 |
| | 25 | 0 |
| | 45 | 0 |

The results of HPLC revealed that the tetrahydrodaidzein synthesis activity is present over a wide range of fractions (fraction No: 15 and subsequent fractions, a retention time of 30 minutes and longer). Given this result, HPLC fraction Nos: 19 to 22 were mixed and concentrated by ultrafiltration (Amicon Ultra Centrifugal UFC801024; MW Cut: 10,000). From about 130 μl of the concentrate, 100 μl was fed to gel filtration HPLC using TSKgel G2000SWXL (Tosoh), under the following conditions.

Column: TSKgel G2000SWXL

Flow rate: 0.6 ml/min

Fraction: 1.2 ml/2 min/fraction

Eluent: 0.05 M potassium phosphate buffer pH 7/1 mM DTT/2.5 mM sodium hydrosulfite/1% isoPrOH/0.3 M NaCl FIG. 12 shows the results of gel filtration HPLC. FIG. 13 shows the results of SDS-PAGE of each fraction performed under reduced conditions. The results showed 28 kDa and 32 kDa bands under reduced conditions in fraction No: 7, a main fraction of tetrahydrodaidzein synthesis activity.

Example B4

Analysis of Amino Acid Sequence of Tetrahydrodaidzein Synthesizing Enzyme

The fraction (fraction No. 7) having tetrahydrodaidzein synthesis activity obtained in Example B3 was used as a sample for MS analysis. More specifically, the sample was separated by SDS-PAGE, and the bands were excised. The excised bands were reduced by alkylation within the gel, and digested with trypsin in the gel. The trypsin-digested peptides were collected and purified for analysis by LC-MS. The data acquired by LC-MS analysis were analyzed by de novo sequencing using the MS analysis support software PEAKS® (Infocom) to calculate and estimate the amino acid sequences of the peptides. Specifically, this was performed according to the procedures below.

(1) Experiment Materials

The experiment used the following materials:

SuperSep HG 10/20% (Wako Pure Chemical Industries, Ltd.); Flamingo Gel staining kit (Bio-Rad); TCEP (Tris[2-carboxyethyl]phosphine) (Pierce); molecular weight marker (Apro Science); DTT (Calbiochem); iodoacetamide (Wako Pure Chemical Industries, Ltd.); acetonitrile (Kanto Kagaku); trypsin (Promega); TFA (Pierce); ammonium bicarbonate (Sigma); ammonium water (Merck); formic acid (Kanto Kagaku); Empore Cation-SR Disk (Sumitomo 3M); MonoCap concentration column (GL Science); MonoCap for Nano Flow 0.1×150 mm (GL Science); FortisTip (AMR); SpeedVac Concentrator (SAVANT); HTS-PAL autosampler (CTC-Analytics); Chorus 220 (CTC-Analytics); QSTAR Pulsar i (Applied Biosystems); and PEAKS® software (Infocom).

(2) SDS-Polyacrylamide Gel Electrophoresis

1 μl of 100 mM TCEP was added to 20 μl of the fraction (fraction No. 7) having tetrahydrodaidzein synthesis activity obtained in Example B3. After reduction at 70° C. for 10 minutes, the entire sample was applied to SuperSep HG, and SDS-PAGE was performed by ordinary method. Following electrophoresis, the gel was stained with Flamingo Gel staining kit (Bio-Rad) (see FIG. 14). Then, bands LG1 and LG2 that appeared after staining were each cut to a size of about 1 $mm^2$. The excised gels were washed with 100 mM ammonium bicarbonate solution, dehydrated with acetonitrile, and dried and solidified with a SpeedVac Concentrator.

(3) Trypsin Digestion in Gel

A DTT solution (1.54 mg/ml in 100 mM ammonium bicarbonate) was added to the dried gels, and the mixture was incubated at 55° C. for 45 minutes to cause reduction. After discarding DTT solution, an iodoacetamide solution (10.1 mg/ml in 100 mM ammonium bicarbonate) was added, and the mixture was incubated at room temperature for 30 minutes in the dark. After discarding the solution, the gels were successively washed with a 50% acetonitrile solution, a 100% acetonitrile solution, a 100 mM ammonium bicarbonate solution, and a 100% acetonitrile solution, followed by drying and solidifying with a SpeedVac Concentrator. Then, a small amount of trypsin solution (12.5 μg/ml in 50 mM ammonium bicarbonate) was added to the dried gels to impregnate the gels for 45 minutes on ice. After impregnation, the excess trypsin solution was removed, and a 50 mM ammonium bicarbonate solution was added until the gels were immersed. Then, a reaction was performed at 37° C. for 16 hours.

(4) Analysis of Amino Acid Sequence by Mass Spectrometry

The trypsin-digested peptides were collected, and pretreated by purifying the peptides with a simple column filled with Empore Cation-SR Disk at the pipette tip. The trypsin-digested peptides were collected by washing with a 0.1% TFA/90% acetonitrile solution. In the simple column, the sample was first treated by an equilibrated, 0.1% TFA/2% acetonitrile solution. After sample adsorption, the column was washed with a 0.1% TFA/90% acetonitrile solution, and the sample was eluted with a 5% ammonia/30% acetonitrile solution. After elution, the digested peptides were dried and concentrated with a SpeedVac Concentrator. The pH of the digested peptide solution was adjusted to about 3 by adding TFA, and the sample was set in autosampler HTS-PAL. The sample set in HTS-PAL was then washed in the column by loading it into a sample concentration column located at the LC-MS injector valve. The sample in the concentration column was separated with an analytical column using nano-HPLC-Chorus 220, and analyzed with QSTAR Pulsar i after ionization with FortisTip set in the analytical column. The conditions of LC-MS analysis are as follows.

LC Chorus220

Solvent A: 0.1% formic acid/2% acetonitrile

Solvent B: 0.1% formic acid/90% acetonitrile

Flow rate=300 nl/min

Gradient 5% A-65% B/20 min

MS

NanoESI Positive mode, Information dependent acquisition mode (m/z=400 to 1,400, over 25 counts, charge state=2 to 4); 4 experiments/1 cycle: Experiment 1 (TOF-MS, m/z=400 to 1,400, accumulation time=1 sec); Experiments 2 to 4 (Positive Product Ion, m/z=100 to 1,400, accumulation time=2 sec)

The data acquired by LC-MS for each of band LG1 and LG2 (see FIG. 14) was analyzed by de novo sequencing using PEAKS® software to estimate the amino acid sequences of the digest peptides.

Example B5

Analysis of Peripheral Genomic DNA Sequence of Dihydrodaidzein Synthesizing (E1) Enzyme Gene (1) Preparation of Genomic DNA Library for Inverse-PCR The genomic DNA of *Lactococcus* 20-92 strain (FERM BP-10036) purified according to Example A5 was digested with restriction enzymes (BamHI, EcoRI, HindIII, KpnI, PstI, SacI, SalI, Sau3AI, XhoI; all available from Takara Bio) at 37° C. for 16 hours to obtain DNA fragments. After phenol-chloroform treatment, the fragments were purified by ethanol precipitation. The purified genomic DNA fragments were self-ligated using TaKaRa Ligation kit ver. 2.1 (Takara Bio). Each ligation solution was diluted ten times with sterilized water to prepare a genomic DNA library for inverse-PCR.

(2) Inverse-PCR

1 μL (equivalent of 40 ng) of the genomic DNA library for inverse-PCR obtained in (1) was used as a template to amplify upstream and downstream regions of genomic DNA near E1 polynucleotide, using inverse-PCR. Fragments treated with PstI and XhoI were used as template DNA for inverse-PCR amplifying the upstream region. For inverse-PCR amplifying the downstream region, fragments treated with HindIII, PstI, SacI, and XhoI were used as template DNA. TaKaRa LA Taq (Takara Bio) was used for inverse-PCR. The first PCR was run using 20 μL of a reaction mixture containing: 1×PCR buffer ($Mg^{2+}$ free); primers, 0.5 nM each; dNTP, 0.5 mM each; $MgCl_2$, 2.5 mM; and TaKaRa LA Taq, 0.2 U. 1 μL (40 ng) of a diluted solution of the genomic DNA library was used as a template. Amplification program: 98° C. for 1 min, (95° C. for 10 sec, 62° C. for 10 sec, 68° C. for 10 min)×35 cycles, 68° C. for 15 min. The subsequent, nested PCR was run using 0.5 μL of the first PCR product as a template, and 30 μL of a reaction mixture containing: 1×PCR buffer ($Mg^{2+}$ free); primers, 0.5 nM each; dNTP, 0.5 mM each; $MgCl_2$, 2.5 mM; and TaKaRa LA Taq, 0.3 U. Amplification program: 98° C. for 1 min, (95° C. for 10 sec, 62° C. for 10 sec, 68° C. for 10 min)×30 cycles, 68° C. for 15 min.

(2-1) Primers

The primer sets used for inverse-PCR are as follows.

(2-1-1) Upstream Side

First-PCR: RACE-N-P3-1 and E1-Bub-N-P1

Nested-PCR: RACE-N-P3-2 and E1-Bub-N-P2

(2-1-2) Downstream Side

First-PCR: RACE-C-P3-1 and E1-Bub-C-P1

Nested-PCR: RACE-C-P3-2 and E1-Bub-C-P2

(2-2) Primer Sequences

The sequences of the primers used for amplification of the upstream and downstream sides by inverse-PCR are as follows.

```
Primer sequences for amplification of the upstream
side
                                   (SEQ ID NO: 43)
RACE-N-P3-1: ATGGAGATAGTGCCGCTGGCAAGGCAACGGCAC

                                   (SEQ ID NO: 44)
RACE-N-P3-2: TCAACGAAGACTCGATTTGAGCGAGAGGCGAGG

                                   (SEQ ID NO: 45)
E1-Bub-N-P1: ACGGTGGAACCGGCATCGTGTTCATGGACAAC

                                   (SEQ ID NO: 46)
E1-Bub-N-P2: GCGTGACCCAGTTCCACCATGTCGGACTGTC

Primer sequences for amplification of the
downstream side
                                   (SEQ ID NO: 47)
RACE-C-P3-1: GACATCCCGTTCGAGCGCAGGATCACCCATGAG

                                   (SEQ ID NO: 48)
RACE-C-P3-2: AGGATCACCCATGAGCGCATCGCTATCATGGAC

                                   (SEQ ID NO: 49)
E1-Bub-C-P1: CATCGCTCTTGCAGTCGTTGTCCAGGAAGTCC

                                   (SEQ ID NO: 50)
E1-Bub-C-P2: TTGTCCAGGAAGTCCATCGCGTACACGACGGAG
```

Note that all oligo DNA used as amplification primers in this Example were synthesized by Sigma-Aldrich Japan.

(3) Purification and Base Sequence Determination of the Inverse-PCR Amplified, Peripheral Genomic DNA Fragments of Dihydrodaidzein Synthesizing Enzyme Gene 10× day was added to the nested-PCR product obtained in (2), in an amount 1/10 the nested-PCR product. Then, 5 μL was electrophorased on 0.8% agarose gel. This confirmed amplification of 0.5 kb (PstI) and 3.5 kb (XhoI) DNA fragments in the upstream region, and 1 kb (HindIII), 1 kb (SacI), and 2.5 kb (XhoI) DNA fragments on the downstream region. In this example, the agarose electrophoresis used ethidium bromide (Nippon Gene) for staining, and λ/StyI (Nippon Gene) and 100 bp ladder (Toyobo) as molecular weight markers. The amplified DNA fragments were excised from the agarose gel, and purified using a QIAGEN Gel-Extraction kit (Qiagen). The base sequences of the purified DNA fragments were then determined by the direct sequence method and the walking method, using the primers used for amplification.

(4) Analysis of Genome Sequence and Estimation of ORF (Open Reading Frame)

The DNA sequences obtained in (3) were subjected to assembly analysis using the sequence-assemble software SEQUENCHER (Gene Codes Inc, USA). In addition, estimation of ORF was made. The analysis determined the sequence of 6,685 bp in the peripheral genome region including E1 enzyme gene. FIG. 15 schematically illustrates the analyzed peripheral genome structure including the dihydrodaidzein synthesizing enzyme gene. Estimation of ORF found three ORFs upstream of E1 enzyme gene (the N terminus unidentified in one of the ORFs), and one ORF on the downstream side. The upstream ORFs were designated US (upstream) 1, US2, and US3, in this order, away from the dihydrodaidzein synthesizing enzyme. The downstream ORF was designated DS (downstream) 1.

Example B6

Collation of Digested Peptide Sequences with Genome Sequence by LC-MS Analysis The estimated amino acid sequences obtained in Example B4 were collated with the data of the peripheral genomic DNA sequence of dihydrodaidzein synthesizing (E1) enzyme gene determined in Example B5. As a result, some of the sequences primarily obtained from LG2 matched the polypeptide sequence inferred from the ORF-US2 nucleotide sequence. This suggests the possibility that ORF-US2 polypeptide may be the tetrahydrodaidzein synthesizing enzyme. The digested peptide sequences that matched the ORF-US2 polypeptide are shown below. FIGS. 16-1, 16-2, and 16-3 show data obtained by LC-MS.

TABLE 1

| m/z | z | Mass | Peptide | Score (%) |
|---|---|---|---|---|
| 629.348 | 2 | 1256.682 | TPGVAASVADEXK (SEQ ID NO: 51) | 100.0 |
| 452.256 | 2 | 902.497 | MPGAPVFGK (SEQ ID NO: 52) | 99.8 |
| 487.847 | 2 | 973.680 | KXXXTGTTK (SEQ ID NO: 53) | 99.8 |
| 654.670 | 3 | 1960.988 | VTQEXXCAHGAFVCGSGR (SEQ ID NO: 54) | 99.6 |
| 644.348 | 2 | 1286.681 | WXSPEESVGQR (SEQ ID NO: 55) | 96.8 |
| 449.795 | 2 | 897.576 | AQEVKVPK (SEQ ID NO: 56) | 74.9 |

In the table above, m/z represents the mass-to-charge ratio, z the number of charges, Mass the mass of the peptide, and Peptide the estimated amino acid sequences. Score represents the percentage accuracy of the sequence calculation performed by PEAKS software (100% being the most accurate). Note that since isoleucine (I) and leucine (L) have the same molecular weight and are indistinguishable, they are both denoted by X in the digested peptide sequences matching the ORF-US2 polypeptide.

Example B7

Synthesis of ORF-US2 Polypeptide Using Acellular Protein-Synthesis System and Confirmation of Tetrahydrodaidzein Synthesis Activity ORF-US2 polypeptide was synthesized using the acellular protein-synthesis system (PURESYSTEM Classic II mini; Post Genome Institute Co., Ltd.), and its tetrahydrodaidzein synthesis activity was confirmed.

(1) Preparation of Template DNA

By a two-step PCR, ORF-US2 polynucleotide template DNA was prepared for acellular protein synthesis.

(1-1) Primers

The primers used for PCR to prepare ORF-US2 template DNA are as follows.

```
                                        (SEQ ID NO: 57)
E2-invitroTS-FP1: ACTTTAAGAAGGAGATATACCAATGGCACAG

GAAGTCAAAGTCC

                                        (SEQ ID NO: 58)
E2-invitroTS-RP: CTAGACCTCGATCTCGCCCTGCATGCCG

                                        (SEQ ID NO: 59)
Universal-Primer: GAAATTAATACGACTCACTATAGGGAGACCA

CAACGGTTTCCCTCTAGAAATAATTTTGTTTAACTTTAAGAAGG

AGATATACCA
```

E2-invitroTS-FP1 and E2-invitroTS-RP were synthesized by Sigma-Aldrich Japan based on the ORF-US2 nucleotide sequence determined in Example B5. The universal primer was obtained from the attachment of PURESYSTEM Classic II mini (Post Genome Institute Co., Ltd.).

(1-2) Preparation of Template DNA by Two-Step PCR

The template DNA used for the synthesis of ORF-US2 polypeptide was prepared by a two-step PCR according to manuals. In this example, the PCR used Easy-A® High-Fidelity PCR Cloning Enzyme (DNA polymerase, Stratagene), and GeneAmp PCR System 9700 (PCR device, Applied Biosystems).

In the first PCR, the genomic DNA of *Lactococcus* 20-92 strain was used as a template to amplify ORF-US2 nucleotide, using the primers E2-invitroTS-FP1 and E2-invitroTS-RP given in (1-1). The resulting PCR product (ORF-US2 nucleotide) was used as a template to perform the second PCR, using the universal primer and E2-invitroTS-RP. 300

μL (50 μL×6) of the PCR product was purified using PCR-Purification kit (Qiagen), and used as template DNA (template DNA for ORF-US2 polypeptide synthesis) to synthesize ORF-US2 polypeptide. The first and second PCR were performed under the following conditions.

First PCR: A 50 μL reaction mixture containing amplification primers, 10 pmol each; dNTP, 2.5 pmol each; *Lactococcus* 20-92 strain-derived genomic DNA, 40 ng; Easy-A buffer (Stratagene); and Easy-A® High-Fidelity PCR Cloning Enzyme, 2U (Stratagene). Amplification program: 95° C. for 2 min (95° C. for 45 sec, 58° C. for 20 sec, 72° C. for 1 min)×30 cycles, 72° C. for 3 min.

Second PCR: A 50 μL reaction mixture containing amplification primers, 10 pmol each; dNTP, 2.5 pmol each; first PCR reaction mixture, 0.5 μL; Easy-A buffer; and Easy-A® High-Fidelity PCR Cloning Enzyme, 2U. Amplification program: 95° C. for 2 min, (95° C. for 45 sec, 45° C. for 20 sec, 72° C. for 1 min)×5 cycles, (95° C. for 45 sec, 60° C. for 20 sec, 72° C. for 1 min)×25 cycles, 72° C. for 3 min.

(2) Acellular Protein Synthesis of ORF-US2 Polypeptide and Confirmation of Tetrahydrodaidzein Synthesis Activity 25 μL of solution A and 10 μL of solution B of PURESYSTEM Classic II mini, preserved at −80° C., were thawed on ice and mixed together. Then, 0.6 μg (60 ng/μL, 10 μL) of ORF-US2 polypeptide synthesizing template DNA (including a T7-promoter sequence and a ribosome binding sequence 5' upstream of the start codon) prepared by the second PCR was added. The total volume was adjusted to 50 μL by adding sterilized water, and the mixture was incubated at 37° C. for 90 minutes to synthesize a target polypeptide. As a positive control of protein synthesis using this system, 0.5 μg (0.2 μg/μL, 2 μL) of dihydrofolate reductase (DHFR) synthesizing template DNA, provided as an attachment of PURESYSTEM Classic II mini, was used. No template DNA was added in a negative control, and only sterilized water was used. For activity measurement, 40 μL of the reaction mixture was added to an enzyme reaction buffer of the composition below, and the mixture was incubated at 37° C. for 6 hours. After reaction, the enzyme reaction mixture was extracted with 3 mL ethyl acetate. The extract was dried and dissolved in phoresis buffer, and tetrahydrodaidzein in the enzyme reaction mixture was assayed by HPLC analysis.

Composition of Enzyme Reaction Buffer 0.1 M potassium phosphate buffer/1 mM PMSF/2 mM DTT/5 mM sodium hydrosulfite (pH 7.0)

2 mM NADPH 2 mM NADH

10 μg/mL dihydrodaidzein

Samples with the dihydrofolate reductase (DHFR) synthesizing template DNA successfully expressed the protein from the DNA, whereas no protein expression was observed in samples with no template DNA. These results suggest that the experiment was indeed appropriate.

The results are shown in FIG. 17. The reaction mixture expressing ORF-US2 polypeptide had a peak for tetrahydrodaidzein at about a 6.7 minute position 6 hours post-reaction, whereas no tetrahydrodaidzein peak was observed in the reaction mixture with no protein synthesis (NC) and the reaction mixture expressing dihydrofolate reductase (DHFR). Further, while the reaction mixture expressing ORF-US2 polypeptide had a reduced level of dihydrodaidzein (substrate) due to tetrahydrodaidzein biosynthesis, a reduction of dihydrodaidzein was not observed in the reaction mixture with no protein synthesis (NC) and the reaction mixture expressing dihydrofolate reductase (DHFR). These results show that ORF-US2 polypeptide has the activity to synthesize tetrahydrodaidzein from dihydrodaidzein. It can therefore be said that ORF-US2 polypeptide corresponds to E2 polypeptide.

Example B8

Expression of Recombinant ORF-US2 Polypeptide Using *Escherichia coli*, and Confirmation of Tetrahydrodaidzein Synthesis Activity The pET system, a recombinant protein expression system using *Escherichia coli*, was used to express ORF-US2 polypeptide, and its tetrahydrodaidzein synthesis activity was confirmed.

(1) Preparation of ORF-US2 Polypeptide Expression Vector

To prepare an ORF-US2 polypeptide expression vector (pET21-US2), the DNA in the open reading frame region of ORF-US2 polypeptide was amplified by PCR.

The following amplification primers were prepared based on the ORF-US2 polypeptide sequence determined in Example B5.

```
                                   (SEQ ID NO: 60)
exp.US2 pet F Nde: TATACATATGGCACAGGAAGTCAAAGTC

                                   (SEQ ID NO: 61)
exp.US2 pet: AATCGAATTCCTAGACCTCGATCTCGCCCTGC
```

For insertion into pET21a (Novagen), the amplification primers exp.US2 pet F Nde and exp.US2 pet were designed to include NdeI and EcoRI restriction sequences, respectively.

A PCR reaction was performed using 25 μL of a reaction mixture containing the primers, 5 pmol each; dNTP, 5 nmol each; genomic DNA of *Lactococcus* 20-92 strain, 40 ng; 10× buffer for KOD-plus DNA polymerase (Toyobo), 2.5 μL; KOD-Plus DNA polymerase, 0.3 U (Toyobo). Amplification program: 95° C. for 3 min, (94° C. for 30 sec, 60° C. for 30 sec, 68° C. for 1 min)×30 cycles, 68° C. for 7 min. PCR device: GeneAmpPCR System 9700 (Applied Biosystems). Analyzing a part of the PCR reaction mixture by agarose gel electrophoresis detected a band of an expected size. The entire PCR product was collected by a QIAGEN PCR Purification kit (Qiagen).

The DNA fragments so collected were cut with restriction enzymes NdeI and EcoRI, and subjected to agarose gel electrophoresis. Then, a portion containing the target band was excised, and purified and collected with a Qiagen Gel Extraction kit (Qiagen). After collection, the DNA fragments were ligated at 16° C. overnight with pET21a digested with NdeI and EcoRI, using a DNA Ligation Kit ver.2.1 (Takara Bio). The ligated reaction mixture was then used to transform *Escherichia coli* JM109 strain (Takara Bio).

The transformant was cultivated at 37° C. overnight on a LB medium agar (GIBCO) plate containing ampicillin (50 μg/mL). The resulting single colonies were cultured overnight in a 3 mL LB medium (GIBCO) containing ampicillin (50 μg/mL). Then, plasmid DNA was extracted using a plasmid auto extractor PI-100 (KURABO).

The base sequence of the inserted DNA in the plasmid was sequenced by the dye terminator method. This confirmed the successful insertion of ORF-US2 polynucleotide, as intended. In this example, the DNA sequence was determined using DNA sequencer ABI3700 (Applied Biosystems).

(2) Expression and Confirmation of Recombinant ORF-US2 Polypeptide in *Escherichia coli*

Recombinant ORF-US2 polypeptide-expressing plasmid pET21-US2 and plasmid pET21a (negative control) were used to transform *Escherichia coli* BL21 (DE3) strain (Novagen). To obtain single colonies, the transformants were cultivated overnight at 37° C. on a LB medium agar plate containing ampicillin (50 μg/mL).

Each *E. coli* BL21 (DE3) transformant was cultured overnight at 37° C. in a 3 mL liquid LB medium containing ampicillin (50 μg/mL). Then, 0.5 mL of the culture was precultured for 3 hours (until OD at 630 nm became about 0.4) by adding 50 mL of liquid LB medium containing the same concentration of ampicillin. After adjusting the final concentration to 1 mM by adding IPTG (isopropyl-β-thiogalactopyranoside; Wako Pure Chemical Industries, Ltd.), the culture was further incubated at 37° C. for 4 hours.

After incubation, the cells were collected by centrifugation (6,000 rpm, 4° C., 15 min) using an Avanti HP25 (Beckman Coulter). The subsequent procedures were performed on ice. After removing the supernatant (the medium), the cells were suspended in 1 mL of 0.1 M potassium phosphate buffer (pH 7.0; KPB-PDH) containing 1 mM PMSF, 2 mM DTT, and 5 mM sodium hydrosulfite. The cell suspension was then placed in a 2 mL assist tube charged with 0.7 mL zirconia-silica beads (BioSpec Products, Inc.) and 400 μL KPB-PDH. The cells were then disrupted by two repeated cycles of a 20-second, 6,500 rpm treatment and 3-minute ice-cooling, using a FastPrep® (Thermo Electron. Corporation). As a result, a suspension of disrupted cells was obtained.

The expression of recombinant ORF-US2 polypeptide in *E. coli* was confirmed by SDS-polyacrylamide-gel electrophoresis (SDS-PAGE).

5 μL of 5× sample buffer (125 mM Tris-HCl (pH 6.5)/25% glycerol/5% SDS/5% 2-mercaptoethanol/BPB 0.5%) was added to 20 μL of the disrupted cell suspension. After heat-denaturing at 98° C. for 5 minutes, the suspension was ice-cooled, and 10 μL was electrophorased by SDS-PAGE. SDS-PAGE was performed with a commercially available gel plate (SuperSep® 5-20%; Wako Pure Chemical Industries, Ltd.), and Quick CBB (Wako Pure Chemical Industries, Ltd.) for staining. Prestained XL-Ladder Broad range (Apro Science) was used as a molecular weight marker.

The results of SDS-PAGE are shown in FIG. 18. A recombinant polypeptide with a molecular weight of about 29 kDa was confirmed in the disrupted cell suspension derived from pET21-US2 transformant.

(3) Confirmation of Dihydrodaidzein Synthesis Activity of Recombinant ORF-US2 Polypeptide The disrupted cell suspension obtained in (2) of this Example was used as an enzyme source to measure the conversion activity from dihydrodaidzein to tetrahydrodaidzein. As a result, the activity was confirmed in the expressed recombinant ORF-US2 polypeptide.

In this example, the measurement of conversion activity from dihydrodaidzein to tetrahydrodaidzein was performed as follows.

An enzyme reaction mixture of the composition below was prepared, and the mixture was incubated at 0° C. for 2 hours.

| Composition of Enzyme Reaction Mixture | |
|---|---|
| Disrupted cell suspension (enzyme source): | 100 μl |
| NADH (100 mM): | 20 μl |
| NADPH (100 mM): | 20 μl |
| Dihydrodaidzein (2 mg/ml): | 5 μl |
| KPB-PDH: | 855 μl |
| Total: | 1,000 μl |

After incubation, 3 mL of ethyl acetate was added to the enzyme reaction mixture for extraction. After drying, the extract was dissolved by the mobile phase (eluent). The dissolved product was analyzed by HPLC to measure the contents of dihydrodaidzein and cis- and trans-tetrahydrodaidzeins in the enzyme reaction mixture.

The results of HPLC analysis are shown in FIG. 19. In the disrupted cell suspension derived from plasmid pET21-US2 transformant expressing the recombinant ORF-US2 polypeptide, the dihydrodaidzein (substrate) added to the enzyme reaction mixture was converted to cis-tetrahydrodaidzein (c-THD) and trans-tetrahydrodaidzein (t-THD), whereas tetrahydrodaidzein was not detected in the enzyme reaction mixture in pET21a transformant (negative control).

These results show that recombinant ORF-US2 polypeptide has the activity to synthesize tetrahydrodaidzein from dihydrodaidzein. It can therefore be said that recombinant ORF-US2 polypeptide corresponds to E2 polypeptide.

Example C

Example C1

Confirmation of Equol Biosynthetic Activity of Bacterial Cell from Tetrahydrodaidzein A *Lactococcus* 20-92 strain (FERM BP-10036) was inoculated in a tetrahydrodaidzein-containing amplification liquid medium (a modified GAM bouillon medium (NISSUI PHARMACEUTICAL CO., LTD.) to which cis- or trans-tetrahydrodaidzein (organically-synthesized by Otsuka Pharmaceutical Co., Ltd.: see Reference Example B1) was added in an amount of 10 μg/mL), and the culture was incubated at 37° C. for 18 hours under anaerobic conditions (using BBL Gas Pack systems). After incubation, 1 mL of the culture was immediately placed in a glass centrifuge tube with cap, and 3 mL of ethyl acetate was added thereto for extraction. The product was dried to prepare a sample for HPLC analysis. As the standard solution for HPLC analysis, a mixed solution of daidzein (2 μg/mL; Funakoshi Corporation), equol (2 μg/mL; Funakoshi Corporation), dihydrodaidzein (2 μg/mL; Trend Research Chemicals Inc.), cis-tetrahydrodaidzein and trans-tetrahydrodaidzein (2 μg/mL; both chemically-synthesized by Otsuka Pharmaceutical Co., Ltd.) was used.

The results are shown in FIG. 20. FIG. 20 shows that the *Lactococcus* 20-92 strain has an activity to biosynthesize equol from both cis- and trans-tetrahydrodaidzeins (FIG. 20, middle and lower charts). Note that in the figures, daidzein is abbreviated as DZN, dihydrodaidzein as DD, cis-tetrahydrodaidzein as c-THD, trans-tetrahydrodaidzein as t-THD, and equol as EQL.

Example C2

Search and Identification of Equol Synthesizing Enzyme by Recombinant Protein Expression System Using *Escherichia coli*

The pET system (Novagen), a recombinant protein expression system using *Escherichia coli*, was used to express polypeptides each corresponding to three ORF polynucleotides (ORF-US3, US1, and DS1) identified in the peripheral genomic DNA sequence of dihydrodaidzein synthesizing (E1) enzyme gene determined in Example B5, in *Escherichia coli*. The activity to catalyze equol conversion from tetrahydrodaidzein was examined to search equol synthesizing (E3) enzyme.

(1) Preparation of ORF Polypeptide Expression Vector

To prepare an expression vector of each ORF polypeptide (ORF-US3, US1, and DS1), the polynucleotide in the open reading frame region of each polypeptide was amplified by PCR and inserted into pET21a vector (Novagen).

(1-1) Amplification Primer

The following amplification primers were prepared based on the peripheral genomic DNA sequence of dihydrodaidzein synthesizing enzyme (E1) determined in Example B5.

```
ORF-US3 polypeptide
                                            (SEQ ID NO: 62)
exp.US3 F: TATACATATGGCAGAATTCGATGTTGAG

                                            (SEQ ID NO: 63)
exp.US3 R: CCGCAAGCTTCTACATAGTGGAGATCGCGTGG ORF-US

ORF-US1 polypeptide
                                            (SEQ ID NO: 64)
exp.US1 F: TATACATATGTTCAAGGGTCCACAGGGC

                                            (SEQ ID NO: 65)
exp.US1 R: GCTCGAATTCTTAGTGCTGCTGTGCCTTTTCAG

ORF-DS1 polypeptide
                                            (SEQ ID NO: 66)
exp.DS1 F: ATATACATATGCAGGATATGGACTTCATGG

                                            (SEQ ID NO: 67)
exp.DS1 R: GCTCGAATTCTCATAGTGACATCAGCGCTCCC
```

For insertion into pET21a (Novagen), the amplification primers exp.US3 F, exp.US1 F, and exp.DS1 F were designed to include NdeI restriction sequence, exp.US3 R to include HindIII restriction sequence, and exp.US1R and exp.DS1 R to include EcoRI restriction sequence.

(1-2) Amplification of Each ORF Polynucleotide

A PCR reaction was performed using 25 μL of a reaction mixture containing the primers, 5 pmol each; dNTP, 5 nmol each; genomic DNA of *Lactococcus* 20-92 strain purified in Example A5, 40 ng; 10× buffer for KOD-plus DNA polymerase (Toyobo Co., Ltd.), 2.5 μL; KOD-Plus DNA polymerase, 0.3 U (Toyobo Co., Ltd.). Amplification program: 95° C. for 3 min, (94° C. for 30 sec, 60° C. for 30 sec, 68° C. for 2 min)×30 cycles, 68° C. for 7 min. PCR device: GeneAmp PCR System 9700 (Applied Biosystems). Analyzing a part of the PCR reaction mixture by agarose gel electrophoresis detected a band of an expected size for each primer. The entire PCR product was collected by a QIAGEN PCR Purification kit (Qiagen).

(1-3) Preparation of ORF Polypeptide Expression Vector

The ORF-US3 polynucleotide fragments collected in process (1-2) were cut with restriction enzymes NdeI and HindIII, and ORF-US1 and ORF-DS1 polynucleotide fragments were cut with restriction enzymes NdeI and EcoRI. The fragments were subjected to agarose gel electrophoresis. Then, a portion containing the target band was excised, and purified and collected with a Qiagen Gel Extraction kit (Qiagen). After collection, the polynucleotide fragments were ligated at 16° C. overnight with pET21a digested with NdeI and HindIII or EcoRI, using a DNA Ligation Kit ver.2.1 (Takara Bio). The ligated reaction mixture was then used to transform *Escherichia coli* JM109 strain (Takara Bio) by an ordinary method. The obtained transformant was cultivated at 37° C. overnight on a LB medium agar (GIBCO) plate containing ampicillin (50 μg/mL). The resulting single colonies were cultured overnight in a 3 mL LB medium (GIBCO) containing ampicillin (50 μg/mL). Then, plasmid DNA was extracted using a plasmid auto extractor PI-100 (KURABO).

The base sequence of the inserted DNA in the plasmid was sequenced by the dye terminator method. This confirmed the successful insertion of each polynucleotide, as intended. Thus, pET-US3, pET-US1, and pET-DS1 were obtained. In this example, the DNA sequence was determined using DNA sequencer ABI3700 (Applied Biosystems).

(2) Expression of Each Recombinant Polypeptide in *Escherichia coli*

(2-1) Preparation of *Escherichia coli* BL21 Transformant

Recombinant ORF polypeptide-expressing plasmids pET-US3, pET-US1, pET-DS1, and pET21a (negative control) were used to transform *Escherichia coli* BL21 (DE3) strain (Novagen) by an ordinary method. To obtain single colonies, the transformants were cultivated overnight at 37° C. on a LB medium agar plate containing ampicillin (50 μg/mL).

(2-2) Induction of Recombinant Polypeptide Expression

Each *E. coli* BL21 (DE3) transformant was cultured overnight at 37° C. in a 3 mL liquid LB medium containing ampicillin (50 μg/mL). Then, 0.5 mL of the culture was precultured for 3 hours (until OD at 630 nm became about 0.4 to 0.7) by adding 50 mL of liquid LB medium containing the same concentration of ampicillin. After adjusting the final concentration to 1 mM by adding IPTG (isopropyl-β-thiogalactopyranoside; Wako Pure Chemical Industries, Ltd.), the culture was further incubated at 37° C. for 4 hours. Thus, recombinant polypeptide expression in *Escherichia coli* was induced.

(2-3) Preparation of Disrupted Cell Suspension

After induction of expression in process (2-2), the cells were collected by centrifugation (6,000 rpm, 4° C., 15 min) using an Avanti HP25 (Beckman Coulter). The subsequent procedures were performed on ice. After removing the supernatant (the medium), the cells were suspended in 1 mL of 0.1 M potassium phosphate buffer (pH 7.0; hereinafter abbreviated as KPB-PDH) containing 1 mM PMSF, 2 mM DTT, and 5 mM sodium hydrosulfite. The cell suspension was then placed in a 2 mL assist tube charged with 0.7 mL zirconia-silica beads (BioSpec Products, Inc.) and 400 μL KPB-PDH. The cells were then disrupted by two repeated cycles of a 20-second, 6,500 rpm treatment and 3-minute ice-cooling, using a FastPrep® (Thermo Electron Corporation). As a result, a suspension of disrupted cells was obtained.

(2-4) Confirmation of Recombinant Polypeptide Expression by SDS-Polyacrylamide-Gel Electrophoresis (SDS-PAGE)

The expression of each recombinant ORF polypeptide in *E. coli* was confirmed by SDS-PAGE. 5 μL of 5× sample buffer (125 mM Tris-HCl (pH 6.5)/25% glycerol/5% SDS/5% 2-mercaptoethanol/BPB 0.5%) was added to 20 μL of the disrupted cell suspension obtained in process (2-3). After heat-denaturing at 98° C. for 5 minutes, the suspension was ice-cooled, and 4 μL was electrophorased by SDS-PAGE. SDS-PAGE was performed with a commercially available gel plate (SuperSep® 5-20%; Wako Pure Chemical Industries, Ltd.), and Quick CBB (Wako Pure Chemical Industries, Ltd.) for staining. Prestained XL-Ladder Broad range (Apro Science) was used as a molecular weight marker. The results of SDS-PAGE are shown in FIG. 21. Expression of recombinant ORF-US3 and ORF-DS1 polypeptides with molecular weights of about 52 kDa and 50 kDa was confirmed in the disrupted cell suspensions derived from pET-US3 and pET-DS1 transformants, respectively. No expression of recombinant ORF-US1 polypeptide was observed in the disrupted cell suspension derived from pET-US1 transformant.

Example C3

Measurement of Equol Synthesis Activity of Recombinant ORF Polypeptide

The disrupted cell suspension obtained in Example C2 was used as an enzyme source to measure the conversion activity from tetrahydrodaidzein to equol. In this example, the measurement of conversion activity from tetrahydrodaidzein to equol was performed as follows.

An enzyme reaction mixture of the composition below was prepared, and the mixture was incubated at 37° C. for 1 hour.

| Composition of Enzyme Reaction Mixture | |
| --- | --- |
| Disrupted cell suspension (enzyme source): | 100 μl |
| NADH (100 mM): | 20 μl |
| NADPH (100 mM): | 20 μl |
| Cis-tetrahydrodaidzein (2 mg/ml): | 5 μl |
| Trans-tetrahydrodaidzein (2 mg/ml): | 5 μl |
| KPB-PDH: | 850 μl |
| Total: | 1,000 μl |

After incubation, 3 mL of ethyl acetate was added to the enzyme reaction mixture for extraction. After drying, the extract was dissolved by the mobile phase (eluent). The dissolved product was analyzed by HPLC to measure the contents of dihydrodaidzein, cis-tetrahydrodaidzein, trans-tetrahydrodaidzein, and equol in the enzyme reaction mixture. As the standard solution for HPLC analysis, a mixed solution of daidzein (2 μg/mL; Funakoshi Corporation), equol (2 μg/mL; Funakoshi Corporation), dihydrodaidzein (2 μg/mL; Trend Research Chemicals Inc.), cis-tetrahydrodaidzein and trans-tetrahydrodaidzein (2 μg/mL; both chemically-ynthesized by Otsuka Pharmaceutical Co., Ltd.) was used.

As a result of HPLC analysis, in the disrupted cell suspension derived from plasmid pET-US3 transformant expressing the recombinant ORF-US3 polypeptide, the tetrahydrodaidzein added to the enzyme reaction mixture was converted to equol (FIG. 22). Additionally, the conversion activity to dihydrodaidzein, which is a precursor of tetrahydrodaidzein, was confirmed during the equol biosynthetic pathway (FIG. 22). As for pET-US1 and pET-DS1 transformants, and pET21a transformant (negative control), only tetrahydrodaidzein was detected in the enzyme reaction mixture. Note that in the figures, aidzein is abbreviated as DZN, dihydrodaidzein as DD, cis-tetrahydrodaidzein as c-THD, trans-tetrahydrodaidzein as t-THD, and equol as EQL.

These results show that ORF-US3 polypeptide has the activity to biosynthesize equol from tetrahydrodaidzein. It can therefore be said that recombinant ORF-US3 polypeptide corresponds to E3 polypeptide.

Example D

Example D1

Expression and Purification of His-Tagged Recombinant Equol Production Related Enzyme Using *Escherichia coli*

Using a pET system (Novagen), which is a recombinant protein expression system using *Escherichia coli*, three equol production related enzymes with His-tag: dihydrodaidzein synthesis enzyme (E1), tetrahydrodaidzein synthesis enzyme (E2), equol synthesis enzyme (E3), were expressed, followed by affinity purification using a His-tagged protein purification (Ni) column.

(1) Production of His-Tagged Enzyme Expression Vector

To produce expression vectors for the enzymes (E1, E2, E3), a polynucleotide in each open reading frame region was amplified by PCR and inserted into a pET21a vector (Novagen).

(1-1) Amplification Primer

Based on the genome sequence in the vicinity of the dihydrodaidzein synthesis enzyme (E1) found in Example B5, the following amplification primers were produced.

```
His-tagged E1 enzyme
                                        (Sequence Number: 41)
exp.E1 pet F Nde: AGCTCATATGAAGAACAAGTTCTATCCGAA

                                        (Sequence Number: 42)
exp.E1 pet His: AATCGAATTCGTACAGGTTGCAGCCAGCGATGT

His-tagged E2 enzyme
                                        (Sequence Number: 60)
exp.US2 pet F Nde: TATACATATGGCACAGGAAGTCAAAGTC

                                        (Sequence Number: 68)
exp.E2 pet His: AATCGAATTCGAGACCTCGATCTCGCCCTGC

His-tagged E3 enzyme
                                        (Sequence Number: 62)
exp.US3 F: TATACATATGGCAGAATTCGATGTTGAG

                                        (Sequence Number: 69)
exp.E3 R His: CCGCAAGCTTGTACATAGTGGAGATCGCGTGG
```

For insertion into pET21a (Novagen), the amplification primers: exp.E1 pet F Nde, exp.US2 pet F, and exp.US3 F were designed to each include a restriction enzyme NdeI cleavage site sequence; exp.E1 pet His and exp.E2 pet His were designed to include a EcoRI cleavage site sequence; and exp.E3 R His was designed to include a HindIII cleavage site sequence.

(1-2) Amplification of His-Tagged Enzyme Polynucleotides

A PCR reaction was performed using 25 μL of a reaction mixture containing the primers, 5 pmol each; dNTP, 5 nmol each; genomic DNA of *Lactococcus* 20-92 strain (FERN BP-10036) purified in Example A5, 40 ng; 10× buffer for KOD-plus DNA polymerase (Toyobo), 2.5 μL; KOD-Plus DNA polymerase (Toyobo) 0.3 U, using an amplification program: 95° C. for 3 min, (94° C. for 30 sec, 60° C. for 30 sec, 68° C. for 2 min)×30 cycles, 68° C. for 7 min (PCR device: GeneAmpPCR System 9700 (Applied Biosystems)). Analyzing a part of the PCR reaction mixture by agarose gel electrophoresis detected a band of an expected size. The whole PCR product was collected by QIAGEN PCR Purification kit (Qiagen).

(1-3) Production of His-Tagged Enzyme Polypeptide Expression Vector

The His-tagged enzyme polynucleotide fragments collected in (1-2) were cut with restriction enzymes NdeI and EcoRI, and subjected to agarose gel electrophoresis. Then, a portion containing the target band was excised, and purified and collected with Qiagen Gel Extraction kit (Qiagen). After collection, the polynucleotide fragments were ligated at 16° C. overnight with pET21a digested with NdeI and EcoRI, using DNA Ligation Kit ver.2.1 (Takara Bio). With the ligated reaction mixture, transformation of *Escherichia coli* JM109 strain (Takara Bio) was performed in a general method. The transformant thus obtained was cultivated at 37° C. overnight on a LB medium agar (GIBCO) plate containing ampicillin (50 μg/mL). The resulting single colonies were cultured overnight in a 3 mL LB medium (GIBCO) containing ampicillin (50 μg/mL). Then, plasmid DNA was extracted using plasmid autoextractor PI-100 (KURABO).

The base sequence of the inserted DNA in the plasmid was sequenced by the dye terminator method. This confirmed successful insertion of ORF-US2 polynucleotide as intended. pET-E1-His, pET-E2-His, and pET-E3-His were obtained. In this example, the DNA sequence was determined using DNA sequencer ABI3700 (Applied Biosystems).

(2) Expression and Affinity Purification of each His-Tagged Recombinant Enzyme Polypeptide in *Escherichia coli*

(2-1) Production of *Escherichia coli*BL21 Transformant

Using plasmid pET-E1-His, pET-E2-His, pET-E3-His for expressing His-tagged enzyme polypeptide, *Escherichia coli* BL21(DE3) strains (Novagen) were transformed using a general method. The transformants were cultivated at 37° C. overnight on LB medium agar (GIBCO) plates containing ampicillin (50 μg/mL), thereby obtaining single colonies.

(2-2) Purification of His-Tagged Recombinant E1 and E2 Enzyme Polypeptide (2-2-1) *Escherichia coli* Cultivation and Induction of Expression of His-Tagged Recombinant E1 and E2 Enzyme Polypeptides Each of *E. coli* BL21 (DE3) transformants, respectively transformed by pET-E1-His and pET-E2-His, was cultured overnight at 37° C. in a 10 mL liquid LB medium containing ampicillin (50 μg/mL). Then, 7.5 mL of the culture was precultured for 2 hours (until OD at 600 nm became about 0.5) by adding 150 mL of liquid LB medium containing the same concentration of ampicillin. After adjusting the final concentration to 0.5 mM by adding IPTG (isopropyl-β-thiogalactopyranoside; Wako Pure Chemical Industries, Ltd.), the culture was further incubated at 30° C. for 4 hours while being mildly shaken, thereby inducing expression of His-tagged recombinant E1 and E2 enzyme polypeptides in *Escherichia coli.*

(2-2-2) Preparation of Lysate

After the expression induction in (2-2), the culture was centrifuged (6000 rpm, 4° C., 10 minutes) using Avanti HP25 (beckman coulter) to collect cells, thereby obtaining His-tagged recombinant E1 and E2 enzyme polypeptides expressed in *Escherichia coli*, respectively in amounts of 0.66 g and 0.73 g. A Bugbuster protein Extraction solution (Novagen) was added to the obtained cells in an amount of 15 mL per gram (wet weight) of the cell. The mixture was suspended gently with a pipet, and Lysozyme (SIGMA) and Benzonase (Novagen) were added to the suspension in the amounts of 2000 units/mL, and 25 units (1 μL)/mL, respectively. Thereafter, the mixture was slowly stirred with a rotator (RT-50:Taitec) at room temperature for 30 minutes, thereby obtaining a lysate (Lysate A). Lysate A was centrifuged (8000 rpm, 4° C., 15 minutes) with Avanti HP25 (beckman coulter) to separate a supernatant (Lysate B).

(2-2-3) Affinity Purification of His-Tagged E1 and E2 Enzyme Polypeptides

Using His GraviTrap (GE Healthcare Bioscience) as a His-tagged protein purification column, affinity purification of the His-tagged E1 and E2 enzyme polypeptides was performed according to the instruction manual except for some modification. More specifically, His GraviTrap was equilibrated with ice-cooled 10 mL binding buffer, and the whole Lysate B prepared in (2-2-2) was poured into the mixture so that the target His-tagged E1 or E2 enzymes were adhered to His GraviTrap by free fall. Thereafter, His GraviTrap was cleaned twice with ice-cooled 10 mL cleaning buffer, followed by elution of the target His-tagged E1 and E2 enzymes from His GraviTrap using 3 mL elution buffer. DTT (dithiothreitol: Wako Pure Chemical Industries, Ltd.) was added to the eluate so that the final concentration became 3 mM. The mixture was divided into 300 μL microtubes. A part of the microtubes was examined for their E1 enzymatic activities and E2 enzymatic activities in the respective eluates. The eluate was preserved at 4° C. until it was used for the enzyme test.

The compositions of the binding buffer, the cleaning buffer, and the elution buffer used for the purification were shown below.

binding buffer: 20 mM Tris-HCl, 20 mM Imidazole (Wako Pure Chemical Industries, Ltd.), 0.5M NaCl (Wako Pure Chemical Industries, Ltd.), 1 mM DTT (dithiothreitol: Wako Pure Chemical Industries, Ltd.), 1 mM PMSF (phenylmethylsulfonyl fluoride: Wako Pure Chemical Industries, Ltd.)

Cleaning Buffer: 20 mM Tris-HCl, 60 mM Imidazole, 0.5M NaCl, 1 mM DTT (dithiothreitol), 1 mM PMSF (phenylmethylsulfonyl fluoride)

Elution Buffer: 20 mM Tris-HCl 500 mM Imidazole, 0.5M NaCl, 1 mM DTT(dithiothreitol), 1 mM PMSF (phenylmethylsulfonyl fluoride)

(2-3)Purification of His-Tagged Recombinant E3 Enzyme Polypeptide (2-3-1) *Escherichia coli* Cultivation and Induction of Expression of His-Tagged Recombinant E3 Enzyme Polypeptide The *E. coli* BL21 (DE3) transformant, transformed by pET-E3-His, was cultured overnight at 37° C. in a 50 mL liquid LB medium containing ampicillin (50 μg/mL). Then, 20 mL of the culture was precultured for 3 hours (until OD at 600 nm became about 0.4) by adding 1 L of liquid LB medium containing the same concentration of ampicillin. After adjusting the final concentration to 0.5 mM by adding IPTG (isopropyl-β-thiogalactopyranoside; Wako Pure Chemical Industries, Ltd.), the culture was further incubated at 37° C. for 4 hours while being shaken, thereby inducing expression of His-tagged recombinant E3 enzyme polypeptide in *Escherichia coli*. After the expression induction, the culture was centrifuged (6000 rpm, 4° C., 10 minutes) using Avanti HP25 (beckman coulter) to collect cells. 0.1 M potassium phosphate buffer containing 1 mM PMSF (phenylmethylsulfonyl fluoride), 2 mM DTT (Wako Pure Chemical Industries, Ltd.) and 5 mM sodiumhydrosulfite (Buffer A, hereinafter: pH 7.0) was added for suspension. After centrifugation (6000 rpm, 4° C., 10 minutes), the culture was kept at −80° C.

(2-3-2) Preparation of Lysate

The cells preserved at −80° C. were quickly thawed and centrifuged (10,000×g 15 min). The cells were suspended by adding 25 mL of new Buffer A. For disruption, the cells were then disrupted by three repeated cycles of a 20-second, 6,500 rpm treatment and 3-minute ice cooling, using FastPrep® (Thermo Electron Corporation). The resulting disrupted cell material was centrifuged (10000×g, 15 min). The supernatant was separated to obtain a lysate.

(2-3-3) Affinity Purification of His-Tagged Recombinant E3 Enzyme Polypeptide 4 mL of the lysate obtained in (2-3-3) was supplied to HisTrap HP (GE Healthcare Bioscience), which is a His-tag fusion protein purification column, to purify the His-tagged recombinant E3 enzyme polypeptide under the purification conditions below. The protein was measured based on the absorption at 280 nm. The fraction using a fraction collector was started after the absorption at 280 nm in the pass-through fraction decreased to the base line.

| | | |
|---|---|---|
| Flow Rate: | 1 ml/min | |
| Fraction: | 2 ml/2 min/Fraction | |
| Eluent A: | 0.1M potassium phosphate buffer (pH 7)/0.5M NaCl/1% isoPrOH | |
| Eluent B: | Eluent A containing 0.5M Imidazole | |
| | Time(min) | (Eluent B)/(Eluent A + Eluent B) |
| Elution Program: | 0 | 0.05 |
| | 5 | 0.05 |
| | 25 | 0.5 |
| | 30 | 1 |
| | 35 | 1 |
| | 37 | 0.05 |

E3 synthesis activity was observed in Fractions No. 7 to 9. Active fractions obtained by a plurality of purifications were pooled, mixed with glycerin at a ratio of 8%, kept at −28° C., and dissolved as required to be used for experiment.

Example D2

Synthesis of Tetrahydrodaidzein from Daidzein Using His-tagged Recombinant E1 and E2 Enzymes Using the His-tagged recombinant E1 and E2 enzymes obtained in process (2-2-3) of Example D1 as an enzyme source, an enzyme reaction mixture of the composition below was prepared, and was reacted at 37° C. for 2 hours to synthesize tetrahydrodaidzein from daidzein. Additionally, reactions using the His-tagged recombinant E1 or E2 enzyme singly as an enzyme source were conducted at the same time.

| Composition of Enzyme Reaction Mixture | |
|---|---|
| His-tagged recombinant E1 enzyme: | 20 μl |
| His-tagged recombinant E2 enzyme: | 20 μl |
| NADH (100 mM): | 20 μl |
| NADPH (100 mM): | 20 μl |
| Daidzein (2 mg/ml): | 5 μl |
| 0.1M potassium phosphate buffer pH 7/1 mM PMSF/2 mM DTT/5 mM sodium hydrosulfite: | 915 μl |
| Total: | 1000 μl |

After incubation, 3 mL of ethyl acetate (Wako Pure Chemical Industries, Ltd.) was added to the obtained enzyme reaction mixture for extraction. After drying, the extract was dissolved by the mobile phase (eluent). The dissolved product was analyzed by HPLC to measure the contents of cis- and trans-tetrahydrodaidzeins in the enzyme reaction mixture.

As the standard solution for HPLC analysis, a mixed solution of daidzein (2 μg/mL; Funakoshi Corporation), equol (2 μg/mL; Funakoshi Corporation), dihydrodaidzein (2 μg/mL; Trend Research Chemicals Inc.), cis-tetrahydrodaidzein (2 μg/mL; Reference Example B1) and trans-tetrahydrodaidzein (2 μg/mL; Reference Example B1) was used.

FIG. 23 shows the results of HPLC analysis. When using the mixture of the His-tagged recombinant E1 and E2 enzymes as an enzyme source, cis- and trans-tetrahydrodaidzeins were confirmed in the product. When using the His-tagged recombinant E1 or E2 enzyme singly as an enzyme source, however, cis- or trans-tetrahydrodaidzeins was not confirmed in the product.

Example D3

Synthesis of Equol from Dihydrodaidzein Using His-Tagged Recombinant E2 and E3 Enzymes Using the His-tagged recombinant E2 and E3 enzymes obtained in processes (2-2-3) and (2-3-3) of Example D1 as an enzyme source, an enzyme reaction mixture of the composition below was prepared, and was reacted at 37° C. for 2 hours to synthesize equol from dihydrodaidzein. Additionally, reactions using the His-tagged recombinant E1 or E2 enzyme singly as an enzyme source were conducted at the same time.

| Composition of Enzyme Reaction Mixture | |
|---|---|
| His-tagged recombinant E2 enzyme: | 20 μl |
| His-tagged recombinant E3 enzyme: | 20 μl |
| NADH (100 mM): | 20 μl |
| NADPH (100 mM): | 20 μl |
| Dihydrodaidzein (2 mg/ml): | 5 μl |
| 0.1M potassium phosphate buffer pH 7/1 mM PMSF/2 mM DTT/5 mM sodium hydrosulfite: | 915 μl |
| Total: | 1000 μl |

After incubation, 3 mL of ethyl acetate (Wako Pure Chemical Industries, Ltd.) was added to the obtained enzyme reaction mixture for extraction. After drying, the extract was dissolved by the mobile phase (eluent). The dissolved product was analyzed by HPLC to measure the content of equol in the enzyme reaction mixture.

FIG. 24 shows the results of HPLC analysis. When using the mixture of the His-tagged recombinant E2 and E3 enzymes as an enzyme source, equol was confirmed in the product. When using the His-tagged recombinant E2 or E3 enzyme singly as an enzyme source, however, equol was not confirmed in the product.

Example D4

Synthesis of Equol from Daidzein Using His-Tagged Recombinant E1, E2, and E3 Enzymes Using the His-tagged recombinant E1, E2, and E3 enzymes obtained in processes (2-2-3) and (2-3-3) of Example D1 as an enzyme source, an enzyme reaction mixture of the composition below was prepared, and was reacted at 37° C. for 2 hours to synthesize equol from daidzein. Additionally, reactions using the His-tagged recombinant E1, E2, or E3 enzyme singly as an enzyme source were conducted at the same time.

| Composition of Enzyme Reaction Mixture | |
|---|---|
| His-tagged recombinant E1 enzyme: | 20 μl |
| His-tagged recombinant E2 enzyme: | 20 μl |
| His-tagged recombinant E3 enzyme: | 20 μl |
| NADH (100 mM): | 20 μl |
| NADPH (100 mM): | 20 μl |
| Dihydrodaidzein (2 mg/ml): | 5 μl |
| 0.1M potassium phosphate buffer pH 7/1 mM PMSF/2 mM DTT/5 mM sodium hydrosulfite: | 895 μl |
| Total: | 1000 μl |

After incubation, 3 mL of ethyl acetate (Wako Pure Chemical Industries, Ltd.) was added to the obtained enzyme reaction mixture for extraction. After drying, the extract was dissolved by the mobile phase (eluent). The dissolved product was analyzed by HPLC to measure the content of equol in the enzyme reaction mixture.

FIG. 25 shows the results of HPLC analysis. When using the His-tagged recombinant E1, E2, or E3 enzyme singly as an enzyme source, equol was not confirmed in the product. When using the mixture of the His-tagged recombinant E1, E2, and E3 enzymes as an enzyme source, however, equol was confirmed in the product.

Example E

Influence of Metal Ions on Dihydrodaidzein Synthesis Activity of His-Tagged Recombinant E1 Enzyme Using the His-tagged recombinant E1 enzyme (E1-His) expressed in *Escherichia coli*, purified by Ni-Sepharose, as an enzyme source, the influence of metal ions on the conversion activity from daidzein to dihydrodaidzein was examined. Various metals ($MnCl_2.2H_2O$, $FeSO_4.7H_2O$, $CaCl_2.2H_2O$, $Zn(CH_3COO)_2.2H_2O$, $CoSO_4.7H_2O$, $MgSO_4.7H_2O$, $NiSO_4.6H_2O$) were dissolved in distilled water to obtain a concentration of 100 mM. Using the metal ion solution, an enzyme reaction mixture of the composition below was prepared, and was reacted at 37° C. for 2 hours to measure the activity.

| Composition of Enzyme Reaction Mixture | |
|---|---|
| His-tagged recombinant E1 enzyme: | 20 μl |
| NADH (100 mM): | 10 μl |
| NADPH (100 mM): | 10 μl |
| Daidzein (1 mg/ml): | 10 μl |
| Metal ion solution: | 100 μl |
| 0.2M KPB-DH: | 850 μl |
| Total: | 1000 μl |

After incubation, 3 mL of ethyl acetate was added to the obtained enzyme reaction mixture for extraction. After drying, the extract was dissolved by the mobile phase (eluent). The dissolved product was analyzed by HPLC to measure the contents of daidzein and dihydrodaidzein in the enzyme reaction mixture. As a result, it was confirmed that $Mn^{2+}$ and $Fe^{2+}$ stimulated the activity (FIG. 26).

BRIEF DESCRIPTION OF THE DRAWINGS

FIG. 2 shows the results of Mono Q HPLC in Example A2 (upper part), and the activity of dihydrodaidzein synthesizing enzyme of each fraction (lower part). The enzyme activity is shown as a peak area corresponding to dihydrodaidzein using daidzein as a substrate.

FIG. 8 shows the results of HPLC analysis in Example A8. Upper part: Control; middle part: pET-E1-His; lower part: pET21a.

FIG. 16-1 shows data from LC-MS analysis, and an example of a digested-peptide amino acid sequence inferred from the LC-MS data in Example B6; L, an amino acid residue denoted by X in the description. The upper figure is for peptide TPGVAASVADEXK, and the lower figure is for peptide MPGAPVFGK.

FIG. 16-2 shows data from LC-MS analysis, and an example of a digested-peptide amino acid sequence inferred from the LC-MS data in Example B6; L, an amino acid residue denoted by X in the description. The upper figure is for peptide KXXXTGTTK and the lower figure is for peptide VTQEXXCAHGAFVCGSGR.

FIG. 16-3 shows data from LC-MS analysis, and an example of a digested-peptide amino acid sequence (WXSPEESVGQR) inferred from the LC-MS data in Example B6; L, an amino acid residue denoted by X in the description.

FIG. 19 shows the results of HPLC analysis in Example B8. Upper chart: Enzyme reaction product using dihydrodaidzein as a substrate, and a disrupted cell suspension derived from recombinant ORF-US2 polypeptide-expressing plasmid pET21-US2 transformant as an enzyme source (pET21-US2); lower chart: Enzyme reaction product using dihydrodaidzein as a substrate, and a disrupted cell suspension derived from pET21a transformant (negative control) as an enzyme source (pET21a). Bar chart: Peak areas corresponding to dihydrodaidzein (DD) and cis- (c-THD) and trans-tetrahydrodaidzeins (t-THD) produced by enzyme reactions in samples using disrupted cell suspensions derived from ORF-US2 polypeptide-expressing reaction mixture and pET21a transformant as an enzyme source.

FIG. 22 shows the results of HPLC analysis in Example C3. Upper part: Standard; middle part: pET-US3; lower part: pET21a.

FIG. 27 shows the alignment of amino acid sequences of SEQ ID NOs: 1, 2 and 3.

FIG. 28 shows the alignment of amino acid sequences of SEQ ID NOs: 7, 8 and 9.

SEQUENCE LISTING FREE TEXT

Figure 1:
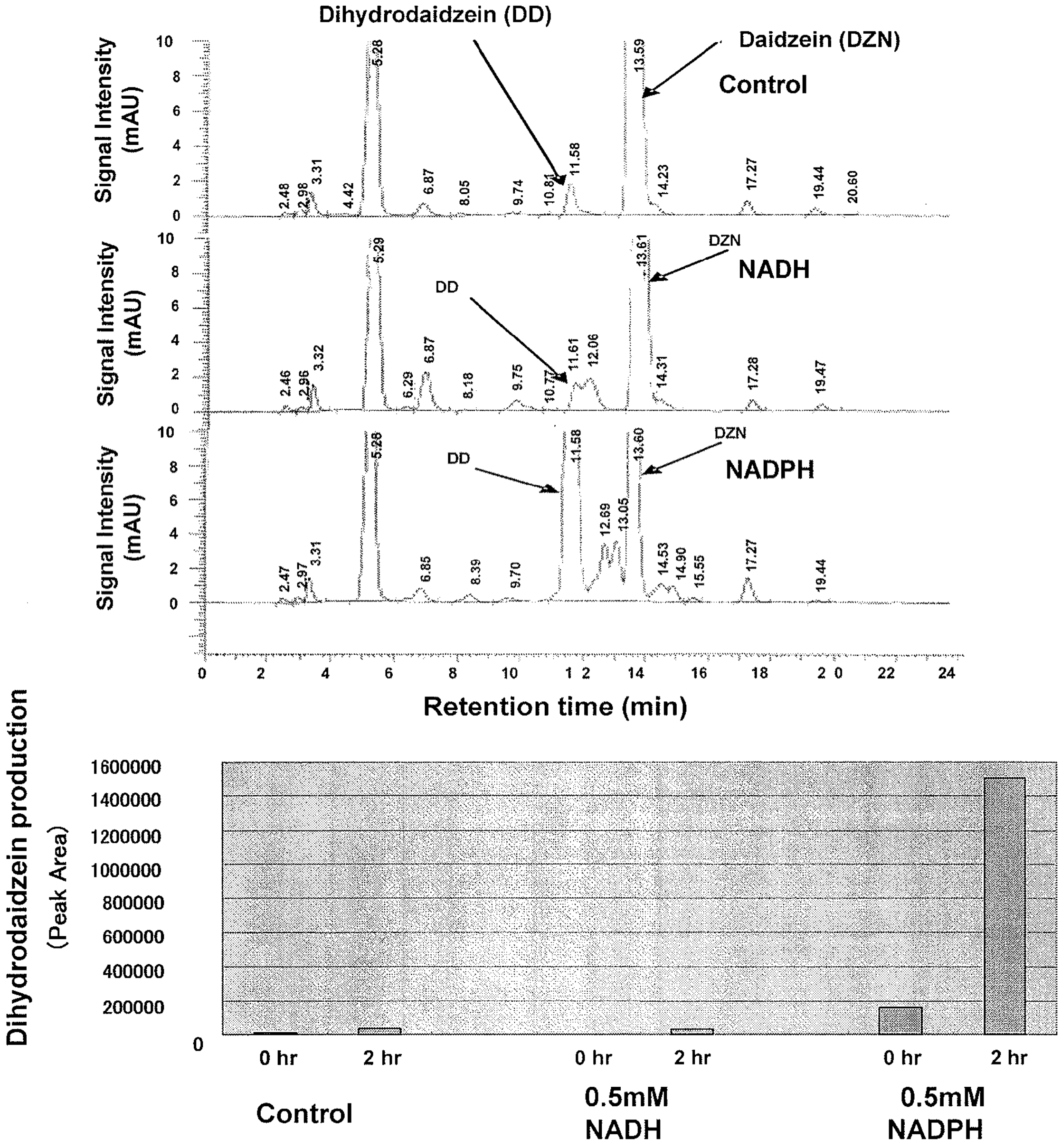
FIG. 1 shows the results of HPLC analysis in Example A1. Upper three chromatographs: Enzyme reaction products using no coenzyme (control), and NADH and NADPH as coenzymes. Bar chart: Peak areas corresponding to dihydrodaidzein in control (no coenzyme) and in samples using NADH and NADPH as coenzymes.
Figure 3:
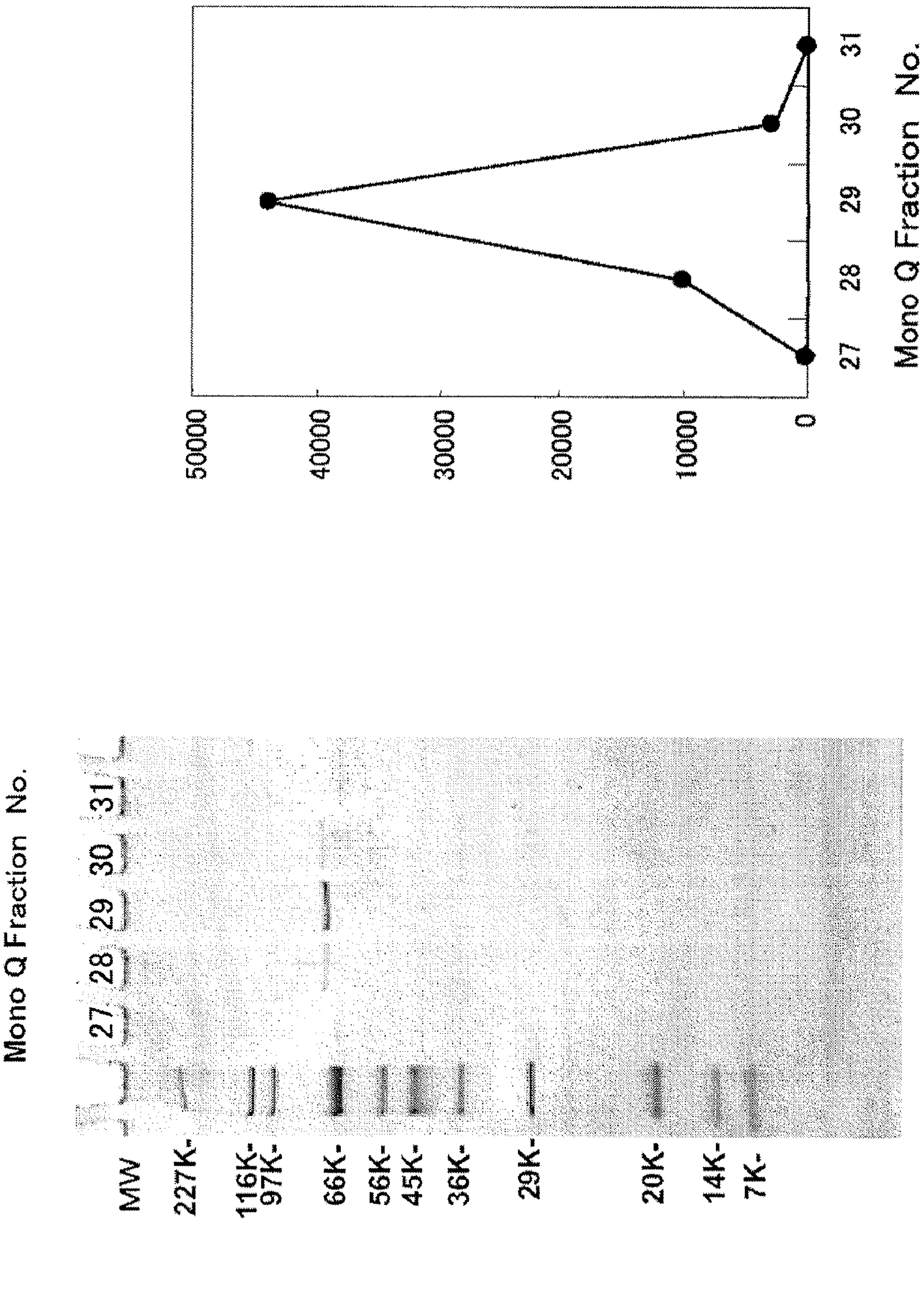
FIG. 3 shows the results of SDS-PAGE in Example A2 (left part), and the activity of dihydrodaidzein synthesizing enzyme of each fraction (right part). The enzyme activity is shown as a peak area corresponding to dihydrodaidzein using daidzein as a substrate. The SuperSep HG 10-20% (Wako Pure Chemical Industries, Ltd.) was used as an electrophoresis gel plate.
Figure 4:
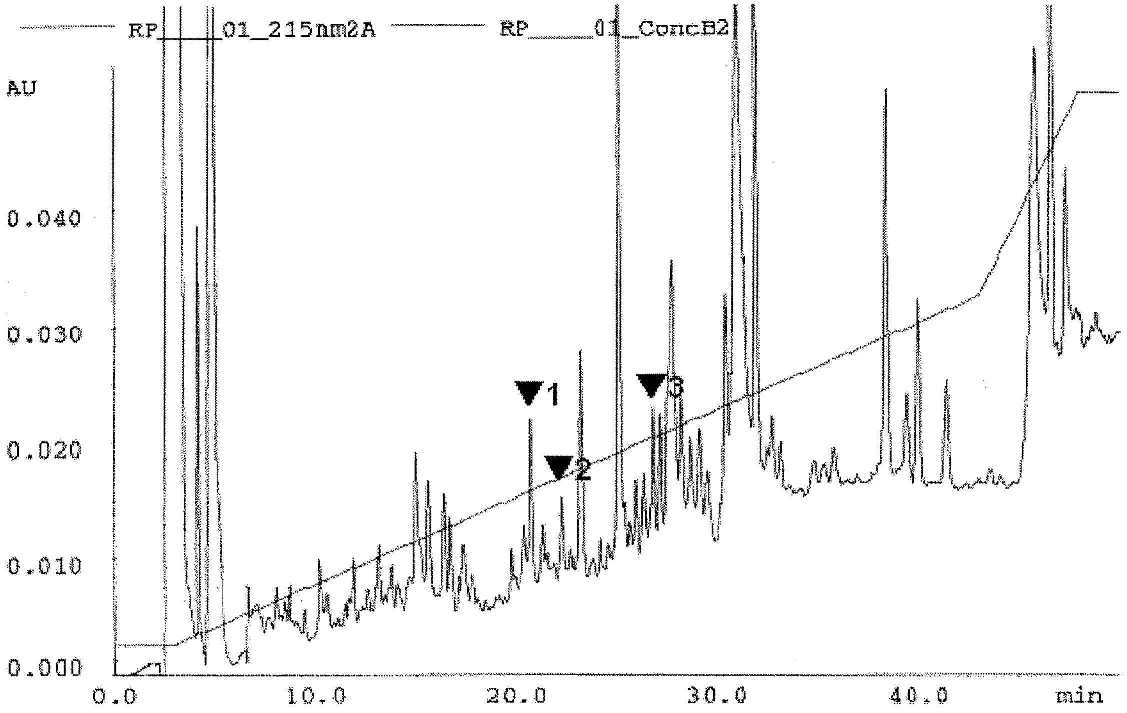
FIG. 4 shows the results of peptide mapping in Example A4, and amino acid sequences of peptides corresponding to peaks. The numbers next to the arrows ▼ in the upper HPLC analysis chart correspond to 1: FDEPVYPQAE, 2:ASRMVMDAVHEGYIAG, and 3: GYIGNLEVENRAIRMPM respectively.
Figure 5:
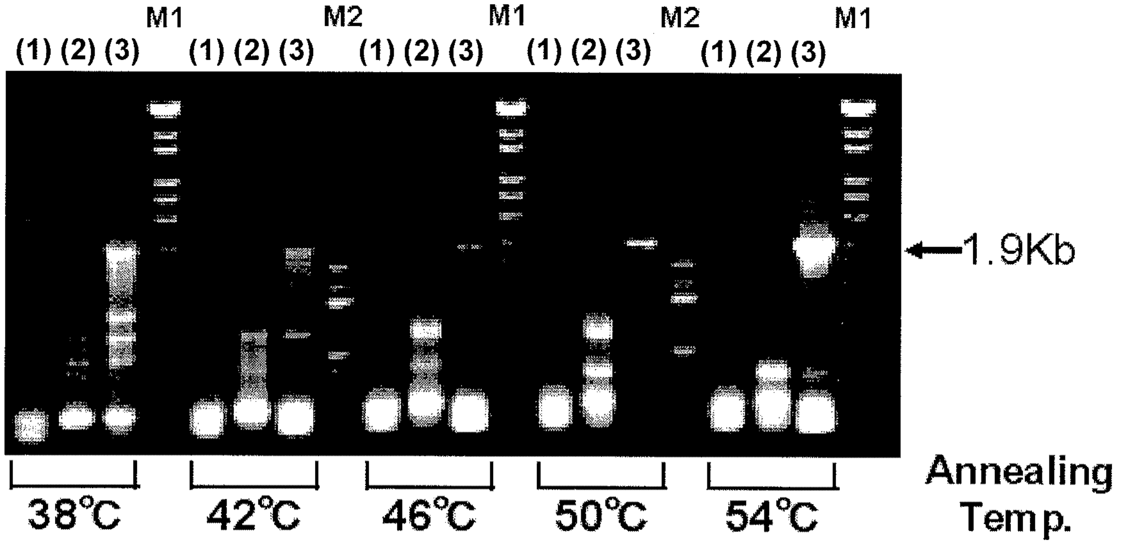
FIG. 5 shows the results of agarose electrophoresis of Denerative-PCR product in Example A5. (1) E1-N-terminal-31 and E1-internal-RP1, (2) E1-N-terminal-37 and E1-internal-RP1, (3) E1-N-terminal-F32 and E1-internal-RP1; marker M1: λ/Styl, M2: 100 bp Ladder
Figure 6:
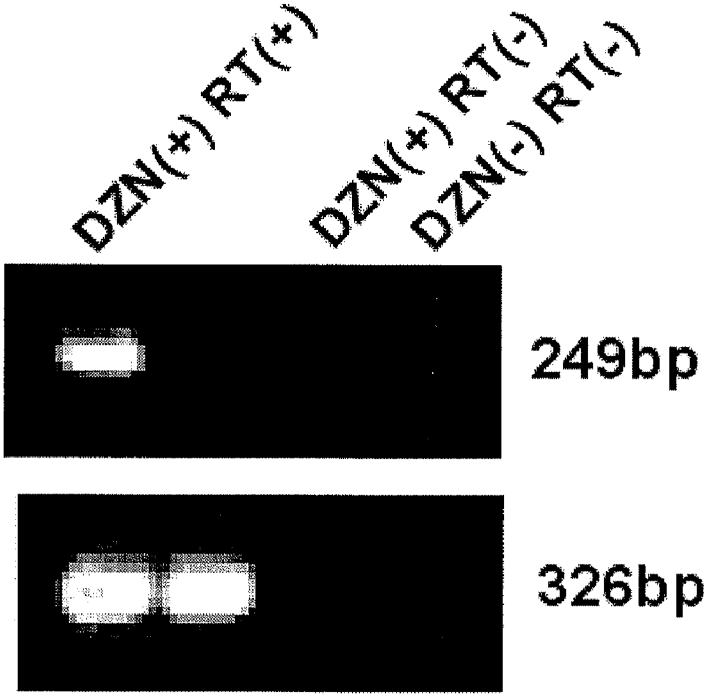
FIG. 6 shows the results of agarose electrophoresis of RT-PCR product in Example A7. Upper part: Dihydrodaidzein synthase; lower part: Ribosomal-RNA.
Figure 7:
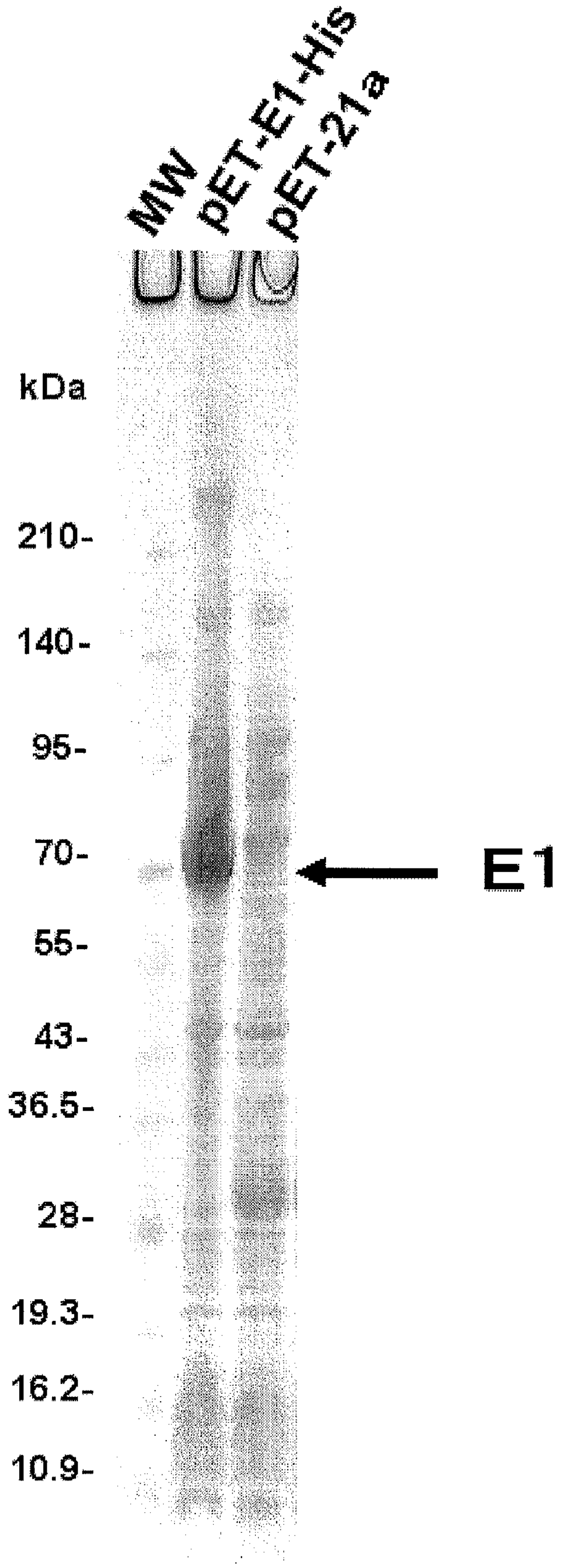
FIG. 7 shows the results of SDS-PAGE in Example A8.
Figure 8:
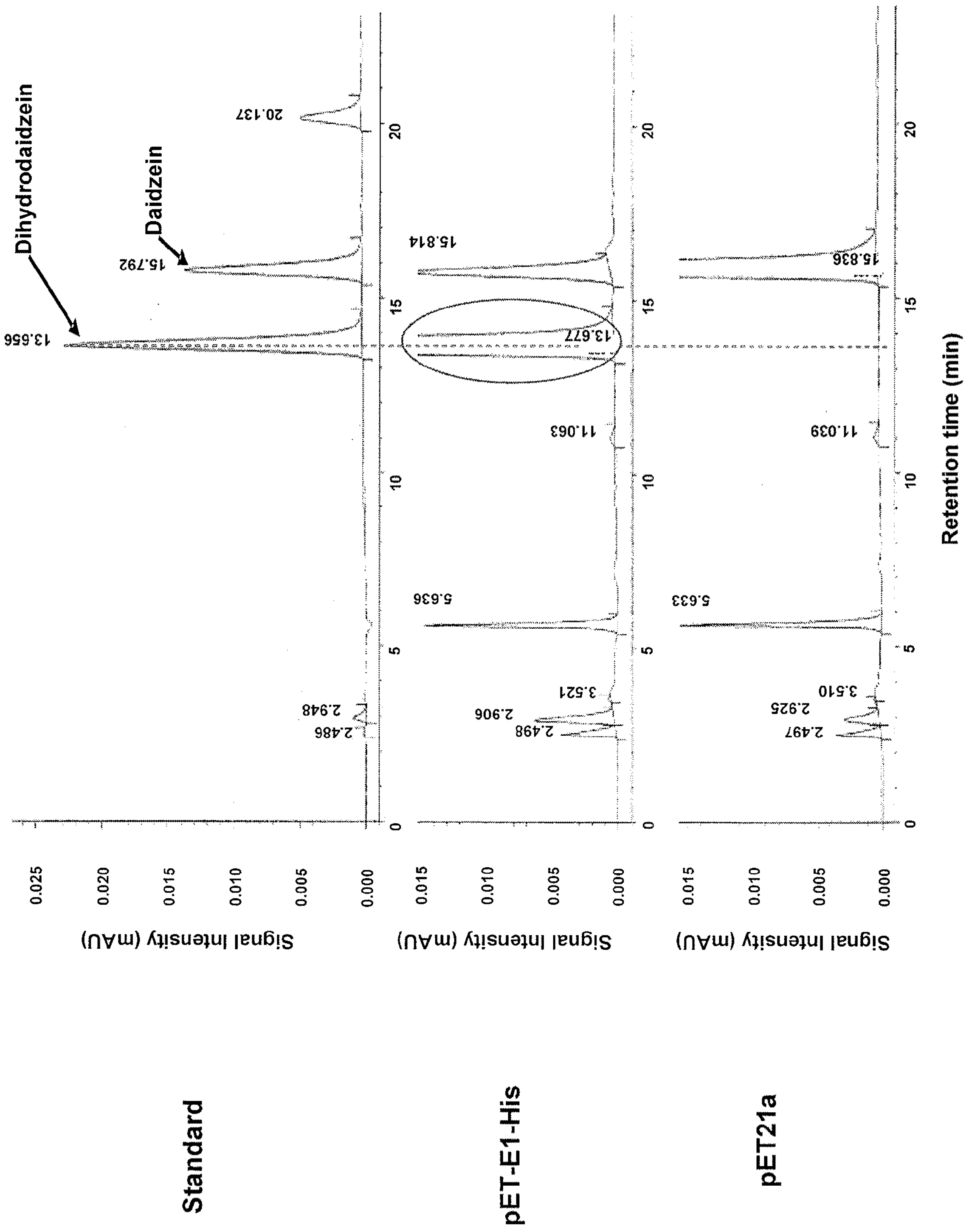
Figure 9:
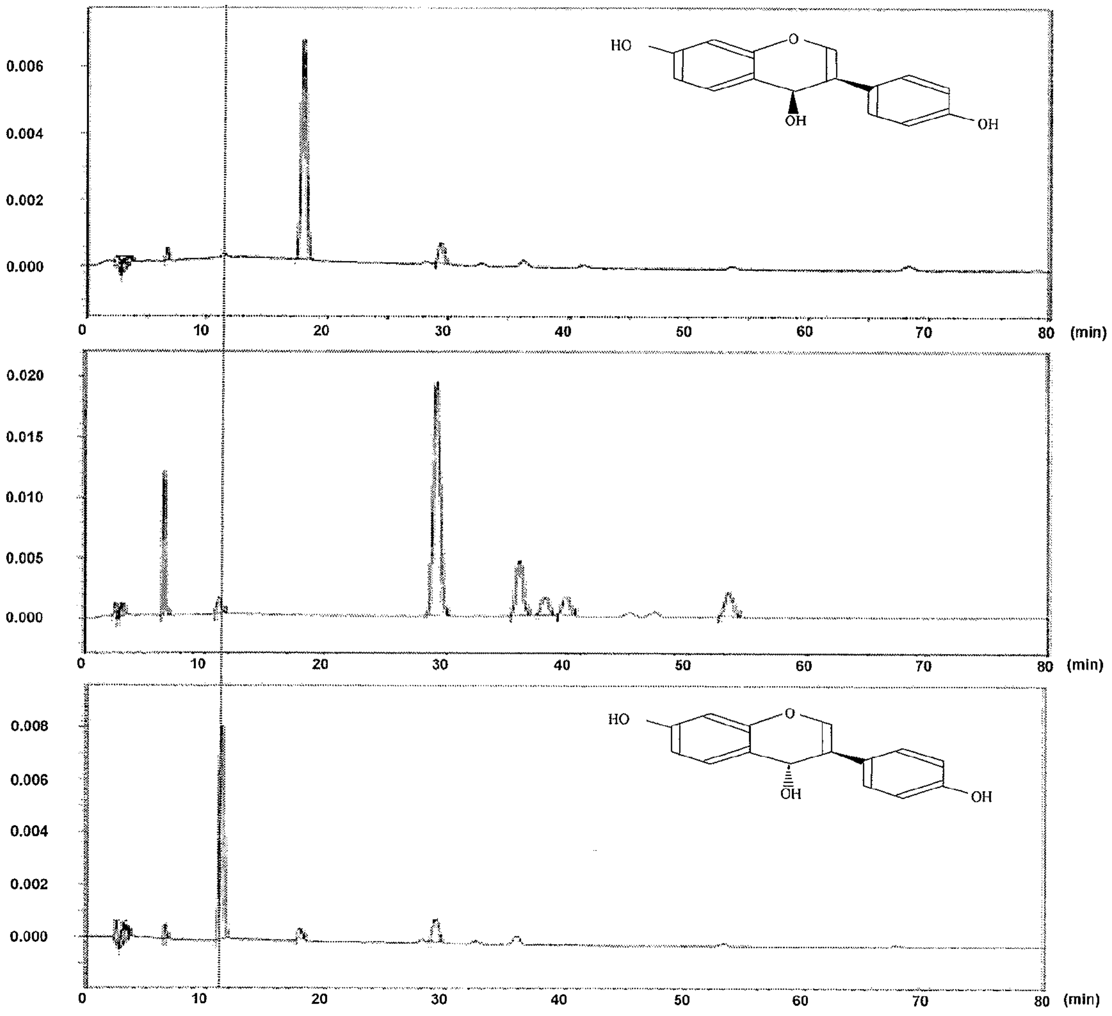
FIG. 9 shows the results of HPLC analysis in Example B1. Upper chart: Cis-tetrahydrodaidzein (REF-000312); middle chart: Enzyme reaction product using dihydrodaidzein as a substrate and disrupted cell material as an enzyme source; lower chart: Trans-tetrahydrodaidzein (REF-000313).
Figure 10:
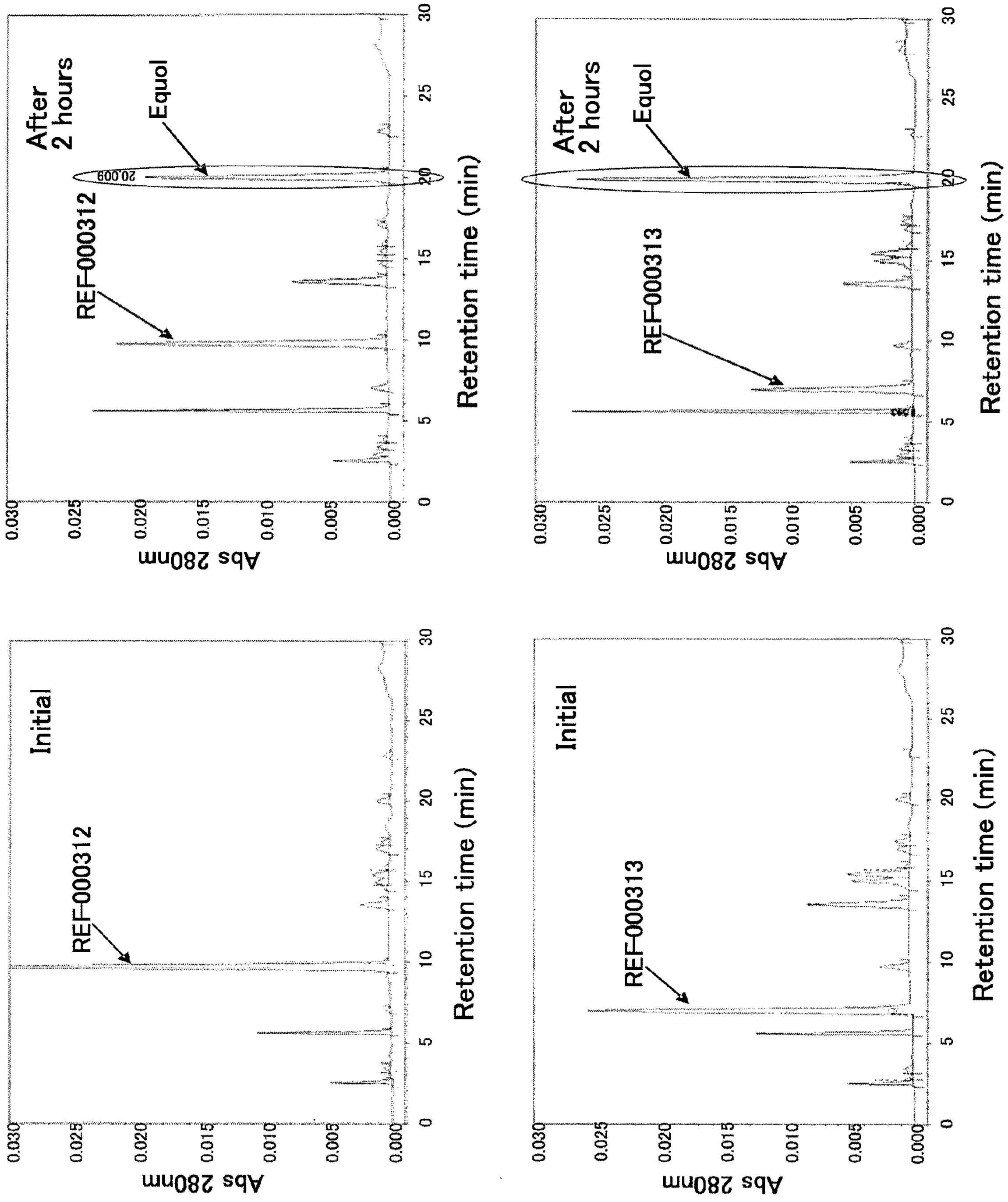
FIG. 10 shows the results of HPLC analysis in Example B1. Upper two charts: Enzyme reaction product using cis-tetrahydrodaidzein (REF-000312) as a substrate and disrupted cell material as an enzyme source; lower two charts: Enzyme reaction product using trans-tetrahydrodaidzein (REF-000313) as a substrate and disrupted cell material as an enzyme source.
Figure 11:
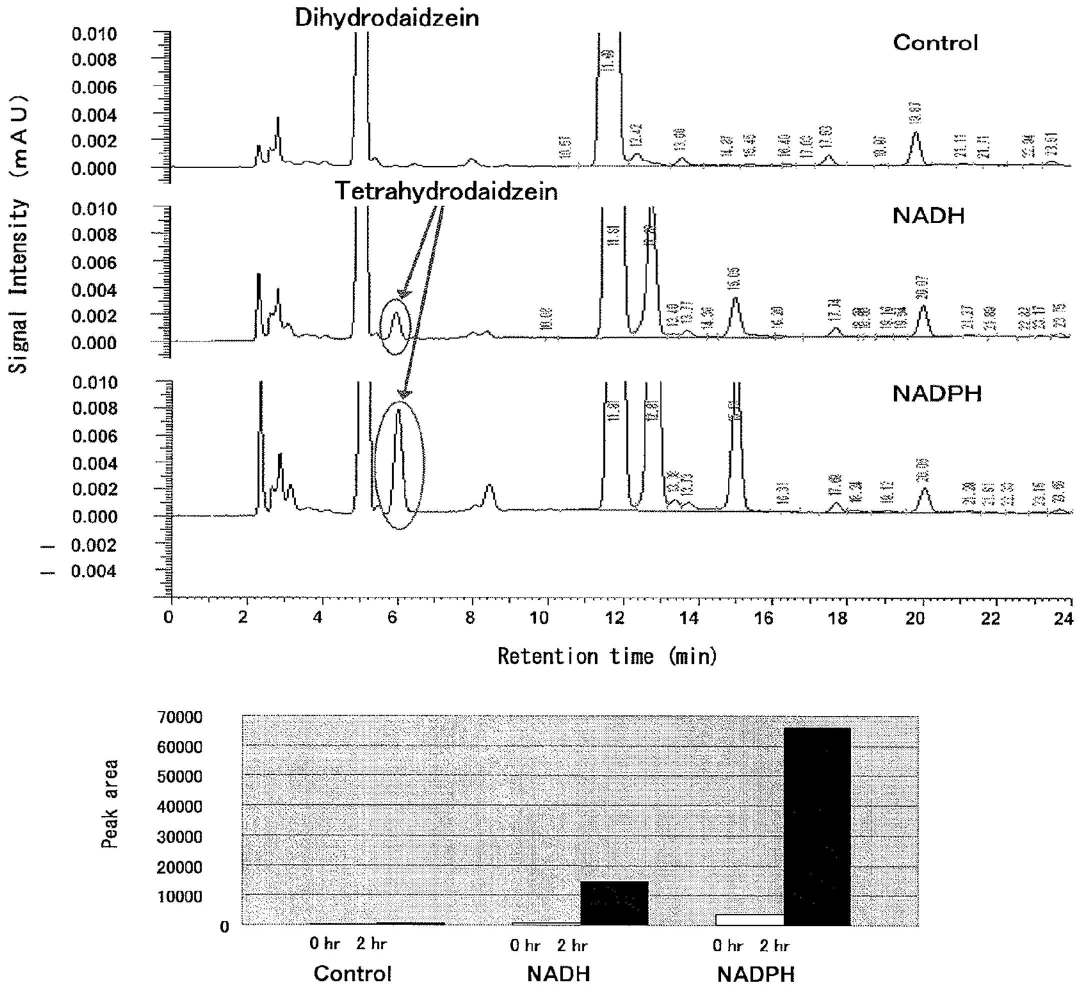
FIG. 11 shows the results of HPLC analysis in Example B2. Upper three charts: Enzyme reaction products using no coenzyme (control), and NADH and NADPH as coenzymes. Bar chart: Peak areas corresponding to tetrahydrodaidzein in control (no coenzyme) and in samples using NADH and NADPH as coenzymes.
Figure 12:
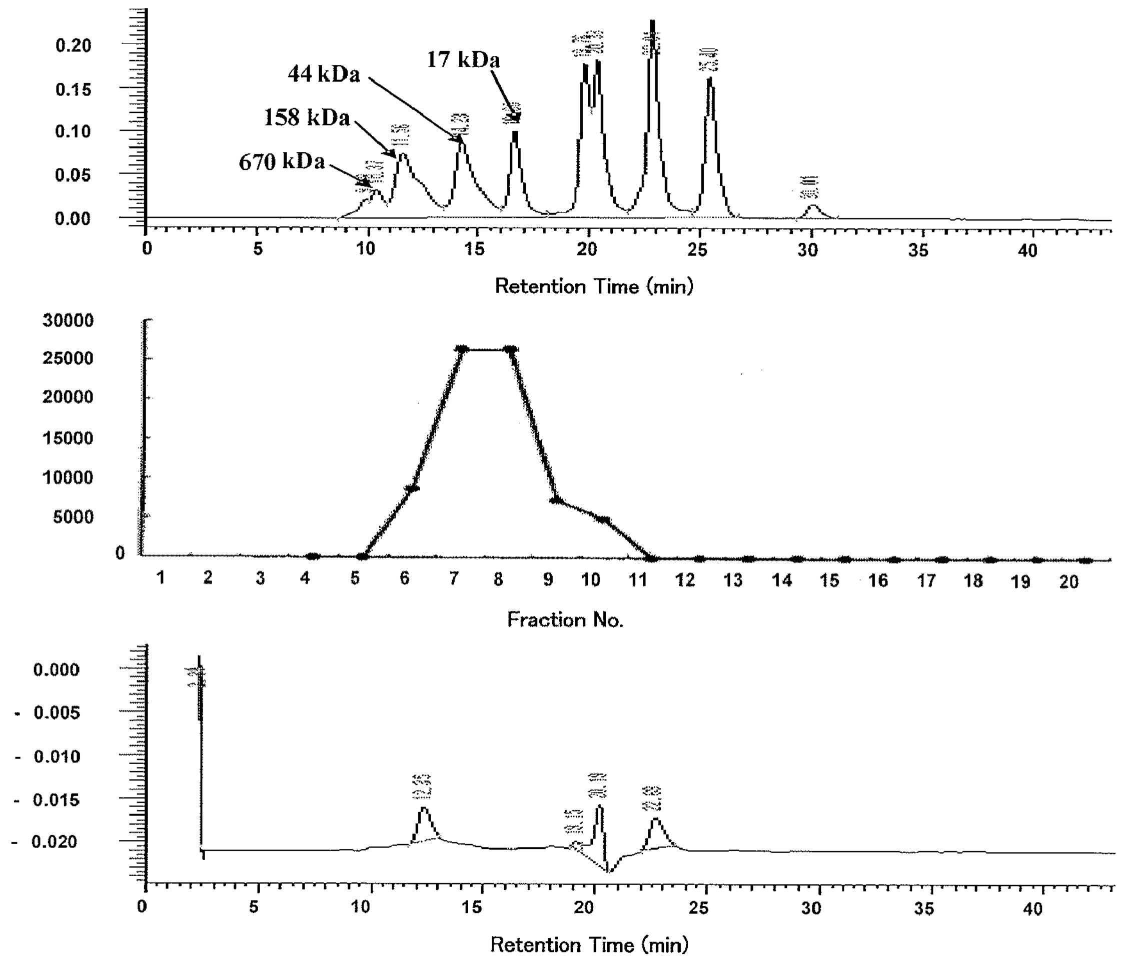
FIG. 12 shows the results of gel filtration HPLC analysis in Example B3. Upper graph: The results for standard protein; middle graph: Enzyme activity of each fraction shown as a peak area corresponding to the product tetrahydrodaidzein; lower graph: Absorption (280 nm) intensity corresponding to the protein of each fraction.
Figure 13:
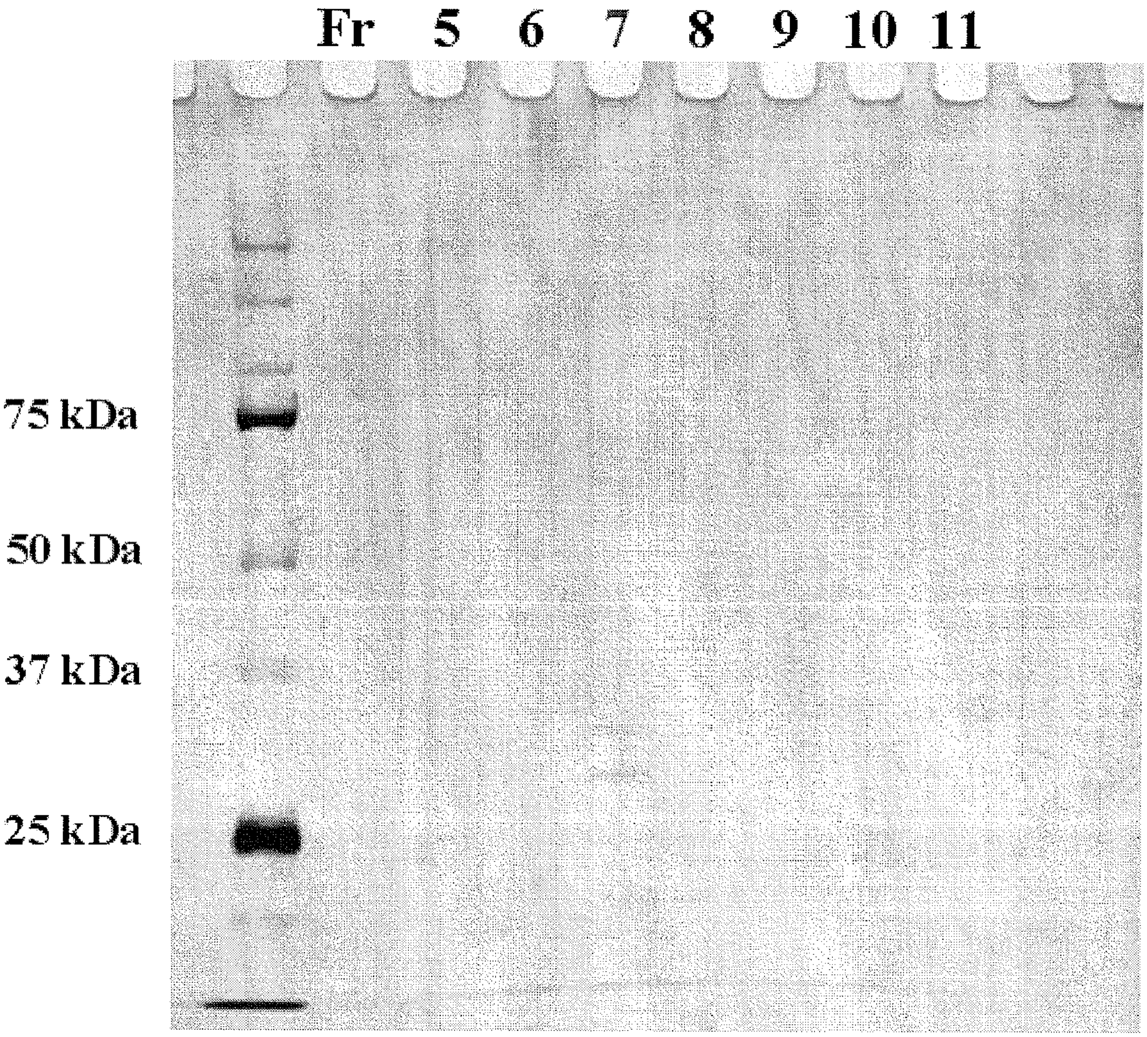
FIG. 13 shows the results of SDS-PAGE in Example B3.
Figure 14:
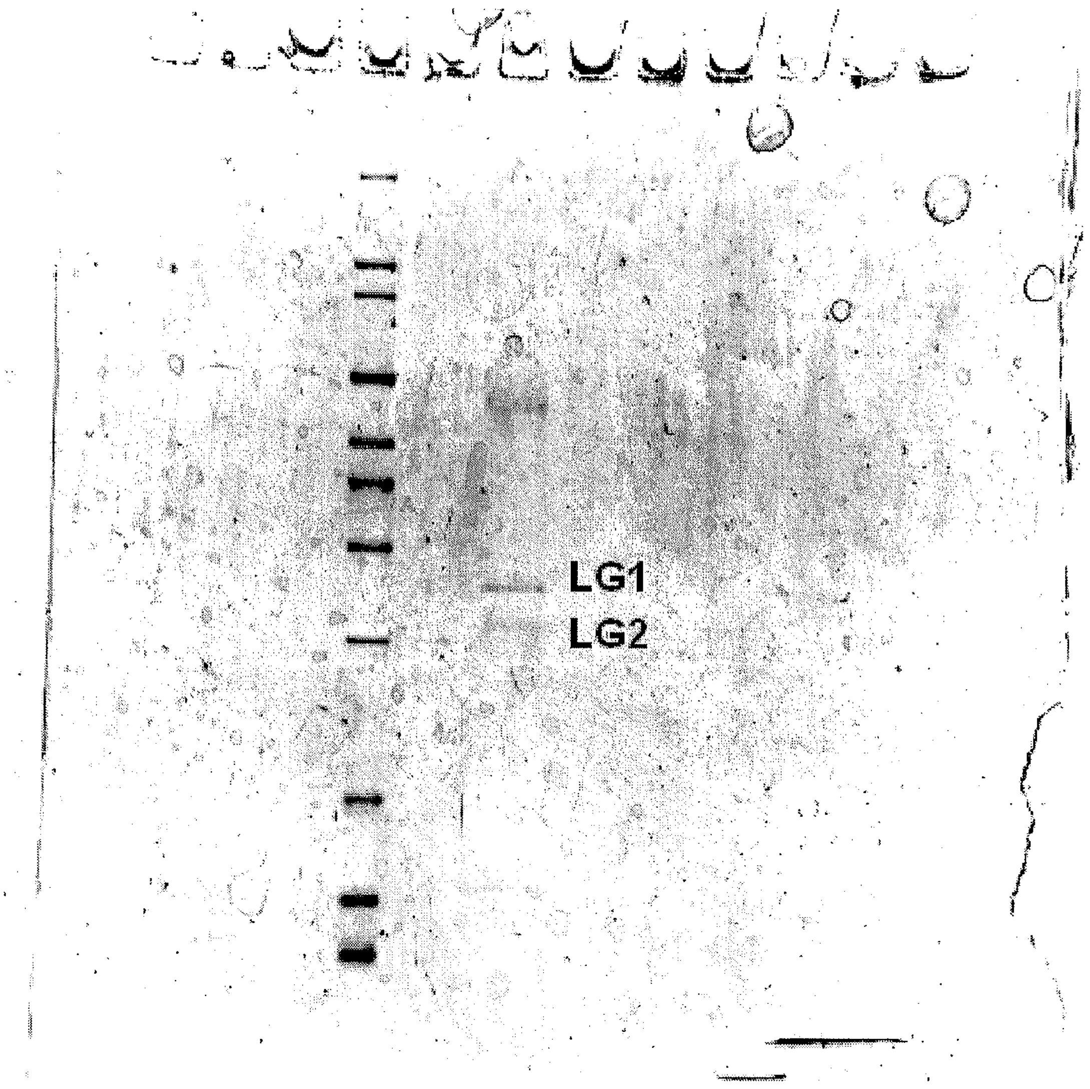
FIG. 14 shows the results of SDS-PAGE in Example B4.
Figure 15:
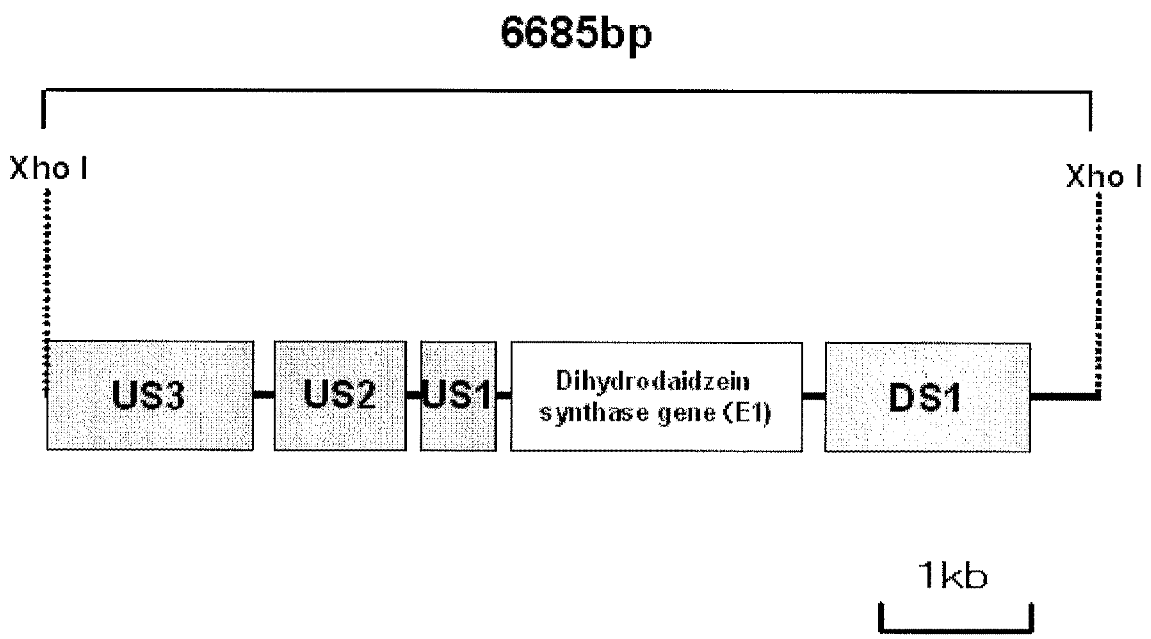
FIG. 15 shows a schematic illustration of a peripheral genome structure of dihydrodaidzein synthesizing (E1) enzyme gene determined in Example B5.
Figures 3, 16:
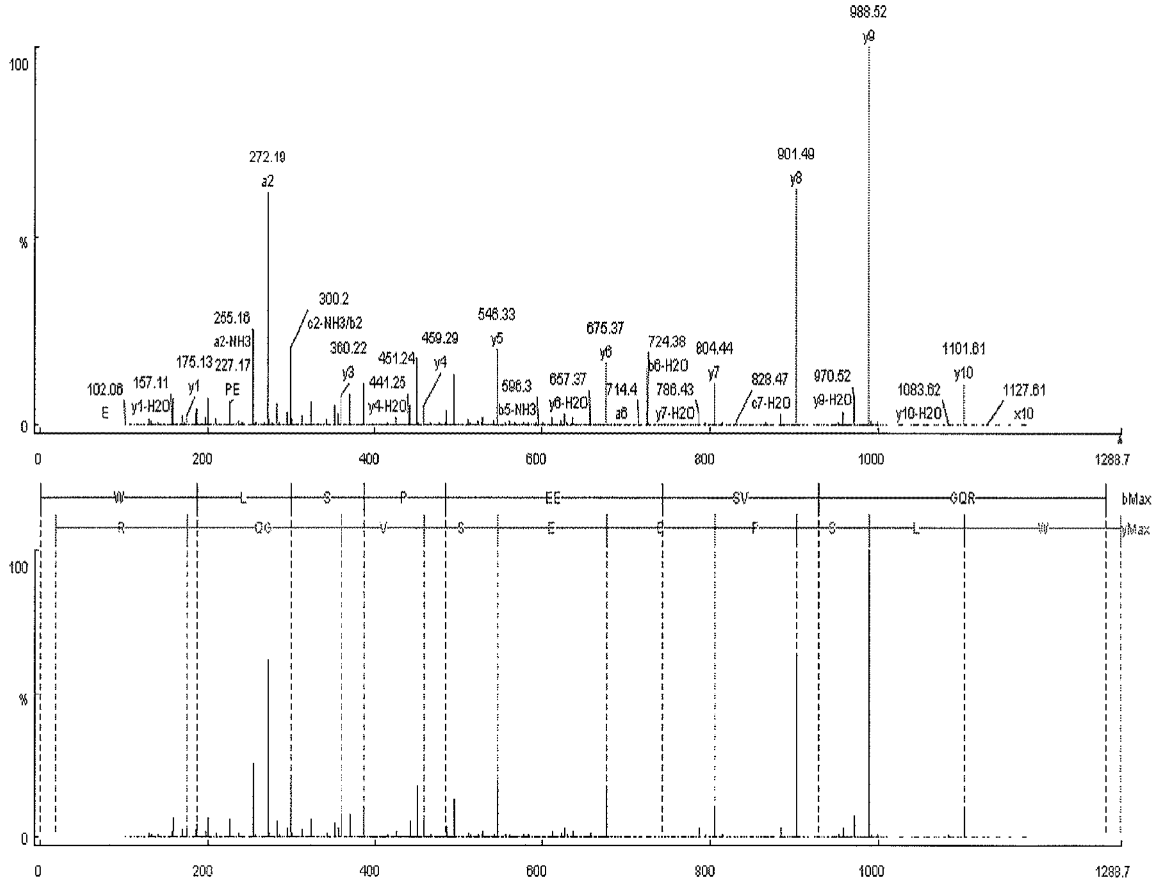
Figure 17:
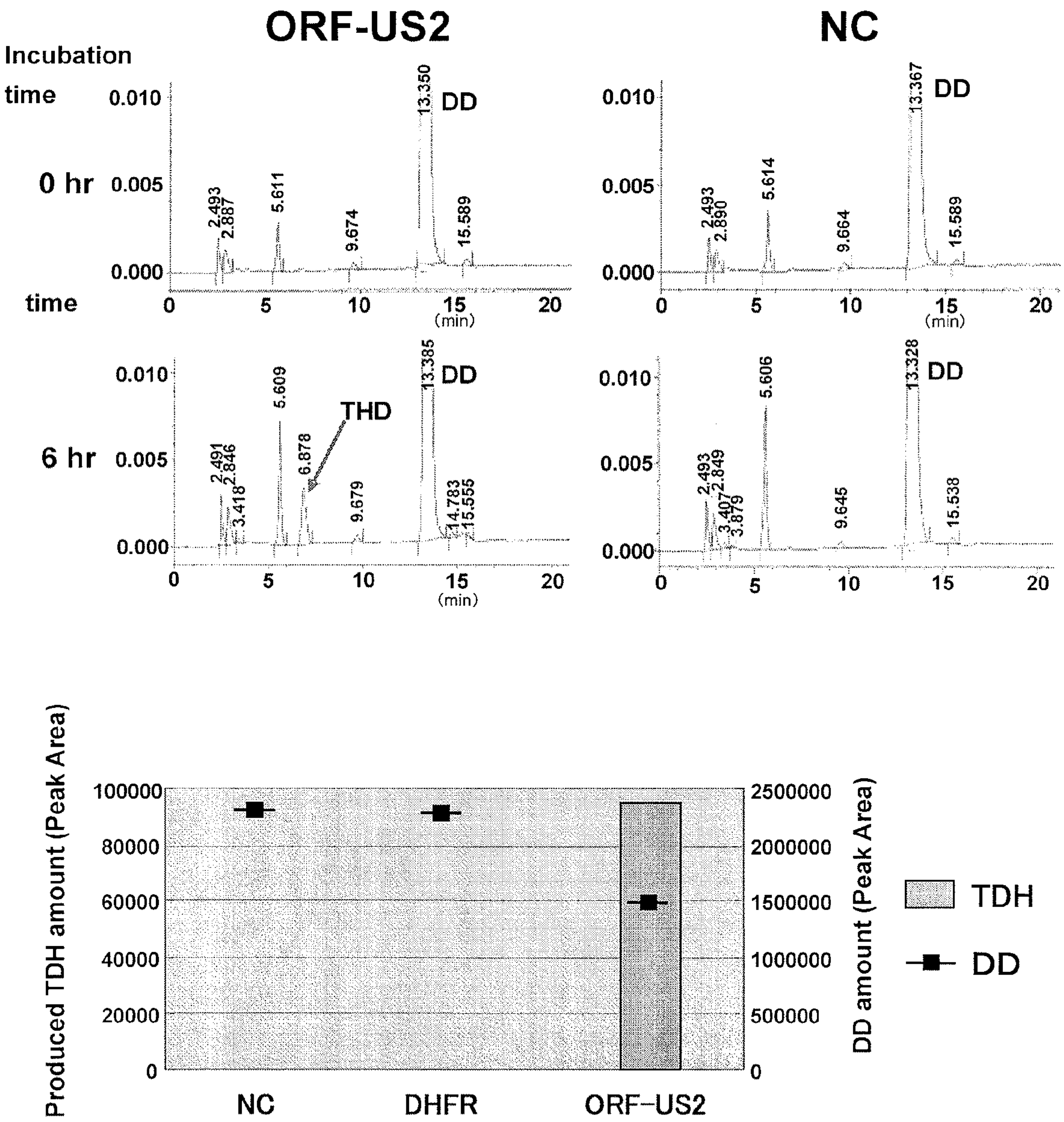
FIG. 17 shows the results of HPLC analysis in Example B7. Upper left charts: Enzyme reaction product using dihydrodaidzein as a substrate and an ORF-US2 polypeptide-expressing reaction mixture as an enzyme source (ORF-US2); upper right charts: Enzyme reaction product using a protein-free reaction mixture as an enzyme source (NC). Bar chart: Peak areas corresponding to dihydrodaidzein (DD) and tetrahydrodaidzein (THD) produced by enzyme reactions in NC (no protein synthesis), and in samples using DHFR (dihydrofolate reductase-expressing reaction mixture) and ORF-US2 (ORF-US2 polypeptide-expressing reaction mixture) as an enzyme source.
Figure 18:
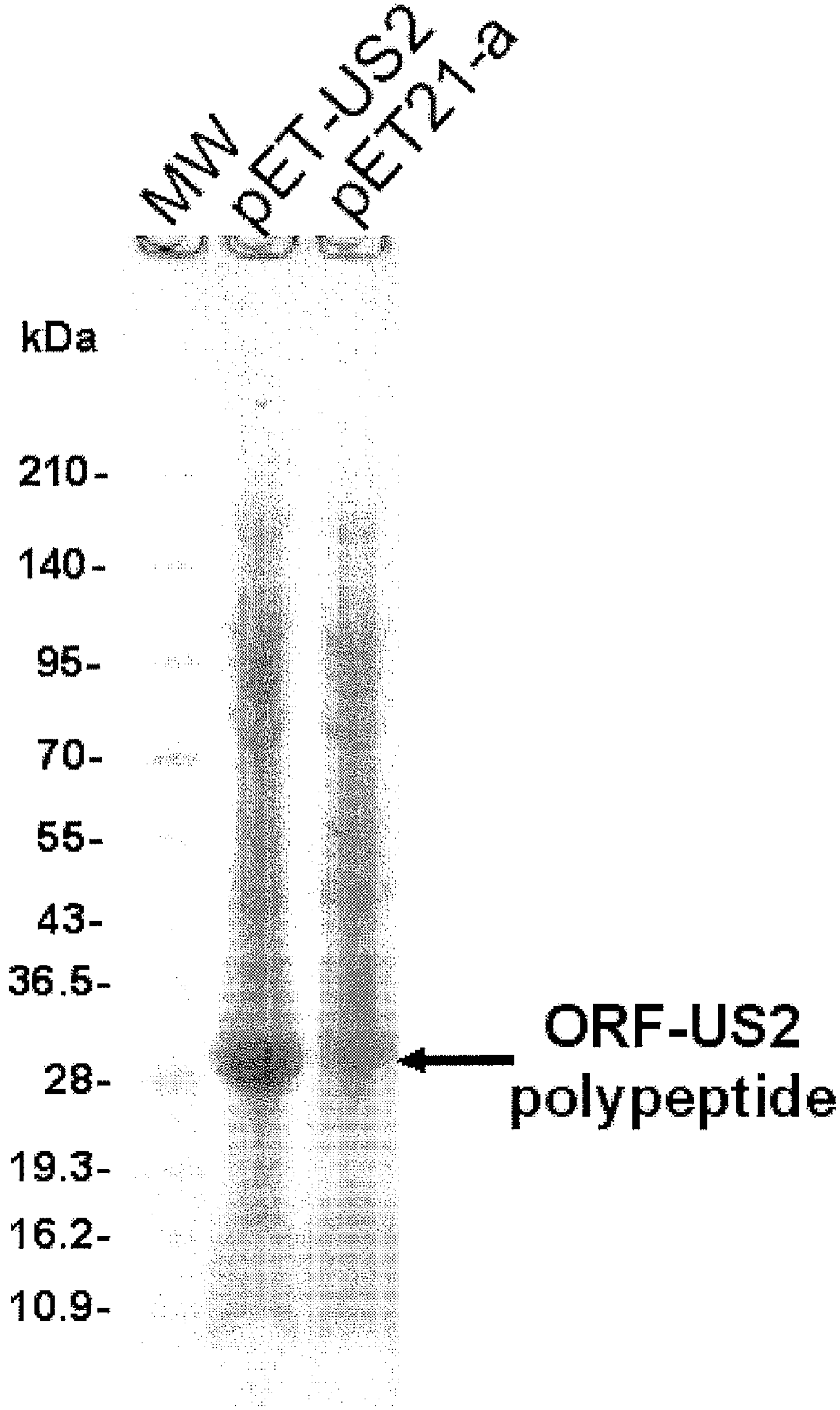
FIG. 18 shows the results of SDS-PAGE in Example B8.
Figure 20:
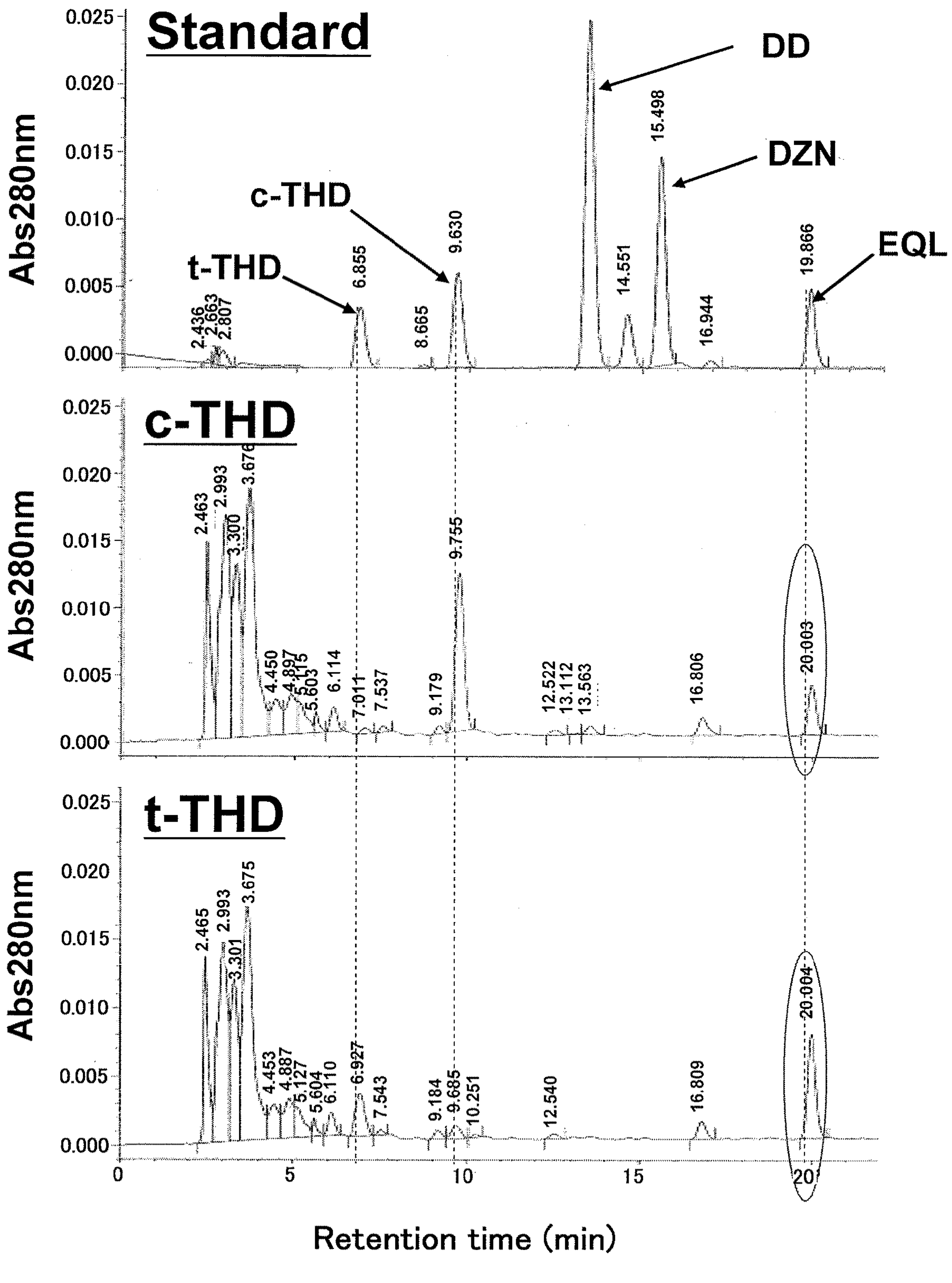
FIG. 20 shows the results of HPLC analysis in Example C1.
Figure 21:
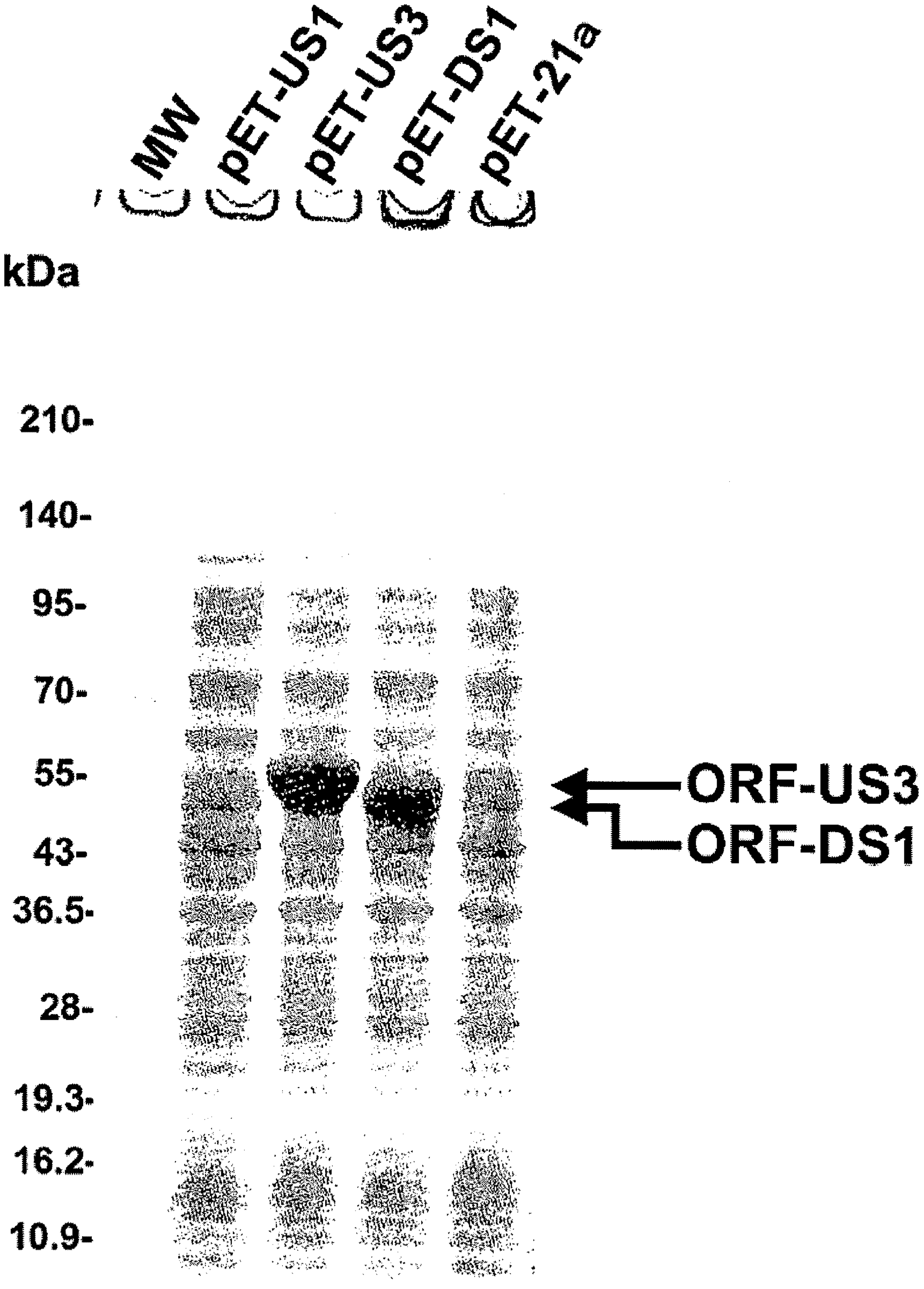
FIG. 21 shows the results of SDS-PAGE in Example C2.
Figure 22:
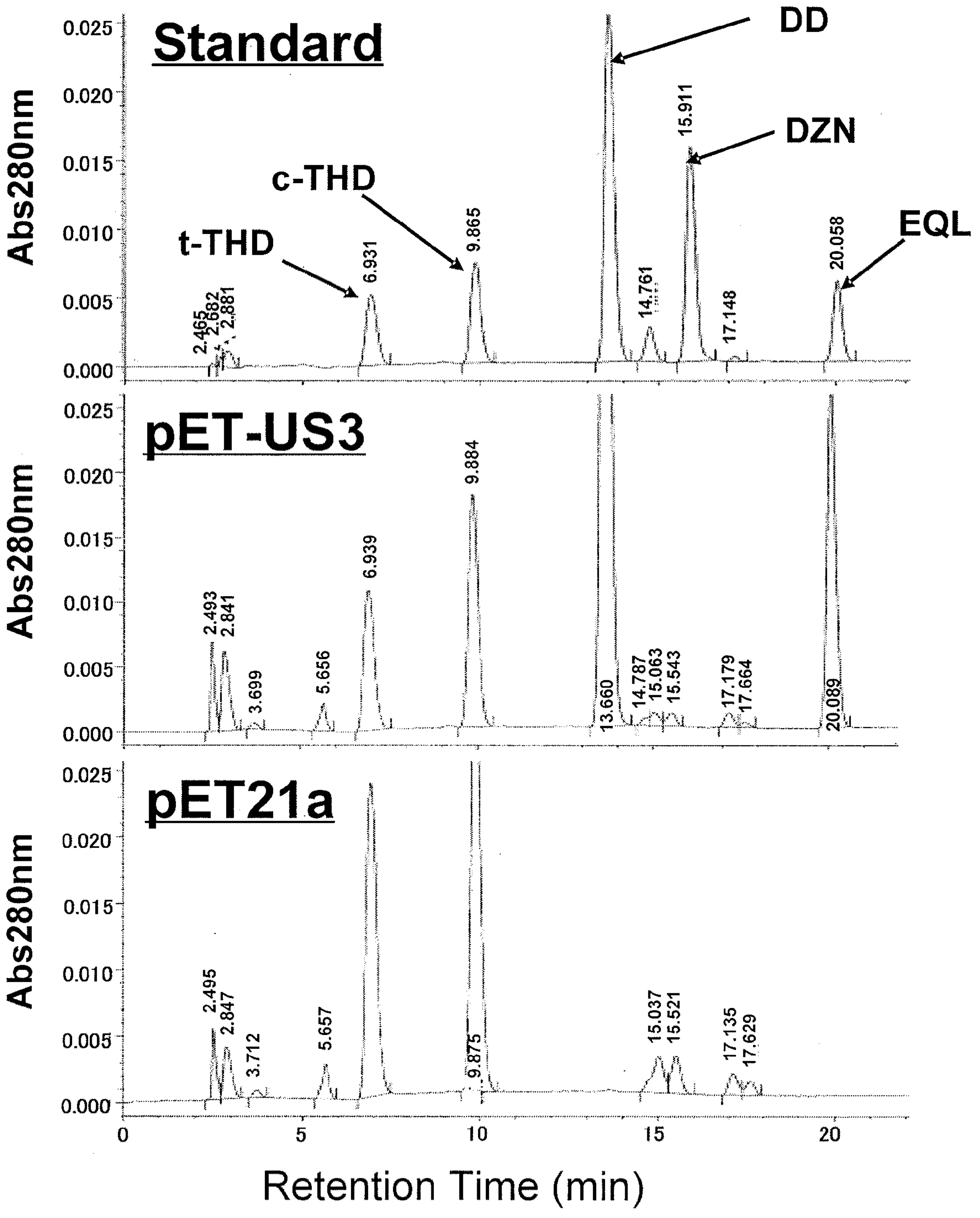
Figure 23:
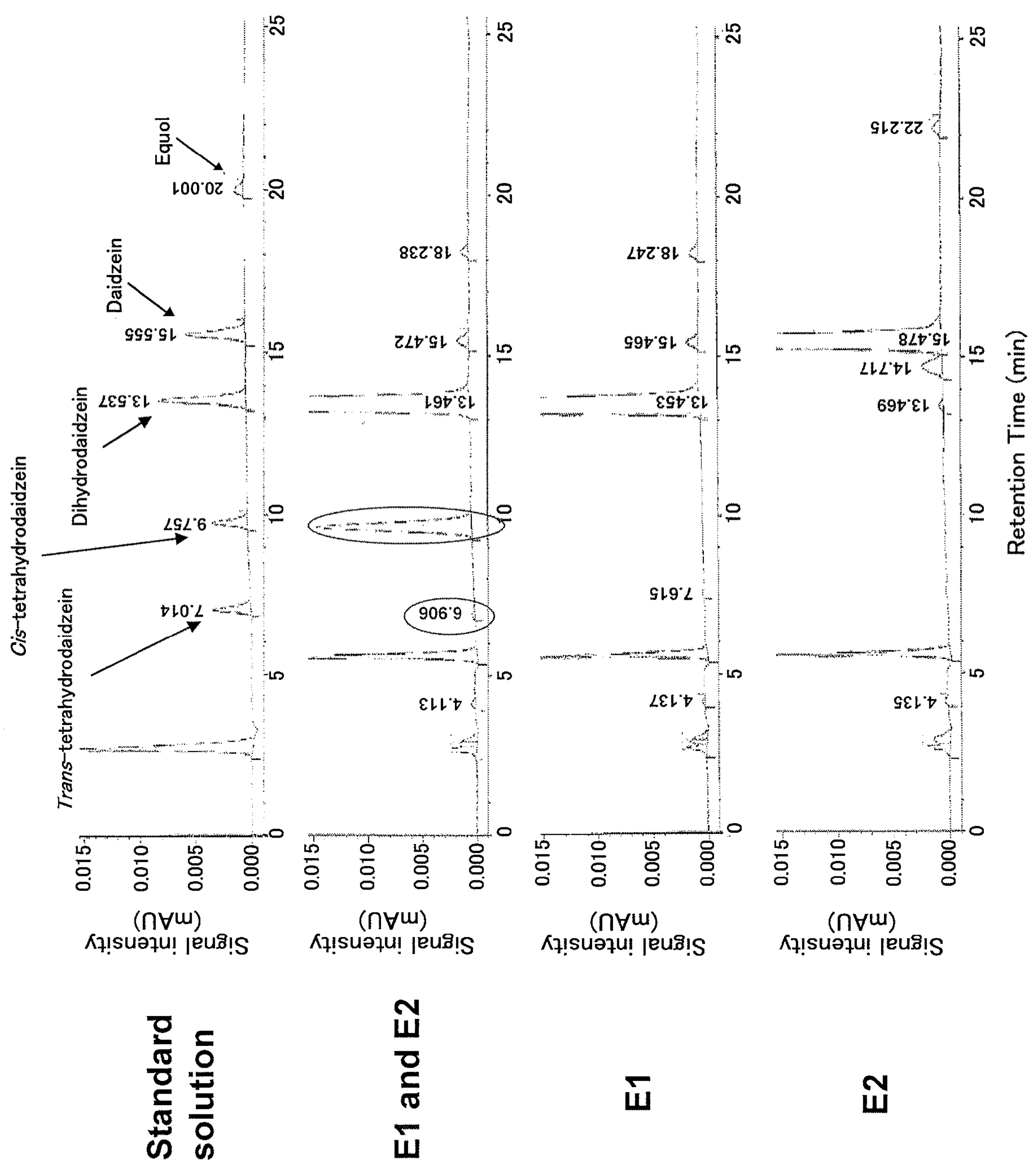
FIG. 23 shows the results of HPLC analysis in Example D2. First from the top: Standard; secand: E1 and E2; third: E1; forth part: E2.
Figure 24:
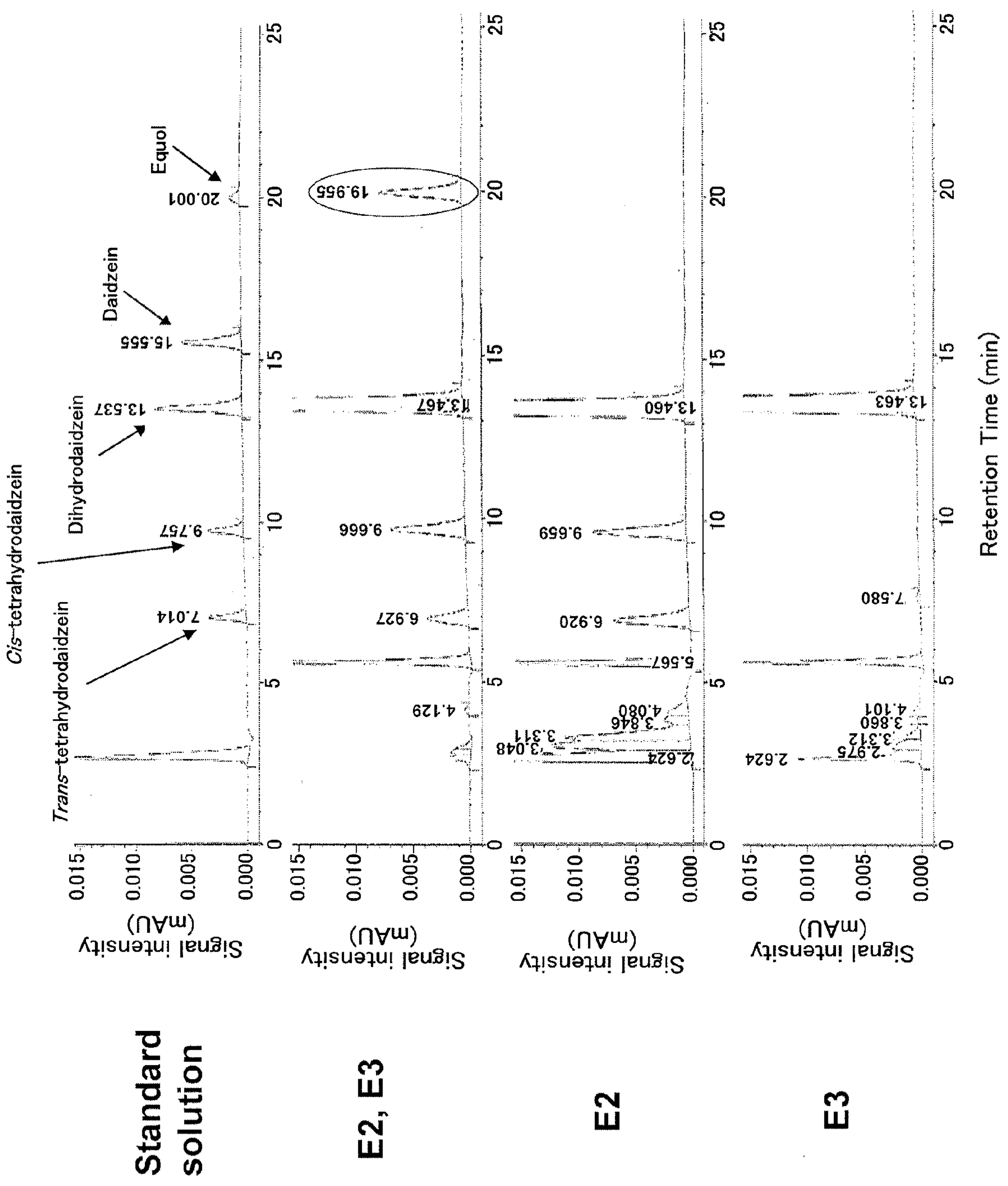
FIG. 24 shows the results of HPLC analysis in Example D3. First from the top: Standard; secand: E2 and E3; third: E2; forth: E3.
Figure 25:
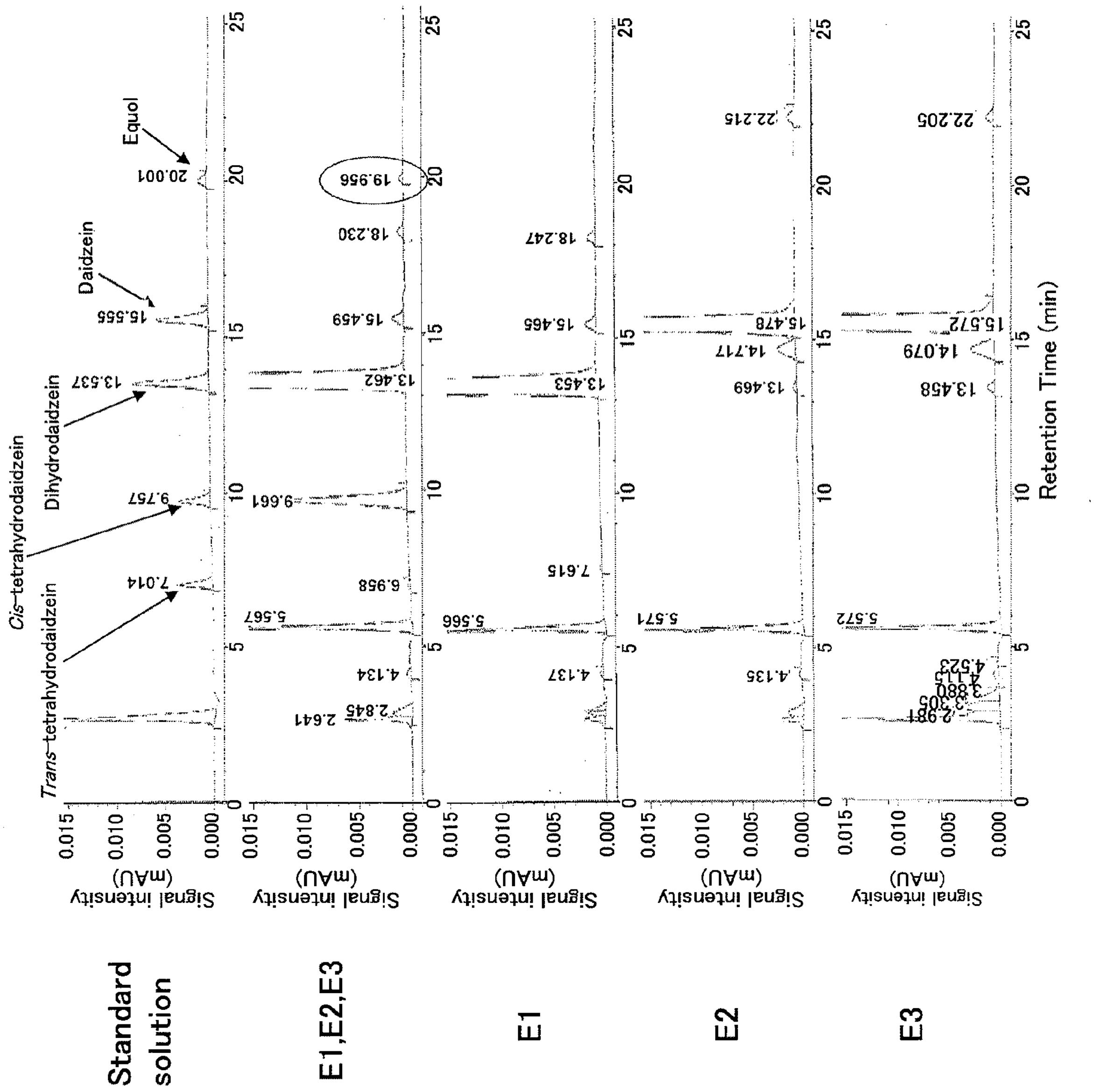
FIG. 25 shows the results of HPLC analysis in Example D4. First from the top: Standard; secand: E1, E2 and E3; third: E1; forth: E2; fifth part: E3.
Figure 26:
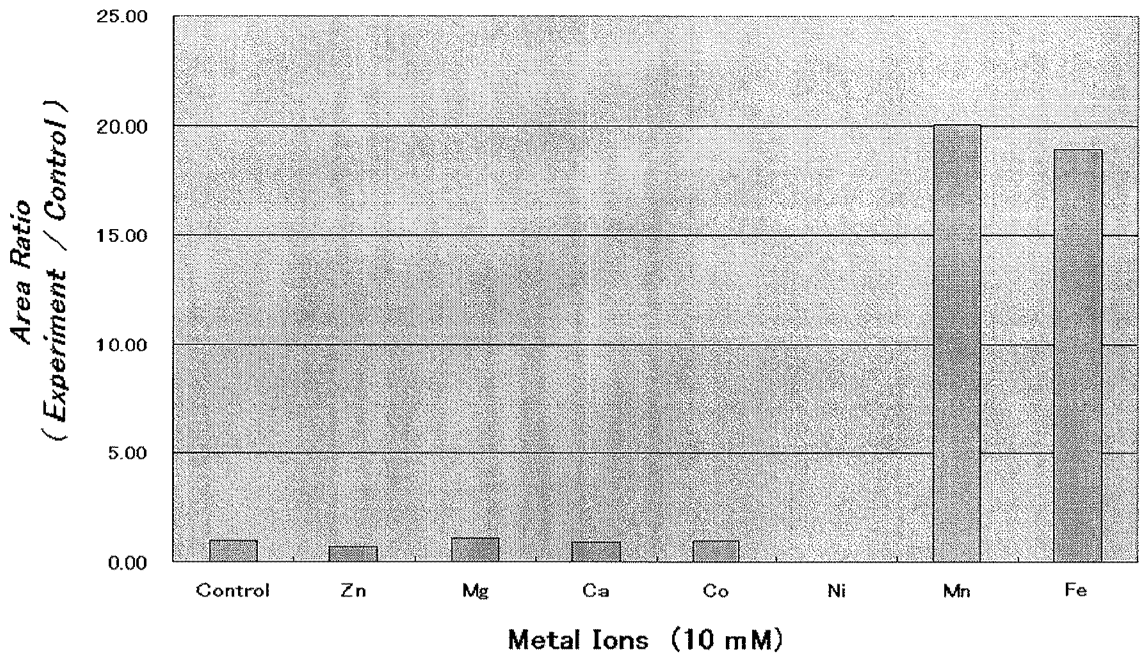
FIG. 26 shows effects of metal ions on E1 enzyme activity.
Figure 29:
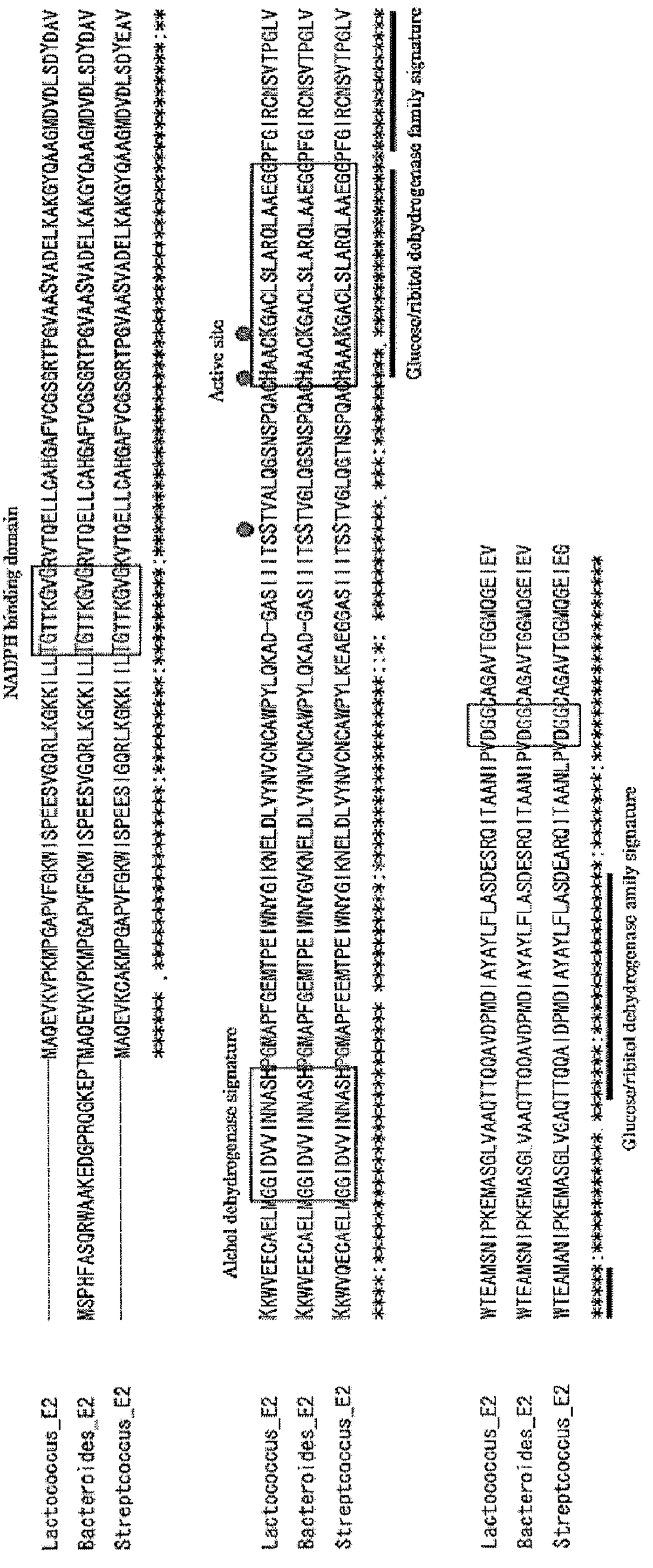
FIG. 29 shows the alignment of amino acid sequences of SEQ ID NOs: 13, 14 and 15.

SEQ ID NO: 23 is the base sequence of primer E1-N-terminal-31.

SEQ ID NO: 24 is the base sequence of primer E1-N-terminal-37.

SEQ ID NO: 25 is the base sequence of primer E1-N-terminal-F32.

SEQ ID NO: 26 is the base sequence of primer E1-internal-RP1.

SEQ ID NO: 27 is the base sequence of primer pUC19-FP-1.

SEQ ID NO: 28 is the base sequence of primer pUC19-RP-1.

SEQ ID NO: 29 is the base sequence of primer pUC19-FP-2.

SEQ ID NO: 30 is the base sequence of primer pUC19-RP-2.

SEQ ID NO: 31 is the base sequence of primer E1-RACE-N-P1.

SEQ ID NO: 32 is the base sequence of primer E1-RACE-RP2-1.

SEQ ID NO: 33 is the base sequence of primer E1-RACE-N-P2.

SEQ ID NO: 34 is the base sequence of primer E1-RACE-RP2-2.

SEQ ID NO: 35 is the base sequence of primer E1-conf-NP.

SEQ ID NO: 36 is the base sequence of primer E1-conf-CP.

SEQ ID NO: 37 is the base sequence of primer E1-FP.

SEQ ID NO: 38 is the base sequence of primer E1-RP.

SEQ ID NO: 39 is the base sequence of primer Gar-16S-Ribo-FP.

SEQ ID NO: 40 is the base sequence of primer Gar-16S-Ribo-RP.

SEQ ID NO: 41 is the base sequence of primer exp.E1 pet F Nde.

SEQ ID NO: 42 is the base sequence of primer exp. E1 pet His.

SEQ ID NO: 43 is the base sequence of primer RACE-N-P3-1.

SEQ ID NO: 44 is the base sequence of primer RACE-N-P3-2.

SEQ ID NO: 45 is the base sequence of primer E1-Bub-N-P1.

SEQ ID NO: 46 is the base sequence of primer E1-Bub-N-P2.

SEQ ID NO: 47 is the base sequence of primer RACE-C-P3-1.

SEQ ID NO: 48 is the base sequence of primer RACE-C-P3-2.

SEQ ID NO: 49 is the base sequence of primer E1-Bub-C-P1.

SEQ ID NO: 50 is the base sequence of primer E1-Bub-C-P2.

SEQ ID NO: 57 is the base sequence of primer E2-invitroTS-FP.

SEQ ID NO: 58 is the base sequence of primer E2-invitroTS-RP.

SEQ ID NO: 59 is the base sequence of primer Universal-Primer.

SEQ ID NO: 60 is the base sequence of primer exp.US2 pet F Nde.

SEQ ID NO: 61 is the base sequence of primer exp.US2 pet.

SEQ ID NO: 62 is the base sequence of primer exp.US3 F.

SEQ ID NO: 63 is the base sequence of primer exp.US3 R.

SEQ ID NO: 64 is the base sequence of primer exp.US1 F.

SEQ ID NO: 65 is the base sequence of primer exp.US1 R.

SEQ ID NO: 66 is the base sequence of primer exp.DS1 F.

SEQ ID NO: 67 is the base sequence of primer exp.DS1 R.

The invention claimed is:

1. An isolated polypeptide comprising an amino acid sequence having at least 80% amino acid sequence identity to the amino acid sequence of SEQ ID NO: 13, and wherein said polypeptide has an activity of synthesizing equol using tetrahydrodaidzein as a substrate.

2. A process for producing equol, comprising having the polypeptide of claim 1 act on tetrahydrodaidzein.

3. The isolated polypeptide of claim 1, wherein said amino acid sequence having at least 80% amino acid sequence identity to the amino acid sequence of SEQ ID NO: 13 has at least 85% amino acid sequence identity to the amino acid sequence of SEQ ID NO: 13.

4. The isolated polypeptide of claim 1, wherein said amino acid sequence having at least 80% amino acid sequence identity to the amino acid sequence of SEQ ID NO: 13 has at least 90% amino acid sequence identity to the amino acid sequence of SEQ ID NO: 13.

5. The isolated polypeptide of claim 1, wherein said amino acid sequence having at least 80% amino acid sequence identity to the amino acid sequence of SEQ ID NO: 13 has at least 95% amino acid sequence identity to the amino acid sequence of SEQ ID NO: 13.

* * * * *

UNITED STATES PATENT AND TRADEMARK OFFICE

CERTIFICATE OF CORRECTION

| | | | |
|---|---|---|---|
| PATENT NO. | : | 8,399,232 B2 | Page 1 of 1 |
| APPLICATION NO. | : | 12/810742 | |
| DATED | : | March 19, 2013 | |
| INVENTOR(S) | : | Shimada et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 283 days.

Signed and Sealed this
First Day of September, 2015

Michelle K. Lee

Michelle K. Lee
*Director of the United States Patent and Trademark Office*

SEQUENCE LISTING

<160> NUMBER OF SEQ ID NOS: 69

<210> SEQ ID NO 1
<211> LENGTH: 644
<212> TYPE: PRT
<213> ORGANISM: Lactococcus garvieae

<400> SEQUENCE: 1

```
Met Lys Asn Lys Phe Tyr Pro Lys Thr Phe Glu Arg Gly Tyr Ile Gly
1               5                   10                  15

Asn Leu Glu Val Glu Asn Arg Ala Ile Arg Met Pro Met Gly Thr Glu
            20                  25                  30

Leu Gly Asn Pro Asp Gly Ser Pro Ser Trp Ala Ser Leu Lys Ala Tyr
        35                  40                  45

Ala Glu Ala Ala Asp Gly Gly Thr Gly Ile Val Phe Met Asp Asn Ala
    50                  55                  60

Gly Val Thr Gln Phe His His Val Gly Leu Ser Leu Ala Ser Asp Asn
65                  70                  75                  80

Tyr Ile Gly Pro Met Ser Val Leu Ala Lys Thr Ile Lys Gln His Gly
                85                  90                  95

Ala Ile Pro Gly Leu Gln Ile Val His Pro Gly Arg Asp Ala Ala Phe
            100                 105                 110

Val Arg Gly Asp Asp Leu Ile Ser Ser Ser Arg Ile Gln Trp Glu Pro
        115                 120                 125

Trp Tyr Glu Asn Gly Gly Ala Val Pro Arg Glu Leu Thr Ile Glu Glu
    130                 135                 140

Ile His Asp Phe Val Gly Tyr Phe Gly Asp Cys Ala Leu Arg Ala Gln
145                 150                 155                 160

Thr Ala Gly Phe Glu Ile Val Asp Val His Ala Ala Cys Gly Val Leu
                165                 170                 175

Leu Ser Asn Phe Leu Ser Pro Arg Asn Asn Thr Arg Asn Asp Met Tyr
            180                 185                 190

Gly Gly Ser Leu His Asn Arg Ala Arg Phe Leu Leu Glu Val Ile Arg
        195                 200                 205

Asp Ile Lys Lys Lys Cys Pro Asn Leu Pro Leu Ala Ile Arg Leu Ser
    210                 215                 220

Gly Ile Asp Phe Glu Pro Asp Gly Ile Thr Ile Glu Glu Thr Cys Glu
225                 230                 235                 240

Val Ala Lys Met Cys Glu Ala Ala Gly Ala Asp Ala Ile Asn Ile Thr
                245                 250                 255

Trp Gly Ser His Ala Glu Val Ile Asn Ala Ala Gly Leu Leu Ser Lys
            260                 265                 270

His Gly Ala Asn His Val Glu Ala Ala Lys Met Ile Lys Asp Ala Val
        275                 280                 285

Ser Ile Pro Thr Met Leu Cys Gly Gly Ile Tyr Ser Pro Glu Ile Gly
    290                 295                 300

Glu Lys Leu Leu Glu Asp Gly Val Cys Asp Phe Ile Gly Ile Gly Lys
305                 310                 315                 320

Pro Ala Leu Ala Asp Pro Met Trp Ala Lys Lys Ala Ala Glu Gly Arg
                325                 330                 335

Pro Glu Asp Ile Arg Pro Cys Ile Gly Cys Gly Val Gly Cys His Asp
            340                 345                 350

Arg Gly Met Leu Ser Gly Gly Val Val Gln Cys Ala Val Asn Ala Ala
        355                 360                 365
```

```
Leu Tyr Lys Phe Asp Glu Pro Val Tyr Pro Gln Ala Glu Val Pro Lys
    370                 375                 380

Lys Val Ile Ile Ile Gly Ala Gly Pro Ala Gly Cys Glu Ala Ala Ile
385                 390                 395                 400

Thr Ala Lys Lys Cys Gly His Asp Val Thr Ile Tyr Glu Lys Arg Lys
                405                 410                 415

Ile Gly Gly Val Leu Lys Glu Ala Thr Val Ser Asp Ser Lys Glu Asp
            420                 425                 430

Leu Gly Arg Leu Ile Thr Tyr Tyr Glu Thr Gln Leu Lys Lys Glu Gly
        435                 440                 445

Ile Glu Val Ile Tyr Glu Glu Ala Thr Ala Asp Thr Val Val Ala Gly
    450                 455                 460

Gly Phe Asp Val Ala Ile Val Ala Cys Gly Ala Thr Val Arg Asn Leu
465                 470                 475                 480

Asn Ile Asp Gly Gln Asp Asp Pro Ser Val Val Tyr Ala Met Asp Phe
                485                 490                 495

Leu Asp Asn Asp Cys Lys Ser Asp Ala Asp Arg Val Val Val Val Gly
            500                 505                 510

Gly Gly Ile Val Gly Ala Glu Thr Ala Leu Ile Leu Ala Glu Glu Arg
        515                 520                 525

Gly Lys Asp Val Thr Ile Thr Thr Arg Ser Pro Glu Phe Phe Val Ser
    530                 535                 540

Gly Val Met Gly Ile Ala Tyr Met Val Arg Leu Gly Met Ala Gly Val
545                 550                 555                 560

Thr Ile Lys Pro Ser Thr Gln Leu Val Ala Val Lys Asp Gly Lys Pro
                565                 570                 575

Met Phe Ala Gly Pro Arg Gly Leu Glu Thr Leu Asp Val Asp Gln Thr
            580                 585                 590

Ile Ile Ser Ser Gly Phe Val Pro Thr Phe Asn Gln Phe Arg Ala Gln
        595                 600                 605

Ile Glu Glu Lys Cys Glu Asp Val Arg Val Ile Gly Ile Gly Asp Cys
    610                 615                 620

Lys Ala Ser Arg Met Val Met Asp Ala Val His Glu Gly Tyr Ile Ala
625                 630                 635                 640

Gly Cys Asn Leu


<210> SEQ ID NO 2
<211> LENGTH: 644
<212> TYPE: PRT
<213> ORGANISM: Bacteroides ovatus

<400> SEQUENCE: 2

Met Lys Asn Lys Phe Tyr Pro Lys Thr Phe Glu Arg Gly Tyr Ile Gly
1               5                   10                  15

Asn Leu Glu Val Glu Asn Arg Ala Ile Arg Met Pro Met Gly Thr Glu
            20                  25                  30

Leu Gly Asn Pro Asp Gly Ser Pro Ser Trp Ala Ser Phe Lys Ala Tyr
        35                  40                  45

Ala Glu Ala Ala Asp Gly Gly Thr Gly Ile Val Phe Met Asp Asn Ala
    50                  55                  60

Gly Val Thr Gln Phe His His Val Gly Leu Ser Leu Ala Ser Asp Asn
65                  70                  75                  80

Tyr Ile Gly Pro Met Ser Val Leu Ala Lys Thr Ile Lys Gln His Gly
                85                  90                  95
```

-continued

```
Ala Ile Pro Gly Leu Gln Ile Val His Pro Gly Arg Asp Ala Ala Phe
            100                 105                 110

Val Arg Gly Asp Asp Leu Ile Ser Ser Ser Arg Ile Gln Trp Glu Pro
        115                 120                 125

Trp Tyr Glu Asn Gly Gly Ala Val Pro Arg Glu Leu Thr Ile Glu Glu
    130                 135                 140

Ile His Asp Phe Val Gly Tyr Phe Gly Asp Cys Ala Leu Arg Ala Gln
145                 150                 155                 160

Thr Ala Gly Phe Glu Ile Val Asp Val His Ala Ala Cys Gly Val Leu
                165                 170                 175

Leu Ser Asn Phe Leu Ser Pro Arg Asn Asn Thr Arg Asn Asp Met Tyr
            180                 185                 190

Gly Gly Ser Leu His Asn Arg Ala Arg Phe Leu Leu Glu Val Ile Arg
        195                 200                 205

Asp Ile Lys Lys Lys Cys Pro Asn Leu Pro Leu Ala Ile Arg Leu Ser
    210                 215                 220

Gly Ile Asp Phe Glu Pro Asp Gly Ile Thr Ile Glu Glu Thr Cys Glu
225                 230                 235                 240

Val Ala Lys Met Cys Glu Ala Ala Gly Ala Asp Ala Ile Asn Ile Thr
                245                 250                 255

Trp Gly Ser His Ala Glu Val Ile Asn Ala Ala Gly Leu Leu Ser Lys
            260                 265                 270

His Gly Ala Asn His Val Glu Ala Ala Lys Met Ile Lys Asp Ala Val
        275                 280                 285

Ser Ile Pro Thr Met Leu Cys Gly Gly Ile Tyr Ser Pro Glu Ile Gly
    290                 295                 300

Glu Lys Leu Leu Glu Asp Gly Val Cys Asp Phe Ile Gly Ile Gly Lys
305                 310                 315                 320

Pro Ala Leu Ala Asp Pro Met Trp Ala Lys Lys Ala Ala Glu Gly Arg
                325                 330                 335

Pro Glu Asp Ile Arg Pro Cys Ile Gly Cys Gly Val Gly Cys His Asp
            340                 345                 350

Arg Gly Met Leu Ser Gly Gly Val Val Gln Cys Ala Val Asn Ala Ala
        355                 360                 365

Leu Tyr Lys Phe Asp Glu Pro Val Tyr Pro Gln Ala Glu Val Pro Lys
    370                 375                 380

Lys Val Ile Ile Ile Gly Ala Gly Pro Ala Gly Cys Glu Ala Ala Ile
385                 390                 395                 400

Thr Ala Lys Lys Cys Gly His Asp Val Thr Ile Tyr Glu Lys Arg Lys
                405                 410                 415

Ile Gly Gly Val Leu Lys Glu Ala Thr Val Ser Asp Ser Lys Glu Asp
            420                 425                 430

Leu Gly Arg Leu Ile Thr Tyr Tyr Glu Thr Gln Leu Lys Lys Glu Gly
        435                 440                 445

Ile Glu Val Ile Tyr Glu Glu Ala Thr Ala Asp Thr Val Val Ala Gly
    450                 455                 460

Gly Phe Asp Val Ala Ile Val Ala Cys Gly Ala Thr Val Arg Asn Leu
465                 470                 475                 480

Asn Ile Asp Gly Gln Asp Asp Pro Ser Val Val Tyr Ala Met Asp Phe
                485                 490                 495

Leu Asp Asn Asp Cys Lys Ser Asp Ala Asp Arg Val Val Val Val Gly
            500                 505                 510

Gly Gly Ile Val Gly Ala Glu Thr Ala Leu Ile Leu Ala Glu Glu Arg
        515                 520                 525
```

```
Gly Lys Asp Val Thr Ile Thr Thr Arg Ser Pro Glu Phe Phe Val Pro
    530                 535                 540

Gly Val Met Gly Ile Ala Tyr Met Val Arg Leu Gly Met Ala Gly Val
545                 550                 555                 560

Thr Ile Lys Pro Ser Thr Gln Leu Val Ala Val Lys Asp Gly Lys Pro
                565                 570                 575

Met Phe Ala Gly Pro Arg Gly Leu Glu Thr Leu Asp Val Asp Gln Thr
            580                 585                 590

Ile Ile Ser Ser Gly Phe Val Pro Thr Phe Asn Gln Phe Arg Ala Gln
        595                 600                 605

Ile Glu Glu Lys Cys Glu Asp Val Arg Val Ile Gly Ile Gly Asp Cys
    610                 615                 620

Lys Ala Ser Arg Met Val Met Asp Ala Val His Glu Gly Tyr Leu Ala
625                 630                 635                 640

Gly Cys Asn Leu


<210> SEQ ID NO 3
<211> LENGTH: 644
<212> TYPE: PRT
<213> ORGANISM: Streptococcus constellatus

<400> SEQUENCE: 3

Met Lys Asn Lys Phe Tyr Pro Lys Thr Phe Glu Arg Gly Tyr Ile Gly
1               5                   10                  15

Asn Leu Glu Val Glu Asn Arg Ala Ile Arg Met Pro Met Gly Thr Glu
            20                  25                  30

Leu Gly Asn Pro Asp Gly Ser Pro Ser Trp Ala Ser Leu Lys Ala Tyr
        35                  40                  45

Ala Glu Ala Ala Asp Gly Gly Thr Gly Ile Val Phe Met Asp Asn Ala
    50                  55                  60

Gly Val Thr Gln Phe His His Val Gly Leu Ser Leu Ala Ser Asp Lys
65                  70                  75                  80

Tyr Ile Gly Pro Met Ser Val Leu Ala Lys Thr Ile Lys Gln His Gly
                85                  90                  95

Ala Ile Pro Gly Leu Gln Ile Val His Pro Gly Arg Asp Ala Ala Phe
            100                 105                 110

Val Arg Gly Asp Asp Leu Ile Ser Ser Ser Arg Ile Gln Trp Glu Pro
        115                 120                 125

Trp Tyr Glu Asn Gly Gly Ala Val Pro Arg Glu Leu Thr Ile Glu Glu
    130                 135                 140

Ile His Asp Phe Val Gly Tyr Phe Gly Asp Cys Ala Leu Arg Ala Gln
145                 150                 155                 160

Thr Ala Gly Phe Glu Ile Ile Asp Val His Ala Ala Cys Gly Val Leu
                165                 170                 175

Leu Ser Asn Phe Leu Ser Pro Arg Asn Asn Thr Arg Asn Asp Met Tyr
            180                 185                 190

Gly Gly Ser Leu His Asn Arg Ala Arg Phe Leu Leu Glu Val Ile Arg
        195                 200                 205

Asp Ile Lys Lys Lys Cys Pro Asn Leu Pro Leu Ala Ile Arg Leu Ser
    210                 215                 220

Gly Ile Asp Phe Glu Pro Gly Gly Ile Thr Val Glu Glu Thr Cys Glu
225                 230                 235                 240

Val Ala Lys Met Cys Glu Ala Ala Gly Ala Asp Ala Ile Asn Ile Thr
                245                 250                 255
```

```
Trp Gly Ser His Ala Glu Val Ile Asn Ala Ala Gly Leu Leu Ser Lys
            260                 265                 270

His Gly Ala Asn His Val Glu Ala Ala Lys Met Ile Lys Asp Ala Val
        275                 280                 285

Ser Ile Pro Thr Met Leu Cys Gly Gly Ile Tyr Ser Pro Glu Ile Gly
    290                 295                 300

Glu Lys Leu Leu Glu Asp Gly Val Cys Asp Phe Ile Gly Ile Gly Lys
305                 310                 315                 320

Pro Ala Leu Ala Asp Pro Met Trp Ala Lys Lys Ala Ala Glu Gly Arg
                325                 330                 335

Pro Glu Asp Ile Arg Pro Cys Ile Gly Cys Gly Val Gly Cys His Asp
            340                 345                 350

Arg Gly Met Leu Ser Gly Gly Val Val Gln Cys Ala Val Asn Ala Ala
        355                 360                 365

Leu Tyr Lys Phe Asp Glu Pro Val Tyr Pro Gln Ala Glu Val Pro Lys
    370                 375                 380

Lys Val Ile Ile Ile Gly Ala Gly Pro Ala Gly Cys Glu Ala Ala Ile
385                 390                 395                 400

Thr Ala Lys Lys Cys Gly His Asp Val Thr Ile Tyr Glu Lys Arg Lys
                405                 410                 415

Ile Gly Gly Val Leu Lys Glu Ala Thr Val Ser Asp Ser Lys Glu Asp
            420                 425                 430

Leu Gly Tyr Leu Ile Thr Tyr Tyr Glu Thr Gln Leu Lys Lys Glu Gly
        435                 440                 445

Ile Glu Val Ile Tyr Glu Glu Ala Thr Ala Ser Thr Val Ala Ala Gly
    450                 455                 460

Gly Phe Asp Val Ala Ile Val Ala Cys Gly Ala Thr Val Arg Asn Leu
465                 470                 475                 480

Asn Ile Asp Gly Gln Asp Asp Pro Ser Val Val Tyr Ala Met Asp Phe
                485                 490                 495

Leu Asp Asn Asp Cys Lys Ser Asp Ala Asp Arg Val Val Val Val Gly
            500                 505                 510

Gly Gly Ile Val Gly Ala Glu Thr Ala Leu Ile Leu Ala Glu Glu Gln
        515                 520                 525

Gly Lys Asp Val Thr Ile Thr Thr Arg Ser Pro Glu Phe Phe Val Pro
    530                 535                 540

Gly Val Met Gly Ile Ala Tyr Met Val Arg Leu Gly Met Ala Gly Val
545                 550                 555                 560

Thr Ile Lys Pro Ser Thr Gln Leu Val Ala Val Lys Asp Gly Lys Pro
                565                 570                 575

Met Phe Ala Gly Pro Arg Gly Leu Glu Thr Leu Asp Val Asp Gln Thr
            580                 585                 590

Ile Ile Ser Ser Gly Phe Val Pro Thr Phe Asn Gln Phe Arg Ala Gln
        595                 600                 605

Ile Glu Glu Lys Cys Glu Asp Val Arg Val Ile Gly Ile Gly Asp Cys
    610                 615                 620

Lys Ala Ser Arg Met Val Met Asp Ala Val His Glu Gly Tyr Ile Ala
625                 630                 635                 640

Gly Cys Asn Leu
```

<210> SEQ ID NO 4
<211> LENGTH: 1935
<212> TYPE: DNA
<213> ORGANISM: Lactococcus garvieae

<400> SEQUENCE: 4

```
atgaagaaca agttctatcc gaagaccttc gagcgcggct acatcggtaa cctagaggtc      60
gagaaccgag cgatccgcat gccgatgggc accgagctgg gcaacccgga cggctctccc     120
agctgggcct ccctcaaggc gtacgctgag gctgccgacg gtggaaccgg catcgtgttc     180
atggacaacg ccggcgtgac ccagttccac catgtcggac tgtccctggc cagcgacaac     240
tacatcggcc ccatgtccgt cctcgcaaag accatcaagc agcacggggc catccccggc     300
ctgcagatcg tccacccggg ccgcgacgcg gcgttcgtgc gcggtgacga cctgatctcc     360
tcttcccgca tccagtggga gccctggtac gagaacggcg gcgctgttcc ccgcgagctc     420
accatcgagg agatccacga cttcgtcggt tacttcggcg actgcgcact ccgcgcgcag     480
accgcgggct tcgaaatcgt cgacgtccac gcggcatgcg gcgtcctgct gagcaacttc     540
ctctcgccgc gcaacaacac ccgcaatgac atgtacggcg gaagcctgca caaccgcgcc     600
cgcttcctgc tcgaggtcat ccgcgacatc aagaagaagt gccccaacct cccgctggct     660
atccgactct ccggcatcga cttcgaaccg gacggcatca ccatcgagga gacctgcgag     720
gtcgccaaga tgtgcgaggc agccggtgcg gacgccatca acatcacctg gggttcccat     780
gcagaggtca taaacgcggc cggcctgctc tccaagcacg gcgccaacca cgtcgaggca     840
gcgaagatga tcaaggacgc tgttagcatc cccaccatgc tgtgcggcgg catctactcc     900
cccgagatcg gcgagaagct gctcgaggac ggcgtctgcg acttcatcgg catcggcaag     960
cccgcgctcg ccgaccccat gtgggccaag aaggcagctg aggggcgtcc tgaggacatc    1020
aggccctgca tcggttgcgg cgtcggctgc catgaccgcg gcatgctctc cggcggcgtc    1080
gtccagtgcg ccgtcaacgc ggccctgtac aagttcgacg aacccgtcta cccgcaggct    1140
gaggttccca agaaggtcat catcatcggc gcaggccccg ctggctgcga ggctgccatc    1200
accgcgaaga agtgcggcca tgacgtcacc atctacgaga agcgcaagat cggtggcgtt    1260
ctgaaggagg ctaccgtctc cgacagcaag gaggacctcg gccgcctcat cacctactac    1320
gagacccagc tcaagaagga gggcatcgag gtcatctacg aggaggccac tgcagacacc    1380
gttgtagccg gcggcttcga cgtcgccatc gtcgcctgcg gcgccaccgt gcgcaacctc    1440
aacatcgacg gccaggacga cccctccgtc gtgtacgcga tggacttcct ggacaacgac    1500
tgcaagagcg atgccgacag ggtcgtcgtt gtcggcggtg gcatcgtggg tgccgagacc    1560
gcgctgatcc tcgcggagga gcggggcaag gatgtcacca tcaccacccg ctccccggag    1620
ttcttcgtct ccggcgtcat gggcatcgcc tacatggttc gcctgggtat ggcgggagtc    1680
acgatcaagc cctccaccca gctcgtcgcc gtcaaggatg gcaagcccat gttcgccggc    1740
ccccgcggcc tggagaccct ggacgtcgac cagacaatca tctcctctgg cttcgtcccg    1800
accttcaacc agttccgcgc ccagatcgag gagaagtgcg aggacgtcag ggtcatcggc    1860
atcggcgact gcaaggcctc ccgcatggtc atggacgctg tccacgaggg ctacatcgct    1920
ggctgcaacc tgtag                                                     1935
```

<210> SEQ ID NO 5
<211> LENGTH: 1935
<212> TYPE: DNA
<213> ORGANISM: Bacteroides ovatus

<400> SEQUENCE: 5

```
atgaagaaca agttctatcc gaagaccttc gagcgcggct acatcggcaa cctagaggtc      60
gagaaccgag cgatccgcat gccgatgggc accgagctgg gcaacccgga cggctctccc     120
```

```
agctgggcct ccttcaaggc gtacgctgag gctgccgacg gtggaaccgg catcgtgttc    180

atggacaacg ccggcgtgac ccagttccac catgtcggac tgtccctggc cagcgacaac    240

tacatcggcc ccatgtccgt cctcgcaaag accatcaagc agcacggggc catccccggc    300

ctgcagatcg tccacccggg ccgcgacgcg gcgttcgtgc gcggtgacga cctgatctcc    360

tcttcccgca tccagtggga gccctggtac gagaacggcg gcgctgttcc ccgcgagctc    420

accatcgagg agatccacga cttcgtcggt tacttcggcg actgcgcact ccgcgcgcag    480

accgcgggct tcgaaatcgt cgacgtccac gcggcatgcg gcgtcctgct gagcaacttc    540

ctctcgccgc gcaacaacac ccgtaacgac atgtacggcg gaagcctgca caaccgcgcc    600

cgcttcctgc tcgaggtcat ccgcgacatc aagaagaagt gccccaacct cccgctggct    660

atccgactct ccggcatcga cttcgaaccg gacggcatca ccatcgagga gacctgcgag    720

gtcgccaaga tgtgcgaggc agccggtgcg gacgccatca acatcacctg ggttcccat     780

gcagaggtca taaacgcggc cggcctgctc tccaagcacg gcgccaacca cgtcgaggca    840

gcgaagatga tcaaggacgc tgttagcatc cccaccatgc tgtgcggcgg catctactcc    900

cccgagatcg gcgagaagct gctcgaggac ggcgtctgcg acttcatcgg catcggcaag    960

cccgcgctcg ccgaccccat gtgggccaag aaggcagctg aggggcgtcc tgaggacatc   1020

aggccctgca tcggttgcgg cgtcggctgc catgaccgcg gcatgctctc cggcggcgtc   1080

gtccagtgcg ccgtcaacgc ggccctgtac aagttcgacg aacccgtcta cccgcaggct   1140

gaggttccca agaaggtcat catcatcggc gcaggccccg ctggctgcga ggctgccatc   1200

accgcgaaga agtgcggcca tgacgtcacc atctacgaga agcgcaagat cggtggcgtt   1260

ctgaaggagg ctaccgtctc cgacagcaag gaggacctcg gccgcctcat cacctactac   1320

gagacccagc tcaagaagga gggcatcgag gtcatctacg aggaggccac tgcagacacc   1380

gttgtagccg gcggcttcga cgtcgccatc gtcgcctgcg gcgccaccgt gcgcaacctc   1440

aacatcgacg gccaggacga cccctccgtc gtgtacgcga tggacttcct ggacaacgac   1500

tgcaagagcg atgccgacag ggtcgtcgtt gtcggcggtg gcatcgtggg cgccgagacc   1560

gcgctgatcc tcgcggagga gcggggcaag gatgtcacca tcaccacccg ctccccggag   1620

ttcttcgtcc ccggcgtcat gggcatcgcc tacatggttc gcctgggtat ggcgggagtc   1680

acgatcaagc cctccaccca gctcgtcgcc gtcaaggacg gcaagcccat gttcgccggc   1740

ccccgcggcc tggagaccct ggacgtcgac cagacaatca tctcctctgg cttcgtcccg   1800

accttcaacc agttccgcgc ccagatcgag gagaagtgcg aggacgtcag ggtcatcggc   1860

atcggcgact gcaaggcctc ccgcatggtc atggacgctg tccacgaggg ctacctcgct   1920

ggctgcaacc tgtag                                                    1935
```

<210> SEQ ID NO 6
<211> LENGTH: 1935
<212> TYPE: DNA
<213> ORGANISM: Streptococcus constellatus

<400> SEQUENCE: 6

```
atgaaaaata agttctatcc gaagaccttc gagcgcggct acatcggtaa cctagaggtc     60

gagaaccgag cgatccgcat gccgatgggc accgagctgg gcaacccgga cggctctccc    120

agctgggcct ccctcaaggc gtacgccgag gctgccgacg gcggtaccgg catcgtgttc    180

atggacaacg ccggcgtgac ccagttccac catgtcggac tttccctggc cagcgacaag    240

tacatcggcc ccatgtccgt cctcgctaag accatcaagc agcacggggc catccccggc    300
```

```
ctgcagatcg tccatccggg ccgcgacgcg gcgttcgtgc gcggtgacga cctgatctcc    360

tcctcccgca tccagtggga gccctggtac gagaacggcg gcgctgttcc ccgcgagctc    420

accatcgagg agatccacga cttcgtcggt tacttcggcg actgcgcact ccgcgcgcag    480

accgcgggct tcgaaatcat cgacgtccac gcggcatgcg gcgtcctgct gagcaacttc    540

ctctcgccgc gcaacaacac ccgcaacgac atgtacggcg gaagcctgca caaccgcgct    600

cgcttcctgc tcgaggtcat ccgcgacatc aagaagaagt gccccaacct cccgctggct    660

atccgactct ccggcatcga tttcgagccg ggcggcatca ccgtcgagga gacctgcgag    720

gtcgccaaga tgtgcgaggc agccggtgcg gacgccatca acatcacctg gggttcccat    780

gcagaggtca tcaacgcggc cggcctgctc tccaagcacg gcgccaacca cgtcgaggca    840

gcgaagatga tcaaggacgc tgttagcatc cccaccatgc tgtgcggcgg catctactcc    900

cccgagatcg gcgagaagct gctcgaggac ggcgtctgcg acttcatcgg catcggcaag    960

ccagcgctcg ctgaccccat gtgggccaag aaggcggctg aggggcgtcc tgaggacatc   1020

aggccctgca tcggttgcgg cgtcggctgc catgaccgcg gcatgctctc cggcggcgtc   1080

gtccagtgcg ccgtcaacgc ggccctgtac aagttcgacg agcccgtcta cccgcaggct   1140

gaggttccca agaaggttat catcatcggc gcaggtcccg ctggctgcga ggctgccatc   1200

accgcgaaga agtgcggcca tgacgtcacc atatacgaga agcgcaagat cggcggcgtt   1260

ctgaaggagg ctaccgtctc cgacagcaag gaggacctcg gctacctcat cacctactac   1320

gagacccagc tcaagaagga gggcatcgag gtcatctacg aggaggccac tgcaagcacc   1380

gttgcagccg gcggcttcga cgtcgccatc gtcgcctgcg gcgccaccgt gcgcaacctc   1440

aacatcgacg gccaggacga cccctccgtc gtgtacgcga tggacttcct ggacaacgac   1500

tgtaagagcg acgccgacag ggtcgtcgtt gtcggcggcg gcatcgtggg tgccgagacc   1560

gcgctgatcc tcgcggagga gcagggcaag gacgtcacca tcactacccg ctccccggag   1620

ttcttcgtcc ccggcgtcat gggtatcgcc tacatggttc gccttggcat ggcgggcgtc   1680

acgatcaagc cctccaccca gctcgtcgcc gtcaaggacg gcaagcccat gttcgccggt   1740

ccccgcggcc tggagaccct ggacgtcgac cagaccatca tctcctctgg cttcgtcccg   1800

accttcaacc agttccgcgc ccagatcgag gagaagtgcg aggacgtcag ggtcatcggc   1860

atcggcgact gcaaggcctc ccgtatggtc atggacgctg tccacgaggg ctacatcgct   1920

ggctgcaacc tgtag                                                    1935
```

<210> SEQ ID NO 7
<211> LENGTH: 286
<212> TYPE: PRT
<213> ORGANISM: Lactococcus garvieae

<400> SEQUENCE: 7

```
Met Ala Gln Glu Val Lys Val Pro Lys Met Pro Gly Ala Pro Val Phe
1               5                   10                  15

Gly Lys Trp Ile Ser Pro Glu Glu Ser Val Gly Gln Arg Leu Lys Gly
            20                  25                  30

Lys Lys Ile Leu Leu Thr Gly Thr Thr Lys Gly Val Gly Arg Val Thr
        35                  40                  45

Gln Glu Leu Leu Cys Ala His Gly Ala Phe Val Cys Gly Ser Gly Arg
    50                  55                  60

Thr Pro Gly Val Ala Ala Ser Val Ala Asp Glu Leu Lys Ala Lys Gly
65                  70                  75                  80

Tyr Gln Ala Ala Gly Met Asp Val Asp Leu Ser Asp Tyr Asp Ala Val
```

```
                85                  90                  95

Lys Lys Trp Val Glu Glu Cys Ala Glu Leu Met Gly Gly Ile Asp Val
            100                 105                 110

Val Ile Asn Asn Ala Ser His Pro Gly Met Ala Pro Phe Gly Glu Met
        115                 120                 125

Thr Pro Glu Ile Trp Asn Tyr Gly Ile Lys Asn Glu Leu Asp Leu Val
    130                 135                 140

Tyr Asn Val Cys Asn Cys Ala Trp Pro Tyr Leu Gln Lys Ala Asp Gly
145                 150                 155                 160

Ala Ser Ile Ile Ile Thr Ser Ser Thr Val Ala Leu Gln Gly Ser Asn
                165                 170                 175

Ser Pro Gln Ala Cys His Ala Ala Cys Lys Gly Ala Cys Leu Ser Leu
            180                 185                 190

Ala Arg Gln Leu Ala Ala Glu Gly Gly Pro Phe Gly Ile Arg Cys Asn
        195                 200                 205

Ser Val Thr Pro Gly Leu Val Trp Thr Glu Ala Met Ser Asn Ile Pro
    210                 215                 220

Lys Glu Met Ala Ser Gly Leu Val Ala Ala Gln Thr Thr Gln Gln Ala
225                 230                 235                 240

Val Asp Pro Met Asp Ile Ala Tyr Ala Tyr Leu Phe Leu Ala Ser Asp
                245                 250                 255

Glu Ser Arg Gln Ile Thr Ala Ala Asn Ile Pro Val Asp Gly Gly Cys
            260                 265                 270

Ala Gly Ala Val Thr Gly Gly Met Gln Gly Glu Ile Glu Val
        275                 280                 285


<210> SEQ ID NO 8
<211> LENGTH: 310
<212> TYPE: PRT
<213> ORGANISM: Bacteroides ovatus

<400> SEQUENCE: 8

Met Ser Pro His Phe Ala Ser Gln Arg Trp Ala Ala Lys Glu Asp Gly
1               5                   10                  15

Pro Arg Gln Gly Lys Glu Pro Thr Met Ala Gln Glu Val Lys Val Pro
            20                  25                  30

Lys Met Pro Gly Ala Pro Val Phe Gly Lys Trp Ile Ser Pro Glu Glu
        35                  40                  45

Ser Val Gly Gln Arg Leu Lys Gly Lys Lys Ile Leu Leu Thr Gly Thr
    50                  55                  60

Thr Lys Gly Val Gly Arg Val Thr Gln Glu Leu Leu Cys Ala His Gly
65                  70                  75                  80

Ala Phe Val Cys Gly Ser Gly Arg Thr Pro Gly Val Ala Ala Ser Val
                85                  90                  95

Ala Asp Glu Leu Lys Ala Lys Gly Tyr Gln Ala Ala Gly Met Asp Val
            100                 105                 110

Asp Leu Ser Asp Tyr Asp Ala Val Lys Lys Trp Val Glu Glu Cys Ala
        115                 120                 125

Glu Leu Met Gly Gly Ile Asp Val Val Ile Asn Asn Ala Ser His Pro
    130                 135                 140

Gly Met Ala Pro Phe Gly Glu Met Thr Pro Glu Ile Trp Asn Tyr Gly
145                 150                 155                 160

Val Lys Asn Glu Leu Asp Leu Val Tyr Asn Val Cys Asn Cys Ala Trp
                165                 170                 175

Pro Tyr Leu Gln Lys Ala Asp Gly Ala Ser Ile Ile Ile Thr Ser Ser
```

```
            180                 185                 190

Thr Val Gly Leu Gln Gly Ser Asn Ser Pro Gln Ala Cys His Ala Ala
        195                 200                 205

Cys Lys Gly Ala Cys Leu Ser Leu Ala Arg Gln Leu Ala Ala Glu Gly
    210                 215                 220

Gly Pro Phe Gly Ile Arg Cys Asn Ser Val Thr Pro Gly Leu Val Trp
225                 230                 235                 240

Thr Glu Ala Met Ser Asn Ile Pro Lys Glu Met Ala Ser Gly Leu Val
                245                 250                 255

Ala Ala Gln Thr Thr Gln Gln Ala Val Asp Pro Met Asp Ile Ala Tyr
            260                 265                 270

Ala Tyr Leu Phe Leu Ala Ser Asp Glu Ser Arg Gln Ile Thr Ala Ala
        275                 280                 285

Asn Ile Pro Val Asp Gly Gly Cys Ala Gly Ala Val Thr Gly Gly Met
    290                 295                 300

Gln Gly Glu Ile Glu Val
305                 310


<210> SEQ ID NO 9
<211> LENGTH: 287
<212> TYPE: PRT
<213> ORGANISM: Streptococcus constellatus

<400> SEQUENCE: 9

Met Ala Gln Glu Val Lys Cys Ala Lys Met Pro Gly Ala Pro Val Phe
1               5                   10                  15

Gly Lys Trp Ile Ser Pro Glu Glu Ser Ile Gly Gln Arg Leu Lys Gly
            20                  25                  30

Lys Lys Ile Ile Leu Thr Gly Thr Thr Lys Gly Val Gly Lys Val Thr
        35                  40                  45

Gln Glu Leu Leu Cys Ala His Gly Ala Phe Val Cys Gly Ser Gly Arg
    50                  55                  60

Thr Pro Gly Val Ala Ala Ser Val Ala Asp Glu Leu Lys Ala Lys Gly
65                  70                  75                  80

Tyr Gln Ala Ala Gly Met Asp Val Asp Leu Ser Asp Tyr Glu Ala Val
                85                  90                  95

Lys Lys Trp Val Gln Glu Cys Ala Glu Leu Met Gly Gly Ile Asp Val
            100                 105                 110

Val Ile Asn Asn Ala Ser His Pro Gly Met Ala Pro Phe Glu Glu Met
        115                 120                 125

Thr Pro Glu Ile Trp Asn Tyr Gly Ile Lys Asn Glu Leu Asp Leu Val
    130                 135                 140

Tyr Asn Val Cys Asn Cys Ala Trp Pro Tyr Leu Lys Glu Ala Glu Gly
145                 150                 155                 160

Gly Ala Ser Ile Ile Ile Thr Ser Ser Thr Val Gly Leu Gln Gly Thr
                165                 170                 175

Asn Ser Pro Gln Ala Cys His Ala Ala Ala Lys Gly Ala Cys Leu Ser
            180                 185                 190

Leu Ala Arg Gln Leu Ala Ala Glu Gly Gly Pro Phe Gly Ile Arg Cys
        195                 200                 205

Asn Ser Val Thr Pro Gly Leu Val Trp Thr Glu Ala Met Ala Asn Ile
    210                 215                 220

Pro Lys Glu Met Ala Ser Gly Leu Val Gly Ala Gln Thr Thr Gln Gln
225                 230                 235                 240

Ala Ile Asp Pro Met Asp Ile Ala Tyr Ala Tyr Leu Phe Leu Ala Ser
```

-continued

```
            245                 250                 255

Asp Glu Ala Arg Gln Ile Thr Ala Ala Asn Leu Pro Val Asp Gly Gly
        260                 265                 270

Cys Ala Gly Ala Val Thr Gly Gly Met Gln Gly Glu Ile Glu Gly
    275                 280                 285


<210> SEQ ID NO 10
<211> LENGTH: 861
<212> TYPE: DNA
<213> ORGANISM: Lactococcus garvieae

<400> SEQUENCE: 10

atggcacagg aagtcaaagt ccccaagatg cccggcgcac ccgtgttcgg caagtggatc      60

tcccccgagg agtccgtcgg ccagcgcctg aagggcaaga agatcctgct caccggcacc     120

accaagggcg tcggcagggt cacccaggag ctgctgtgcg cacacggcgc cttcgtctgc     180

ggctccggcc gcaccccgg cgtggcagcc tccgtcgccg acgagctgaa ggccaagggc     240

taccaggccg ccggcatgga cgtcgacctg tctgactacg acgccgtgaa gaagtgggtt     300

gaggagtgcg ccgagctcat gggcggcatc gacgtcgtca tcaacaacgc gtcccacccc     360

ggcatggccc ccttcggcga gatgaccccg gagatctgga actacggcat caagaacgag     420

ctcgacctcg tctacaacgt ctgcaactgc gcatggccct acctgcagaa ggcagacggc     480

gcctccatca tcatcacctc ctccaccgtc gccctccagg gcagcaactc ccctcaggcc     540

tgtcacgctg cctgcaaggg cgcctgcctg tccctggccc gccagctcgc cgctgagggc     600

ggccccttcg gcatccgctg caactccgtc accccgggcc tggtctggac cgaggccatg     660

tccaacatcc ccaaggagat ggcaagcggc ctggtcgcag cccagaccac ccagcaggct     720

gtcgacccga tggacatcgc ctacgcctac ctgttcctgg catccgacga gtcccgccag     780

atcaccgctg ccaacatccc cgtcgacggc ggctgcgccg gcgctgtgac cggcggcatg     840

cagggcgaga tcgaggtcta g                                               861


<210> SEQ ID NO 11
<211> LENGTH: 933
<212> TYPE: DNA
<213> ORGANISM: Bacteroides ovatus

<400> SEQUENCE: 11

atgagcccgc attttgcgag ccaaagatgg gctgcaaagg aagacggccc aagacaagga      60

aaggaaccaa ccatggcaca ggaagtcaaa gtccccaaga tgcccggcgc acccgtgttc     120

ggcaagtgga tctcccccga ggagtccgtc ggccagcgcc tgaagggcaa gaagatcctg     180

ctcaccggca ccaccaaggg cgtcggcagg gtcacccagg agctgctgtg cgcacacggc     240

gccttcgtct gcggctccgg ccgcaccccc ggcgtggcag cctccgtcgc cgacgagctg     300

aaggccaagg gctaccaggc cgccggcatg gacgtcgacc tgtctgacta cgacgccgtg     360

aagaagtggg ttgaggagtg cgccgagctc atgggcggca tcgacgtcgt catcaacaac     420

gcgtcccacc ccggcatggc cccctcggc gagatgaccc cggagatctg gaactacggc     480

gtcaagaacg agctcgacct cgtctacaac gtctgcaact gcgcatggcc ctacctgcag     540

aaggcagacg gcgcctccat catcatcacc tcctccaccg tcggcctcca gggcagcaac     600

tcccctcagg cctgccacgc tgcctgcaag ggcgcctgcc tgtccctggc ccgccagctc     660

gccgctgagg gcggcccctt cggcatccgc tgcaactccg tcaccccggg cctggtctgg     720

accgaggcca tgtccaacat ccccaaggag atggcaagcg gcctggtcgc agcccagacc     780
```

acccagcagg ctgtcgaccc gatggacatc gcctacgcct acctgttcct ggcatccgac 840
gagtcccgcc agatcaccgc tgccaacatc cccgtcgacg gcggctgcgc cggcgctgtg 900
accggcggca tgcagggcga gatcgaggtc taa 933

<210> SEQ ID NO 12
<211> LENGTH: 864
<212> TYPE: DNA
<213> ORGANISM: Streptococcus constellatus

<400> SEQUENCE: 12
atggcacagg aagtcaaatg cgccaagatg cccggagcgc ccgtcttcgg caagtggatc 60
agccccgagg agtcgatcgg ccagcgcctc aagggcaaga agatcattct caccggcacc 120
actaagggcg tcggcaaggt cacccaagag ctgctgtgcg cccacggcgc cttcgtctgc 180
ggctccggtc gtacccccgg cgtggccgct tccgtggccg acgagctgaa ggccaagggc 240
taccaggccg ccggcatgga cgtcgacctg tccgactacg aggccgtgaa gaagtgggtc 300
caagagtgcg ccgagctcat gggcggcatc gacgtcgtca tcaacaacgc ctcccacccg 360
ggcatggccc ccttcgagga gatgaccccc gagatctgga actacggcat caagaacgag 420
ctcgacctgg tctacaacgt gtgcaactgc gcttggccgt acctgaagga agccgagggc 480
ggcgcttcca tcatcatcac ctcctccacc gtcggcctcc agggcaccaa ctccccgcag 540
gcctgccacg ccgccgccaa gggcgcatgc ctgtccctgg cccgccagct ggcagctgaa 600
ggcggcccct tcggcatccg ctgcaactcc gtcacccccg gcctggtgtg gaccgaggcc 660
atggccaaca tcccgaagga aatggcatcc ggcctggtcg gtgcgcagac cacccagcag 720
gctatcgacc ccatggacat cgcctacgct tacctcttcc tggcctccga tgaggctcgc 780
cagatcaccg cagcgaacct tcccgtcgac ggcggctgcg ccggcgctgt gaccggcggc 840
atgcagggcg agatcgaagg ctaa 864

<210> SEQ ID NO 13
<211> LENGTH: 486
<212> TYPE: PRT
<213> ORGANISM: Lactococcus garvieae

<400> SEQUENCE: 13

Met Ala Glu Phe Asp Val Glu Tyr Asp Leu Val Val Val Gly Gly Gly
1               5                   10                  15

Ala Ser Gly Lys Ser Ala Ala Leu Ile Ala Ala Arg Glu Gly Lys Arg
            20                  25                  30

Val Val Val Leu Glu Lys Met Pro Glu Thr Gly Gly Leu Ser Met Tyr
        35                  40                  45

Ala Glu Gly Thr Ala Ala Phe Glu Ser Ser Ile Gln Asn Glu Leu Gly
    50                  55                  60

Thr Pro Arg Leu Ser Lys Tyr His Phe Pro Thr Lys Gln Glu Gly Ile
65                  70                  75                  80

Glu Lys Phe Met Gly Tyr Ser His Gln Arg Ala Asn Tyr Asp Val Val
                85                  90                  95

Arg Ala Phe Val Glu Asn Ser Ala Glu Thr Ile Asp Ile Tyr Arg Asp
            100                 105                 110

Leu Gly Val Val Tyr Lys Ala Cys Asp Ile Ala Ala Glu Asp Asp Pro
        115                 120                 125

Asn Glu Val Trp Thr Phe His Leu Pro Glu Gly Leu Gly Ala His Cys
    130                 135                 140

Gln Glu Val Leu Leu Asp Ala Ile Gln Lys Leu Asp Val Asp Ile Phe

-continued

```
145                 150                 155                 160

Thr Ser Thr Pro Ala Lys Glu Leu Ile Ile Glu Asp Gly Ala Val Val
                165                 170                 175

Gly Val Val Ala Glu Ser Asp Gly Glu Pro Leu Arg Val Gly Gly Lys
            180                 185                 190

Ala Val Ile Leu Ala Thr Gly Gly Met Gly Ser Ser Pro Glu Arg Ile
        195                 200                 205

Phe Lys Tyr Ser Trp Phe Ala Pro Ala Ala Tyr Asn Met Asn Thr Leu
    210                 215                 220

Thr Pro Leu Gln Asn Val Gly Asp Gly Leu Asp Leu Ala Leu Ser Ala
225                 230                 235                 240

Gly Ala Asp Pro Thr Tyr Ile Thr Thr Cys Pro Ile Leu Ala Ala Gly
                245                 250                 255

Gly Arg Asp Met Thr Met Asp Ser Gln Val Gly Gly Ala Gly Val Asn
            260                 265                 270

Pro Gly Val Trp Ile Asn Lys Thr Gly Arg Arg Phe Ala Ala Glu Ser
        275                 280                 285

Val Ala Glu Asn Ile Gly Asp Ile Gly Thr Tyr Tyr Gly Lys Gln Pro
    290                 295                 300

Gly Gly Val Val Trp Ser Ile Leu Ser Gln Ala Asp Ile Asp Arg Leu
305                 310                 315                 320

Val Ala Glu Gly Ser Glu Ile Ala Ile Gly Glu Phe Val Val Tyr His
                325                 330                 335

Lys Pro Met Glu Arg Leu Pro Ile Glu Leu Glu Ala His Leu Glu Ser
            340                 345                 350

Gly Leu Val Lys Lys Ala Gly Ser Phe Glu Glu Leu Ala Ala Leu Ile
        355                 360                 365

Asp Val Pro Val Asp Thr Phe Val Ala Thr Met Ala Asp Tyr Asn Glu
    370                 375                 380

Ala Cys Glu Lys Gly Tyr Asp Asp Ala Phe Met Lys Lys Pro Gln Tyr
385                 390                 395                 400

Leu Arg Pro Met Val Glu Gly Pro Phe Tyr Ala Ile Pro Leu Ala Thr
                405                 410                 415

Gly Thr Met Gly Ser Ala Gly Gly Ile Arg Ile Asn Gly Asn Met Gln
            420                 425                 430

Val Val Asp Ala Asp Tyr Asn Ala Ile Pro Gly Leu Tyr Ala Val Gly
        435                 440                 445

Leu Asp Ala Thr Gly Leu Tyr Gly Asp Ser Tyr Asn Met Glu Val Pro
    450                 455                 460

Gly Ala Ala Asn Gly Phe Ala His Thr Ser Gly Arg Ile Ala Ala Arg
465                 470                 475                 480

His Ala Ile Ser Thr Met
                485


<210> SEQ ID NO 14
<211> LENGTH: 486
<212> TYPE: PRT
<213> ORGANISM: Bacteroides ovatus

<400> SEQUENCE: 14

Met Ala Gln Phe Asp Val Glu Tyr Asp Leu Val Val Val Gly Gly Gly
1               5                   10                  15

Ala Ser Gly Lys Ser Ala Ala Leu Ile Ala Ala Arg Glu Gly Lys Arg
            20                  25                  30

Val Val Val Leu Glu Lys Met Pro Glu Thr Gly Gly Leu Ser Met Tyr
```

```
        35                  40                  45

Ala Glu Gly Thr Ala Ala Phe Glu Ser Ser Ile Gln Asn Glu Leu Gly
    50                  55                  60

Thr Pro Arg Leu Ser Lys Tyr His Phe Pro Thr Lys Gln Glu Gly Ile
65                  70                  75                  80

Glu Lys Phe Met Gly Tyr Ser His Gln Arg Ala Asn Tyr Asp Val Val
                85                  90                  95

Arg Ala Phe Val Glu Asn Ser Ala Glu Thr Ile Asp Ile Tyr Arg Asp
            100                 105                 110

Leu Gly Val Val Tyr Lys Ala Cys Asp Ile Ala Ala Glu Asp Asp Pro
        115                 120                 125

Asn Glu Val Trp Thr Phe His Leu Pro Glu Gly Leu Gly Ala His Cys
    130                 135                 140

Gln Glu Val Leu Leu Asp Ala Ile Gln Lys Leu Asp Val Asp Ile Phe
145                 150                 155                 160

Thr Ser Thr Pro Ala Lys Glu Leu Ile Ile Glu Glu Gly Ala Val Val
                165                 170                 175

Gly Val Val Ala Glu Ser Asp Gly Glu Pro Leu Arg Val Gly Gly Lys
            180                 185                 190

Ala Val Ile Leu Ala Thr Gly Gly Met Gly Ser Ser Pro Glu Arg Ile
        195                 200                 205

Phe Lys Tyr Ser Trp Phe Ala Pro Ala Ala Tyr Asn Met Asn Thr Leu
    210                 215                 220

Thr Pro Leu Gln Asn Val Gly Asp Gly Leu Asp Leu Ala Leu Ser Ala
225                 230                 235                 240

Gly Ala Asp Pro Thr Tyr Ile Thr Thr Cys Pro Ile Leu Ala Ala Gly
                245                 250                 255

Gly Arg Asp Met Thr Met Asp Ser Gln Val Gly Gly Ala Gly Val Asn
            260                 265                 270

Pro Gly Val Trp Ile Asn Lys Thr Gly Arg Arg Phe Ala Ala Glu Ser
        275                 280                 285

Val Ala Glu Asn Ile Gly Asp Ile Gly Thr Tyr Tyr Gly Lys Gln Pro
    290                 295                 300

Gly Gly Val Val Trp Ser Ile Leu Ser Gln Ala Asp Ile Asp Arg Leu
305                 310                 315                 320

Val Ala Glu Gly Ser Glu Ile Ala Ile Gly Glu Phe Val Val Tyr His
                325                 330                 335

Lys Pro Met Glu Arg Leu Pro Ile Glu Leu Glu Ala His Leu Glu Ser
            340                 345                 350

Gly Leu Val Lys Lys Ala Gly Ser Phe Glu Glu Leu Ala Ala Leu Ile
        355                 360                 365

Asp Val Pro Val Asp Thr Phe Val Ala Thr Met Ala Asp Tyr Asn Glu
    370                 375                 380

Ala Cys Glu Lys Gly Tyr Asp Asp Ala Phe Met Lys Lys Pro Gln Tyr
385                 390                 395                 400

Leu Arg Pro Met Val Glu Gly Pro Phe Tyr Ala Ile Pro Leu Ala Thr
                405                 410                 415

Gly Thr Met Gly Ser Ala Gly Gly Ile Arg Ile Asn Gly Asn Met Gln
            420                 425                 430

Val Val Asp Ala Asp Tyr Asn Ala Ile Pro Gly Leu Tyr Ala Val Gly
        435                 440                 445

Leu Asp Ala Thr Gly Leu Tyr Gly Asp Ser Tyr Asn Met Glu Val Pro
    450                 455                 460
```

```
Gly Ala Ala Asn Gly Phe Ala His Thr Ser Gly Arg Ile Ala Ala Arg
465                 470                 475                 480

His Ala Ile Ser Thr Met
                485


<210> SEQ ID NO 15
<211> LENGTH: 487
<212> TYPE: PRT
<213> ORGANISM: Streptococcus constellatus

<400> SEQUENCE: 15

Met Ala Glu Phe Asp Val Glu Tyr Asp Leu Val Val Val Gly Gly Gly
1               5                   10                  15

Ala Ser Gly Lys Ser Ala Ala Leu Ile Ala Ala Arg Ala Gly Lys Ser
            20                  25                  30

Val Val Val Leu Glu Lys Met Pro Glu Thr Gly Gly Leu Ser Met Tyr
        35                  40                  45

Ala Glu Gly Thr Ala Ala Phe Glu Ser Ser Ile Gln Lys Glu Leu Gly
    50                  55                  60

Thr Pro Arg Leu Ser Lys Tyr His Phe Pro Thr Lys Gln Glu Gly Val
65                  70                  75                  80

Glu Lys Phe Met Gly Tyr Ser His Gln Arg Ala Ser Tyr Asp Val Val
                85                  90                  95

Arg Ala Phe Val Glu Asn Ser Ala Glu Thr Ile Asp Ile Tyr Arg Glu
            100                 105                 110

Leu Gly Val Val Tyr Lys Thr Cys Asp Ile Ala Ala Glu Asp Asp Pro
        115                 120                 125

Ser Glu Val Trp Thr Phe His Leu Pro Glu Gly Leu Gly Ala His Cys
    130                 135                 140

Gln Glu Val Leu Leu Asp Ala Ile Gln Lys Leu Asp Val Asp Ile Phe
145                 150                 155                 160

Thr Ser Thr Pro Ala Lys Glu Leu Ile Ile Glu Asp Gly Lys Val Val
                165                 170                 175

Gly Val Val Ala Glu Ser Asp Gly Glu Pro Leu Arg Val Gly Gly Lys
            180                 185                 190

Ala Val Ile Leu Ala Thr Gly Gly Met Gly Ser Asn Pro Asp Arg Ile
        195                 200                 205

Phe Lys Tyr Ser Trp Phe Ala Pro Ala Ala Tyr Asn Met Asn Val Leu
    210                 215                 220

Thr Pro Leu Gln Asn Met Gly Asp Gly Leu Asp Leu Ala Leu Ser Ala
225                 230                 235                 240

Gly Ala Asp Asp Thr Ala Ile Thr Thr Cys Pro Ile Leu Ala Ala Gly
                245                 250                 255

Gly Arg Asp Met Thr Met Asp Ser Gln Val Gly Gly Ala Gly Val Asn
            260                 265                 270

Pro Gly Val Trp Ile Asn Lys Ser Gly Lys Arg Phe Cys Ala Glu Ser
        275                 280                 285

Val Ala Glu Asn Ile Gly Asp Ile Gly Thr Tyr Tyr Gly Lys Gln Pro
    290                 295                 300

Gly Gly Ile Val Trp Ser Ile Leu Ser Gln Ala Asp Ile Asp Arg Leu
305                 310                 315                 320

Val Asn Glu Gly Ser Glu Ile Ala Ile Gly Glu Phe Val Val Tyr His
                325                 330                 335

Lys Pro Met Glu Arg Leu Pro Ile Glu Leu Asn Ala His Leu Glu Ser
            340                 345                 350
```

```
Gly Leu Val Lys Lys Ala Asp Cys Phe Glu Glu Leu Ala Glu Lys Met
        355                 360                 365

Asp Val Pro Ala Gly Ala Phe Val Asp Thr Met Asn Ala Tyr Asn Glu
    370                 375                 380

Ala Cys Glu Lys Gly Tyr Asp Asp Ala Phe Met Lys Lys Pro Glu Tyr
385                 390                 395                 400

Leu Arg Ala Glu Thr Gln Ala Pro Phe Tyr Ala Ile Pro Leu Ala Thr
                405                 410                 415

Gly Thr Met Gly Ser Ala Gly Gly Ile Lys Ile Asn Gly Asn Met Gln
            420                 425                 430

Val Ile Asp Ser Asp Ala Asn Pro Ile Pro Gly Leu Tyr Ala Val Gly
        435                 440                 445

Leu Asp Ala Thr Gly Leu Tyr Gly Asp Ser Tyr Asn Met Glu Val Pro
    450                 455                 460

Gly Ala Ala Asn Gly Phe Ala His Thr Ser Gly Arg Ile Ala Ala Arg
465                 470                 475                 480

His Ala Leu Ser Thr Met Glu
                485


<210> SEQ ID NO 16
<211> LENGTH: 1461
<212> TYPE: DNA
<213> ORGANISM: Lactococcus garvieae

<400> SEQUENCE: 16

atggcagaat tcgatgttga gtatgatctt gttgtcgttg gaggaggcgc ctctggaaag     60

tctgcagcgc tgatcgccgc ccgtgagggc aagcgcgtcg tggtgctcga gaagatgccc    120

gagaccggag gcctctccat gtacgccgaa ggcaccgctg ccttcgagtc ctctattcag    180

aacgagctcg gcaccccgcg tctttccaag taccacttcc cgaccaagca ggagggcatc    240

gagaagttca tgggctacag ccatcagcgc gcgaactacg acgtcgtccg cgctttcgtt    300

gagaactccg cagagaccat cgacatctac cgcgacctcg gcgtcgtcta caaggcctgc    360

gacatcgccg cagaggacga ccccaacgag gtctggacct tccatctgcc cgagggcctc    420

ggcgcccatt gccaggaagt cctgctcgac gccatccaga agctcgacgt cgacatcttc    480

acctccaccc ccgccaagga gctcatcatc gaggacggcg ctgtcgtcgg tgtcgtcgca    540

gagtctgacg gcgagcccct gcgcgtcggc ggcaaggccg ttatcctggc aaccggcggc    600

atgggctcca gcccggagcg catcttcaag tacagctggt tcgcccccgc tgcctacaac    660

atgaacaccc tcaccccgct gcagaacgtc ggcgacggcc tcgacctcgc cctctccgcg    720

ggcgcagacc ccacctacat caccacctgc ccgattctcg cagcaggcgg ccgtgacatg    780

accatggact cccaggtcgg cggcgcgggc gtcaaccccg gcgtgtggat caacaagacc    840

ggcaggcgct tcgcggccga gtccgttgcc gagaacatcg gcgacatcgg aacctactac    900

ggcaagcagc ccggcggcgt ggtctggtcc atcctctccc aggcggacat cgaccgtctg    960

gtggccgagg gttccgagat cgcgatcggc gagttcgtcg tgtaccacaa gccgatggag   1020

cgcctcccta tcgagctcga ggctcatctc gagtccggcc tggtgaagaa ggctggcagc   1080

ttcgaggagc tcgcagccct cattgacgtg cctgtagaca ccttcgtcgc aactatggcc   1140

gactacaacg aggcatgcga gaagggctac gacgacgcct ttatgaagaa gccccagtac   1200

ctccgcccga tggtcgaggg tcccttctat gccatccctc tggctaccgg caccatgggt   1260

tctgctggcg gcatccgcat taacggcaac atgcaggtcg tcgacgccga ctacaacgcc   1320

attcccggtc tctacgcggt cggtctggac gccacgggtc tctacggcga ttcctacaac   1380
```

atggaggttc ccggcgcagc aaacggtttc gcccacacct ccggacgcat cgccgcccgc 1440
cacgcgatct ccactatgta g 1461

<210> SEQ ID NO 17
<211> LENGTH: 1461
<212> TYPE: DNA
<213> ORGANISM: Bacteroides ovatus

<400> SEQUENCE: 17
atggcacaat tcgatgttga gtatgatctt gttgtcgttg gaggaggcgc ctctggaaag 60
tctgcagcgc tgatcgccgc ccgtgagggc aagcgcgtcg tggtgctcga gaagatgccc 120
gagaccggag gcctctccat gtacgccgaa ggcaccgctg ccttcgagtc ctctattcag 180
aacgagctcg gcaccccgcg tctttccaag taccacttcc cgaccaagca ggagggcatc 240
gagaagttca tgggctacag ccatcagcgc gcgaactacg acgtcgtccg cgctttcgtt 300
gagaactccg cagagaccat cgacatctac cgcgacctcg gcgtcgtcta caaggcctgc 360
gacatcgccg cagaggacga ccccaacgag gtctggacct tccatctgcc cgagggcctc 420
ggcgcccatt gccaggaagt cctgctcgac gccatccaga agctcgacgt cgacatcttc 480
acctccaccc ccgccaagga gctcatcatc gaggaaggcg ctgtcgtcgg tgtcgtcgca 540
gagtctgacg gcgagcccct gcgcgtcggc ggcaaggccg ttatcctggc aaccggcggc 600
atgggctcca gcccggagcg catcttcaag tacagctggt tcgcccccgc tgcctacaac 660
atgaacaccc tcaccccgct gcagaacgtc ggcgacggcc tcgacctcgc cctctccgcg 720
ggcgcagacc ccacctacat caccacctgc ccgattctcg cagcaggcgg ccgtgacatg 780
accatggact cccaggtcgg cggcgcgggc gtcaaccccg gcgtgtggat caacaagacc 840
ggcaggcgct tcgcggccga gtccgttgcc gagaacatcg gcgacatcgg aacctactac 900
ggcaagcagc ccggcggcgt ggtctggtcc atcctctccc aggcggacat cgaccgtctg 960
gtggccgagg gttccgagat cgcgatcggc gagttcgtcg tgtaccacaa gccgatggag 1020
cgcctcccta tcgagctcga ggctcatctc gagtccggcc tggtgaagaa ggctggcagc 1080
ttcgaggagc tcgcagccct cattgacgtg cctgtagaca ccttcgtcgc aactatggcc 1140
gactacaacg aggcatgcga gaagggctac gacgacgcct ttatgaagaa gccccagtac 1200
ctccgcccga tggtcgaggg tcccttctat gccatccctc tggctaccgg caccatgggt 1260
tctgctggcg gcatccgcat taacggcaac atgcaggtcg tcgacgccga ctacaacgcc 1320
attcccggtc tctacgcggt cggtctggac gccacgggtc tctacggcga ctcctacaac 1380
atggaggttc ccggcgcagc aaacggtttc gcccacacct ccggacgcat cgccgcccgc 1440
cacgcgatct ccactatgta g 1461

<210> SEQ ID NO 18
<211> LENGTH: 1464
<212> TYPE: DNA
<213> ORGANISM: Streptococcus constellatus

<400> SEQUENCE: 18
atggctgagt tcgatgttga gtacgacctg gtcgtcgtcg gcggcggcgc atccggcaag 60
tccgcggcct tgatcgcggc tcgcgccggc aagagcgtcg tcgttctcga gaagatgccc 120
gagacgggcg gcctgtccat gtacgccgag gggaccgcgg cgttcgagtc ttccattcag 180
aaggaactcg gtacccccg tctgagcaag taccatttcc ccacgaagca agagggcgtg 240
gagaagttca tgggatacag tcaccagcgc gcgagctacg acgtggtgcg cgccttcgtg 300

-continued

```
gagaattccg ctgagaccat cgacatctac cgcgagctgg gcgtcgtcta caagacctgc    360

gacatcgccg cagaggacga tcccagcgag gtctggacct tccacctgcc cgagggcctc    420

ggcgcccact gccaggaggt tctgctcgac gccatccaga agctcgacgt ggacatcttc    480

acctccacgc ccgccaagga gctgattatc gaggacggca aggtcgtcgg cgtcgtggcc    540

gagtccgacg gagagccgct gcgcgtcggc ggcaaggccg tcatcctcgc gaccggcggc    600

atgggctcga accccgaccg catcttcaag tacagctggt tcgcccccgc tgcctacaac    660

atgaacgttc tgaccccgct gcagaatatg ggcgacggcc ttgatctggc cctgtccgca    720

ggcgcagatg acacggccat caccacctgc ccgattttgg cggctggcgg ccgtgacatg    780

accatggatt cccaggtcgg cggcgcaggc gtcaaccccg gcgtgtggat caacaagtcc    840

ggcaagcgct tctgcgccga atccgtcgcc gagaacatcg gcgacatcgg cacctactac    900

ggcaagcagc ccggcggcat cgtgtggtcc atcctctccc aggccgacat cgaccgcctg    960

gtcaacgagg gctccgaaat cgccatcggc gagttcgtcg tgtaccacaa gcccatggag   1020

cgcctaccca tcgagctcaa tgcgcacctg gagtccggcc tggtcaagaa ggccgactgc   1080

ttcgaagagc tggctgagaa gatggacgtt cccgccggcg ccttcgtaga caccatgaac   1140

gcctacaacg aggcgtgcga gaagggctac gacgacgcct tcatgaagaa gcccgagtac   1200

ctgcgtgccg agacccaggc ccccttctac gccatcccct tggcaacggg caccatgggc   1260

tctgccggcg gcatcaagat caacggcaac atgcaggtca tcgattccga cgcgaacccc   1320

atccccggcc tgtacgctgt gggcctggat gccaccggcc tgtacggcga ctcctacaac   1380

atggaggttc ccggcgccgc taacggcttt gcccacacct ccggccgcat tgcggcacgc   1440

cacgccctct ccacgatgga gtaa                                          1464
```

```
<210> SEQ ID NO 19
<211> LENGTH: 22
<212> TYPE: PRT
<213> ORGANISM: Lactococcus garcieae

<400> SEQUENCE: 19

Met Lys Asn Lys Phe Tyr Pro Lys Thr Phe Glu Arg Gly Tyr Ile Gly
1               5                   10                  15

Asn Leu Glu Val Glu Asn
            20


<210> SEQ ID NO 20
<211> LENGTH: 10
<212> TYPE: PRT
<213> ORGANISM: Lactococcus garcieae

<400> SEQUENCE: 20

Phe Asp Glu Pro Val Tyr Pro Gln Ala Glu
1               5                   10


<210> SEQ ID NO 21
<211> LENGTH: 16
<212> TYPE: PRT
<213> ORGANISM: Lactococcus garcieae

<400> SEQUENCE: 21

Ala Ser Arg Met Val Met Asp Ala Val His Glu Gly Tyr Ile Ala Gly
1               5                   10                  15


<210> SEQ ID NO 22
<211> LENGTH: 17
```

<212> TYPE: PRT
<213> ORGANISM: Lactococcus garcieae

<400> SEQUENCE: 22

```
Gly Tyr Ile Gly Asn Leu Glu Val Glu Asn Arg Ala Ile Arg Met Pro
1               5                   10                  15

Met
```

<210> SEQ ID NO 23
<211> LENGTH: 31
<212> TYPE: DNA
<213> ORGANISM: Artificial sequence
<220> FEATURE:
<223> OTHER INFORMATION: E1-N-terminal-31primer
<220> FEATURE:
<221> NAME/KEY: misc_feature
<222> LOCATION: (11)..(11)
<223> OTHER INFORMATION: n stands for inosine
<220> FEATURE:
<221> NAME/KEY: misc_feature
<222> LOCATION: (14)..(14)
<223> OTHER INFORMATION: n stands for inosine
<220> FEATURE:
<221> NAME/KEY: misc_feature
<222> LOCATION: (20)..(20)
<223> OTHER INFORMATION: n stands for adenine, guanine, cytosine or thymine
<220> FEATURE:
<221> NAME/KEY: misc_feature
<222> LOCATION: (26)..(26)
<223> OTHER INFORMATION: n stands for adenine, guanine, cytosine or thymine

<400> SEQUENCE: 23

```
tgaagaataa nttntayccn aaracnttyg a                                31
```

<210> SEQ ID NO 24
<211> LENGTH: 37
<212> TYPE: DNA
<213> ORGANISM: Artificial sequence
<220> FEATURE:
<223> OTHER INFORMATION: E1-N-terminal-37 primer
<220> FEATURE:
<221> NAME/KEY: misc_feature
<222> LOCATION: (11)..(11)
<223> OTHER INFORMATION: n stands for inosine
<220> FEATURE:
<221> NAME/KEY: misc_feature
<222> LOCATION: (14)..(14)
<223> OTHER INFORMATION: n stands for inosine
<220> FEATURE:
<221> NAME/KEY: misc_feature
<222> LOCATION: (20)..(20)
<223> OTHER INFORMATION: n stands for inosine
<220> FEATURE:
<221> NAME/KEY: misc_feature
<222> LOCATION: (26)..(26)
<223> OTHER INFORMATION: n stands for inosine
<220> FEATURE:
<221> NAME/KEY: misc_feature
<222> LOCATION: (35)..(35)
<223> OTHER INFORMATION: n stands for adenine, guanine, cytosine or thymine

<400> SEQUENCE: 24

```
tgaagaataa nttntayccn aaracnttyg arrgngg                          37
```

<210> SEQ ID NO 25
<211> LENGTH: 32
<212> TYPE: DNA
<213> ORGANISM: Artificial sequence
<220> FEATURE:
<223> OTHER INFORMATION: E1-N-terminal-F32 primer

```
<220> FEATURE:
<221> NAME/KEY: misc_feature
<222> LOCATION: (21)..(21)
<223> OTHER INFORMATION: n stands for adenine, guanine, cytosine or
      thymine
<220> FEATURE:
<221> NAME/KEY: misc_feature
<222> LOCATION: (27)..(27)
<223> OTHER INFORMATION: n stands for adenine, guanine, cytosine or
      thymine

<400> SEQUENCE: 25

atgaagaata agttttaycc naaracntty ga                                 32


<210> SEQ ID NO 26
<211> LENGTH: 38
<212> TYPE: DNA
<213> ORGANISM: Artificial sequence
<220> FEATURE:
<223> OTHER INFORMATION: E1-internal-RP1 primer
<220> FEATURE:
<221> NAME/KEY: misc_feature
<222> LOCATION: (24)..(24)
<223> OTHER INFORMATION: n stands for adenine, guanine, cytosine or
      thymine
<220> FEATURE:
<221> NAME/KEY: misc_feature
<222> LOCATION: (33)..(33)
<223> OTHER INFORMATION: n stands for adenine, guanine, cytosine or
      thymine

<400> SEQUENCE: 26

cctgcaatat aaccttcatg tacngcrtcc atnaccat                           38


<210> SEQ ID NO 27
<211> LENGTH: 30
<212> TYPE: DNA
<213> ORGANISM: Artificial sequence
<220> FEATURE:
<223> OTHER INFORMATION: pUC19-FP-1 primer

<400> SEQUENCE: 27

acacaggaaa cagctatgac catgattacg                                    30


<210> SEQ ID NO 28
<211> LENGTH: 30
<212> TYPE: DNA
<213> ORGANISM: Artificial sequence
<220> FEATURE:
<223> OTHER INFORMATION: pUC19-RP-1 primer

<400> SEQUENCE: 28

agctggcgaa agggggatgt gctgcaaggc                                    30


<210> SEQ ID NO 29
<211> LENGTH: 30
<212> TYPE: DNA
<213> ORGANISM: Artificial sequence
<220> FEATURE:
<223> OTHER INFORMATION: pUC19-FP-2 primer

<400> SEQUENCE: 29

atgattacgc caagcttgca tgcctgcagg                                    30


<210> SEQ ID NO 30
<211> LENGTH: 30
<212> TYPE: DNA
<213> ORGANISM: Artificial sequence
<220> FEATURE:
<223> OTHER INFORMATION: pUC19-RP-2 primer
```

<400> SEQUENCE: 30
ccagtcacga cgttgtaaaa cgacggccag 30

<210> SEQ ID NO 31
<211> LENGTH: 34
<212> TYPE: DNA
<213> ORGANISM: Artificial sequence
<220> FEATURE:
<223> OTHER INFORMATION: E1-RACE-N-P1 primer

<400> SEQUENCE: 31
atgcggatcg ctcggttctc gacctctagg ttac 34

<210> SEQ ID NO 32
<211> LENGTH: 33
<212> TYPE: DNA
<213> ORGANISM: Artificial sequence
<220> FEATURE:
<223> OTHER INFORMATION: E1-RACE-RP2-1 primer

<400> SEQUENCE: 32
atcgaggaga agtgcgagga cgtcagggtc atc 33

<210> SEQ ID NO 33
<211> LENGTH: 31
<212> TYPE: DNA
<213> ORGANISM: Artificial sequence
<220> FEATURE:
<223> OTHER INFORMATION: E1-RACE-N-P2 primer

<400> SEQUENCE: 33
ttctcgacct ctaggttacc gatgtagccg c 31

<210> SEQ ID NO 34
<211> LENGTH: 32
<212> TYPE: DNA
<213> ORGANISM: Artificial sequence
<220> FEATURE:
<223> OTHER INFORMATION: E1-RACE-RP2-2 primer

<400> SEQUENCE: 34
acgtcagggt catcggcatc ggcgactgca ag 32

<210> SEQ ID NO 35
<211> LENGTH: 34
<212> TYPE: DNA
<213> ORGANISM: Artificial sequence
<220> FEATURE:
<223> OTHER INFORMATION: E1-conf-NP primer

<400> SEQUENCE: 35
tgccggtgca atggctgaca tcatgttcaa cctg 34

<210> SEQ ID NO 36
<211> LENGTH: 34
<212> TYPE: DNA
<213> ORGANISM: Artificial sequence
<220> FEATURE:
<223> OTHER INFORMATION: E1-conf-CP primer

<400> SEQUENCE: 36
tcctccatcg ttcctccaat cagtaagaca cgcg 34

<210> SEQ ID NO 37
<211> LENGTH: 23

<212> TYPE: DNA
<213> ORGANISM: Artificial sequence
<220> FEATURE:
<223> OTHER INFORMATION: E1-FP primer

<400> SEQUENCE: 37
ctacatcggt aacctagagg tcg 23

<210> SEQ ID NO 38
<211> LENGTH: 23
<212> TYPE: DNA
<213> ORGANISM: Artificial sequence
<220> FEATURE:
<223> OTHER INFORMATION: E1-RP primer

<400> SEQUENCE: 38
ccgtgctgct tgatggtctt tgc 23

<210> SEQ ID NO 39
<211> LENGTH: 21
<212> TYPE: DNA
<213> ORGANISM: Artificial sequence
<220> FEATURE:
<223> OTHER INFORMATION: Gar-16S-Ribo-FP primer

<400> SEQUENCE: 39
tgcgtagata tatggaggaa c 21

<210> SEQ ID NO 40
<211> LENGTH: 21
<212> TYPE: DNA
<213> ORGANISM: Artificial sequence
<220> FEATURE:
<223> OTHER INFORMATION: Gar-16S-Ribo-RP primer

<400> SEQUENCE: 40
cttatctcta aggatagcac g 21

<210> SEQ ID NO 41
<211> LENGTH: 30
<212> TYPE: DNA
<213> ORGANISM: Artificial sequence
<220> FEATURE:
<223> OTHER INFORMATION: exp.E1 pet F Nde primer

<400> SEQUENCE: 41
agctcatatg aagaacaagt tctatccgaa 30

<210> SEQ ID NO 42
<211> LENGTH: 33
<212> TYPE: DNA
<213> ORGANISM: Artificial sequence
<220> FEATURE:
<223> OTHER INFORMATION: exp. E1 pet His primer

<400> SEQUENCE: 42
aatcgaattc ctacaggttg cagccagcga tgt 33

<210> SEQ ID NO 43
<211> LENGTH: 33
<212> TYPE: DNA
<213> ORGANISM: Artificial sequence
<220> FEATURE:
<223> OTHER INFORMATION: RACE-N-P3-1

<400> SEQUENCE: 43
atggagatag tgccgctggc aaggcaacgg cac 33

<210> SEQ ID NO 44
<211> LENGTH: 33
<212> TYPE: DNA
<213> ORGANISM: Artificial sequence
<220> FEATURE:
<223> OTHER INFORMATION: RACE-N-P3-2

<400> SEQUENCE: 44
tcaacgaaga ctcgatttga gcgagaggcg agg 33

<210> SEQ ID NO 45
<211> LENGTH: 32
<212> TYPE: DNA
<213> ORGANISM: Artificial sequence
<220> FEATURE:
<223> OTHER INFORMATION: E1-Bub-N-P1

<400> SEQUENCE: 45
acggtggaac cggcatcgtg ttcatggaca ac 32

<210> SEQ ID NO 46
<211> LENGTH: 31
<212> TYPE: DNA
<213> ORGANISM: Artificial sequence
<220> FEATURE:
<223> OTHER INFORMATION: E1-Bub-N-P2

<400> SEQUENCE: 46
gcgtgaccca gttccaccat gtcggactgt c 31

<210> SEQ ID NO 47
<211> LENGTH: 33
<212> TYPE: DNA
<213> ORGANISM: Artificial sequence
<220> FEATURE:
<223> OTHER INFORMATION: RACE-C-P3-1

<400> SEQUENCE: 47
gacatcccgt tcgagcgcag gatcacccat gag 33

<210> SEQ ID NO 48
<211> LENGTH: 33
<212> TYPE: DNA
<213> ORGANISM: Artificial sequence
<220> FEATURE:
<223> OTHER INFORMATION: RACE-C-P3-2

<400> SEQUENCE: 48
aggatcaccc atgagcgcat cgctatcatg gac 33

<210> SEQ ID NO 49
<211> LENGTH: 32
<212> TYPE: DNA
<213> ORGANISM: Artificial sequence
<220> FEATURE:
<223> OTHER INFORMATION: E1-Bub-C-P1

<400> SEQUENCE: 49
catcgctctt gcagtcgttg tccaggaagt cc 32

<210> SEQ ID NO 50
<211> LENGTH: 33
<212> TYPE: DNA
<213> ORGANISM: Artificial sequence
<220> FEATURE:
<223> OTHER INFORMATION: E1-Bub-C-P2

<400> SEQUENCE: 50
ttgtccagga agtccatcgc gtacacgacg gag 33

<210> SEQ ID NO 51
<211> LENGTH: 13
<212> TYPE: PRT
<213> ORGANISM: Lactococcus garvieae
<220> FEATURE:
<221> NAME/KEY: MISC_FEATURE
<222> LOCATION: (12)..(12)
<223> OTHER INFORMATION: Xaa stands for isoleucine or leucine

<400> SEQUENCE: 51

Thr Pro Gly Val Ala Ala Ser Val Ala Asp Glu Xaa Lys
1 5 10

<210> SEQ ID NO 52
<211> LENGTH: 9
<212> TYPE: PRT
<213> ORGANISM: Lactococcus garvieae

<400> SEQUENCE: 52

Met Pro Gly Ala Pro Val Phe Gly Lys
1 5

<210> SEQ ID NO 53
<211> LENGTH: 9
<212> TYPE: PRT
<213> ORGANISM: Lactococcus garvieae
<220> FEATURE:
<221> NAME/KEY: MISC_FEATURE
<222> LOCATION: (2)..(4)
<223> OTHER INFORMATION: Xaa stands for isoleucine or leucine

<400> SEQUENCE: 53

Lys Xaa Xaa Xaa Thr Gly Thr Thr Lys
1 5

<210> SEQ ID NO 54
<211> LENGTH: 18
<212> TYPE: PRT
<213> ORGANISM: Lactococcus garvieae
<220> FEATURE:
<221> NAME/KEY: MISC_FEATURE
<222> LOCATION: (5)..(6)
<223> OTHER INFORMATION: Xaa stands for isoleucine or leucine

<400> SEQUENCE: 54

Val Thr Gln Glu Xaa Xaa Cys Ala His Gly Ala Phe Val Cys Gly Ser
1 5 10 15

Gly Arg

<210> SEQ ID NO 55
<211> LENGTH: 11
<212> TYPE: PRT
<213> ORGANISM: Lactococcus garvieae
<220> FEATURE:
<221> NAME/KEY: MISC_FEATURE
<222> LOCATION: (2)..(2)
<223> OTHER INFORMATION: Xaa stands for isoleucine or leucine

<400> SEQUENCE: 55

Trp Xaa Ser Pro Glu Glu Ser Val Gly Gln Arg
1 5 10

<210> SEQ ID NO 56

<211> LENGTH: 8
<212> TYPE: PRT
<213> ORGANISM: Lactococcus garvieae

<400> SEQUENCE: 56

Ala Gln Glu Val Lys Val Pro Lys
1 5

<210> SEQ ID NO 57
<211> LENGTH: 44
<212> TYPE: DNA
<213> ORGANISM: Artificial sequence
<220> FEATURE:
<223> OTHER INFORMATION: E2-invitroTS-FP1

<400> SEQUENCE: 57
actttaagaa ggagatatac caatggcaca ggaagtcaaa gtcc 44

<210> SEQ ID NO 58
<211> LENGTH: 28
<212> TYPE: DNA
<213> ORGANISM: Artificial sequence
<220> FEATURE:
<223> OTHER INFORMATION: E2-invitroTS-RP

<400> SEQUENCE: 58
ctagacctcg atctcgccct gcatgccg 28

<210> SEQ ID NO 59
<211> LENGTH: 85
<212> TYPE: DNA
<213> ORGANISM: Artificial sequence
<220> FEATURE:
<223> OTHER INFORMATION: Universal-Primer

<400> SEQUENCE: 59
gaaattaata cgactcacta tagggagacc acaacggttt ccctctagaa ataattttgt 60
ttaactttaa gaaggagata tacca 85

<210> SEQ ID NO 60
<211> LENGTH: 28
<212> TYPE: DNA
<213> ORGANISM: Artificial sequence
<220> FEATURE:
<223> OTHER INFORMATION: exp.US2 pet F Nde

<400> SEQUENCE: 60
tatacatatg gcacaggaag tcaaagtc 28

<210> SEQ ID NO 61
<211> LENGTH: 32
<212> TYPE: DNA
<213> ORGANISM: Artificial sequence
<220> FEATURE:
<223> OTHER INFORMATION: exp. US2 pet

<400> SEQUENCE: 61
aatcgaattc ctagacctcg atctcgccct gc 32

<210> SEQ ID NO 62
<211> LENGTH: 28
<212> TYPE: DNA
<213> ORGANISM: Artificial sequence
<220> FEATURE:
<223> OTHER INFORMATION: exp.US3 F primer

<400> SEQUENCE: 62

-continued tatacatatg gcagaattcg atgttgag 28

<210> SEQ ID NO 63
<211> LENGTH: 32
<212> TYPE: DNA
<213> ORGANISM: Artificial sequence
<220> FEATURE:
<223> OTHER INFORMATION: exp.US3 R primer

<400> SEQUENCE: 63
ccgcaagctt ctacatagtg gagatcgcgt gg 32

<210> SEQ ID NO 64
<211> LENGTH: 28
<212> TYPE: DNA
<213> ORGANISM: Artificial sequence
<220> FEATURE:
<223> OTHER INFORMATION: exp.US1 F primer

<400> SEQUENCE: 64
tatacatatg ttcaagggtc cacagggc 28

<210> SEQ ID NO 65
<211> LENGTH: 33
<212> TYPE: DNA
<213> ORGANISM: Artificial sequence
<220> FEATURE:
<223> OTHER INFORMATION: exp.US1 R primer

<400> SEQUENCE: 65
gctcgaattc ttagtgctgc tgtgcctttt cag 33

<210> SEQ ID NO 66
<211> LENGTH: 30
<212> TYPE: DNA
<213> ORGANISM: Artificial sequence
<220> FEATURE:
<223> OTHER INFORMATION: exp.DS1 F primer

<400> SEQUENCE: 66
atatacatat gcaggatatg gacttcatgg 30

<210> SEQ ID NO 67
<211> LENGTH: 32
<212> TYPE: DNA
<213> ORGANISM: Artificial sequence
<220> FEATURE:
<223> OTHER INFORMATION: exp.DS1 R primer

<400> SEQUENCE: 67
gctcgaattc tcatagtgac atcagcgctc cc 32

<210> SEQ ID NO 68
<211> LENGTH: 31
<212> TYPE: DNA
<213> ORGANISM: Artificial sequence
<220> FEATURE:
<223> OTHER INFORMATION: exp.E2 pet His primer

<400> SEQUENCE: 68
aatcgaattc gagacctcga tctcgccctg c 31

<210> SEQ ID NO 69
<211> LENGTH: 32
<212> TYPE: DNA
<213> ORGANISM: Artificial sequence -continued

```
<220> FEATURE:
<223> OTHER INFORMATION: exp.E3 R His primer

<400> SEQUENCE: 69

ccgcaagctt gtacatagtg gagatcgcgt gg                                    32
```